(12) United States Patent
Hanna et al.

(10) Patent No.: US 10,940,189 B2
(45) Date of Patent: *Mar. 9, 2021

(54) SYSTEMS, COMPOSITIONS, AND METHODS FOR TRANSPLANTATION

(71) Applicant: Cytonics Corporation, Jupiter, FL (US)

(72) Inventors: Lewis Hanna, Naples, FL (US); John David Laughlin, Jupiter, FL (US); Shawn Robert Browning, Jupiter, FL (US)

(73) Assignee: CYTONICS CORPORATION, Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,477

(22) Filed: Mar. 2, 2018

(65) Prior Publication Data

US 2019/0046617 A1 Feb. 14, 2019

Related U.S. Application Data

(62) Division of application No. 14/380,234, filed as application No. PCT/US2013/027159 on Feb. 21, 2013.

(60) Provisional application No. 61/601,434, filed on Feb. 21, 2012, provisional application No. 61/726,815, filed on Nov. 15, 2012, provisional application No. 61/726,840, filed on Nov. 15, 2012, provisional application No. 61/727,433, filed on Nov. 16, 2012, provisional application No. 61/740,218, filed on Dec. 20, 2012.

(51) Int. Cl.
| | |
|---|---|
| *A61K 38/57* | (2006.01) |
| *A61K 38/17* | (2006.01) |
| *C07K 14/81* | (2006.01) |
| *A61K 35/19* | (2015.01) |
| *A61K 35/16* | (2015.01) |
| *A61K 35/28* | (2015.01) |
| *A61K 45/06* | (2006.01) |
| *A61M 1/34* | (2006.01) |

(52) U.S. Cl.
CPC .............. *A61K 38/57* (2013.01); *A61K 35/16* (2013.01); *A61K 35/19* (2013.01); *A61K 35/28* (2013.01); *A61K 38/1722* (2013.01); *A61K 45/06* (2013.01); *A61M 1/34* (2013.01); *C07K 14/81* (2013.01); *C07K 14/8107* (2013.01)

(58) Field of Classification Search
CPC .... A61K 38/57; A61K 38/1722; C07K 14/81; C07K 14/8107

See application file for complete search history.

(56) References Cited

U.S. PATENT DOCUMENTS

| | | |
|---|---|---|
| 4,518,584 A | 5/1985 | Mark et al. |
| 4,683,195 A | 7/1987 | Mullis et al. |
| 4,683,202 A | 7/1987 | Mullis |
| 4,708,713 A | 11/1987 | Lentz |
| 4,800,159 A | 1/1989 | Mullis et al. |
| 5,143,854 A | 9/1992 | Pirrung et al. |
| 5,242,974 A | 9/1993 | Holmes |
| 5,384,261 A | 1/1995 | Winkler et al. |
| 5,405,783 A | 4/1995 | Pirrung et al. |
| 5,409,818 A | 4/1995 | Davey et al. |
| 5,412,087 A | 5/1995 | McGall et al. |
| 5,424,186 A | 6/1995 | Fodor et al. |
| 5,429,807 A | 7/1995 | Matson et al. |
| 5,436,327 A | 7/1995 | Southern et al. |
| 5,445,934 A | 8/1995 | Fodor et al. |
| 5,472,672 A | 12/1995 | Brennan |
| 5,527,681 A | 6/1996 | Holmes et al. |
| 5,529,756 A | 6/1996 | Brennan |
| 5,532,128 A | 7/1996 | Eggers et al. |
| 5,545,531 A | 8/1996 | Rava et al. |
| 5,554,293 A | 9/1996 | Uhoch |
| 5,554,501 A | 9/1996 | Coassin et al. |
| 5,554,527 A | 9/1996 | Fickenscher |

(Continued)

FOREIGN PATENT DOCUMENTS

| | | |
|---|---|---|
| EP | 1320308 A1 | 6/2003 |
| EP | 1098664 B1 | 8/2003 |

(Continued)

OTHER PUBLICATIONS

Sottrup-Jensen et al., J. Biol. Chem., 1984, vol. 259(13):8318-8327.*
A2M and Chronic Wounds. 7 pages. Feb. 18, 2014.
A2M Peptide Biomarkers. 8 pgs.
Abrams, et al. Hip Synovial Fluid Cytokine Profiling in Patients with and without Arthritis. Poster No. 1801. ORS 2012 Annual Meeting.
Barilla, et al. Fibronectin fragments and their role in inflammatory arthritis. Semin Arthritis Rheum. Feb. 2000;29(4):252-65.

(Continued)

*Primary Examiner* — Xiaozhen Xie
(74) *Attorney, Agent, or Firm* — Wilson Sonsini Goodrich & Rosati

(57) ABSTRACT

Systems and methods for purification and concentration of autologous alpha-2-macroglobulin (A2M) from whole blood are provided. Also provided are diagnostic methods for identifying sites in the synovial joints, spine, tendons or ligaments for treatment of pain, degeneration, or inflammation with autologous A2M. Methods for utilizing autologous A2M in combination with other autologous treatments (e.g. platelets and other growth factors) are provided in addition to combinations with exogenous drugs or carriers. Also provided is a method of producing recombinant A2M wild type or variants thereof where the bait region was modified to enhance the inhibition characteristics of A2M and/or to prolong the half life of the protein in joints and spine disc or epidural space.

13 Claims, 32 Drawing Sheets

Specification includes a Sequence Listing.

(56) References Cited

U.S. PATENT DOCUMENTS

| | | | |
|---|---|---|---|
| 5,556,752 | A | 9/1996 | Lockhart et al. |
| 5,561,071 | A | 10/1996 | Hollenberg et al. |
| 5,563,120 | A | 10/1996 | Kuznetsov |
| 5,571,639 | A | 11/1996 | Hubbell et al. |
| 5,593,839 | A | 1/1997 | Hubbell et al. |
| 5,599,695 | A | 2/1997 | Pease et al. |
| 5,624,711 | A | 4/1997 | Sundberg et al. |
| 5,658,734 | A | 8/1997 | Brock et al. |
| 5,700,637 | A | 12/1997 | Southern et al. |
| 5,728,554 | A | 3/1998 | Bayer et al. |
| 5,747,251 | A | 5/1998 | Carson et al. |
| 5,807,522 | A | 9/1998 | Brown et al. |
| 5,837,832 | A | 11/1998 | Chee et al. |
| 5,876,980 | A | 3/1999 | DeFrees et al. |
| 5,922,577 | A | 7/1999 | Defrees et al. |
| 6,004,755 | A | 12/1999 | Wang |
| 6,010,627 | A | 1/2000 | Hood, III |
| 6,030,815 | A | 2/2000 | DeFrees et al. |
| 6,040,138 | A | 3/2000 | Lockhart et al. |
| 6,040,166 | A | 3/2000 | Erlich et al. |
| 6,045,996 | A | 4/2000 | Cronin et al. |
| 6,218,114 | B1 | 4/2001 | Peck et al. |
| 6,218,122 | B1 | 4/2001 | Friend et al. |
| 6,271,002 | B1 | 8/2001 | Linsley et al. |
| 6,284,460 | B1 | 9/2001 | Fodor et al. |
| 6,342,157 | B1 | 1/2002 | Hood, III |
| 6,472,140 | B1 * | 10/2002 | Tanzi ............... C07K 14/8107 435/4 |
| 6,566,331 | B1 | 5/2003 | Lezdey et al. |
| 6,607,885 | B1 | 8/2003 | Larossa et al. |
| 6,683,155 | B1 | 1/2004 | Silbiger et al. |
| 6,806,254 | B2 | 10/2004 | Godbole et al. |
| 6,903,201 | B2 | 6/2005 | Kekuda et al. |
| 7,011,852 | B2 | 3/2006 | Sukavaneshvar et al. |
| 7,186,695 | B2 | 3/2007 | Hogg |
| 7,291,450 | B2 | 11/2007 | Sowemimo-Coker et al. |
| 7,354,515 | B2 | 4/2008 | Coull et al. |
| 7,485,298 | B2 | 2/2009 | Powell |
| 7,709,215 | B2 | 5/2010 | Scuderi |
| 7,803,279 | B2 | 9/2010 | Coull et al. |
| 7,806,845 | B2 | 10/2010 | Arm et al. |
| 7,858,296 | B2 | 12/2010 | Sowemimo-Coker et al. |
| D632,801 | S | 2/2011 | Kyle et al. |
| 7,888,313 | B2 | 2/2011 | Greenspan et al. |
| 7,923,203 | B2 | 4/2011 | Sowemimo-Coker et al. |
| 7,927,344 | B2 | 4/2011 | Burba et al. |
| 8,101,077 | B2 | 1/2012 | Sukavaneshvar et al. |
| 8,551,068 | B2 | 10/2013 | Kyle et al. |
| 9,352,021 | B2 | 5/2016 | Hanna et al. |
| 10,265,388 | B2 | 4/2019 | Hanna et al. |
| 2002/0028207 | A1 | 3/2002 | Srivastava et al. |
| 2002/0037290 | A1 | 3/2002 | Armen |
| 2003/0127390 | A1 | 7/2003 | Davis |
| 2003/0180722 | A1 | 9/2003 | Godbole et al. |
| 2003/0180835 | A1 | 9/2003 | Bayer |
| 2004/0072993 | A1 | 4/2004 | Srivastava et al. |
| 2004/0138103 | A1 | 7/2004 | Patt |
| 2005/0037432 | A1 | 2/2005 | Tortorella et al. |
| 2006/0165710 | A1 | 7/2006 | Srivastava et al. |
| 2006/0204951 | A1 | 9/2006 | Folkman et al. |
| 2007/0244306 | A1 | 10/2007 | Tanahashi et al. |
| 2007/0259030 | A1 | 11/2007 | Drapeau |
| 2008/0040153 | A1 | 2/2008 | Davis |
| 2008/0044852 | A1 | 2/2008 | Kanayinkal et al. |
| 2009/0123452 | A1 | 5/2009 | Madison |
| 2009/0247456 | A1 | 10/2009 | Srivastava et al. |
| 2010/0085606 | A1 | 4/2010 | Daos |
| 2010/0098684 | A1 | 4/2010 | Scuderi et al. |
| 2011/0305663 | A1 | 12/2011 | Gosselin et al. |
| 2013/0059371 | A1 | 3/2013 | Shevitz |

FOREIGN PATENT DOCUMENTS

| | | | |
|---|---|---|---|
| EP | 2022506 | A2 | 2/2009 |
| JP | S5732225 | A | 2/1982 |
| JP | 2004256436 | A | 9/2004 |
| WO | WO-9736614 | A1 | 10/1997 |
| WO | WO-9831826 | A1 | 7/1998 |
| WO | WO-9936507 | A1 | 7/1999 |
| WO | WO-0226077 | A1 | 4/2002 |
| WO | WO-03015712 | A2 | 2/2003 |
| WO | WO-03031464 | A2 | 4/2003 |
| WO | WO-03068822 | A2 | 8/2003 |
| WO | WO-03090686 | A2 | 11/2003 |
| WO | WO-2004074454 | A2 | 9/2004 |
| WO | WO-03099846 | A3 | 5/2005 |
| WO | WO-2006003388 | A3 | 4/2006 |
| WO | WO-2006044614 | A2 | 4/2006 |
| WO | WO-2006044614 | A3 | 8/2006 |
| WO | WO-2006023911 | A3 | 1/2007 |
| WO | WO-2007016250 | A1 | 2/2007 |
| WO | WO-2008045148 | A3 | 10/2008 |
| WO | WO-2008074029 | A3 | 12/2008 |
| WO | WO-2010045024 | A1 | 4/2010 |
| WO | WO-2010085606 | A1 | 7/2010 |
| WO | WO-2010075249 | A3 | 10/2010 |

OTHER PUBLICATIONS

Bedi, et al. The effect of matrix metalloproteinase inhibition on tendon-to-bone healing in a rotator cuff repair model. J Shoulder Elbow Surg. Apr. 2010;19(3):384-91. Epub Oct. 2, 2009.

Bhattacharjee, et al. The conformation-dependent interaction of alpha 2-macroglobulin with vascular endothelial growth factor. A novel mechanism of alpha 2-macroglobulin/growth factor binding. J Biol Chem. Sep. 1, 2000;275(35):26806-11.

Binder, R. Purification of alpha2-macroglobulin and the construction of immunogenic alpha2-macroglobulin-peptide complexes for use as cancer vaccines. Methods. Jan. 2004;32(1):29-31.

Biocompare Editor, Product Review for "Centricon® Centrifugal Filter Units from Millipore" (Dec. 21, 2006).

Borth, W. Alpha 2-macroglobulin. A multifunctional binding and targeting protein with possible roles in immunity and autoimmunity. Ann N Y Acad Sci. Sep. 10, 1994;737:267-72.

Bowen, et al. Bait region involvement in the dimer-dimer interface of human alpha 2-macroglobulin and in mediating gross conformational change. Evidence from cysteine variants that form interdimer disulfides. J Biol Chem. Jan. 16, 1998;273(3):1825-31.

Braun, et al. The effect of local anaesthetics on synoviocytes: a possible indirect mechanism of chondrolysis. Knee Surg Sports Traumatol Arthrosc. Jun. 21, 2012. 1468-74.

Browning, et al. Platelet-rich plasma increases matrix metalloproteinases in cultures of human synovial fibroblasts. J Bone Joint Surg Am. Dec. 5, 2012;94(23):e1721-7. doi: 10.2106/JBJS.K.01501.

Burton-Wurster, et al. Fibronectin and water content of articular cartilage explants after partial depletion of proteoglycans. J Orthop Res. 1986;4(4):437-45.

Castillo, et al. Comparison of growth factor and platelet concentration from commercial platelet-rich plasma separation systems. Am J Sports Med. 2011;39(2):266-271.

Cote, et al. Generation of human monoclonal antibodies reactive with cellular antigens. Proc Natl Acad Sci U S A. Apr. 1983;80(7):2026-30.

Cuellar, et al. Can Intra-articular cytokine profiling predict the development of knee pain? Four-year follow-up of asymptomatic controls. Poster No. 1793. ORS 2012 Annual Meeting.

Cuellar, et al. Cytokine evaluation in individuals with low back pain using discographic lavage. Spine J. Mar. 2010;10(3):212-8.

Cuellar, et al. Cytokine Expression in the Epidural Space: A Model of Non-compressive Disc Herniation-induced Inflammation. Spine (Phila Pa 1976). 2012 May 29, 2012. 38(1):17-23.

Cuellar, et al. Cytokine profiling in acute anterior cruciate ligament injury. Arthroscopy. Oct. 2010;26(10):1296-301.

(56) References Cited

OTHER PUBLICATIONS

Cuellar, et al. Diagnostic utility of cytokine biomarkers in the evaluation of acute knee pain. J Bone Joint Surg Am. Oct. 2009;91(10):2313-20.
Cuellar, et al. Does a fibronectin and aggrecan complex play a role in painful vertebral disks? PM R. Apr. 2013;5(4):297-302; quiz 302. doi: 10.1016/j.pmrj.2013.01.002. Epub Mar. 13, 2013.
Cuellar, et al. Is there a chondroprotective effect of autologous protease inhibitor concentrate on an osteoarthritis rabbit model? A pilot study. 11th Annual Pain Medicine Meeting. Miami, Florida. Nov. 15, 2012.
Cytonics Publication Summary. 2 pages.
De Grauw, et al. Arthrogenic lameness of the fetlock: synovial fluid markers of inflammation and cartilage turnover in relation to clinical joint pain. Equine Vet J. Jul. 2006;38(4):305-11.
Demaille, et al. Human alpha-2 macroglobulin: isolation and composition (L alpha-2 macroglobuline humaine: isolement et composition). C R Seances Soc Biol Fil. 1970;164(3):626-31.
Demirag, et al. Enhancement of tendon-bone healing of anterior cruciate ligament grafts by blockage of matrix metalloproteinases. J Bone Joint Surg Am. Nov. 2005;87(11):2401-10.
Demirag, et al. The effect of alpha-2 macroglobulin on the healing of ruptured anterior cruciate ligament in rabbits. Connect Tissue Res. 2004;45(1):23-27.
Dissemond, et al. EPA made easy. Wounds International. 2013; 4(2):1-6.
Dumfarth, et al. Prophylactic low-energy shock wave therapy improves wound healing after vein harvesting for coronary artery bypass graft surgery: a prospective, randomized trial. Ann Thorac Surg. Dec. 2008;86(6):1909-13. doi: 10.1016/j.athoracsur.2008.07.117.
Dunn, et al. The alpha 2-macroglobulin of human plasma. I. Isolation and composition. J Biol Chem. Dec. 10, 1967;242(23):5549-55.
Edsberg, et al. Analysis of the proteomic profile of chronic pressure ulcers. Wound Repair Regen. May-Jun. 2012;20(3):378-401. doi: 10.1111/j.1524-475X.2012.00791.x.
Eming, et al. The inhibition of matrix metalloproteinase activity in chronic wounds by a polyacrylate superabsorber. Biomaterials. Jul. 2008;29(19):2932-40. doi: 10.1016/j.biomaterials.2008.03.029. Epub Apr. 9, 2008.
European search report and search opinion dated Jan. 7, 2016 for EP Application No. 13751112.7.
FOSANG—ADAMTS-5: the story so far. Eur Cell Mater. Feb. 5, 2008;15:11-26.
Frechette, et al. Platelet-rich plasmas: growth factor content and roles in wound healing. J. Dent. Res. 2005;84(5):434-439.
Freshney, I. Culture of Animal Cells: A Manual of Basic Technique. Wiley-Liss; 5th edition 2005.
Gajendran, et al. Is the fibronectin-aggrecan complex present in cervical disk disease? PM R. Nov. 2011;3(11):1030-4. doi: 10.1016/j.pmrj.2011.07.003.
Gene Cloning and Analysis: Current Innovations, 1997 pp. 99-115.
Gibson, et al. MMPs made easy. Wounds International. 2009; 1:1-6.
Golish, et al. Are persistently symptomatic vertebral compression fractures associated with abnormal inflammatory profiles? A prospective study. J Spinal Disord Tech. Apr. 2011;24(2):121-5.
Golish, et al. Functional outcome after lumbar epidural steroid injection is predicted by a complex of fibronectin and aggrecan.
Golish, et al. Outcome of lumbar epidural steroid injection is predicted by assay of a complex of fibronectin and aggrecan from epidural lavage. Spine (Phila Pa 1976). Aug. 15, 2011;36(18):1464-9.
Greenwald. Thirty-six years in the clinic without an MMP inhibitor. What hath collagenase wrought? Ann N Y Acad Sci. Jun. 30, 1999;878:413-9.
Grinnell, et al. Degradation of fibronectin and vitronectin in chronic wound fluid: analysis by cell blotting, immunoblotting, and cell adhesion assays. J Invest Dermatol. Apr. 1992;98(4):410-6.
Grinnell, et al. Fibronectin degradation in chronic wounds depends on the relative levels of elastase, alphal-proteinase inhibitor, and alpha2-macroglobulin. J Invest Dermatol. Feb. 1996;106(2):335-41.
Hadler, et al. Protease Inhibitors in Inflammatory Synovial effusions. Annals of Rheumatic diseases. 1981; 40:55-59.
Harlow, et al. Antibodies: a laboratory manual. vol. 559. Cold Spring Harbor, NY: Cold Spring Harbor Laboratory, 1988.
Hashimoto, et al. ADAMTS4 (aggrecanase-1) interaction with the C-terminal domain of fibronectin inhibits proteolysis of aggrecan. J Biol Chem. Jul. 30, 2004;279(31):32483-91. Epub May 25, 2004.
Henikoff, et al. Amino acid substitution matrices from protein blocks. Proc Natl Acad Sci U S A. Nov. 15, 1992;89(22):10915-9.
Hermanson, Bioconjugate Techniques 1996, Academic Press, Inc., San Diego.
Hofheinz, E. Eureka! Rush Researchers Find Breakthrough in OA. Jan. 3, 2013. Available at http://ryortho.com/breaking/eureka-rush-researchers-find-breakthrough-in-oa/. Accessed Jul. 11, 2013.
Holland, et al. Detection of specific polymerase chain reaction product by utilizing the 5'-3' exonuclease activity of Thermus aquaticus DNA polymerase. Proc Natl Acad Sci U S A. Aug. 15, 1991;88(16):7276-80.
Honjo, et al. Kinetics of {alpha}2-macroglobulin and {alpha}1-acid glycoprotein in rats subjected to repeated acute inflammatory stimulation. Lab Anim. Apr. 2010;44(2):150-4. Epub Oct. 26, 2009.
Hunt, et al. Inflammatory Cytokines in the Painful Ankle Joint: Arthritis and Osteochondral Lesions.
Huse, et al. Generation of a large combinatorial library of the immunoglobulin repertoire in phage lambda. Science. Dec. 8, 1989;246(4935):1275-81.
Ikai, et al. A recombinant bait region mutant of human alpha2-macroglobulin exhibiting an altered proteinase-inhibiting spectrum. Cytotechnology. Sep. 1999;31(1-2):53-60. doi: 10.1023/A:1008011919876.
Imber, et al. Clearance and Binding of Two Electrophoretic 'fast' forms of Human A2-macroglobulin. J. Bio. Chem. Aug. 10, 1981; 256(15):8134-8139.
Inada, et al. Critical roles for collagenase-3 (Mmp13) in development of growth plate cartilage and in endochondral ossification. Proc Natl Acad Sci U S A. Dec. 7, 2004;101(49):17192-7. Epub Nov. 24, 2004.
Inman, E. Researchers create "truth serum" to explain knee pain. http://www.stanforddaily.com/2011/02/17/researchers-create-%E2%80%9Ctruth-serum%E2%80%9D-to-explain-knee-pain/ Accessed Dec. 3, 2014.
Innis, et al., eds. PCR protocols: a guide to methods and applications. Academic press, New York. 1990.
International search report and written opinion dated Aug. 7, 2013 for PCT/US2013/027159.
Jackson. Cytokine Biomarkers in Orthopedics Offer an Enormous Diagnosis and Prognosis Potential. Orthopedics Today. Jan. 2010. 3 pgs.
Kimmel, et al. Preparation of cDNA and the generation of cDNA libraries: overview. Methods Enzymol. 1987;152:307-16.
Kohler, et al. Continuous cultures of fused cells secreting antibody of predefined specificity. Nature. Aug. 7, 1975;256(5517):495-7.
Kozbor, et al. Specific immunoglobulin production and enhanced tumorigenicity following ascites growth of human hybridomas. J Immunol Methods. Jul. 16, 1985;81(1):31-42.
Liang, et al. Distribution and cloning of eukaryotic mRNAs by means of differential display: refinements and optimization. Nucleic Acids Res. Jul. 11, 1993;21(14):3269-75.
Lindena, et al. Efficacy and safety of a polyester leukocyte removal filter for whole blood and red cell concentrate filtration. J Clin Chem Clin Biochem. May 1989;27(5):331-6.
Lindhorst, et al. Increase in degraded collagen type II in synovial fluid early in the rabbit meniscectomy model of osteoarthritis. Osteoarthritis Cartilage. Feb. 2005;13(2):139-45.
Lobmann, et al. Expression of matrix-metalloproteinases and their inhibitors in the wounds of diabetic and non-diabetic patients. Diabetologia. Jul. 2002;45(7):1011-6. Epub May 25, 2002.
Lobmann, et al. Proteases and the diabetic foot syndrome: mechanisms and therapeutic implications. Diabetes Care. Feb. 2005;28(2):461-71.

(56) References Cited

OTHER PUBLICATIONS

Luan, et al. Inhibition of ADAMTS-7 and ADAMTS-12 degradation of cartilage oligomeric matrix protein by alpha-2-macroglobulin. Osteoarthritis Cartilage. Nov. 2008;16(11):1413-20. Epub May 15, 2008.
Maniatis, et al. Molecular Cloning: A Laboratory Manual, Cold Spring Harbor Laboratory Press, Cold Spring Harbor, N.Y., USA 1982.
Masters, et al. Effects of nitric oxide releasing poly(vinyl alcohol) hydrogel dressings on dermal wound healing in diabetic mice. Wound Repair Regen. Sep.-Oct. 2002;10(5):286-94.
Mccafferty, et al. Phage antibodies: filamentous phage displaying antibody variable domains. Nature. Dec. 6, 1990;348(6301):552-4.
Miller, et al. CCR2 chemokine receptor signaling mediates pain in experimental osteoarthritis. Proc Natl Acad Sci U S A. Dec. 11, 2012;109(50):20602-7. doi: 10.1073/pnas.1209294110. Epub Nov. 26, 2012.
Morrison et al. Chimeric human antibody molecules: mouse antigen-binding domains with human constant region domains. Proc Natl Acad Sci U S A. Nov. 1984;81(21):6851-5.
Nakayama, et al. Removal of trypsin complexed alpha-2 macroglobulin by plasma fractionation. ASAIO Journal. 1993; M297-M300.
Needleman, et al. A general method applicable to the search for similarities in the amino acid sequence of two proteins. J Mol Biol. Mar. 1970;48(3):443-53.
Neuberger et al. Recombinant antibodies possessing novel effector functions. Nature. Dec. 13-19, 1984;312(5995):604-8.
Nguyen, et al. Applications of platelet-rich plasma in musculoskeletal and sports medicine: An evidence-based approach. PM R. 2011;3(3):226-250.
Notice of Allowance dated Dec. 8, 2018 for U.S. Appl. No. 14/380,234.
Notice of Allowance dated Mat 29, 2019 for U.S. Appl. No. 15/528,387.
Office action dated Jan. 6, 2017 for U.S. Appl. No. 14/380,234.
Office action dated May 26, 2016 for U.S. Appl. No. 14/380,234.
Office action dated Aug. 6, 2015 for U.S. Appl. No. 14/380,234.
Office action dated Aug. 11, 2017 for U.S. Appl. No. 14/380,234.
Office action dated Oct. 8, 2015 for U.S. Appl. No. 14/380,234.
Office Action dated Dec. 21, 2017 for U.S. Appl. No. 14/380,234.
Ohara, et al. One-sided polymerase chain reaction: the amplification of cDNA. Proc Natl Acad Sci U S A. Aug. 1989;86(15):5673-7.
Organs, et al. A2M Prior Art. Technical and clinical aspects of cascade filtration plasma exchange (CFPE). 3pages.
Plasmaflo: OP series, Asahi hollow fiber plasma seprarator. Asahi Kasei Medical Co., Ltd. Jan. 1, 2012. www.asahi-kasei.co.jp/medical/en/pdf/apheresis/plasmaflo-op_catalog.pdf.
Poller, et al. Cloning of the human alpha 2-macroglobulin gene and detection of mutations in two functional domains: the bait region and the thiolester site. Hum Genet. Jan. 1992;88(3):313-9.
Poller, et al. Sequence polymorphism in the human alpha-2-macroglobulin (A2M) gene. Nucleic Acids Research. 2001; 19(1):198.
PR Newswire. Interpore Cross Receives FDA Clearance to Market New Device That Simplifies AGF(TM) Process. New York. Aug. 22, 2022:1.
Quaranta, et al. Technical and clinical aspects of cascade filtration plasma exchange (CFPE). Int J Artif Organs. Nov. 1983;6(6):309-14.
Rao, et al. Alpha 1-antitrypsin is degraded and non-functional in chronic wounds but intact and functional in acute wounds: the inhibitor protects fibronectin from degradation by chronic wound fluid enzymes. J Invest Dermatol. Oct. 1995;105(4):572-8.
Rayment, et al. Attenuation of protease activity in chronic wound fluid with bisphosphonate-functionalised hydrogels. Biomaterials. Apr. 2008;29(12):1785-95. doi: 10.1016/j.biomaterials.2007.12.043. Epub Jan. 31, 2008.
Re: Cytonics Patent Status and Strategy Summary letter. McHale & Slavin, P.A. Dated Mar. 23, 2011. 37 pages.
Rheofilter ER-4000. Asahi Kasei Medical Co., Ltd. Jan. 2012. www.asahi-kasei.co.jp/medical/en/pdf/apheresis/rheofilter-er_catalog.pdf.
Rompaey, et al. Design of a new protease inhibitor by the manipulation of the bait region of alpha 2-macroglobulin: inhibition of the tobacco etch virus protease by mutant alpha 2-macroglobulin. Biochem J. Nov. 15, 1995;312 ( Pt 1):191-5.
Roukis, et al. Autologous platelet-rich plasma for wound and osseous healing: a review of the literature and commercially available products. Adv Ther. Mar.-Apr. 2006;23(2):218-37.
Sambrook, et al. Molecular cloning: a laboratory manual. Cold Spring Harbor Laboratory Press, Cold Spring Harbor, NY 11: 18. 2nd Ed. 1989.
San Giovanni, et al. Correlation of intra-articular ankle pathology with cytokine biomarkers and matrix degradation products. Foot Ankle Int. Aug. 2012;33(8):627-31.
Sanchez, et al. Intra-articular injection of an autologous preparation rich in growth factors for the treatment of knee OA: a retrospective cohort study. Clin Exp Rheumatol. Sep.-Oct. 2008;26(5):910-3.
Sato, et al. Relationship of calcitonin gene-related peptide in synovial tissues and temporomandibular joint pain in humans. Oral Surg Oral Med Oral Pathol Oral Radiol Endod. Nov. 2004;98(5):533-40.
Scopes. Protein purification: Principles and Practice, Springer-Verlag (1994).
Scuderi, et al. A critical evaluation of discography in patients with lumbar intervertebral disc disease. Spine J. Jul.-Aug. 2008;8(4):624-9. Epub Jan. 10, 2007.
Scuderi, et al. Cytokine assay of the epidural space lavage in patients with lumbar intervertebral disk herniation and radiculopathy. J Spinal Disord Tech. Jun. 2006;19(4):266-9.
Scuderi, et al. Epidural interferon gamma-immunoreactivity: a biomarker for lumbar nerve root irritation. Spine (Phila Pa 1976). Oct. 1, 2009;34(21):2311-7.
Scuderi, et al. Identification of a complex between fibronectin and aggrecan G3 domain in synovial fluid of patients with painful meniscal pathology. Clin Biochem. Jul. 2010;43(10-11):808-14. Epub May 11, 2010.
Scuderi, et al. Identification of a novel fibronectin-aggrecan complex in the synovial fluid of knees with painful meniscal injury. J Bone Joint Surg Am. Feb. 16, 2011;93(4):336-40.
Search report dated Jul. 12, 2013 for GB Application No. 1306788.9.
Search report dated Oct. 14, 2013 for GB Application No. 1315212.9.
Second ESR dated Apr. 11, 2019 for EP Appl. No. 13751112.7.
Shena, et al. Parallel human genome analysis: microarray-based expression monitoring of 1000 genes. Proc Natl Acad Sci USA. Oct. 1, 1996;93(20):10614-9.
Shena, et al. Quantitative monitoring of gene expression patterns with a complementary DNA microarray. Science. Oct. 20, 1995;270(5235):467-70.
Snyder, et al. Using a diagnostic tool to identify elevated protease activity levels in chronic and stalled wounds: a consensus panel discussion. Ostomy Wound Manage. Dec. 2011;57(12):36-46.
Sottrup-Jensen et al., (1984), Primary STructure of Human a2-Macroglobulin, vol. 25, No. 13, Jul. 10, pp. 8318-8327.
Srikrishna, et al. Endogenous damage-associated molecular pattern molecules at the crossroads of inflammation and cancer. Neoplasia. Jul. 2009;11(7):615-28.
Stanton, et al. Investigating ADAMTS-mediated aggrecanolysis in mouse cartilage. Nat Protoc. Mar. 2011;6(3):388-404. Epub Mar. 3, 2011.
Struglics, et al. Human osteoarthritis synovial fluid and joint cartilage contain both aggrecanase- and matrix metalloproteinase-generated aggrecan fragments. Osteoarthritis Cartilage. Feb. 2006;14(2):101-13. Epub Sep. 26, 2005.
Sundman, et al. Growth Factor and Catabolic Cytokine Concentrations are Influenced by the Cellular Composition of Platelet-Rich Plasma. Am J Sports Med. Oct. 2011;39(10):2135-40. Epub Aug. 16, 2011.

(56) References Cited

OTHER PUBLICATIONS

Swenson, et al. Structural characterization of human alpha2-macroglobulin subunits. J Biol Chem. Jun. 10, 1979;254(11):4452-6.
Takeda, et al. Construction of chimaeric processed immunoglobulin genes containing mouse variable and human constant region sequences. Nature. Apr. 4-10, 1985;314(6010):452-4.
Tchetverikov, et al. MMP profile in paired serum and synovial fluid samples of patients with rheumatoid arthritis. Ann Rheum Dis. Jul. 2004;63(7):881-3.
Tetlow, et al. Matrix metalloproteinase and proinflammatory cytokine production by chondrocytes of human osteoarthritic cartilage: associations with degenerative changes. Arthritis Rheum. Mar. 2001;44(3):585-94.
Trengove, et al. Analysis of the acute and chronic wound environments: the role of proteases and their inhibitors. Wound Repair Regen. Nov.-Dec. 1999;7(6):442-52.
Twining, SS. Fluorescein isothiocyanate-labeled casein assay for proteolytic enzymes. Anal Biochem. Nov. 15, 1984;143(1):30-4.
Van Den Dolder, et al. Platelet-rich plasma: quantification of growth factor levels and the effect on growth and differentiation of rat bone marrow cells. Tissue Eng. 2006;12(11):3067-3073.
Ventura, et al. A pseudobiospecific hollow fiber cartridge for in vitro adsorbtion of autoantibodies from pathological serum. Braz. J. Chem. Eng. vol. 17 n.4-7 São Paulo Dec. 2000.
Wang, et al. Identification of α2-macroglobulin as a master inhibitor of cartilage-degrading factors that attenuates the progression of posttraumatic osteoarthritis. Arthritis Rheumatol. Jul. 2014;66(7):1843-53. doi: 10.1002/art.38576.
Weibrich, et al. Curasan PRP kit vs. PCCS PRP system. Collection efficiency and platelet counts of two different methods for the preparation of platelet-rich plasma. Clin Oral Implants Res. Aug. 2002;13(4):437-43.
Weibrich, et al. Growth factor levels in platelet-rich plasma and correlations with donor age, sex, and platelet count. J Craniomaxillofac Surg. 2002;30(2):97-102.
Weibrich, et al. Growth factor levels in the platelet-rich plasma produced by 2 different methods: curasan-type PRP kit versus PCCS PRP system. Int J Oral Maxillofac Implants. 2002;17(2):184-190.
Wild. Biomarkers Predict Response to Steroid Injections in Radiculopathy Patients. Jan. 2011; vol. 37:1. http://www.anesthesiologynews.com/default.aspx. Accessed on Dec. 5, 2014. 2 pages.
Wildeboer, et al. Specific protease activity indicates the degree of Pseudomonas aeruginosa infection in chronic infected wounds. Eur J Clin Microbiol Infect Dis. Sep. 2012;31(9):2183-9. doi: 10.1007/s10096-012-1553-6. Epub Jan. 26, 2012.
Woodell-May, et al. Autologous protein solution inhibits MMP-13 production by IL-1β and TNFα-stimulated human articular chondrocytes. J Orthop Res. Sep. 2011;29(9):1320-6. doi: 10.1002/jor.21384. Epub Mar. 15, 2011.
Wysocki, et al. Wound fluid from chronic leg ulcers contains elevated levels of metalloproteinases MMP-2 and MMP-9. J Invest Dermatol. Jul. 1993;101(1):64-8.
Yager, et al. Ability of chronic wound fluids to degrade peptide growth factors is associated with increased levels of elastase activity and diminished levels of proteinase inhibitors. Wound Repair and Regeneration. 1997; 5:23-32.
Zack, et al. Identification of fibronectin neoepitopes present in human osteoarthritic cartilage. Arthritis Rheum. Sep. 2006;54(9):2912-22.
Zhang, et al. Inhibition of bone morphogenetic protein 1 by native and altered forms of alpha2-macroglobulin. J Biol Chem. Dec. 22, 2006;281(51):39096-104. Epub Oct. 27, 2006.
Zhang, et al. Phosphoprotein analysis using antibodies broadly reactive against phosphorylated motifs. J Biol Chem. Oct. 18, 2002;277(42):39379-87. Epub Jul. 31, 2002.
Zhang, et al. Poster 108: Characterization of fibronectin fragments in human surgical intervertebral disk specimens. Archives of Phyisical medicine and rehabilitation. 2007;88(9):e40.

* cited by examiner

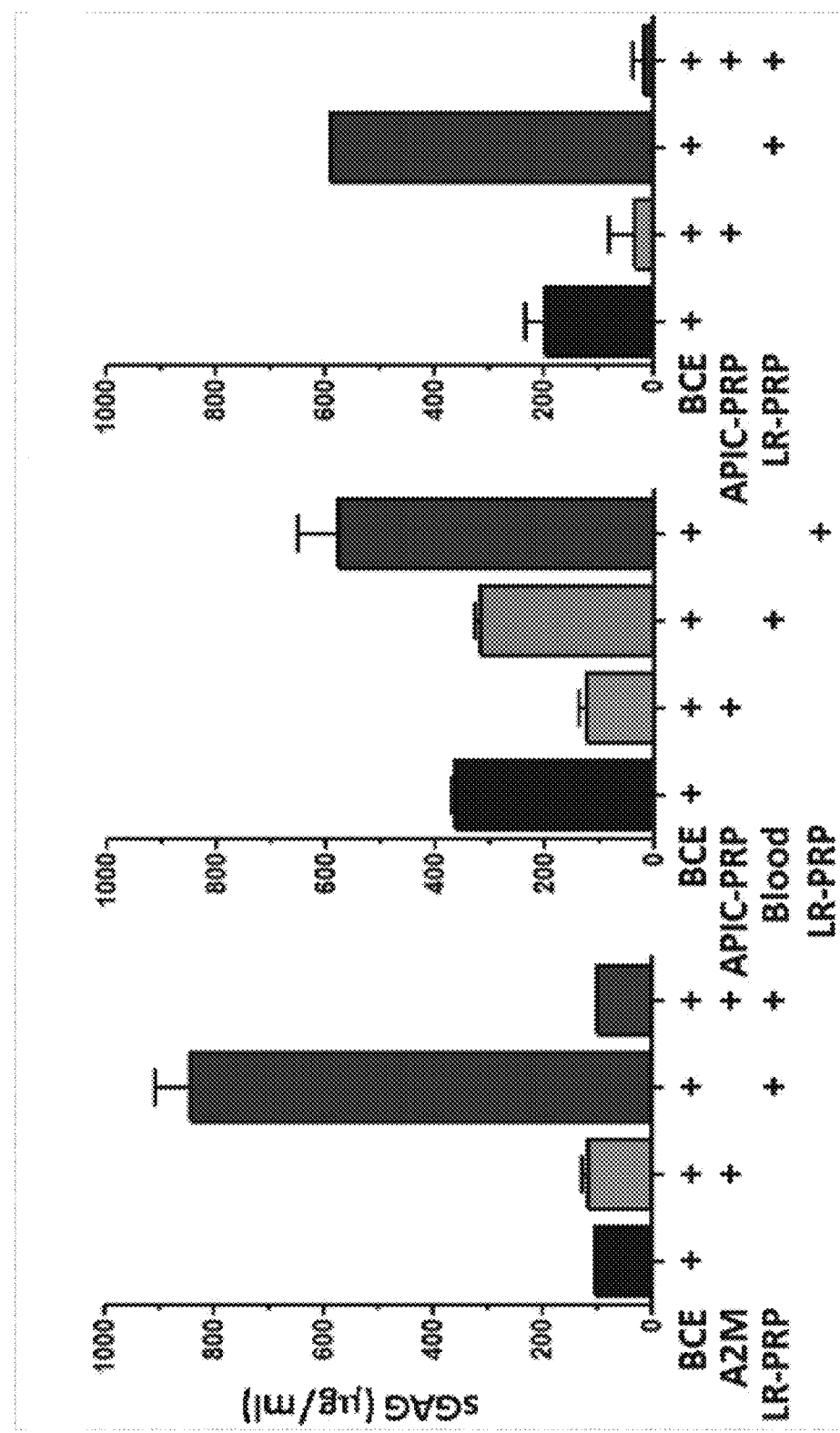

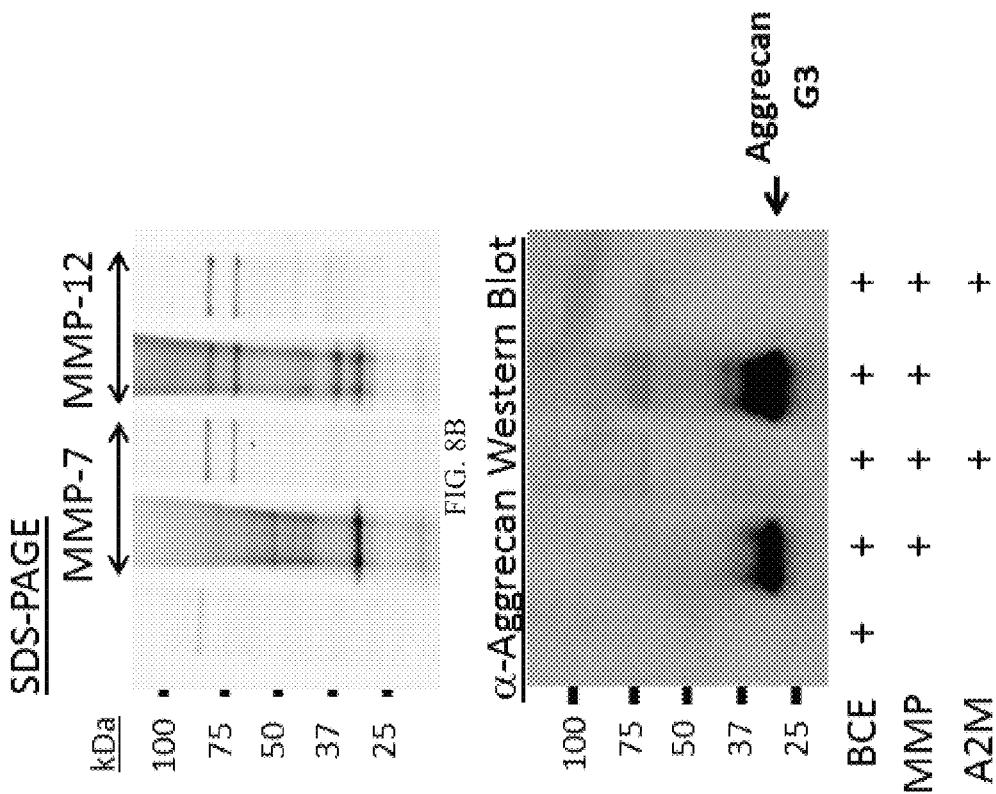
FIG. 8B
FIG. 8C
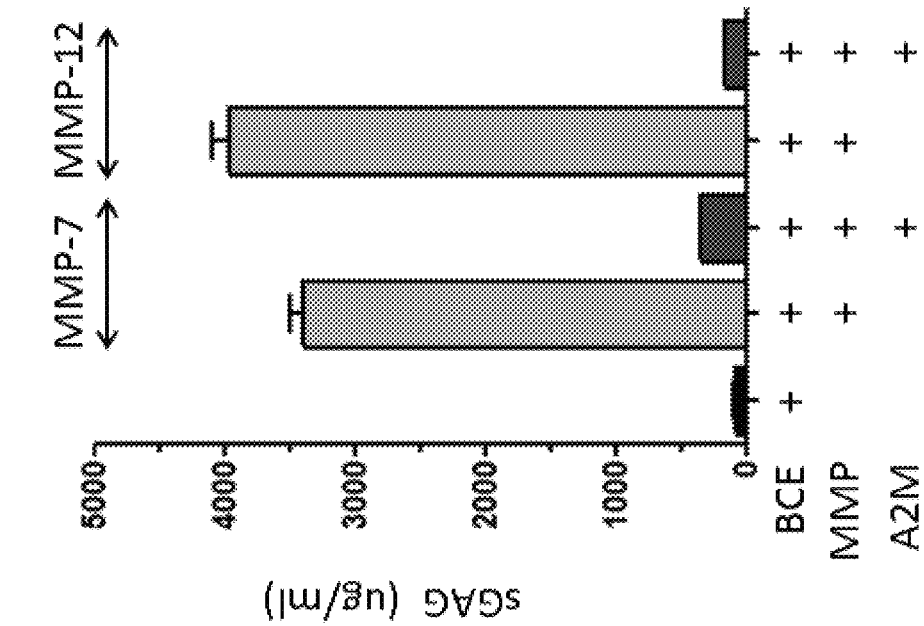
FIG. 8A

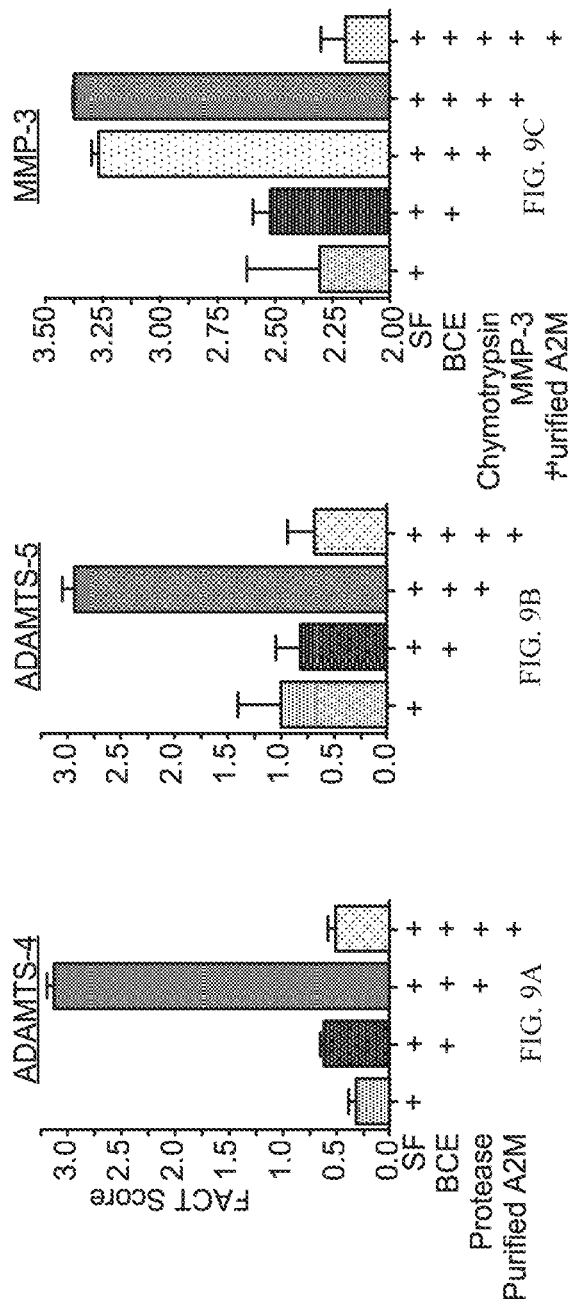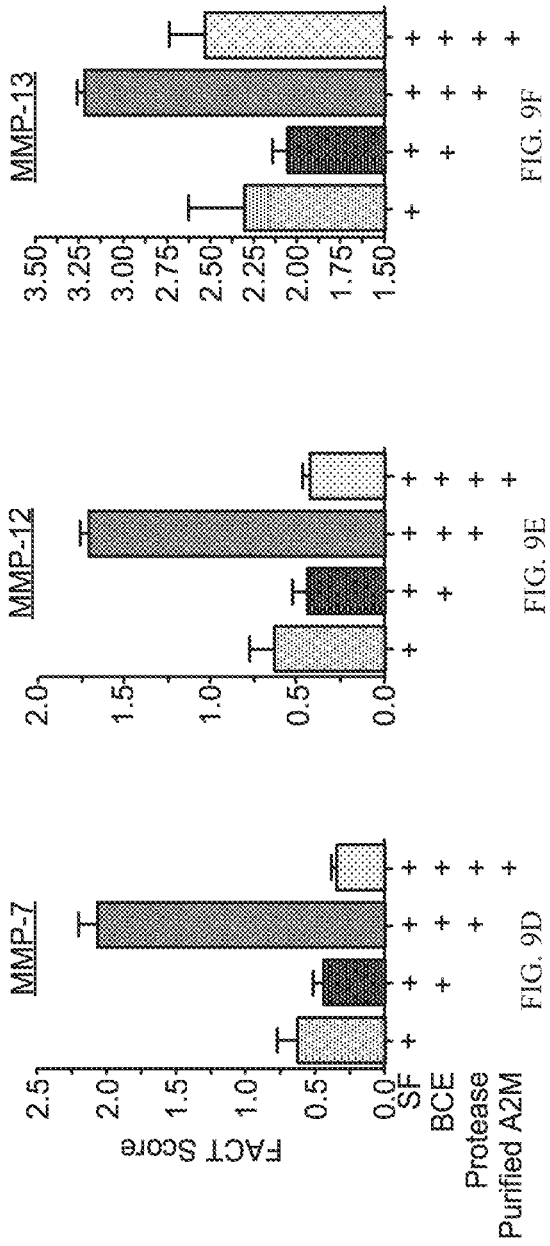

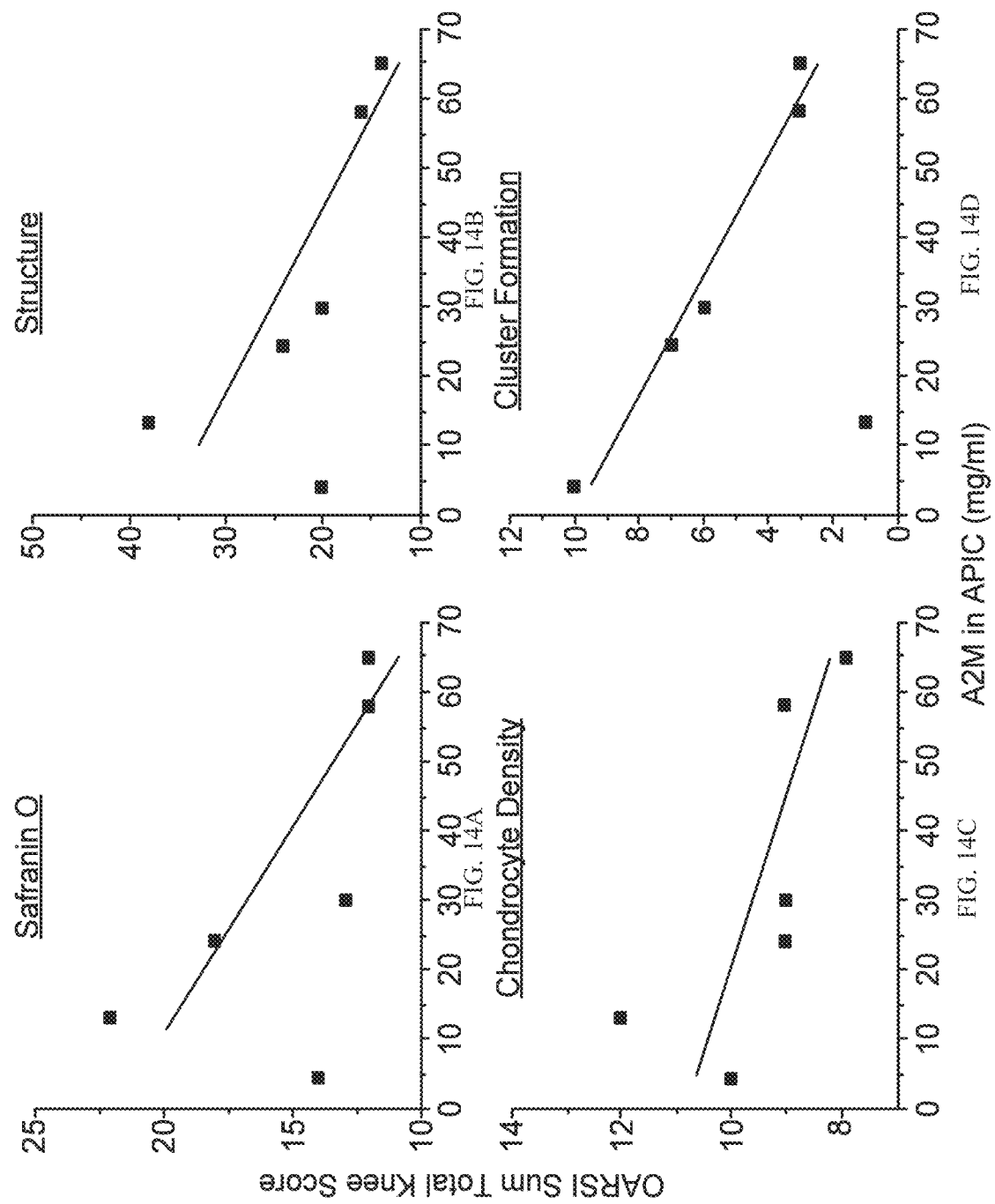

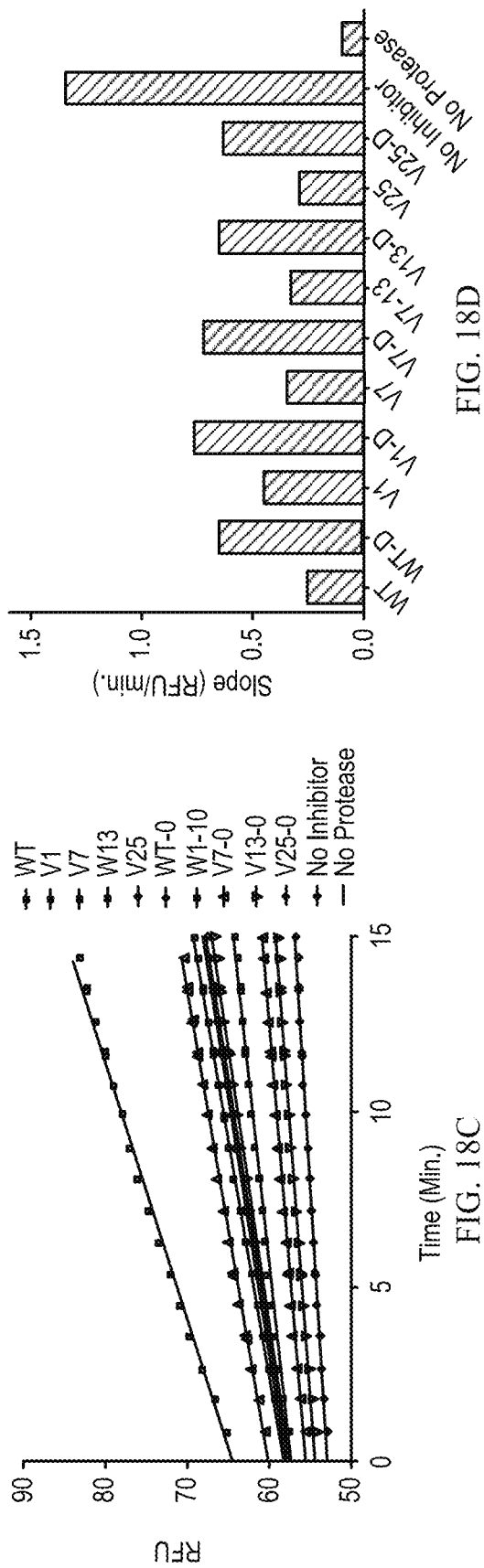
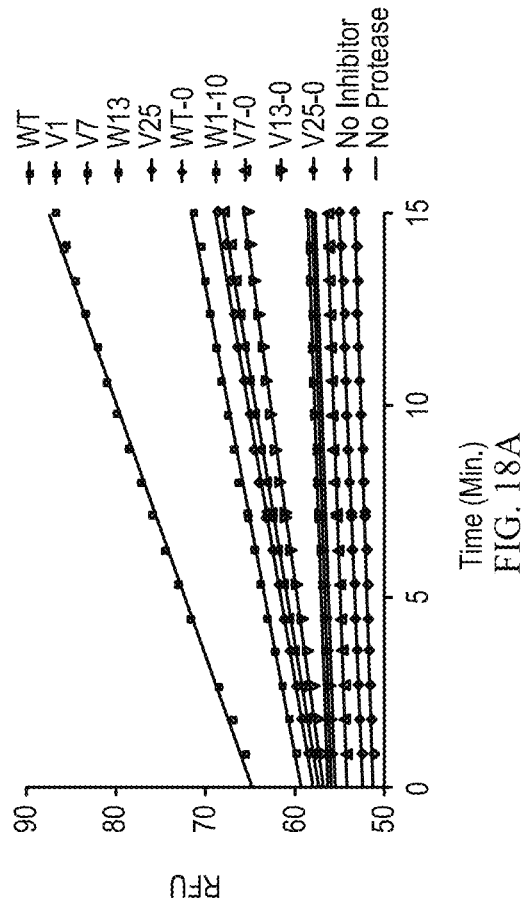

|  | TS4 | TS5 | MMP1 | MMP2* | MMP3 | MMP8 | MMP9* | MMP12** | MMP13 | Cath K | Trypsin | Chymo |
|---|---|---|---|---|---|---|---|---|---|---|---|---|
| APL34 | 202 | 314 | 154 | 109 | 118 | 100 | 121 | 100 | 185 | 100 | 100 | 100 |
| APL43 | 75 | 140 | 344 | 115 | 394 | 100 | 81 | 100 | 350 | 100 | 100 | 100 |
| APL52 | 95 | 355 | 197 | 120 | 394 | 100 | 66 | 100 | 867 | 100 | 100 | 71 |
| APL54 | 100 | 435 | 106 | 116 | 122 | 100 | 113 | 100 | 770 | 100 | 100 | 80 |

\* MMP2 cuts IGD poorly, leading to low differentiation between variants
\*\* MMP8 and MMP12 were completely inhibited by WT and all variants, so no difference could be determined
\*\*\* MMP9 cleaved IGD does not show up on Western, so quantitation was done on remaining intact IGD only, which is less accurate

Bait sequences:

APL34  LEQYEMHGPEGLRVCGEGEGEGTYESDVMERGHARLVHVEEPHTKL

APL43  LEQYEMHGPEGLRVCEAIPMSIPTSEDLVVQIPENFFGVKL

APL52  LEQYEMHGPEGLRVCKEEEGLGSIPENFFGVSELEGRGSKL

APL54  LEQYEMHGPEGLRVCSELEGRGSTYESDVMERGHARLVHVEEPHTKL

FIG. 20

SYSTEMS, COMPOSITIONS, AND METHODS FOR TRANSPLANTATION

CROSS-REFERENCE

This application is a divisional of U.S. application Ser. No. 14/380,234, filed on Aug. 21, 2014, now issued as U.S. Pat. No. 10,265,388 on Apr. 23, 2019, which claims the benefit International Application No. PCT/US2013/027159, filed on Feb. 21, 2013, which claims the benefit of U.S. Provisional Application No. 61/601,434, filed on Feb. 21, 2012, U.S. Provisional Application No. 61/726,815, filed on Nov. 15, 2012, U.S. Provisional Application No. 61/726,840, filed on Nov. 15, 2012, U.S. Provisional Application No. 61/727,433, filed on Nov. 16, 2012, and U.S. Provisional Application No. 61/740,218, filed on Dec. 20, 2012, which applications are incorporated herein by reference in their entirety.

All publications and patent applications mentioned in this specification are herein incorporated by reference to the same extent as if each individual publication or patent application was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Mar. 22, 2013, is named 37151-701.601_SL.txt and is 85,619 bytes in size.

BACKGROUND OF THE INVENTION

Inflammation causing spinal and joint pain can be difficult to treat. Increasing degrees of inflammation and force applied to joints result in joint injury. Abnormal joint anatomy can be a hallmark of aging, but joint injury can be also a result of trauma, such as chondral lesions often seen in athletes. While joint injury resulting from trauma can be typically associated with acute inflammation, aberrant joint anatomy resulting from aging (e.g., osteoarthritis) can be a chronic condition. Physicians currently do not have a system or method available to differentiate between acute injury due to trauma and age related joint deteriorations.

Presently, it can be difficult to determine the appropriate course of treatment for a given patient since it can be frequently unclear whether the particular condition the patient suffers from may be acute or chronic or if pathology in the joint is the cause of the pain.

Spinal-related pain can be typically classified as discogenic, facetogenic or radiculopathic pain. The manifestation of radiculopathic pain has traditionally been attributed to various physical and/or mechanical abnormalities, such as compression or mechanical irritation of the nerve root related to conditions such as disc herniation, stenosis, spondylolisthesis, sciatica, piriformis syndrome, obturator syndrome, cystic lesions (e.g., ganglion and synovial), tumors, and other pathology, such as chemically mediated causes.

Numerous studies have attempted to elucidate the pathophysiology of spinal-related pain, and several molecular pathways have been implicated tentatively. However, no clear causal pathway leading from injury or degeneration to the painful state has been confirmed. Molecular markers can be linked to clinical symptoms, and serve as potential targets for the development of diagnostics and therapeutic tools. Although some studies have provided evidence that the epidural space can be affected by an intervertebral disc herniation, none has measured concentrations of biomolecules in the epidural space in an attempt to detect the differences between affected and non-affected persons.

Tendons, which connect muscle to bone, and ligaments, which connect bones to other bones, are both composed of bands of fibrous connective tissue. The cells of the fibrous connective tissue are mostly made up of fibroblasts the irregular, branching cells that secrete strong fibrous proteins (such as collagens, reticular and elastic fibers, and glycoproteins) as an extracellular matrix. The extracellular matrix can be defined in part as any material part of a tissue that is not part of any cell. So defined, the extracellular matrix (ECM) can be the significant feature of the fibrous connective tissue.

The ECM's main component can be various glycoproteins. In most animals, the most abundant glycoprotein in the ECM can be collagen. Collagen can be tough and flexible and gives strength to the connective tissue. Indeed, the main element of the fibrous connective tissue is collagen (or collagenous) fiber. The ECM also contains many other components: proteins such as fibrin and elastin, minerals such as hydroxyapatite, or fluids such as blood plasma or serum with secreted free flowing antigens. Given this diversity, it can serve any number of functions, such as providing support and anchorage for cells (which attach via focal adhesions), providing a way of separating the tissues, and regulating intercellular communication. Therefore, the ECM can function in a cell's dynamic behavior.

Injury to tendons and ligaments causes damage not only to the connective tissue, but to the extracellular matrix as well. Damage to the ECM can interrupt cell behavior in the connective tissue and decrease and/or limit healing. After injury, continuing damage can be caused by production of matrix metalloproteinases (MMPs) by the body. MMPs are enzymes that degrade all components of the ECM. This can lead to an imbalance between the synthesis and degradation of the ECM, as the body tries to heal itself while the enzymes remodel the ECM. An overabundance of remodeling by MMPs cause damage to previously connected tissue which results in the formation of scar tissue. In addition, scar tissue adhesion to surrounding tissue can cause further pulling and/or stretching of the tendons or ligaments and resultant pain.

Currently, treatment of injury to tendons and ligaments includes some simple measures such as: avoiding activities that aggravate the problem; resting the injured area; icing the area the day of the injury; and taking over-the-counter anti-inflammatory medicines. However, these simple remedies do not always cure the injury and often more advanced treatments are needed. These treatments include: corticosteroid injections, platelet-rich plasma (PRP), hyaluronic acid (HA) injection, physical therapy and even surgery. Corticosteroids are often used because they can work quickly to decrease the inflammation and pain. Physical therapy can include range of motion exercises and splinting (such as for the fingers, hands, and forearm). Surgery can be only rarely needed for severe problems not responding to the other treatments. It can be appreciated that additional treatment measures are needed to treat and prevent extracellular matrix degradation for quicker and improved healing of tendons and ligaments.

Alpha-2-macroglobulin (A2M) is a highly conserved protease inhibitor present in plasma at relatively high concentrations (0.1-6 mg/ml). It is unique in its ability to inhibit all the major classes of proteases (Bhattacharjee et al (2000) J. Biol. Chem. 275, 26806-26811). A2M can be produced by several cell types, such as hepatocytes, lung fibroblasts, macrophages, astrocytes and tumor cells (Borth W, "Alpha 2-macroglobulin, A multifunctional binding and targeting protein with possible roles in immunity and autoimmunity," Ann. N.Y. Acad. Sci. 737:267-272 (1994)). A2M often exists as a tetramer of four identical 180 kDa subunits that forms a hollow cylinder-like structure. It can present multiple target peptide bonds to attacking proteases in its central "bait" domain. A2M can be the major protease inhibitor acting on foreign proteases, such as snake venoms. However, there are many other protease inhibitors in the circulation and it has been proposed that A2M can have other functions including binding to and regulation of cytokine and growth factor activity, promotion of tumoricidal capabilities of macrophages, and enhancement of antigen presentation. A2M can also be a targeting carrier for cytokines or growth factors.

Therefore, it is an object of the invention to provide compositions, systems, methods, and kits for the detection, diagnosis, and treatment of inflammation, pain in the spine or joint, degradation of extracellular matrix, and inhibiting fibronectin aggrecan complex (FAC) (FIG. 1). It is another object of the invention to provide biomarkers and methods for identifying sites in the spine or joint for treating pain. It is another object of the invention to provide biomarkers that can be used to diagnose or assist in the diagnosis be of the presence of pathologies that are causative of spinal- or joint-related pain. It is another object of the invention to provide methods for diagnosing or assisting in the diagnosis of the presence of pathologies that are causative of spinal- or joint related pain. Yet another object of the invention is to provide biomarkers and methods to determine an appropriate therapy for a subject experiencing spinal- or joint-related pain. Another object of the invention is to provide biomarkers and methods to monitor and assess the efficacy of a treatment for spinal- or joint-related pain. Another object of the invention is to provide compositions and methods for treating spinal or joint pain and for selecting treatment sites in the spine or joint for treatment to inhibit or reduce pain.

It is another object of the invention to provide variant polypeptides for treating inflammation and pain. It is another object of the invention to provide variant A2M polypeptides that inhibit the formation of fibronectin aggrecan complex (FAC). It is another object of the invention to provide variant A2M polypeptides with a higher protease inhibitory activity than a wild-type A2M polypeptide. It is another object of the invention to provide methods of making variant polypeptides for the treatment of inflammation and pain.

SUMMARY OF THE INVENTION

In one aspect, provided herein is a liquid composition comprising: (a) alpha-2-macroglobulin (A2M) isolated from a biological sample from a mammal, wherein the A2M is present at a concentration of at least 1.1 times higher than the concentration of A2M present in the biological sample from the mammal; and (b) plasma, bone marrow aspirate (BMA), or another body fluid from the biological sample. In some embodiments, any composition provided herein further comprises proteins with a molecular weight higher than 500 kDa wherein the proteins with a molecular weight higher than 500 kDa are present at a concentration of at least 1.1 times higher than found in the biological sample from the mammal. In some embodiments, the concentration of molecules with a molecular weight less than 500 kDa is less than 90%, 70%, 50%, 30%, or 10% of the concentration of those proteins and/or fold concentration of A2M present in the biological sample from the mammal. In some embodiments, the molecules with a molecular weight less than 500 kDa comprise cytokines; chemokines; other immunomodulatory mediators including peptides, proteins, DNA, RNA, carbohydrates and small molecules; proteases; and other degradative proteins with a molecular weight of less than 500 kDa. In some embodiments, the cytokines comprise interleukins, tumor necrosis factors (TNFs), monocyte chemoattractant proteins (MCPs), macrophage inflammatory proteins (MIPs), tumor growth factors (TGFs), and matrix metalloproteases (MMPs). In some embodiments, the concentration of A2M present in the biological sample is between about 0.1 mg/mL to 6 mg/mL. In some embodiments, the biological sample is a blood sample, BMA, or other body fluid. In some embodiments, any of the compositions provided herein further comprise one or more additional non-blood derived components. In some embodiments, the one or more additional non-blood derived components comprise an anti-coagulant, wherein the anti-coagulant comprises EDTA, tri-sodium citrate, water for injection (WFI), or saline. In some embodiments, any of the compositions provided herein further comprise one or more additional blood-derived components. In some embodiments, the one or more additional blood-derived components comprise platelets. In some embodiments, the composition is substantially free of cells and particles larger than and comprises a reduced concentration of proteins and other molecules with a molecular weight of 500 kDa or less compared to the biological sample. In some embodiments, the composition is for autologous delivery into one or more joints of the mammal, and wherein the one or more joints are selected from the synovial, diarthrodial, amphiarthrodial, synarthrodial, symphyseal, and cartilaginous joint. In some embodiments, the mammal is a human. In some embodiments, the A2M is present at a concentration of at least 1.5 times higher than the concentration of A2M present in the biological sample from the mammal. In some embodiments, the A2M is present at a concentration of at least 2 times higher than the concentration of A2M present in the biological sample from the mammal, optionally wherein the A2M is present at a concentration of at least 3, 5, 10, or 20 times higher than the concentration of A2M present in the biological sample from the mammal. In some embodiments, any of the compositions provided herein further comprise platelets.

In one aspect, provided herein is a method for enrichment of A2M from a sample obtained from a mammal comprising: (a) flowing the sample through one or more filters, thereby separating the sample into a filtrate and a retentate; and (b) collecting the retentate, wherein the retentate is enriched for A2M and wherein the concentration in said retentate of proteins having a molecular weight of less than about 500 kDa is less than 90% of the concentration of those proteins and/or fold concentration of A2M in the sample. In some embodiments, the concentration of A2M in the retentate is at least 1.1, 1.5, 2, 3, 4, 5, 10, or 20 times higher than the concentration of A2M in the mammalian sample. In some embodiments, the retentate comprises less than 90%, 80%, 60%, 30%, or 10% fold concentration of A2M and/or concentration of the proteins with a molecular weight less than about 500 kDa from the mammalian sample. In some embodiments, the mammalian sample comprises plasma. In some embodiments, red blood cells and white blood cells have been removed from the mammalian sample. In some embodiments, the mammalian sample further comprises one or more blood derived components. In some embodiments, the one or more blood derived components comprise platelets. In some embodiments, red blood cells, white blood cells, and platelets are removed from the mammalian sample. In some embodiments, the red blood cells, white blood cells, and platelets are removed by flowing or passing the mammalian sample through the one or more filters. In some embodiments, the one or more filters is characterized by having a pore size of at most 0.1 µm, 0.6 µm, 1 µm, or higher. In some embodiments, the one or more filters is a hollow fiber tangential flow filter, is characterized by having a molecular weight cut-off of at most 500 kDa, or a combination thereof. In some embodiments, the one or more other filters comprise a charge, immobilized molecules, or a combination thereof, thereby enhancing the selectivity of the one or more filters. In some embodiments, the immobilized molecules comprise antibodies, proteins, receptors, ligands, carbohydrates, nucleotides, RNA, or DNA. In some embodiments, enhancing the selectivity of the one or more filters comprises enhancing the ability of the one or more filters to retain A2M, enhancing the ability of the one or more filters to not retain molecules that are not A2M, or a combination thereof. In some embodiments, flowing the sample through one or more filters comprises applying tangential force filtration, one or more centrifugation steps, gravitational forces, mechanical forces, or any combination thereof. In some embodiments, the mechanical force comprises a pump, centrifugal force, gas pressure, or a force that can flow a liquid through the one or more filters. In some embodiments, any of the methods provided herein further comprise adding one or more non-blood derived components, one or more blood derived components, or a combination thereof, to the mammalian sample before or during step (a), to the retentate after step (a), or both. In some embodiments, the one or more additional non-blood derived components comprises an anti-coagulant, preservative, excipient, diluent, or other additive. In some embodiments, the anti-coagulant comprises EDTA, tri-sodium citrate, water for injection (WFI), saline, or ACD-A. In some embodiments, the diluent is a WFI solution or a saline solution. In some embodiments, the one or more additional blood derived components comprise platelets. In some embodiments, the retentate is substantially free of cells and particles larger than 0.1 µm, 0.2 µm, 0.6 µm, and/or 1 µm and comprises a reduced concentration of proteins and other molecules with a molecular weight of 500 kDa or less compared to the A2M concentration in the biological sample. In some embodiments, the mammalian sample is from a human subject. In some embodiments, the human subject has a disease or condition treatable with the retentate. In some embodiments, the diseases or conditions treatable with the retentate comprise cancer, degenerative diseases, traumatic diseases, and/or inflammatory diseases, whose pathogenesis includes the activity of proteases. In some embodiments, the cancer, degenerative diseases, traumatic diseases, and/or inflammatory diseases whose pathogenesis includes the activity of proteases comprises osteoarthritis, inflammatory arthritides, enthesopathies, tendinopathies, ligamentous injuries, and degenerative diseases of the bone, cartilage, tendons, and ligaments, post operation of tendons, wound healing, and other musculoskeletal diseases. In some embodiments, the biological sample is collected with the aid of an additional absorbent, adsorbent, or capillary materials or devices selected from the group of needle-syringe combo, sponges, wicks, pledgets, sutures, hydrophilic catheters, hydrophobic catheters, hollow-lumen catheters, or any combination thereof.

In one aspect, provided herein is a method for enrichment of A2M from a mammalian sample comprising: (a) flowing or passing the sample through one or more first filters, thereby separating the sample into a first filtrate and a first retentate; (b) flowing the first filtrate through one or more second filters, thereby separating the sample into a second filtrate and a second retentate enriched in A2M; and (c) collecting the second retentate. In some embodiments, the one or more first filters are characterized by having a pore size of at most 0.1 µm, 0.6 or 1 µm. In some embodiments, the one or more second filters are characterized by having a molecular weight cut-off of at most 500 kDa. In some embodiments, the retentate is obtained in less than about 15 minutes, 30 minutes, 45 minutes, 1 hour, or 3 hours.

In one aspect, provided herein is a system for enrichment of A2M from a mammalian sample comprising: (a) one or more filters; and (b) a centrifuge, a pump, or a combination thereof, wherein cells, particles, and other molecules larger than 1 µm and proteins with a molecular weight of less than about 500 kDa are removed from the sample by flowing the sample through the one or more filters in sequence. In some embodiments, the flow filtration module is a dead end and/or tangential flow filtration module. In some embodiments, any system provided herein further comprises one or more waste modules. In some embodiments, the sample is flowed or passed through the one or more filters in sequence by applying centrifugal force, using the pump, or a combination thereof; thereby producing an A2M enriched retentate. In some embodiments, any system provided herein further comprises a collection module, wherein the A2M enriched retentate is collected after passing the sample through the one or more filters. In some embodiments, cells, particles, and other molecules larger than 0.6 µm and proteins with a molecular weight of less than about 500 kDa removed from the sample by flowing the sample through the one or more filters in sequence are deposited into the one or more waste modules. In some embodiments, any system provided herein further comprises a sample loading module operable to introduce the sample into the system. In some embodiments, the sample loading module is directly or indirectly attached to the blood stream of a subject.

In one aspect, provided herein is a system for concentrating A2M from a fluid sample comprising: a flow filtration module comprising an inlet, an outlet, and two or more filters; wherein the two or more filters are fluidly connected in series between the filter unit inlet and outlet; wherein a flow of fluid sample passes through the at least two filters to produce an A2M concentrated serum; wherein a first of the two or more filters screens out cells, particles, and other molecules larger than 0.1 µm; and wherein a second of the two or more filters retain molecules of weight more than about 500 kDa. In some embodiments, the flow filtration module is a dead end and/or tangential flow filtration module. In some embodiments, any system provided herein further comprises a pump adapted to be fluidly coupled to the filtration module either upstream of the inlet or downstream of the outlet of the filtration module, said pump further adapted to produce a flow of the fluid sample that passes through the filter unit from the inlet to the outlet. In some embodiments, the first and the second of two or more filters comprise a first and a second cross flow filter. In some embodiments, the filter module further comprises a first and a second permeate collection reservoir, and wherein the first permeate collection reservoir stores a permeate from the first cross flow filter and a retentate of the first cross flow filter, and wherein the second permeate collection reservoir stores a permeate from the second cross flow filter and the concentrated A2M from serum or plasma comprises a retentate of the second cross flow filter. In some embodiments, the concentrated A2M from serum or plasma remains in the first permeate collection reservoir. In some embodiments, the retentate of the first cross flow filter remains in a collection bag. In some embodiments, the first permeate from the first cross flow filter flows through the second cross flow filter. In some embodiments, any system provided herein further comprises a centrifuge and/or centrifugation step. In some embodiments, the first and the second of two or more filters comprise a first and a second cross flow filter.

In one aspect, provided herein is a system for concentrating A2M from a fluid sample comprising: a filtration module comprising an inlet, an outlet, and one or more filters; wherein the one or more filters are fluidly connected in series between the filter module inlet and outlet; wherein a flow of the fluid sample passes through the one or more filters to produce a concentrated A2M serum; wherein a first of the one or more filters screens out cells, particles, and other molecules larger than 1 μm; and wherein a second of the one or more filters retains molecules of weight more than about 500 kDa. In some embodiments, any system provided herein further comprises a pump adapted to be fluidly coupled to the filtration module either upstream of the inlet or downstream of the outlet of the filtration module, said pump further adapted to produce a flow of the fluid sample that passes through one or more filters of the filter module. In some embodiments, the first and the second of two or more filters comprise a first and a second cross flow filter. In some embodiments, the filter module further comprises a first and a second permeate collection reservoirs, and wherein the first permeate collection reservoir stores a permeate from the first cross flow filter, and wherein the first permeate flows through the second cross flow filter and a retentate of the first cross flow filter will remain in a first retentate collection reservoir, and wherein the second permeate collection reservoir stores a permeate from the second cross flow filter and the retentate of the second cross flow filter comprises concentrated A2M the fluid sample.

In one aspect, provided herein is a system for concentrating A2M from a fluid sample comprising: a centrifuge; a filtration module comprising an inlet, an outlet, and one or more filters; and a supernatant of the fluid sample obtained from by centrifuging the fluid sample with the centrifuge, wherein the one or more filters are fluidly connected in series between the filter module inlet and outlet, wherein a flow of the fluid sample passes through the one or more filters to produce a concentrated A2M serum, wherein the flow of the fluid sample that passes through the filtration module comprises the supernatant of the fluid sample, wherein the one or more filters of the filtration module comprise at least one 500 kDa cross flow filter configured to retain molecules of weight more than about 500 kDa in a retentate reservoir, wherein the permeate from the 500 kDa cross flow filter is collected in a permeate reservoir, and wherein the retentate of the 500 kDa cross flow filter comprises concentrated A2M.

In one aspect, provided herein is a method of concentrating A2M in a fluid sample comprising: providing a filtration module, wherein the filtration module comprises an inlet, an outlet, and one or more filters fluidly connected in series between the inlet and outlet; pumping the fluid sample through the filtration module inlet, the one or more filters and the outlet to produce a concentrated A2M serum, wherein pumping the fluid sample is accomplished with a pump fluidly connected to the filtration module either upstream of the inlet or downstream of the outlet; and removing cells from the fluid sample, wherein at least one 500 kDa filter of the one or more filters retains molecules of weight more than about 500 kDa. In some embodiments, removing cells from the fluid sample comprises providing a centrifuge, centrifuging the fluid sample, and obtaining a resultant supernatant of the fluid sample. In some embodiments, removing cells from the fluid sample comprises pumping the fluid sample through a first filter of the filtration module, wherein the filter screens out cells, particles and other molecules larger than 1 In some embodiments, the first filter comprises a first cross-flow filter and the at least one 500 kDa filter comprises a second cross-flow filter. In some embodiments, any of the methods provided herein further comprise filtering a permeate of the first cross-flow filter with the second cross-flow filter; and retaining a retentate of the second cross-flow filter, wherein the retentate of the second cross flow filter comprises concentrated A2M. In some embodiments, any of the methods provided herein further comprise storing the retentate of the second cross-flow filter containing the concentrated A2M in a second cross-flow filter retentate reservoir. In some embodiments, any of the methods provided herein further comprise storing the retentate of the first-cross flow filter in a first cross-flow filter retentate reservoir. In some embodiments, any of the methods provided herein further comprise retaining a pellet of the centrifuged fluid sample.

In one aspect provided herein is a method of concentrating A2M in a fluid sample comprising: providing a flow filtration module, wherein the filtration module comprises an inlet, an outlet, and two or more filters fluidly connected in series between the inlet and outlet; and pumping the fluid sample through the filtration module inlet, the two or more filters and the outlet to produce a concentrated A2M serum or plasma, and wherein pumping the fluid sample is accomplished with a pump fluidly connected to the filtration module either upstream of the inlet or downstream of the outlet, and wherein a first of the two or more filters screens out cells, particles, and other molecules larger than 0.1 μm, and wherein a second of the two or more filters retain molecules of weight more than about 500 kDa. In some embodiments, the flow filtration module is a dead end and/or tangential flow filtration module. In some embodiments, the first and second of the at least two filters comprise a first and a second cross flow filter. In some embodiments, the filtration module further comprises: retaining a permeate of the first cross flow filter in the first permeate collection reservoir; and passing a permeate of the first cross flow filter to the second cross flow filter; and retaining a permeate of the second cross flow filter in a second permeate collection reservoir, wherein the concentrated A2M from serum or plasma comprises a retentate of the second cross flow filter in a collection bag. In some embodiments, any of the methods provided herein further comprise centrifuging the fluid sample to remove cells and particles, thereby forming plasma or serum, and placing the plasma and/or serum into the collection bag.

In one aspect, provided herein is a method of treating a subject, comprising administering to a subject in need thereof an effective amount of any composition described herein or a composition obtainable by any method described herein. In some embodiments, the composition is administered into an anatomic site relevant to a pathology of the subject. In some embodiments, protease activity is inhibited at an anatomic site of administration; thereby decreasing the degeneration rate of tissue, the degeneration rate of cartilage, the degeneration rate of discs, or synovial inflammation, or a combination thereof. In some embodiments, the subject has one or more conditions comprising: arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof; wherein inflammation comprises joint or disc inflammation caused by surgery, joint or disc inflammation caused by a joint or disc replacement, or a combination thereof. In some embodiments, the subject has been previously diagnosed with the one or more conditions. In some embodiments, the administration is to a joint selected from the group comprising a wrist, spinal, shoulder, elbow, carpal, metacarpal, phalangeal, acromioclavicular, sternoclavicular, scapular, costal, sacroiliac, hip, knee, ankle, tarsal, and a metatarsal joint.

In one aspect, provided herein is a method of inhibiting the formation or causing the dissociation of the fibronectin-aggrecan complex (FAC) in a subject with a condition comprising administering an agent to the subject, wherein the agent inhibits one or more proteins or cells associated with formation of the FAC, thereby inhibiting FAC formation. In some embodiments, the condition comprises cancer, arthritis, inflammation, ligament injury, tendon injury, bone injury, cartilage degeneration, cartilage injury an autoimmune disease, back pain, joint pain, joint degeneration, disc degeneration, spine degeneration, bone degeneration, inflammation in joint or disc surgery, inflammation in joint or disc replacement, or any combination thereof. In some embodiments, the agent comprises an antibody, polypeptide, nucleotide, or small molecule. In some embodiments, the agent binds to the FAC but not to the individual components of the complex separately. In some embodiments, the agent comprises a recombinant aggrecan G3 domain, wherein the domain contains the aggrecan G3 Lectin domain and competitively binds to fibronectin; and wherein the newly formed complex lacks the binding site to Pathogen Associated Molecular Patterns (PAMP) receptor and the binding site Damage Associated Molecular Patterns (DAMP) receptor. In some embodiments, the agent comprises a recombinant fibronectin fragment, wherein the fragment comprises a G3 binding domain and competitively binds to aggrecan, and wherein the newly formed fibronectin fragment aggrecan G3 complex lacks the binding site to PAMP receptor, and the DAMP receptor. In some embodiments, the agent comprises an aggrecan antibody. In some embodiments, the agent comprises a fibronectin antibody. In some embodiments, the agent comprises an antibody that binds to the PAMP receptor recognition domain of aggrecan, the DAMP receptor recognition domain of aggrecan, or both, thereby inhibiting activation of monocytes and other cells. In some embodiments, the agent comprises an antibody that binds to the PAMP receptor recognition domain of fibronectin, the DAMP receptor recognition domain of fibronectin, or both, thereby inhibiting activation of monocytes and other cells. In some embodiments, the agent comprises a PAMP receptor or DAMP receptor that binds to the PAMP domain of aggrecan G3, the DAMP domain of aggrecan G3, or both, thereby inhibiting activation of monocytes and other cells. In some embodiments, the agent comprises a soluble form of the PAMP receptor or DAMP receptor that binds to the PAMP domain of fibronectin, the DAMP domain of fibronectin, or both, thereby inhibiting activation of monocytes and other cells. In some embodiments, the agent inhibits production of proinflammatory cytokines, chemokines, proteases, or any combination thereof. In some embodiments, the agent inhibits fibroblast cells, thereby inhibiting production of fibronectin, recruitment of other fibroblast cells, or a combination thereof. In some embodiments, the small molecule or polypeptide is identified using one or more high-throughput screening methods. In some embodiments, the small molecule or polypeptide inhibits FAC formation, causes the dissociation of FAC, inhibits activation of monocytes, inhibits increased production of fibronectin, inhibits recruitment of fibroblast cells, binds to the DAMP domain of fibronectin, binds to the DAMP domain of aggrecan G3, binds to the PAMP domain of fibronectin, or binds to the PAMP domain of aggrecan G3. In some embodiments, the small molecule or polypeptide inhibits FAC formation by competitively binding to fibronectin or aggrecan. In some embodiments, the small molecule or polypeptide binds to the FAC complex resulting in dissociation or degradation of the FAC complex. In some embodiments, inhibiting the formation of the fibronectin-aggrecan complex (FAC) comprises inhibiting of one or more steps in FAC formation. In some embodiments, the one or more steps in FAC formation comprise production of fibronectin in the ECM, production of proteases and metalloproteases, production of inflammatory cytokines and chemokines, degradation of aggrecan in cartilage, and production of aggrecan G3 domain fragment.

In one aspect, provided herein is an agent for use in therapy, wherein said agent inhibits the formation of the fibronectin-aggrecan complex (FAC) in a subject with a condition, and wherein the agent inhibits one or more proteins or cells associated with formation of the FAC, thereby inhibiting FAC formation. In some embodiments, the agent comprises an antibody, polypeptide, nucleotide, or small molecule. In some embodiments, the agent binds to the FAC but not to the individual components of the complex separately. In some embodiments, the agent comprises a recombinant aggrecan G3 domain, wherein the domain contains the aggrecan G3 Lectin domain and competitively binds to fibronectin; and wherein the newly formed complex lacks the binding site to Pathogen Associated Molecular Patterns (PAMP) receptor and the binding site Damage Associated Molecular Patterns (DAMP) receptor. In some embodiments, the agent comprises a recombinant fibronectin fragment, wherein the fragment comprises a G3 binding domain and competitively binds to aggrecan, and wherein the newly formed fibronectin fragment aggrecan G3 complex lacks the binding site to PAMP receptor, and the DAMP receptor. In some embodiments, the agent comprises an aggrecan antibody. In some embodiments, the agent comprises a fibronectin antibody. In some embodiments, the agent comprises an antibody that binds to the PAMP receptor recognition domain of aggrecan, the DAMP receptor recognition domain of aggrecan, or both, thereby inhibiting activation of monocytes and other cells. In some embodiments, the agent comprises an antibody that binds to the PAMP receptor recognition domain of fibronectin, the DAMP receptor recognition domain of fibronectin, or both, thereby inhibiting activation of monocytes and other cells. In some embodiments, the agent comprises a PAMP receptor or DAMP receptor that binds to the PAMP domain of aggrecan G3, the DAMP domain of aggrecan G3, or both, thereby inhibiting activation of monocytes and other cells. In some embodiments, the agent comprises a soluble form of the PAMP receptor or DAMP receptor that binds to the PAMP domain of fibronectin, the DAMP domain of fibronectin, or both, thereby inhibiting activation of monocytes and other cells. In some embodiments, the agent inhibits production of proinflammatory cytokines, chemokines, proteases, or any combination thereof. In some embodiments, the agent inhibits fibroblast cells, thereby inhibiting production of fibronectin, recruitment of other fibroblast cells, or a combination thereof. In some embodiments, the small molecule or polypeptide is identified using one or more high-throughput screening methods. In some embodiments, the small molecule or polypeptide inhibits FAC formation, inhibits activation of monocytes, inhibits increased production of fibronectin, inhibits recruitment of fibroblast cells, binds to the DAMP domain of fibronectin, binds to the DAMP domain of aggrecan G3, binds to the PAMP domain of fibronectin, or binds to the PAMP domain of aggrecan G3. In some embodiments, the small molecule or polypeptide inhibits FAC formation by competitively binding to fibronectin or aggrecan. In some embodiments, the small molecule or polypeptide binds to the FAC complex resulting in dissociation or degradation of the FAC complex. In some embodiments, inhibiting the formation of the fibronectin-aggrecan complex (FAC) comprises inhibiting of one or more steps in FAC formation. In some embodiments, the one or more steps in FAC formation comprise production of fibronectin in the ECM, production of proteases and metalloproteases, production of inflammatory cytokines and chemokines, degradation of aggrecan in cartilage, and production of aggrecan G3 domain fragment. In some embodiments, the condition comprises arthritis, inflammation, ligament injury, tendon injury, bone injury, cartilage degeneration, cartilage injury an autoimmune disease, back pain, joint pain, joint degeneration, disc degeneration, spine degeneration, bone degeneration, inflammation in joint or disc surgery, inflammation in joint or disc replacement, or any combination thereof.

In one aspect, provided herein is a composition comprising a variant A2M polypeptide, comprising a bait region, wherein the bait region of the variant A2M polypeptide comprises a plurality of protease recognition sites arranged in series. In some embodiments, the variant A2M polypeptide protein is a recombinant protein. In some embodiments, the variant A2M polypeptide protein is produced in a host comprising bacteria, yeast, fungi, insect, or mammalian cells, or a cell free system. In some embodiments, the variant A2M polypeptide protein is characterized by an enhanced nonspecific inhibition of serine proteases, threonine proteases, cysteine proteases, aspartate proteases, metalloproteases, glutamic acid proteases, or any combination thereof. In some embodiments, the variant A2M polypeptide protein further comprises PEG with abnormal glycosylation sites. In some embodiments, the variant A2M polypeptide protein has a longer half life than the half life of a wild type A2M protein when disposed within a joint or spine disc of a subject. In some embodiments, the plurality of protease recognition sites comprise one or more protease substrate bait regions from one or more proteins other than A2M, one or more additional protease bait regions from A2M, one or more non-natural protein sequences, or any combination thereof, wherein the modified A2M protein is characterized by at least a 10% increase in protease inhibitory effectiveness compared to the protease inhibitory effectiveness of a wild type A2M protein. In some embodiments, the non-natural protein sequences comprise one or more protease recognition sites that can function as bait for proteases. In some embodiments, the one or more protease substrate bait regions comprise consensus sequences for serine proteases, threonine proteases, cysteine proteases, aspartate proteases, metalloproteinases, glutamic acid proteases, or any combination thereof. In some embodiments, the protease substrate bait regions comprise one or more consensus sequences for one or more proteases from one or more organisms. In some embodiments, the one or more organisms comprise animals, plants, bacteria, yeast, fish, reptiles, amphibians, or fungi. In some embodiments, one or more of the one or more protease substrate bait regions from the one or more proteins other than A2M are the same. In some embodiments, one or more of the one or more protease substrate bait regions from A2M are the same. In some embodiments, one or more of the one or more protease substrate bait regions from the one or more non-natural protein sequences are the same. In some embodiments, one or more of the one or more protease substrate bait regions from the one or more proteins other than A2M or from the one or more non-natural protein sequences comprise a suicide inhibitor; wherein the suicide inhibitor is operable to covalently attach a protease to A2M. In some embodiments, one or more of the one or more protease substrate bait regions are from different species.

In one aspect, provided herein is a composition comprising an isolated variant A2M polypeptide, wherein the variant A2M polypeptide comprises one or more non-natural bait regions, wherein the one or more non-natural bait regions comprise one or more protease recognition sites not present in a wild-type A2M polypeptide. In some embodiments, the modified A2M polypeptide is characterized by at least a 10% enhanced inhibition of one or more proteases compared to a wild-type A2M inhibition of the one or more proteases. In some embodiments, the enhanced inhibition comprises enhanced nonspecific inhibition. In some embodiments, the enhanced inhibition comprises enhanced specific inhibition. In some embodiments, the protease comprises a serine protease, threonine protease, cysteine protease, aspartate protease, metalloprotease, glutamic acid protease, or any combination thereof. In some embodiments, the protease comprises MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11), Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xcol4, *xenopus* collagenase), MMP19 (RASI-1, stromelysin-4), MMP20 (Enamelysin), MMP21 (X-MMP), MMP23A (CA-MMP), MMP23B MMP24 (MT5-MMP), MMP25 (MT6-MMP), MMP26 (Matrilysin-2, endometase), MMP27 (MMP-22, C-MMP), MMP28 (Epilysin); A Disintegrin and Metalloproteinase with Thrombospondin Motifs protease, such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMPSTE2; acetylcholinesterase; or a combination thereof. In some embodiments, the protease comprises ADAMTS4, ADAMTS 5, MMP13, or a combination thereof. In some embodiments, the modified A2M polypeptide is characterized by at least a 10% enhanced inhibition of FAC formation compared to a wild-type A2M inhibition of FAC formation. In some embodiments, the one or more non-natural bait regions are derived from one or more proteins other than A2M. In some embodiments, the one or more proteins other than A2M are from a non-human organism. In some embodiments, the non-human organism comprises an animal, plant, bacterium, yeast, fish, reptile, amphibian, or fungi. In some embodiments, the one or more non-natural bait regions comprise SEQ ID NOs 5-66. In some embodiments, the variant A2M polypeptide comprises SEQ ID NO 4, or a fragment thereof. In some embodiments, the one or more non-natural bait regions comprise SEQ ID NOs 5-66, or fragments thereof. In some embodiments, the wild-type A2M polypeptide comprises SEQ ID NO 3, or a fragment thereof. In some embodiments, one or more of the one or more non-natural bait regions comprise a suicide inhibitor; wherein the suicide inhibitor is operable to covalently attach a protease to the variant A2M polypeptide. In some embodiments, the one or more protease recognition sites comprise 2 or more copies of the one or more protease recognition sequences. In some embodiments, the one or more non-natural bait regions comprise 2 or more copies of the one or more non-natural bait regions. In some embodiments, the variant A2M polypeptide comprises a wild-type A2M bait region sequence. In some embodiments, the variant A2M polypeptide is a recombinant polypeptide. In some embodiments, the one or more protease recognition sites comprise a consensus sequence for a protease. In some embodiments, the variant A2M polypeptide comprises one or more modified glycosylation sites. In some embodiments, the one or more modified glycosylation sites are functionalized with PEG. In some embodiments, the variant A2M polypeptide has at least a 10% longer half life than the half life of a wild type A2M polypeptide when disposed within a subject.

In one aspect, provided herein is a method of treating a subject with one or more conditions, comprising administering to the subject an effective amount of any composition provided herein, a wild-type A2M protein, A2M variant, or a combination thereof. In some embodiments, nonspecific inhibition of one or more proteases in the subject, inhibition Aggrecan G3 fragment formation, inhibition FAC formation, or a combination thereof, is increased. In some embodiments, the rate of degeneration of tissue, cartilage and discs, synovial inflammation, or a combination thereof, is decreased in the subject. In some embodiments, treating results in a reduction in severity, occurrence, rate of progression, or a combination thereof, of the one or more conditions. In some embodiments, any of the methods provided herein further comprise administering one or more additional carriers or drugs. In some embodiments, the one or more additional carriers or drugs comprise hydrogels, hyaluronic acid preparations, polymer microspheres, corticosteroids, microparticles, chitosan, local anaesthetics, growth factors, cytokines, protease inhibitors, steroids, hyaluranic Acid (HA), or other biologically active autogenous or endogenous mediators. In some embodiments, the one or more conditions are treatable with any composition provided herein. In some embodiments, the one or more conditions comprise cancer, degenerative diseases, traumatic diseases, and/or inflammatory diseases, whose pathogenesis includes the activity of proteases. In some embodiments, the cancer, degenerative diseases, traumatic diseases, and/or inflammatory diseases whose pathogenesis includes the activity of proteases comprises osteoarthritis, inflammatory arthritides, chondrosis, chondral injuries, enthesopathies, tendinopathies, ligamentous injuries, degenerative diseases of the bone, cartilage, tendons, and ligaments, post-operative conditions and wound healing, and other musculoskeletal diseases. In some embodiments, the one or more conditions comprise cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof. In some embodiments, inflammation comprises joint or disc inflammation caused by surgery, joint or disc inflammation caused by a joint or disc replacement, or a combination thereof. In some embodiments, the subject is a human, pig, mouse, rat, rabbit, cat, dog, monkey, frog, horse or goat. In some embodiments, the subject has been previously diagnosed with the one or more conditions. In some embodiments, the composition is administered into an anatomic site relevant to the host pathology. In some embodiments, the administration comprises injection with a hollow-lumen device or flexible catheter combinations. In some embodiments, the hollow-lumen device comprises a needle, syringe, or combination thereof. In some embodiments, the administration occurs during a surgical procedure.

In one aspect, provided herein is a composition comprising an isolated variant A2M polynucleotide, wherein the variant A2M polynucleotide encodes for one or more non-natural bait regions, wherein the one or more non-natural bait regions comprise one or more protease recognition sites not present in a wild-type A2M polypeptide. In some embodiments, the non-natural bait regions comprise a sequence with at least 60% identity to SEQ ID NOs 5-66, or fragments thereof. In some embodiments, the variant A2M polynucleotide comprises at least 90% identity to SEQ ID NO 2, or a fragment thereof. In some embodiments, the wild-type A2M polynucleotide comprises SEQ ID NO 1, or a fragment thereof. In some embodiments, the variant A2M polynucleotide is within an expression vector.

In one aspect, provided herein is a method for determining the enhanced inhibition of a protease by a variant A2M polypeptide comprising: (a) providing a variant A2M polypeptide comprising a sequence of one or more of SEQ ID NOs 5-66; (b) contacting the variant A2M polypeptide with the protease and a substrate cleaved by the protease; (c) contacting a wild-type A2M polypeptide with the protease and the substrate cleaved by the protease; and (d) comparing the amount of cleavage of the substrate from step (b) to the amount of cleavage of the substrate from step (c), thereby determining the enhanced inhibition of the protease by the variant A2M polypeptide.

In one aspect, provided herein is a method for making a variant A2M polynucleotide comprising: (a) providing a vector containing a variant A2M polynucleotide comprising a sequence of SEQ ID NO 2; (b) digesting the vector containing a variant A2M polynucleotide with restriction endonucleases to form a linear vector; (c) ligating one end of the one or more polynucleotides encoding one or more of the non-natural bait regions of SEQ ID NOs 5-66 to one end of the linear vector; and (d) ligating the other end of the one or more polynucleotides encoding one or more of the non-natural bait regions of SEQ ID NOs 5-66 to the other end of the linear vector, thereby forming a vector containing a variant A2M polynucleotide comprising the non-natural bait regions of SEQ ID NOs 5-66.

In one aspect, provided herein is a composition comprising A2M, wherein the composition is obtainable by any method provided herein. In some embodiments, the composition is for autologous administration.

In one aspect, provided herein is a composition comprising A2M for use in therapy wherein the composition is (a) any liquid composition provided herein (b) a composition obtainable by any method provided herein, or (c) any variant A2M composition provided herein In some embodiments, the composition is for use in autologous therapy or for use in non-autologous therapy. In some embodiments, the composition is for use in the treatment of cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof; wherein inflammation comprises joint or disc inflammation caused by surgery, joint or disc inflammation caused by a joint or disc replacement, or a combination thereof.

In one aspect, provided herein is a use of (a) any liquid composition provided herein (b) a composition obtainable by any method provided herein, or (c) any variant A2M composition provided herein, for the manufacture of a medicament for use in therapy. In some embodiments, the medicament is for use in autologous therapy or for use in non-autologous therapy. In some embodiments, the medicament is for use in the treatment of cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof; wherein inflammation comprises joint or disc inflammation caused by surgery, joint or disc inflammation caused by a joint or disc replacement, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the event of a conflict between a term herein and a term incorporated by reference, the term herein controls.

BRIEF DESCRIPTION OF THE DRAWINGS

The novel features are set forth with particularity in the appended claims. A better understanding of the features and advantages will be obtained by reference to the following detailed description that sets forth illustrative embodiments, in which the principles of devices, methods, and compositions are utilized, and the accompanying drawings of which:

FIG. 5A depicts a graph demonstrating treatment of Bovine Cartilage Explants (BCE) with leukocyte-rich Platelet Rich Plasma (LR-PRP), which induces cartilage catabolism, and treatment with purified A2M to inhibit cartilage degradation.

FIG. 5B depicts a graph demonstrating treatment of Bovine Cartilage Explants (BCE) with APIC-PRP, blood, or leukocyte-rich Platelet Rich Plasma (LR-PRP) from the same patient. LR-PRP, but not blood, induces cartilage catabolism. Treatment of BCE with APIC-PRP inhibits cartilage degradation below endogenous levels.

FIG. 5C depicts a graph demonstrating leukocyte-rich Platelet Rich Plasma (LR-PRP) induces cartilage catabolism in a Bovine Cartilage Explant (BCE) model. Treatment with APIC-PRP inhibits the cartilage degradation induced by treatment with LR-PRP.

FIG. 8A depicts a graph demonstrating the sulfated glycosaminoglycan (sGAG) released upon cartilage catabolism in a BCE model with and without treatment of MMP-7 and MMP-12. Treatment with purified A2M inhibited the MMP-induced cartilage catabolism.

FIG. 8B depicts a stained SDS-PAGE gel of samples produced in FIG. 9A. The MMP-7- or MMP-12-induced degradation of cartilage, and the production of cartilage protein fragments visible in the gel, was inhibited with addition of purified A2M.

FIG. 8C depicts a Western Blot with α-Aggrecan G3 antibody using the gel from FIG. 8B and the samples from FIG. 8A. The degradation of cartilage by MMP-7 or MMP-12 produces an Aggrecan G3 fragment at ~30 kDa which can be inhibited with addition of purified A2M.

FIG. 9A, FIG. 9B, FIG. 9C, FIG. 9D, FIG. 9E, and FIG. 9F are exemplary graphs depicting the results of an ELISA test that recognizes complexes of Fibronectin and Aggrecan G3 (FACT, Fibronectin Aggrecan Complex Test). Culture media from BCE treated with or without the listed proteases in the presence or absence of A2M were incubated with Synovial Fluid (SF) spiked with free Fibronectin and tested on the FACT assay. In each case where degradation of cartilage led to Aggrecan fragments the result was formation of additional Fibronectin Aggrecan Complexes above the SF background control. Treatment with A2M, however, which prevented cartilage catabolism, subsequently preventing FAC formation.

FIG. 14A, FIG. 14B, FIG. 14C, and FIG. 14D are exemplary graphs of histopathology evaluation of the rabbit knees from experiments depicted in FIGS. 12 and 13 including structure, chondrocyte density, Safarin-O staining, and cluster formation evaluations; and shows an inverse correlation between A2M concentration in each rabbit's APIC and the scoring criteria. One outlying rabbit is excluded from calculations in the line but is included in the figures.

FIG. 18A depicts the raw data (left) and FIG. 18B depicts the calculated slope (right) of digestion of FTC-casein by bovine trypsin in the presence of tagged wild-type A2M (WT) or the four chosen A2M variants. The samples without the "−D" are prepared with a 1:1 molar ratio of A2M: protease. Those with the "−D" are prepared at a 0.5:1 ratio of A2M:protease.

FIG. 18C depicts the raw data (left) and FIG. 18D depicts the calculated slope (right) of digestion of FTC-casein by chymotrypsin in the presence of tagged wild-type A2M (WT) or the four chosen A2M variants. The samples without the "−D" are prepared with a 1:1 molar ratio of A2M: protease. Those with the "−D" are prepared at a 0.5:1 ratio of A2M:protease.

FIG. 20 depicts a chart of the inhibition of IGD fragment proteolysis by the indicated variants as a percentage of wild-type A2M (top) and the sequences of the bait sequences (SEQ ID NOS 75, 29, 5 and 76, respectively, in order of appearance) corresponding to the indicated A2M variants (bottom).

DETAILED DESCRIPTION OF THE DISCLOSURE

Figure 1:
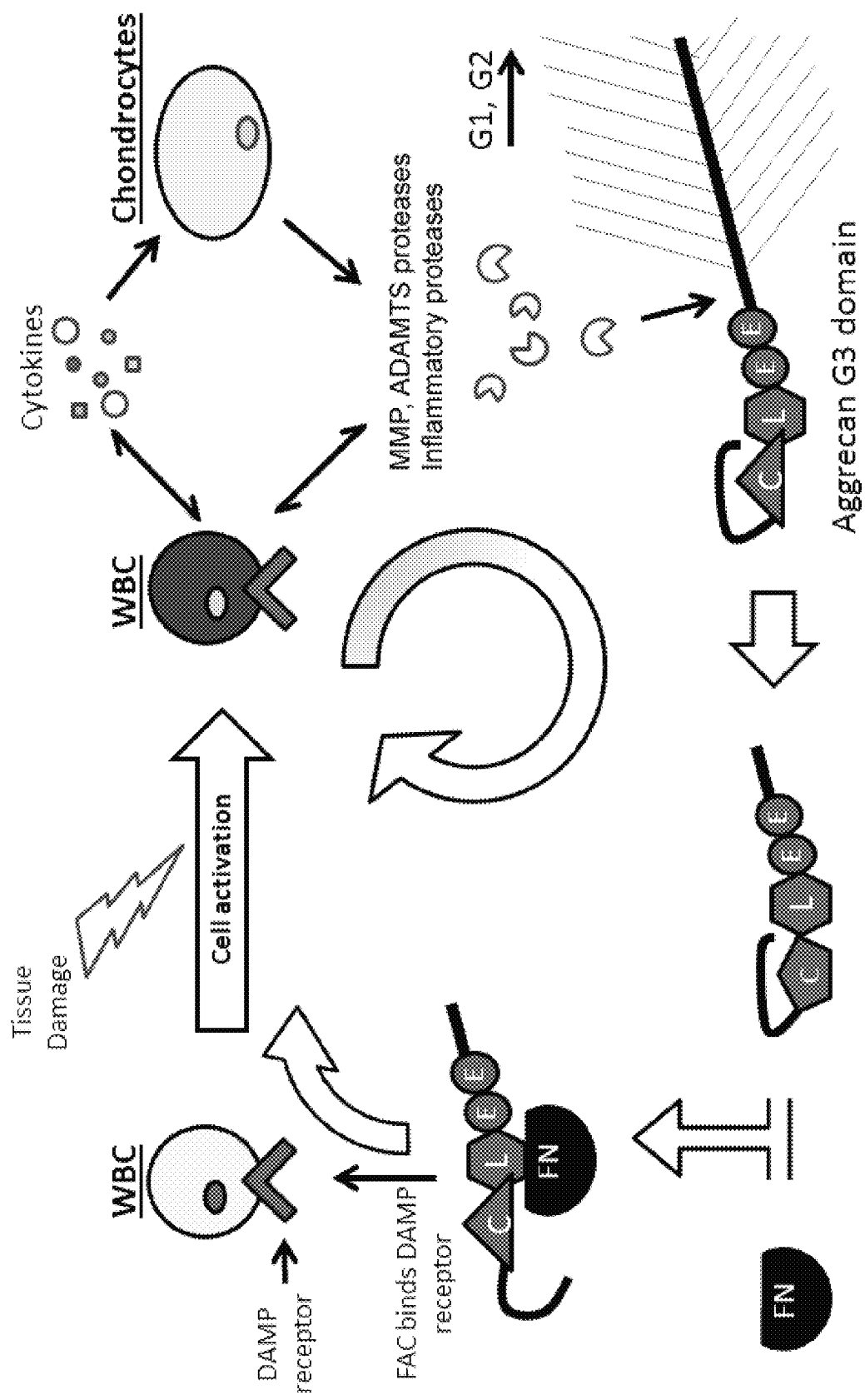
FIG. 1 depicts a schematic of the steps and signaling pathways associated with formation of a fibronectin-aggrecan complex (FAC) and the FAC-induced activation of Damage-Associated-Molecular Pattern (DAMP) receptor signaling in cells. The combination of the two processes creates a cyclic process that continually degrades cartilage.
Figures 2A, 2B:
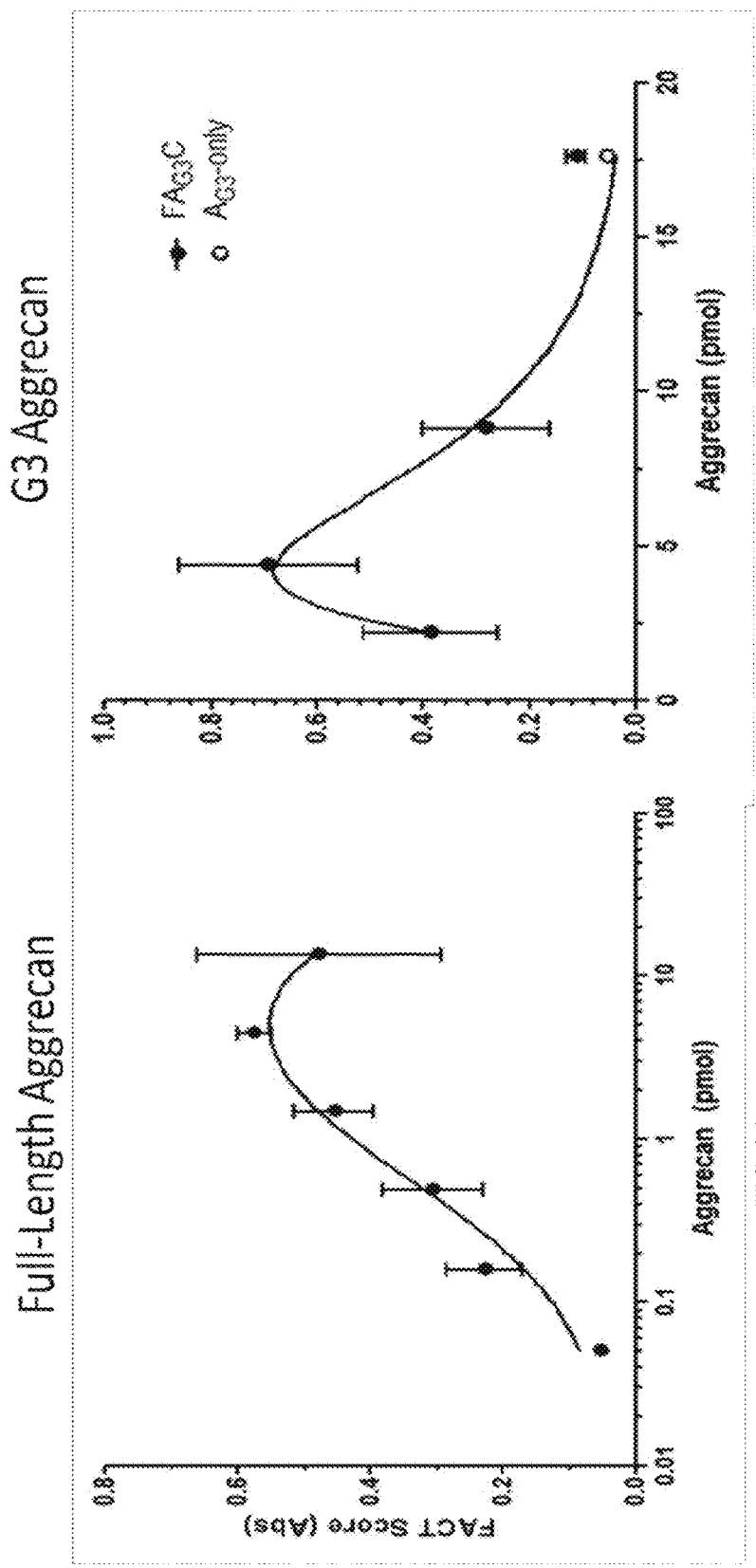
FIG. 2A and FIG. 2B are exemplary graphs depicting FAC formation using fibronectin to form a complex with purified full length Aggrecan or recombinant G3 Aggrecan. Both Aggrecan and the G3 domain bind fibronectin to form FAC.

Provided herein are compositions, methods, kits and systems for the detection, diagnosis, and treatment of inflammation, pain in the spine or joint, and degradation of extracellular matrix.

The details of one or more inventive embodiments are set forth in the accompanying drawings, the claims, and in the description herein. Other features, objects, and advantages of inventive embodiments disclosed and contemplated herein will be apparent from the description and drawings, and from the claims. As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment. As used herein, unless otherwise indicated, some inventive embodiments herein contemplate numerical ranges. When ranges are present, the ranges include the range endpoints. Additionally, every subrange and value within the range is present as if explicitly written out.

Definitions

The term "substantially non-immunogenic" or "substantially non-antigenic" means that the composition being administered to a subject does not elicit an immune response to the composition.

A "subject" refers to a donor, recipient or host of the composition of the present invention. In some embodiments, the donor and the recipient are the same. In some embodiments the subject is a human subject.

A "proteoglycan" refers to a special class of proteins that are heavily glycosylated. A proteoglycan is made up of a core protein with numerous covalently attached high sulphated glycosaminoglycan chain(s). Non-limiting example of extracellular matrix proteoglycans include aggrecan and certain collagens, such as collagen IX.

A "glycosaminoglycan" or "GAG" as used herein refers to a long unbranched polysaccharide molecules found on the cell surface or within the extracellular matrix. Non-limiting examples of glycosaminoglycan include heparin, chondroitin sulfate, dextran sulfate, dermatan sulfate, heparan sulfate, keratan sulfate, hyaluronic acid, hexuronyl hexosaminoglycan sulfate, and inositol hexasulfate.

The term "non-autologous" refers to tissue or cells which originate from a donor other than the recipient. Non-autologous can refer to, for example, allogeneic or xenogeneic. The term "autologous" as in an autologous composition, refers to a composition in which the donor and recipient is the same individual. Likewise, "allogeneic" refers to a donor and a recipient of the same species; "syngeneic" refers to a donor and recipient with identical genetic make-up (e.g. identical twins or autogeneic) and "xenogeneic" refers to donor and recipient of different species.

The term "variant" (or "analog") refers to any molecule differing from the naturally occurring molecule.

The term "variant polynucleotide" (or "analog") refers to any polynucleotide differing from the naturally occurring polynucleotide. For example, "variant A2M polynucleotide" refers to any A2M polynucleotide differing from naturally occurring A2M polynucleotides. A variant A2M polynucleotide includes a polynucleotide sequence different from the wild-type A2M polynucleotide sequence (SEQ ID NO: 1). Variant polynucleotides can be characterized by nucleic acid insertions, deletions, and substitutions, created using, for example, recombinant DNA techniques. A variant A2M polynucleotide preferably includes a mutation, insertion, deletion, or a combination thereof, in the bait region of a wild-type A2M polynucleotide sequence. As used herein, when referring to polypeptides, the "bait region" includes the region of an A2M polynucleotide that encodes the region of the A2M polypeptide that binds to proteases, for example, regions that contain protease recognition sites. A variant A2M polynucleotide includes an "A2M acceptor sequence" (SEQ ID NO: 2) which includes a polynucleotide sequence of A2M with point mutations that can aid in creating variant A2M polynucleotides by recombinant DNA techniques, for example, by creating restriction enzyme cloning sites to aid in inserting various polynucleotide sequences encoding the variant bait regions. Bait regions include SEQ ID NOs: 5-66 and sequences substantially similar to SEQ ID NOs: 5-66.

The term "variant polypeptide" refers to any polypeptide differing from the naturally occurring polypeptide. For example, "variant A2M polypeptide" refers to any A2M polypeptide differing from naturally occurring A2M polypeptides. Variant polypeptides can be characterized by amino acid insertions, deletions, and substitutions, created using, for example, recombinant DNA techniques. A variant A2M polypeptide includes a polypeptide sequence different from the wild-type A2M polypeptide sequence. A variant A2M polypeptide preferably includes a mutation, insertion, deletion, or a combination thereof, in the bait region of a wild-type A2M protein. When referring to polypeptides, the "bait region" includes the region of an A2M polypeptide that binds to proteases, for example, a stretch of amino acids that contains one or more protease recognition sites. A variant A2M polypeptide includes a polypeptide (SEQ ID NO: 3) encoded by an A2M acceptor sequence (SEQ ID NO: 2). A "variant A2M polypeptide" can have at least one amino acid sequence alteration in the bait region as compared to the amino acid sequence of the corresponding wild-type polypeptide. An amino acid sequence alteration can be, for example, a substitution, a deletion, or an insertion of one or more amino acids. A variant A2M polypeptide can have any combination of amino acid substitutions, deletions or insertions.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence. Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as inhibition of proteases, ligand-binding affinities, interchain affinities, or degradation/turnover rate. Variant nucleotides can also be used to generate polypeptides that are better suited for expression, scale up and the like in the host cells chosen for expression.

For example, cysteine residues can be deleted or substituted with another amino acid residue in order to eliminate disulfide bridges.

An amino acid "substitution" includes replacing one amino acid with another amino acid having similar structural and/or chemical properties, for example, conservative amino acid replacements. "Conservative" amino acid substitutions can be made on the basis of similarity in polarity, charge, solubility, hydrophobicity, hydrophilicity, the amphipathic nature of the residues involved, or a combination thereof. Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid. "Insertions" or "deletions" are preferably in the range of about 1 to 50 amino acids, more preferably 1 to 30 amino acids. The variation allowed can be experimentally determined by inserting, deleting, or substituting amino acids in a polypeptide using recombinant DNA techniques and assaying the resulting recombinant variants for activity, for example, protease inhibition activity.

The terms "purified" or "substantially purified" as used herein denotes that the indicated nucleic acid or polypeptide is present in the substantial absence of other biological macromolecules, for example, polynucleotides, proteins, and the like. The polynucleotide or polypeptide can be purified such that it constitutes at least 95% by weight, for example, at least 99% by weight, of the indicated biological macromolecules present. Water, buffers, and other small molecules with a molecular weight of less than 1000 Daltons, can be present in any amount. The term "isolated" as used herein refers to a polynucleotide or polypeptide separated from at least one other component present with the polynucleotide or polypeptide in its natural source. In some embodiments, the polynucleotide or polypeptide can be found in the presence of only a solvent, buffer, ion, or other components normally present in a solution of the same. The terms "isolated" and "purified" do not encompass polynucleotides or polypeptides present in their natural source.

As used herein, "recombinant polypeptides" include polypeptides or proteins derived from recombinant expression systems, for example, microbial, insect, or mammalian expression systems. Polypeptides or proteins expressed in most bacterial cultures will be free of glycosylation modifications; polypeptides or proteins expressed in yeast can have a glycosylation pattern in general different from those expressed in mammalian cells.

The term "expression vector" refers to a plasmid or phage or virus or vector, for expressing a polypeptide from a DNA or RNA sequence. An expression vector can include a transcriptional unit comprising an assembly of a genetic element or elements having a regulatory role in gene expression, for example, promoters or enhancers, a structural or coding sequence which is transcribed into mRNA and translated into protein, and appropriate transcription initiation and termination sequences. Structural units intended for use in yeast or eukaryotic expression systems can include a leader sequence enabling extracellular secretion of translated protein by a host cell. Alternatively, where recombinant protein is expressed without a leader or transport sequence, it can include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems can be used to express heterologous polypeptides or proteins upon induction of the regulatory elements linked to the DNA segment or synthetic gene to be expressed. This term includes host cells which have stably integrated a recombinant genetic element or elements having a regulatory role in gene expression, for example, promoters or enhancers. Recombinant expression systems can be used to express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly, for example soluble proteins, or partially, for example receptors, from the cell in which they are expressed. "Secreted" proteins also include proteins transported across the membrane of the endoplasmic reticulum. "Secreted" proteins also include proteins containing non-typical signal sequences.

Where desired, an expression vector may be designed to contain a "signal sequence" which will direct the polypeptide through the membrane of a cell. A signal sequence can be naturally present on the polypeptides described herein or provided from heterologous protein sources.

As used herein, "substantially equivalent" or "substantially similar" can refer both to nucleotide and amino acid sequences, for example a variant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35%. For example, the number of individual residue substitutions, additions, and/or deletions in a substantially equivalent sequence, as compared to the corresponding reference sequence, divided by the total number of residues in the substantially equivalent sequence is about 0.35 or less. A substantially equivalent sequence includes sequences with 65% sequence identity to the reference sequence. A substantially equivalent sequence of the invention can vary from a reference sequence by no more than 30% (70% sequence identity), no more than 25% (75% sequence identity), no more than 20% (80% sequence identity), no more than 10% (90% sequence identity), or no more that 5% (95% sequence identity). Substantially equivalent amino acid sequences according to the invention preferably have at least 80% sequence identity with a reference amino acid sequence, at least 85% sequence identity, at least 90% sequence identity, at least 95% sequence identity, at least 98% sequence identity, or at least 99% sequence identity. Substantially equivalent polynucleotide sequences of the invention can have lower percent sequence identities, taking into account, for example, the redundancy or degeneracy of the genetic code. Preferably, the polynucleotide sequence has at least about 65%, at least about 75%, at least about 80%, at least 85%, at least 90%, at least 95%, at least 98%, or at least 99% sequence identity. Sequences having substantially equivalent biological activity and substantially equivalent expression characteristics are considered substantially equivalent. Identity between sequences can be determined by methods known in the art, such as by alignment of the sequences or varying hybridization conditions.

As used herein the term "effective amount" or "therapeutically effective amount" means a dosage sufficient to treat, inhibit, or alleviate spinal pain in a subject in need thereof.

By "degenerate variant" can be intended nucleotide fragments which differ from a nucleic acid fragment of the present invention (e.g., an ORF) by nucleotide sequence but, due to the degeneracy of the genetic code, encode an identical polypeptide sequence.

The terms polypeptide, peptide, and protein can be used interchangeably and can refer to a polymer of amino acid residues or a variant thereof. Amino acid polymers can have one or more amino acid residues and can be an artificial chemical mimetic of a corresponding naturally occurring amino acid, as well as to naturally occurring amino acid polymers, those containing modified residues, and non-naturally occurring amino acid polymers. A variant polypeptide can have at least one amino acid sequence alteration as compared to the amino acid sequence of the corresponding wild-type polypeptide. An amino acid sequence alteration can be, for example, a substitution, a deletion, or an insertion of one or more amino acids. A variant polypeptide can have any combination of amino acid substitutions, deletions or insertions. An amino acid sequence alteration can be formed by altering the nucleotide sequence from which it is derived, such as a mutation, for example, a frameshift mutation, nonsense mutation, missense mutation, neutral mutation, or silent mutation. For example, sequence differences, when compared to a wild-type nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid, for example, if the change in the nucleic acid sequence causes a frame shift, the frame shift can result in a change in the encoded amino acids, and/or can result in the generation of a premature stop codon, causing generation of a truncated polypeptide.

The term "fragment" can refer to any subset of the polypeptide that can be a shorter polypeptide of the full length protein. Fragments of A2M can include 20, 30, 40, 50 or more amino acids from A2M that can be detected with anti-A2M antibodies. Other fragments of A2M include various domains of A2M and combinations thereof.

"Platelet-rich plasma" ("PRP") can refer to blood plasma that has been enriched with platelets.

Compositions for Autologous Treatment of Pain and Inflammation

An autologous composition of the present disclosure can comprise alpha-2-macroglobulin (A2M) and can be used to treat a subject with a condition. The A2M can be from a biological sample, such as from a human subject; or can be any fragment thereof. In preferred embodiments the autologous compositions of the present invention are substantially non-immunogenic, namely do not elicit an immune response.

An autologous composition can comprise an elevated concentration of A2M compared to the concentration of A2M found in a biological sample, such as the blood of normal subjects, or the blood from a subject in need of autologous treatment with the autologous composition. The concentration of A2M in an autologous composition can be at least about 1.1 times higher than the concentration of A2M found in a biological sample, such as blood, of normal subjects. For example, the concentration of A2M can be at least about 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample, such as blood, of normal subjects, or the blood from a subject in need of autologous treatment with the autologous composition. For example, the concentration of A2M can be at least about 2 times higher than the concentration of A2M found in the biological sample.

In some embodiments, an autologous composition can further comprise a reduced concentration of components other than A2M compared to the normal concentration of the other components. An autologous composition can comprise a reduced concentration of other components isolated from a biological sample compared to the normal concentration of the other components in the biological sample. The concentration of other components can be at least about 10% less than the concentration of the other components normally found in a biological sample. For example, the concentration of other components can be at least about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than the concentration of the other components normally found in a biological sample, such as an endogenous concentration of the other components in a biological sample. For example, the concentration of other components can be at least about 20% less than the concentration of the other components normally found in a biological sample. The concentration of other components can be at least about 0.1 times less than the concentration of the other components normally found in a biological sample. For example, the concentration of other components can be at least about 0.2, 0.3, 0.4, 0.5, 0.6, 0.7, 0.8, 0.9, 1, 2, 2, 3, 4, 5, 6, 7, 8, 9, 10, 15, 20, 25, 30, 35, 40, 45, 50, 55, 60, 65, 70, 75, 80, 85, 90, 95, 100, 150, 200, 300, 400, 500, 600, 700, 800, 900, or 1000 times less than the concentration of the other components normally found in a biological sample. For example, the concentration of other components can be at least about 2 times less than the concentration of the other components normally found in a biological sample.

In some embodiments, an autologous composition can comprise an elevated concentration of one or more proteins with a molecular weight higher than 100 kDa. The concentration of one or more proteins with a molecular weight higher than 100 kDa can be at least about 1.1 times higher than the concentration of the one or more proteins with molecular weight higher than 100 kDa found in a normal biological sample, such as blood from a subject. The concentration of one or more proteins with a molecular weight higher than 100 kDa found in a normal biological sample can be the concentration of the endogenous level of the one or more proteins with a molecular weight higher than 100 kDa in the biological sample, such as a normal or control biological sample. For example, the concentration of one or more proteins with molecular weight higher than 100 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than 100 kDa found in a normal biological sample or the endogenous concentration in a normal biological sample. For example, the concentration of one or more proteins with molecular weight higher than 100 kDa can be at least about 1.5 times higher than the concentration of the one or more proteins with molecular weight higher than 100 kDa found in a normal biological sample or the endogenous concentration in a normal biological sample.

Proteins with a molecular weight higher than 100 kDa can include, but are not limited to, immunoglobulin G, immunoglobulin M, fibronectin, fibrinogen and other proteins. Proteins with a molecular weight less than about 100 kDa can comprise cytokines, chemokines, proteases, pro-proteases, enzymes, pro-enzymes, immune-modulators and other proteins known in the art with a molecular weight of less than 100 kDa.

In some embodiments, an autologous composition can comprise an elevated concentration of one or more proteins with a molecular weight higher than 500 kDa. The concentration of one or more proteins with a molecular weight higher than 500 kDa can be at least about 1.1 times higher than the concentration of the one or more proteins with molecular weight higher than 500 kDa found in a normal biological sample, such as blood from a subject. The concentration of one or more proteins with a molecular weight higher than 500 kDa found in a normal biological sample can be the concentration of the endogenous level of the one or more proteins with a molecular weight higher than 500 kDa in a biological sample, such as a normal or control biological sample. For example, the concentration of one or more proteins with molecular weight higher than 100 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than 500 kDa found in a normal biological sample or the endogenous concentration in a normal biological sample, or the blood from a subject in need of autologous treatment with the autologous composition. For example, the concentration of one or more proteins with molecular weight higher than 500 kDa can be at least about 1.5 times higher than the concentration of the one or more proteins with molecular weight higher than 100 kDa found in a normal biological sample or the endogenous concentration in a normal biological sample. Proteins with a molecular weight higher than 500 kDa include, but are not limited to, IgM and Complement Component C4 binding proteins. Proteins with a molecular weight less than about 500 kDa can comprise cytokines, chemokines, proteases, pro-proteases, enzymes, pro-enzymes, immune-modulators and other proteins with a molecular weight of less than 500 kDa.

In some embodiments, proteins with a molecular weight between about 300 kDa and 500 kDa, such as fibronectin, fibrinogen, and fibrin monomers or polymers may be partially concentrated using the methods described herein. In some embodiments, an autologous composition can comprise an elevated concentration of one or more proteins with a molecular weight higher between about 300 kDa and 500 kDa. In some embodiments, the concentration of one or more proteins with a molecular weight higher than between about 300 kDa and 500 kDa can be at least about 1.1 times higher than the concentration of the one or more proteins with molecular weight between about 300 kDa and 500 kDa found in a normal biological sample, such as blood from a subject. The concentration of one or more proteins with a molecular weight between about 300 kDa and 500 kDa found in a normal biological sample can be the concentration of the endogenous level of the one or more proteins with a molecular weight between about 300 kDa and 500 kDa in a biological sample, such as a normal or control biological sample. For example, the concentration of one or more proteins with molecular weight between about 300 kDa and 500 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight between about 300 kDa and 500 kDa found in a normal biological sample or the endogenous concentration in a normal biological sample.

An autologous composition can comprise an elevated concentration of A2M compared to the concentration of A2M found in a biological sample and a reduced concentration of components other than A2M compared to the normal concentration of the other components found in a biological sample. The concentration of A2M in an autologous composition can be at least about 1.5 times higher than the concentration of A2M found in a biological sample and the concentration of other components other than A2M can be at least about 10% less than the concentration of the other components normally found in a biological sample. For example, the concentration of A2M can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of components other than A2M can be at least about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 300, 400, 500, 600, 700, 800, 900, or 1000 times less than the concentration of the other components normally found in a biological sample. For example, the concentration of the concentration of A2M can be at least about 2 times higher than the concentration of A2M found in a biological sample and the concentration of components other than A2M can be at least about 2 times less than the concentration of the other components normally found in a biological sample. As another example, the concentration of A2M can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of other components can be at least about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than the concentration of the other components normally found in a biological sample. For example, the concentration of A2M can be at least about 2 times higher than the concentration of A2M found in a biological sample and the concentration of other components can be at least about 20% less than the concentration of the other components normally found in a biological sample.

In some embodiments, an autologous composition can comprise an elevated concentration of A2M compared to the concentration of A2M found in a biological sample and an elevated concentration of one or more proteins with molecular weight higher than 100 kDa found in a biological sample. The concentration of A2M in an autologous composition can be at least about 1.5 times higher than the concentration of A2M found in a biological sample and the concentration of one or more proteins with molecular weight higher than 100 kDa can be at least about 1.5 times higher than the concentration of the one or more proteins with molecular weight higher than 100 kDa found in a biological sample. For example, the concentration of the concentration of A2M can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 100 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 100 kDa found in a biological sample. For example, the concentration of A2M can be at least about 2 times higher than the concentration of A2M found in a biological sample and the concentration of one or more proteins with molecular weight higher than 100 kDa can be at least about 2 times higher than the concentration of the one or more proteins with molecular weight higher than about 100 kDa found in a biological sample. Proteins with a molecular weight higher than about 100 kDa can be, for example, proteins with a molecular weight more than about 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, 2000 kDa, or more.

The concentration of A2M and other proteins with a molecular weight higher than 100 kDa can be present at a concentration of at least about 1.5 times higher than their concentration in a biological sample after retention by one or more filters using the methods or systems described herein. For example, the concentration of A2M and other proteins with a molecular weight higher than 100 kDa can be present at a concentration of at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein. For example, the concentration of A2M and other proteins with a molecular weight higher than 100 kDa can be present at a concentration of at least about 1.5 times higher than their concentration in a biological sample after retention by one or more filters using the methods or systems described herein.

The concentration of proteins with molecular weight less than about 100 kDa can be less than about 10% of the concentrations of those proteins in a biological sample when not retained by the one or more filters using the methods or systems described herein. For example, the concentration of proteins with molecular weight less than about 100 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when not retained by the one or more filters using the methods or systems described herein. For example, the concentration of proteins with molecular weight less than about 100 kDa can be less than about 20% less than their concentration in a biological sample when not retained by the one or more filters using the methods or systems described herein. Proteins with a molecular weight less than about 100 kDa can be, for example, proteins with a molecular weight less than about 95 kDa, 90 kDa, 85 kDa, 80 kDa, 75 kDa, 70 kDa, 65 kDa, 60 kDa, 55 kDa, 50 kDa, 45 kDa, 40 kDa, 35 kDa, 30 kDa, 25 kDa, 20 kDa, 15 kDa, 10 kDa, 5 kDa, or less.

The concentration of A2M and other proteins with a molecular weight higher than 100 kDa can be present at a concentration of at least about 1.5 times higher than their concentration in a biological sample after retention by one or more filters using the methods or systems described herein and the concentration of proteins with molecular weight less than about 100 kDa can be less than about 10% of the concentrations of those proteins in a biological sample when not retained by the one or more filters using the methods or systems described herein. For example, the concentration of A2M and other proteins with a molecular weight higher than 100 kDa can be present at a concentration of at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein, and the concentration of proteins with molecular weight less than about 100 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when not retained by the one or more filters using the methods or systems described herein. For example, the concentration of A2M and other proteins with a molecular weight higher than 100 kDa can be present at a concentration of at least about 1.5 times higher than their concentration in a biological sample after retention by one or more filters using the methods or systems described herein, and the concentration of proteins with molecular weight less than about 100 kDa can be less than about 10% less than their concentration in a biological sample when not retained by the one or more filters.

In some embodiments, an autologous composition can comprise an elevated concentration of A2M compared to the concentration of A2M found in a biological sample and an elevated concentration of one or more proteins with molecular weight higher than 500 kDa found in a biological sample. The concentration of A2M in an autologous composition can be at least about 1.5 times higher than the concentration of A2M found in a biological sample and the concentration of one or more proteins with molecular weight higher than 500 kDa can be at least about 1.5 times higher than the concentration of the one or more proteins with molecular weight higher than 500 kDa found in a biological sample. For example, the concentration of the concentration of A2M can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 500 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 500 kDa found in a biological sample. For example, the concentration of A2M can be at least about 2 times higher than the concentration of A2M found in a biological sample and the concentration of one or more proteins with molecular weight higher than 500 kDa can be at least about 2 times higher than the concentration of the one or more proteins with molecular weight higher than about 500 kDa found in a biological sample. Proteins with a molecular weight higher than about 500 kDa can be, for example, proteins with a molecular weight higher than about 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, 2000 kDa, or higher.

The concentration of A2M and other proteins with a molecular weight higher than 500 kDa can be present at a concentration of at least about 1.5 times higher than their concentration in a biological sample after retention by one or more filters using the methods or systems described herein. For example, the concentration of A2M and other proteins with a molecular weight higher than 500 kDa can be present at a concentration of at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein. For example, the concentration of A2M and other proteins with a molecular weight higher than 500 kDa can be present at a concentration of at least about 1.5 times higher than their concentration in a biological sample after retention by one or more filters using the methods or systems described herein.

In some embodiments, the concentration of proteins with molecular weight less than about 500 kDa can be less than about 10% of the concentrations of those proteins in a biological sample when not retained by the one or more filters. For example, the concentration of proteins with molecular weight less than about 500 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when not retained by the one or more filters. For example, the concentration of proteins with molecular weight less than about 500 kDa can be less than about 20% less than their concentration in a biological sample when not retained by the one or more filters. Proteins with a molecular weight less than about 500 kDa can be, for example, proteins with a molecular weight less than about 450 kDa, 400 kDa, 350 kDa, 300 kDa, 250 kDa, 200 kDa, 150 kDa, 100 kDa, 50 kDa, 45 kDa, 40 kDa, 35 kDa, 30 kDa, 25 kDa, 20 kDa, 15 kDa, 10 kDa, 5 kDa, or less.

The concentration of A2M and other proteins with a molecular weight higher than 500 kDa can be present at a concentration of at least about 1.5 times higher than their concentration in a biological sample after retention by one or more filters using the methods or systems described herein and the concentration of proteins with molecular weight less than about 500 kDa can be less than about 10% of the concentrations of those proteins in a biological sample when not retained by the one or more filters. For example, the concentration of A2M and other proteins with a molecular weight higher than 500 kDa can be present at a concentration of at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein, and the concentration of proteins with molecular weight less than about 500 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when not retained by the one or more filters. For example, the concentration of A2M and other proteins with a molecular weight higher than 500 kDa can be present at a concentration of at least about 1.5 times higher than their concentration in a biological sample after retention by one or more filters using the methods or systems described herein, and the concentration of proteins with molecular weight less than about 500 kDa can be less than about 10% less than their concentration in a biological sample when not retained by the one or more filters.

The concentration of A2M found in a biological sample, such as a blood sample from a normal subject, can be between about 0.1 mg/mL to about 6 mg/mL. For example, the concentration of A2M found in a blood sample from a normal subject or a normal biological sample can be between about 0.1 mg/mL to 5.5 mg/mL, 0.1 mg/mL to 5 mg/mL, 0.1 mg/mL to 4.5 mg/mL, 0.1 mg/mL to 4 mg/mL, 0.1 mg/mL to 3.5 mg/mL, 0.1 mg/mL to 3 mg/mL, 0.1 mg/mL to 2.5 mg/mL, 0.1 mg/mL to 2 mg/mL, 0.1 mg/mL to 1.5 mg/mL, 0.1 mg/mL to 1 mg/mL, 0.1 mg/mL to 0.75 mg/mL, 0.1 mg/mL to 0.5 mg/mL, 0.1 mg/mL to 0.25 mg/mL, 1 mg/mL to 6 mg/mL, 1 mg/mL to 5.5 mg/mL, 1 mg/mL to 5 mg/mL, 1 mg/mL to 4.5 mg/mL, 1 mg/mL to 4 mg/mL, 1 mg/mL to 3.5 mg/mL, 1 mg/mL to 3 mg/mL, 1 mg/mL to 2.5 mg/mL, 1 mg/mL to 2 mg/mL, 1 mg/mL to 1.5 mg/mL, 2 mg/mL to 6 mg/mL, 2 mg/mL to 5.5 mg/mL, 2 mg/mL to 5 mg/mL, 2 mg/mL to 4.5 mg/mL, 2 mg/mL to 4 mg/mL, 2 mg/mL to 3.5 mg/mL, 2 mg/mL to 3 mg/mL, 2 mg/mL to 2.5 mg/mL, 3 mg/mL to 6 mg/mL, 3 mg/mL to 5.5 mg/mL, 3 mg/mL to 5 mg/mL, 3 mg/mL to 4.5 mg/mL, 3 mg/mL to 4 mg/mL, 3 mg/mL to 3.5 mg/mL, 4 mg/mL to 6 mg/mL, 4 mg/mL to 5.5 mg/mL, 4 mg/mL to 5 mg/mL, 4 mg/mL to 4.5 mg/mL, 5 mg/mL to 6 mg/mL, or 5 mg/mL to 5.5 mg/mL.

In some embodiments, an autologous composition with an elevated concentration of A2M can be characterized by a reduction in the concentration of or a change in the ratios of cytokines, chemokines, other immunomodulatory mediators, for example, cytokines, chemokines, other immunomodulatory mediators with a molecular weight less than about 100 kDa. In some embodiments, an autologous composition with an elevated concentration of A2M can be characterized by a reduction in the concentration of or a change in the ratios of cytokines, chemokines, other immunomodulatory mediators, for example, cytokines, chemokines, other immunomodulatory mediators with a molecular weight less than about 500 kDa. Other immunomodulatory mediators can include peptides, proteins, DNA, RNA, carbohydrates, other small molecules, proteases, and other degradative proteins.

Cytokines, chemokines and other molecules can be involved in inflammation. Cytokines can be small cell-signaling protein molecules that are secreted by one or more cells and are a category of signaling molecules that can be used in intercellular communication. Cytokines can be classified as proteins, peptides, or glycoproteins, chemokines, interleukins, tumor necrosis factors (TNFs), monocyte chemoattractant proteins (MCPs), IL-1-like cytokines, gamma chain cytokines, beta chain cytokines, IL-6-like cytokines, IL-10-like cytokines, interferons, tumor necrosis factors, TGF-beta, macrophage inflammatory proteins (MIPs), tumor growth factors (TGFs), and matrix metalloproteases (MMPs). For example, cytokines can be interleukins, such as IL-1-like, IL-1α (hematopoietin-1), IL-1β (catabolin), IL-1RA (IL-1 receptor antagonist), IL-18 (interferon-γ inducing factor), Common g chain (CD132), IL-2 (T cell growth factor), IL-4 (BSF-1), IL-7, IL-9 (T cell growth factor P40), IL-13 (P600), IL-15, Common b chain (CD131), IL-3 (multipotential CSF, MCGF), IL-5 (BCDF-1), GM-CSF (CSF-2), IL-6-like, IL-6 (IFN-(β2, BSF-2), IL-11 (AGIF), G-CSF (CSF-3), IL-12 (NK cell stimulatory factor), LIF (leukemia inhibitory factor), OSM (oncostatin M), IL-10-like, IL-10 (CSIF), IL-20, IL-14 (HMW-BCGF), IL-16 (LCF), and IL-17 (CTLA-8); interferons, such as IFN-α, IFN-β, and IFN-γ, tumor necrosis factors (TNFs), such as CD154 (CD40L, TRAP), LT-β, TNF-α (cachectin), TNF-β (LT-α), 4-1BBL, APRIL (TALL-2), CD70 (CD27L), CD153 (CD30L), CD178 (FasL), GITRL, LIGHT, OX40L, TALL-1, TRAIL (Apo2L), TWEAK (Apo3L), and TRANCE (OPGL); tumor growth factors, such as TGF-β1, (TGF-β), TGF-β2, and TGF-β3; and hematopoietins, such as Epo (erythropoietin), Tpo (MGDF), Flt-3L, SCF (stem cell factor, c-kit ligand), M-CSF (CSF-1), and MSP (Macrophage stimulating factor). Other cytokines can include MST-1, CD40LG (TNFSF5), IFNA2, IL10, IL13, IL17C, IL1A, IL1B, IL1F10, IL36RN, IL36A, IL37, IL36B, IL36G, IL22, IL5, IL8, IL9, LTA, LTB, MIF, AIMP1, SPP1, and TNF. Exemplary, cytokine receptors can be IFNA2, IL10RA, IL10RB, IL13, IL13RA1, IL5RA, IL9, and IL9R.

Chemokines can be a family of small cytokines, or proteins secreted by cells. Some chemokines can be pro-inflammatory and can be induced during an immune response to recruit cells of an immune system to a site of infection, while others can be homeostatic and can be involved in controlling the migration of cells during normal processes of tissue maintenance or development. For example, chemokines can be XCL1 (lymphoactin a, SCM-1a, ATAC), XCL2 (lymphoactin b, SCM-1b, ATAC,) CCL1 (I-309), CCL2 (MCP-1, MCAF), CCL3 (MIP-1α, LD78α), CCL4 (MIP-1β, LAG-1, ACT-2), CCL5 (RANTES), CCL7 (MCP-3), CCL8 (MCP-2), CCL11 (eotaxin), CCL13 (MCP-4), CCL14 (HCC-1), CCL15 (HCC-2, Lkn-1, MIP-1d, MIP-5), CCL16 (HCC-4, LEC, LMC, LCC-1), CCL17 (TARC), CCL18 (DC-CK1, PARC, AMAC-a, MIP-4), CCL19 (MIP-3β, ELC, exodus-3), CCL20 (MIP-3α, LARC, exodus-1), CCL21 (6Ckine, SLC, exodus-2), CCL22 (MDC, STCP-1), CCL23 (MPIF-1, MIP-3, CKb-8), CCL24 (MPIF-2, eotaxin-2, CKb-6), CCL25 (TECK, MIP-4a), CCL26 (eo-taxin-3), CCL27 (Eskine, CTACK, ILC), CXCL1 (GROa, MGSA-a), CXCL2 (GROb, MGSA-b, MIP-2a), CXCL3 (GROg, MGSA-g, MIP-2b), CXCL4 (PF4, oncostatin A), CXCL5 (ENA-78, CXCL6 (GCP-2), CXCL7 (NAP-2, PPBP), CXCL8 (IL-8, NAP-1, NAF, MDNCF), CXCL9 (Mig), CXCL10 (IP-10), CXCL11(I-TAC), CXCL12 (SDF-1α/β), CXCL13 (BLC, BCA-1), CXCL14 (BRAK), CX3CL1 (fractaline). Chemokine receptors can be CCL13 (mcp-4), CCR1, CCR2, CCR3, CCR4, CCR5, CCR6, CCR7, CCR8, CCR9, CX3CR1, CXCR1, XCR1 (CCXCR1). Other proteins involved in inflammation can be ABCF1, BCL6, C3, C4A, CEBPB, CRP, CARD18, IL1R1, IL1RN, CXCR2, LTB4R, and TOLLIP.

Any of the autologous compositions described herein comprising A2M can further comprise one or more additional non-blood derived components. Non-blood derived components can be added before, during, or after isolation by any of the methods described herein. A non-blood derived component can be obtained from non-blood tissues. A non-blood derived component can be an anti-coagulant. For example, a non-blood derived component or an anti-coagulant can be EDTA, tri-sodium citrate, water for injection (WFI), acid-citrate-dextrose (ACD), citrate-phosphate-dextrose (CPD), citrate-phosphate-double dextrose (CP2D), citrate-phosphate-dextrose-adenine (CPDA1), or saline.

Any of the autologous compositions described herein can comprise one or more additional blood products or blood-derived components. Blood products or blood-derived components can be added before, during, or after isolation by any of the methods described herein. Blood products or blood-derived components can be cells, peptides, proteins, DNA, RNA, carbohydrates, or other small molecules. For example, blood products or blood-derived components can be red blood cells, white blood cells, platelets, packed red blood cells, platelet-rich plasma, platelet concentrates, fresh plasma, fresh frozen plasma, frozen plasma, cryoprecipitate and cryosupernant.

In some embodiments, an autologous composition can contain platelet rich plasma ("PRP"). PRP is an autologous blood product that can be used in conjunction with autograft or allograft bone. The scientific rationale for this clinical use is that PRP is a recognized material frequently used by orthopedic healthcare providers due to the ability of platelet concentrates to release growth factors to the surgical site along with bone graft. Platelets can be prepared by any means known in the art. The cellular components of PRP products generally include platelets with concentrations that vary between 2 and 10-fold over whole blood. PRP products can also comprise variable concentrations of other growth factors released upon platelet degranulation, including, but not limited to, transforming growth factor-beta (TGF-β), insulin-like growth factor-1 (IGF-1), vascular endothelial growth factor (VEGF), epidermal growth factor (EGF), fibroblast growth factor (FGF), and other factors. The growth factor content in various PRP products can vary between both patients and the method of preparation.

In some embodiments, an autologous composition can contain platelets. Typically, platelets can be prepared by separating platelets in blood from other blood components. In some embodiments, platelets can be obtained from any of the methods or systems described herein. In some embodiments, PRP can be separated from whole blood via centrifugation. Centrifugation can be used to separate plasma and platelets, which can be retained, from red and white blood cells, which can be discarded. In some embodiments, centrifugation parameters can be designed to achieve plasma containing approximately 70-100% of the platelets contained in the original blood sample, and to avoid the collection of leukocytes, such as less than 5%, for further processing. In some embodiments, concentrated platelets in blood plasma can be obtained by apheresis or pheresis (centrifugal separation during the donor process while other components are returned to the donor) or by selective removal from whole blood after gravity or centrifugal sedimentation of blood cells.

Though PRP preparations contain growth factors, other molecular mediators are also present, including cytokines, proteases and plasma proteins. Some of these mediators are potentially pro-inflammatory or catabolic, and are thought to be derived from leukocytes. Though all PRP preparations contain concentrated platelets, leukocytes and other blood derived cells may also be present and contribute to the molecular profile of the PRP products. It is an object of the current invention to concentrate platelets and, in some embodiments, allow for the retention of platelet-released growth factors, while, in some embodiments, using a molecular weight cutoff of a filter and a tangential flow ultrafiltration (TFF) step to avoid the concentration of potentially proinflammatory cytokines and catabolic proteases. After obtaining PRP, tangential flow ultrafiltration (TFF) can be used to concentrate platelets to a desired concentration range using the methods described herein, resulting in an autologous platelet integrated concentrate in which low molecular weight proteins, such as cytokines and proteases, such as those less than about 500 kDa in mass, have not been concentrated. In some embodiments, filter parameters can be chosen to concentrate platelets but to avoid concentration of cytokines, proteases, and potentially undesirable plasma proteins.

Methods of A2M Enrichment and Preparation of Autologous Compositions

Methods of enrichment of A2M from a subject are also provided herein. The methods can be used to produce any of the autologous compositions described herein.

A method for enrichment of A2M from a biological sample, such as a mammalian biological sample, can comprise flowing or passing a biological sample through one or more filters. Flowing or passing a sample through one or more filters can comprise flowing the sample through 1, 2, 3, 4, 5, 6, 7, 8, 9, 10, or more filters. A sample can be separated into one or more filtrates and one or more retentates, for example a first filtrate and a first retentate. For example, a sample can be separated into 2, 3, 4, 5, 6, 7, 8, 9, 10, or more filtrates and 2, 3, 4, 5, 6, 7, 8, 9, 10, or more retentates upon flowing or passing the sample through one or more filters. For example, a sample can be separated into 2 or more filtrates and 2 or more retentates upon flowing or passing the sample through two or more filters. An A2M enriched sample can be a first, second, third, fourth, fifth, or more retentate upon flowing or passing a biological sample through one or more filters. One or more A2M enriched samples or retentates can be diluted, such as with a diluent. A diluent can be a liquid or a solution, such as a hypotonic, hypertonic, or isotonic solution. For example, a diluent can be a WFI solution or a saline solution.

A method for enrichment of A2M from a biological sample, such as a mammalian biological sample can comprise separating cells from a cellular biological sample, such as blood. In some embodiments, red blood cells can be separated from white blood cells and platelets by performing one or more centrifugation steps. White blood cells can be separated from platelets by performing one or more centrifugation steps. A supernatant of a centrifuged blood sample can contain A2M. In some embodiments, the supernatant can contain A2M and platelets. In some embodiments, the supernatant can contain A2M and not contain platelets.

In some embodiments, it is preferable to separate red blood cells and white blood cells from the biological sample and platelets within the biological sample prior to flowing the sample through one or more filters by performing one or more centrifugation steps. In some embodiments, it is preferable to separate red blood cells, white blood cells, and platelets from the biological sample prior to flowing or passing the sample through the one or more filter by performing one or more centrifugation steps.

In some embodiments, it is preferable to separate red blood cells and white blood cells from the biological sample and platelets within the biological sample by flowing or passing the biological sample through one or more filters. In some embodiments, it is preferable to separate red blood cells, white blood cells, and platelets from the biological sample by flowing or passing the biological sample through one or more filters. The one or more filters used to remove the cells and other large particles from the biological sample can have a pore size of at least about 0.1 µm. For example, the one or more filters used to remove the cells and other large particles from the biological sample can have a pore size of at least about 0.2 µm, 0.3 µm, 0.4 µm, 0.5 µm, 0.6 µm, 0.7 µm, 0.7 µm, 0.8 µm, 0.9 µm, 1µm, 1.1 µm, 1.2 µm, 1.3 µm, 1.4 µm, 1.5 µm, 1.6 µm, 1.7 µm, 1.8 µm, 1.9 µm, 2 µm, 2.1 µm, 2.2 µm, 2.3 µm, 2.4 µm, 2.5 µm, 2.6 µm, 2.7 µm, 2.8 µm, 2.9 µm, or 3 µm, or higher. As a non-limiting example, a biological sample, such as blood, can be flowed through one or more filters with a pore size of at least about 0.2 µm wherein the red blood cells and white blood cells are retained by the filter and are in the retentate and non-cellular components and platelets are not retained by the filter and are in the filtrate. As another non-limiting example, a biological sample, such as blood, can be flowed through one or more filters with a pore size of at least about 0.2 µm wherein the red blood cells, white blood cells, and platelets are retained by the filter in the retentate and non-cellular components are not retained by the filter and are in the filtrate.

In some embodiments, one or more of the filters can have a charge, immobilized molecules, or a combination thereof and can thereby enhance the selectivity of the filters. Immobilized molecules can be antibodies, proteins, receptors, ligands, carbohydrates, nucleotides, RNA, DNA or any combination thereof. For example, enhancing the selectivity of filters can enhance the ability of a filter to retain A2M in the retentate upon flowing or passing a biological sample through the filter or, as another example, enhance the ability of a filter to not retain molecules that are not A2M upon flowing a biological sample through the filter.

Additionally, one or more filters with a molecular weight cut-off can be used and can allow a percentage of particles in the biological sample, such as cells and proteins, with a molecular weight higher than the molecular weight cut-off of the filter to be retained by the filter. The retained sample can be a retentate and the sample that flows through the filter can be a filtrate. A filter with a molecular weight cut-off can allow less than about 10%, 15%, 20%, 25%, 30%, 35%, 40%, 45%, or 50% of particles in a filtrate, such as cells and proteins, with a molecular weight higher than the molecular weight cut-off of the filter to be retained by the filter. For example, one or more filters can remove 100% of cells, cellular debris, or a combination thereof, from a blood sample and can remove or reduce the ratio of proteins with a molecular weight less than 500 kDa from a biological sample containing A2M relative to A2M concentration.

One or more filtrates obtained from the methods described herein can be passed through one or more other filters by applying a gravitational, centrifugal, or mechanical force to the one or more filtrates. A sample can be separated into one or more other filtrates and one or more other retentates, for example a second filtrate and a second retentate. For example, a sample can be separated into 2, 3, 4, 5, 6, 7, 8, 9, 10, or more other filtrates and 2, 3, 4, 5, 6, 7, 8, 9, 10, or more other retentates upon flowing the sample through one or more other filters. For example, a sample can be separated into 2 other filtrates and 2 other retentates upon flowing or passing the sample through one or more other filters. An A2M enriched sample can be a first, second, third, fourth, fifth, or more other retentate upon flowing a biological sample through one or more other filters. One or more other retentates, filtrates, or A2M enriched samples can be diluted, such as with a diluent. For example, a diluent can be a liquid, such as a WFI solution or a saline solution.

In some embodiments, after separating the cells from a biological sample according to the methods described herein, the resulting biological sample, lacking red blood cells, white blood cells and platelets, can be flowed or passed through one or more filters to obtain one or more filtrates and retentates, such as an A2M enriched retentate or A2M concentrated retentate. The resulting biological sample lacking red blood cells, white blood cells and platelets can be flowed through one or more filters with a molecular weight cut-off of at most about 500 kDa to obtain one or more filtrates and retentates, such as an A2M enriched or concentrated retentate. For example, the resulting biological sample lacking red blood cells, white blood cells and platelets can be flowed through one or more filters with a molecular weight cut-off of at most about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa or lower to obtain one or more filtrates and retentates, such as an A2M enriched retentate or A2M concentrated retentate.

A retentate, such as an A2M enriched or concentrated retentate obtained by flowing or passing a biological sample lacking red blood cells, white blood cells and platelets through one or more filters with a molecular weight cut-off of at most about 500 kDa, can comprise an elevated concentration of A2M compared to the concentration of A2M found in a biological sample and an elevated concentration of one or more proteins with molecular weight higher than 500 kDa found in a biological sample. The concentration of A2M in a retentate obtained by flowing a biological sample lacking red blood cells, white blood cells and platelets through one or more filters with a molecular weight cut-off of at most about 500 kDa can be at least about 1.5 times higher than the concentration of A2M found in a biological sample and the concentration of one or more proteins with molecular weight higher than 500 kDa can be at least about 1.5 times higher than the concentration of the one or more proteins with molecular weight higher than 500 kDa found in a biological sample. For example, the concentration of A2M in a retentate obtained by flowing a biological sample lacking red blood cells, white blood cells and platelets through one or more filters with a molecular weight cut-off of at most about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, 500 kDa, or lower, can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 500 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 500 kDa found in a biological sample. For example, the concentration of A2M in a retentate obtained by flowing a biological sample lacking red blood cells, white blood cells and platelets through one or more filters with a molecular weight cut-off of at most about 500 kDa can be at least about 2 times higher than the concentration of A2M found in a biological sample and the concentration of one or more proteins with molecular weight higher than 500 kDa can be at least about 2 times higher than the concentration of the one or more proteins with molecular weight higher than about 500 kDa found in a biological sample.

In some embodiments, after separating the cells from a biological sample according to the methods described above, the resulting biological sample lacking red blood cells and white blood cells, but not lacking platelets, can be flowed through one or more filters to obtain one or more filtrates and retentates, such as an A2M enriched or concentrated retentate. The resulting biological sample lacking red blood cells, white blood cells, but not lacking platelets, can be flowed through one or more filters with a molecular weight cut-off of at most about 500 kDa to obtain one or more filtrates and retentates, such as an A2M enriched or concentrated retentate. For example, the resulting biological sample lacking red blood cells and white blood cells, but not lacking platelets, can be flowed through one or more filters with a molecular weight cut-off of at most about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa or lower to obtain one or more filtrates and retentates, such as an A2M enriched or concentrated retentate.

A retentate, such as an A2M enriched or concentrated retentate obtained by flowing or passing a biological sample lacking red blood cells and white blood cells, but not lacking platelets, through one or more filters with a molecular weight cut-off of at most about 500 kDa, can comprise an elevated concentration of A2M compared to the concentration of A2M found in a biological sample and an elevated concentration of one or more proteins with molecular weight higher than 500 kDa found in a biological sample. The concentration of A2M in a retentate obtained by flowing a biological sample lacking red blood cells and white blood cells, but not lacking platelets, through one or more filters with a molecular weight cut-off of at most about 500 kDa can be at least about 1.5 times higher than the concentration of A2M found in a biological sample and the concentration of one or more proteins with molecular weight higher than 500 kDa can be at least about 1.5 times higher than the concentration of the one or more proteins with molecular weight higher than 500 kDa found in a biological sample. For example, the concentration of A2M in a retentate obtained by flowing a biological sample lacking red blood cells and white blood cells, but not lacking platelets, through one or more filters with a molecular weight cut-off of at most about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, 500 kDa, or lower, can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 500 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 500 kDa found in a biological sample. For example, the concentration of A2M in a retentate obtained by flowing a biological sample lacking red blood cells, white blood cells, but not lacking platelets, through one or more filters with a molecular weight cut-off of at most about 500 kDa can be at least about 2 times higher than the concentration of A2M found in a biological sample and the concentration of one or more proteins with molecular weight higher than 500 kDa can be at least about 2 times higher than the concentration of the one or more proteins with molecular weight higher than about 500 kDa found in a biological sample.

In some embodiments, after passing a sample through one or more filters according to the methods described herein, at least about 10% of particles, and proteins with a molecular weight less than 500 kDa can be removed from the sample. For example, at least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than 500 kDa can be removed from the sample. For example, at least about 20% of particles and proteins with a molecular weight less than 500 kDa can be removed from the sample. At least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and proteins with a molecular weight less than about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, or less can be removed from the sample. For example, at least about 20% of particles and small proteins with a molecular weight less than 500 kDa, can be removed from the sample. An autologous composition described herein can be isolated after passing a sample through one or more filters according to the methods described herein.

In some embodiments, after passing a biological sample through one or more filters according to the methods described herein, at least about 10% of cells, particles, and small proteins with a molecular weight less than 100 kDa can be removed from the sample For example, at least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than 100 kDa can be removed from the sample. For example, at least about 20% of cells, particles, and small proteins with a molecular weight less than 100 kDa can be removed from the sample. At least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than 95 kDa, 90 kDa, 85 kDa, 80 kDa, 75 kDa, 70 kDa, 65 kDa, 60 kDa, 55 kDa, 50 kDa, 45 kDa, 40 kDa, 35 kDa, 30 kDa, 25 kDa, 20 kDa, 15 kDa, 10 kDa, 5 kDa, or less can be removed from the sample. For example, at least about 20% of cells, particles, and small proteins with a molecular weight less than 100 kDa, can be removed from the sample. An autologous composition described herein can be isolated after passing a sample through one or more filters according to the methods described herein.

One or more centrifugation cycles can be used or applied to provide centrifugal force to flow or push a biological sample through one or more filters. Gravitational, centrifugal or mechanical force can also be used or applied to provide force to flow or push a biological sample through one or more filters. Mechanical force can be a pump, centrifugal force, gas pressure, or any other force that is operable to provide enough force to flow a sample through one or more filters as described herein.

Filters can be positively charged, negatively charged, or not charged. Filters can be made of Polyesteramide (Nylon), Mixed Cellulose Ester (MEC), Polyfluortetraethylene, Polyether sulfone, Polyvinylidene Fluoride (PVDF), Phosphocellulose (PH), DEAE (DE), Polypropylene, Cellulose Acetate, Glass Fiber, or any combination thereof.

Filters can be characterized by a molecular weight cut-off. For example, a filter can be characterized as having a molecular weight cut-off of 500 kDa or less, such as about 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, or less.

A filter with a molecular weight cut-off can allow a large percentage of particles in a sample, such as cells and proteins, with a molecular weight less than the molecular weight cut-off of the filter to pass through the filter. The sample that flows through the filter can be the filtrate. For example, a filter with a molecular weight cut-off can allow more than about 5%, 10%, 15% 20%, 25%, 30%, 35%, 40%, 45%, 50%, 55%, 60%, 65%, 70%, 75%, 80%, 85%, 90%, 95%, or 100% of particles in a sample, such as cells and proteins, with a molecular weight less than the molecular weight cut-off of the filter to pass through the filter. For example, a filter with a molecular weight cut-off can allow more than about 50% of particles in a sample, such as cells and proteins, with a molecular weight less than the molecular weight cut-off of the filter to pass through the filter.

After passing one or more filtrates through one or more other filters according to the methods described herein, at least about 10% of cells, particles, and small proteins with a molecular weight less than 500 kDa can be removed from a filtrate. For example, at least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than 500 kDa can be removed from a filtrate. For example, at least about 20% of cells, particles, and small proteins with a molecular weight less than 500 kDa can be removed from a filtrate. For example, at least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than about 100 kDa, 150 kDa, 200 kDa, 250 kDa, 300 kDa, 350 kDa, 400 kDa, or 450 kDa can be removed from a filtrate. For example, at least about 20% of cells, particles, and small proteins with a molecular weight less than about 500 kDa can be removed from a filtrate. After passing a filtrate through one or more filters according to the methods described herein, a composition described herein can be isolated.

One or more additional non-blood derived components can be added to the one or more filtrates or retentates. Non-blood derived components can be added before, during, or after isolation by any of the methods described herein. A non-blood derived component can be an anti-coagulant. For example, an anti-coagulant can be EDTA, tri-sodium citrate, water for injection (WFI), or saline.

One or more additional blood products or blood-derived components can be added to the one or more filtrates or retentates. Blood products or blood-derived components can be added before, during, or after isolation by any of the methods described herein. Blood products or blood derived components can be cells, peptides, proteins, DNA, RNA, carbohydrates, or other small molecules. For example, blood products or blood-derived components can be red blood cells, white blood cells, or platelets.

Platelets can be isolated from a biological sample according to any method known in the art, such as by centrifugation of a blood sample. Red blood cells and white blood cells can be sedimented by centrifugation at relatively low centrifugal force, for example, less than 1000 g. Platelets can be isolated by centrifugation of the platelet containing plasma obtained from a first centrifugation. A platelet containing plasma can be centrifuged, for example, between about 3000 g to 5000 g, to sediment platelets. The above procedure can also be performed in one centrifugation step.

In some embodiments, one or more other filtrates or retentates, for example a second filtrate or second retentate can be collected. One or more additional non-blood derived components can be added to the one or more other filtrates or other retentates. Non-blood derived components can be added before, during, or after isolation by any of the methods described herein. A non-blood derived component can be an anti-coagulant. For example, an anti-coagulant can be EDTA, tri-sodium citrate, water for injection (WFI), or saline.

One or more additional blood products or blood-derived components can be added to the one or more other filtrates or other retentates. Blood products or blood-derived components can be added before, during, or after flowing or passing the biological sample through one or more filters according to any of the methods described herein. Blood products or blood-derived components can be cells, peptides, proteins, DNA, RNA, carbohydrates, or other small molecules. For example, blood products or blood-derived components can be red blood cells, white blood cells, or platelets.

Systems for Production of Autologous A2M Compositions

Also provided herein are systems that can be used with the methods described herein and can be used to produce any of the compositions described herein. A system for enrichment of A2M from a mammalian sample is provided. A system can have one or more filters, a centrifuge, a pump, or a combination thereof. A system can have one or more waste or permeate collection modules.

One aspect of the invention is directed at a system for concentrating A2M from a fluid sample. Typically, the fluid sample is blood derived from a patient and the system concentrates the A2M from the blood into a concentrated A2M blood serum or concentrated A2M blood plasma. An exemplary embodiment of the system comprises a filtration module comprising an inlet and an outlet and one or more filters. A flow of the fluid sample flows into the filtration module and through at least the inlet and one or more filters of the filtration module. The flow may also pass through the outlet of the module after passing through the inlet and one or more filters. The one or more filters are typically connected in series between the inlet and the outlet of the filter module. The inlet and outlet may have selectively closed valves to control flow of the fluid sample therein and the module may comprise multiple inlets or multiple outlets or any combination thereof. The filtration module may be a dead-end filtration module. Alternatively, the filtration module may be a tangential flow filtration module.

In some embodiments the one or more filters of the filtration module comprise at least a first and a second filter. The first filter screens out cells, particles, and other molecules larger than 1 micron. The second filter screens out molecules having a weight less than about 500 kDa. The second filter may also retain molecules having a weight of more than about 500 kDa. In some embodiments the first and the second filters comprise cross-flow filters.

Some embodiments of the invention further comprise a pump adapted to be fluidly coupled with the filtration module either upstream of the inlet of the filtration module or downstream of the outlet of the filtration module. The pump is further adapted to produce a flow of the fluid sample that passes through the one or more filters of the filter module. In some embodiments of the invention, the filter module further comprises at least one reservoir.

In an exemplary embodiment of the invention wherein the first filter comprises a cross-flow filter that screens out cells particles and other molecules lager than 1 micron. A retentate of this filter containing the cells, particles, and other molecules larger than 1 micron of the fluid sample is stored in a first retentate reservoir. Alternatively, the retentate of the first filter is discarded. A permeate of the first filter is directed to a first permeate reservoir, the first permeate reservoir is then typically connected to the second filter. The permeate of the first filter flows through the second filter. The second filter may typically be a cross flow filter adapted to retain molecules of weight more than about 500 kDa. A retentate of the second filter comprises these molecules of weight more than about 500 kDa may be retained in the first permeate collection reservoir. The retentate of the second filter typically comprises the concentrated A2M of the fluid sample. A permeate of the second filter may directed to a separate second filter permeate reservoir. Alternatively, the permeate of the second reservoir may be redirected through the outlet of the filtration module and circulated back to the inlet of the filtration module such that the fluid sample is processed by the filtration module multiple times or continuously.

In other exemplary embodiments of the invention the system for concentrating A2M further comprises a centrifuge. The fluid sample is centrifuged to produce a supernatant and a pellet, the supernatant containing small molecules and A2M but not large particles such as cells. The pellet contains the large particles such as cells present in the fluid sample. The supernatant is then directed through the filtration module. The filtration module comprising at least one filter adapted to retain molecules of weight more than about 500 kDa. The at least one filter typically comprises a 500 kDa cross flow filter as describe above. The retentate of the 500 kDa cross flow filter typically comprising the A2M of the supernatant is retained in a retentate reservoir. The permeate of the at least one filter may be directed to a waste reservoir or discarded. Alternatively, the permeate of the at least one filter may be directed to the filter module outlet where it is redirected to the filter module inlet such that the supernatant of the fluid sample passes through the filter module multiple times.

Another aspect of the invention comprises a method of concentrating A2M from a fluid sample comprising providing a filtration module. The filtration module comprises an inlet, an outlet and one or more filters fluidly connected in series between the inlet and the outlet. The method further comprises removing cells from the fluid sample. The method also further comprises pumping the fluid sample through the filtration module inlet and the one or more filters to produce a concentrated A2M serum or plasma. The fluid sample may also be pumped through the outlet. Pumping the fluid sample is accomplished with a pump fluidly connected to the filtration module either upstream of the inlet or downstream of the outlet. The one or more filters of the filtration module comprises at least one 500 kDA filter configured to retain molecules of weight more than about 500 kDa.

In some embodiments of the method described above, removing cells from the fluid sample comprises providing a centrifuge, centrifuging the fluid sample, and obtaining a resultant supernatant of the fluid sample. A resultant pellet of the fluid sample comprising cells and large molecules may be retained. The resultant supernatant of the fluid sample typically comprises A2M and small molecules but not cells and large molecules. The supernatant of the fluid sample is then pumped through the filtration module to concentrate the A2M. The 500 kDa filter of the filtration module is typically a 500 kDa cross-flow filter, a retentate of the 500 kDa cross-flow filter is retained and comprises the concentrated A2M serum.

In some embodiments, removing cells from the fluid sample comprises filtering the fluid sample with a first filter of the filtration module adapted to screen out cells, particles, and molecules larger than 1 micron. Typically the first filter is a cross-flow filter and a permeate of the first filter is directed to the at least one 500 kDa filter of the filtration module. The permeate of the first filter may be stored in a first permeate reservoir. The 500 kDa filter of the filtration module is typically a 500 kDa cross-flow filter, a retentate of the 500 kDa cross-flow filter is retained in the first permeate reservoir and comprises the concentrated A2M serum. A permeate of the 500 kDa cross flow filter may be stored, discarded, or directed to the inlet of the filtration module such that it be further filtered.

It should be understood that features of the above described method and system embodiments may be combined and interchanged with one another.

Cells and particles with a size of 0.6 µm or more, and other molecules with a molecular weight of 500 kDa or less can be removed from the sample by flowing or passing a sample through one or more filters contained within the system in sequence. Removed cells and particles can be disposed of or collected in a waste module. For example, cells and particles of 0.6 µm, 0.7 µm, 0.8 µm, 0.9 µm, 1µm, 2 µm, or 3 µm or more, and other molecules with a molecular weight of 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, or less can be removed by the one or more filters and can be deposited into one or more waste modules. A sample can be flowed through one or more filters by applying centrifugal force using the centrifuge of the system, using the pump of the system, or a combination thereof. A system can further comprise a collection module. A retentate or filtrate can be collected or isolated in the collection module, for example a retentate with an A2M enriched sample can be isolated in a collection module, after passing a sample through one or more filters. A system can further comprise a sample loading module. A sample loading module can be operable to introduce the sample into the system. A sample loading module can be directly or indirectly attached to the blood stream of a subject.

The first step in the system can be either a centrifugation step or filtration step. The collected blood can be centrifuged at a particular centrifugal force that allows the precipitation of the red blood cells and white blood cells and other particles and debris, allowing plasma proteins and platelets in the supernatant. This process can also be achieved by filtration using a hollow fiber membrane that will allow the plasma proteins and platelets to go through the membrane into the filtrate and prevent the red blood cells and white blood cells and other particles and debris to remain in the retentate. In some embodiments, the supernatant from the centrifugation step or the filtrate from the filtration step can be filtered on the second filter where proteins 500 kDa or larger can be retained by the filter and smaller proteins than 500 kDa and other molecules can pass through the membrane into the filtrate. In some embodiments, the supernatant from the centrifugation step or the filtrate from the filtration step can be filtered on the second filter where proteins 100 kDa or larger can be retained by the filter and smaller proteins than 100 kDa and other molecules can pass through the membrane into the filtrate. The concentrated retentate can then be collected and injected into the patient.

In some embodiments, a collection receptacle with platelets and plasma can be connected to any of the systems described herein, such as with hematologic tubing, and passed through a filter, such as hollow fiber tangential flow filter (HFTFF), that uses a molecular weight cutoff membrane, such as a 500 kDa molecular weight cutoff membrane, of modified polyethersulfone using a pump, such as a peristaltic pump. In some embodiments, the flow-through port of the filter can be connected using hematologic tubing back to the collection bottle in a closed-loop. In some embodiments, the filtrate port of the filter can also be connected using tubing connected to waste. In some embodiments, no priming of the flow-circuit is necessary.

As a non-limiting example, a system, such as an APIC system (Autologous Platelet Integrated Concentrate system) can be run until the plasma reaches between 2-10 times the concentrations as found in whole blood, for a total remaining volume of approximately 4-6 mL. In some embodiments, this process or a similar process can be performed in approximately 10 to 30 minutes, 15 to 35 minutes, 20 to 40 minutes, or 30 to 45 minutes. The total waste volume of approximately 36 mL, containing low molecular weight proteins, including potentially pro-inflammatory cytokines and proteases, can be discarded. The resulting autologous platelet concentrate can be drawn into a syringe and provided for mixing as needed for clinical administration with autograft or allograft bone. TFF is a filtration process whereby the solution is constantly flowing over the membrane to prevent pores from becoming clogged by cells and proteins. As used in the systems and methods described herein, TFF discourages platelets and other large proteins from blocking the membrane pores and allowing the flow of small molecules and proteins. The use of hollow fiber membranes can increase the surface area that is available for filtration. The 500 kDa molecular weight cutoff of the membrane permits small molecules and proteins such as cytokines, chemokines, and proteases to pass through, eventually leading to waste, but retaining larger particles (>500 kDa) such as platelets.

Figure 24:
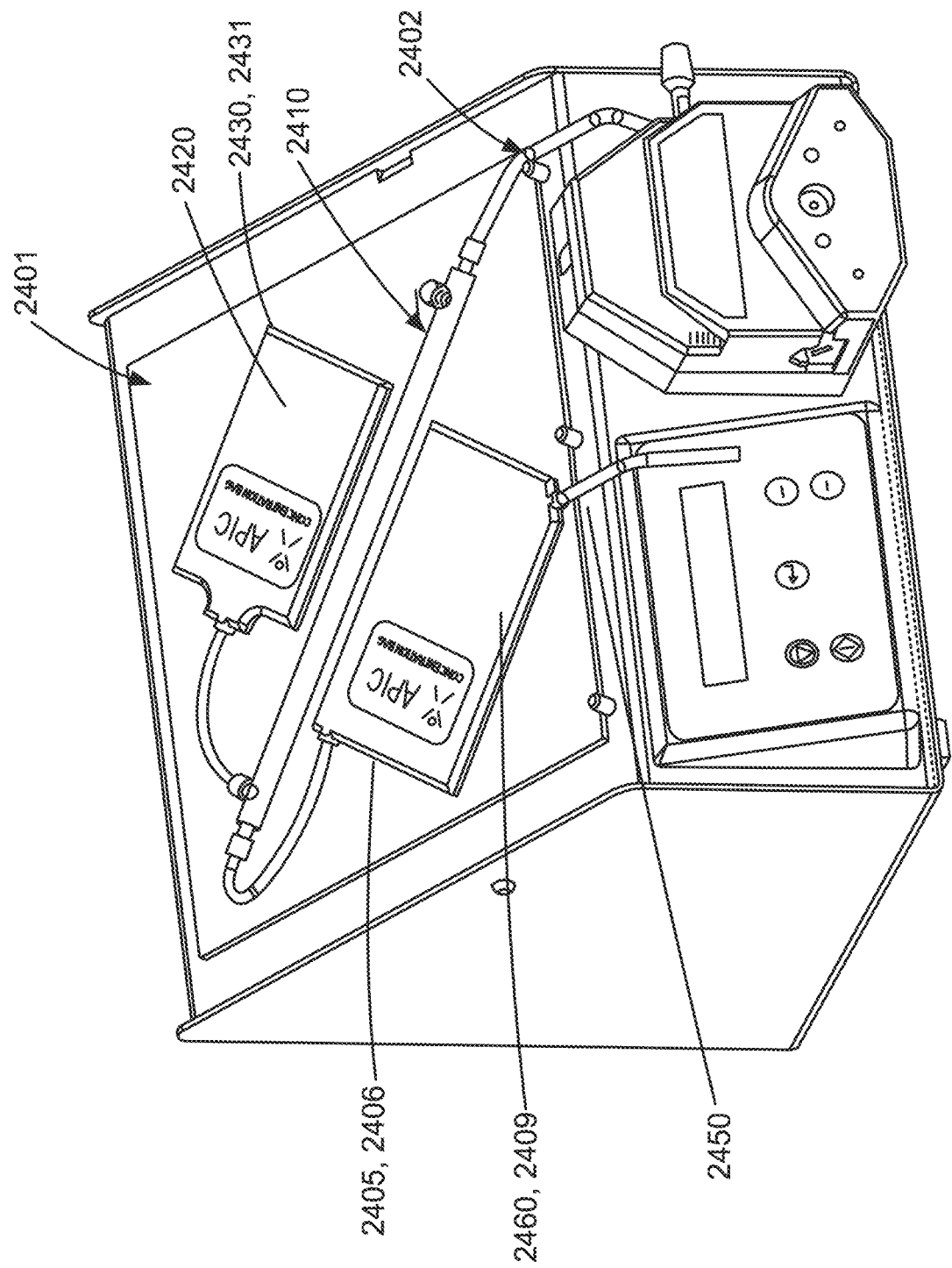
FIG. 24 depicts a schematic of a system as described herein.
Figure 25:
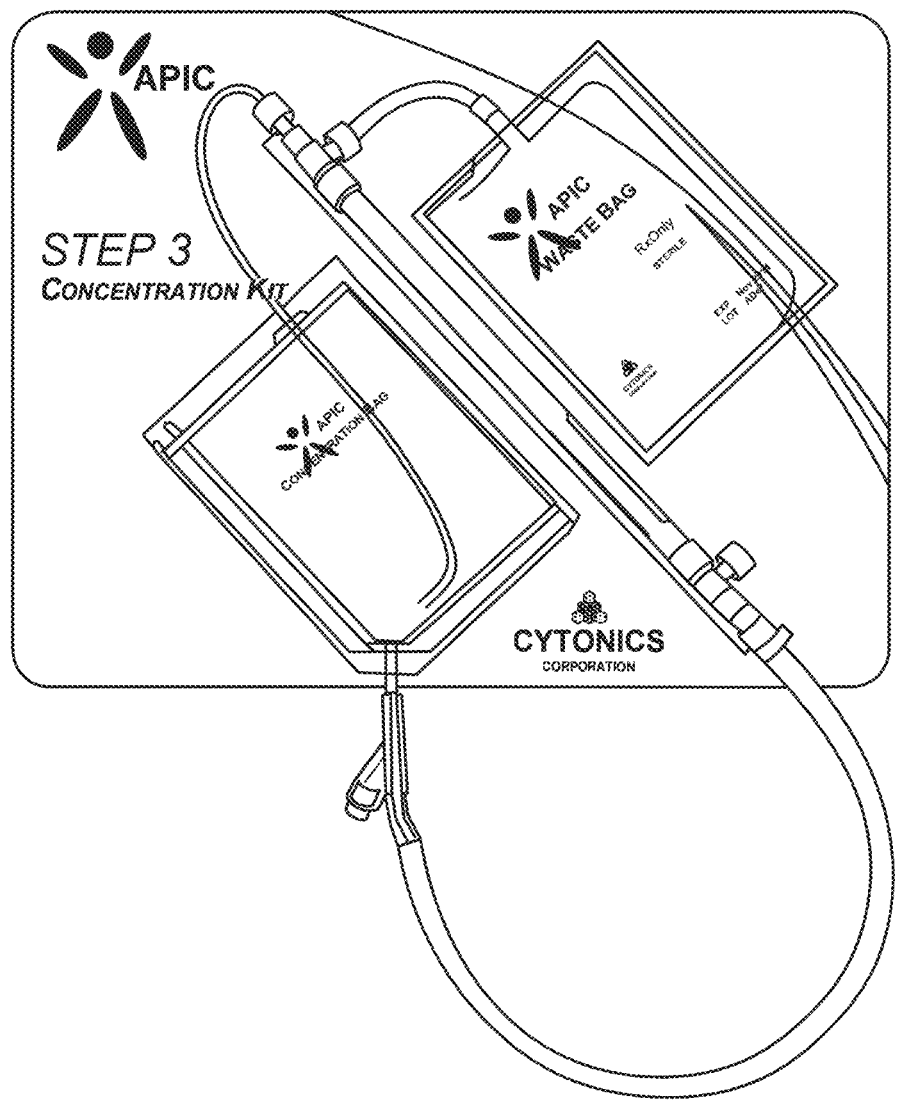
FIG. 25 a picture of the concentration kit/tray of a system described herein showing one filter, a concentration bag and the filtrate bag.
Figure 26:
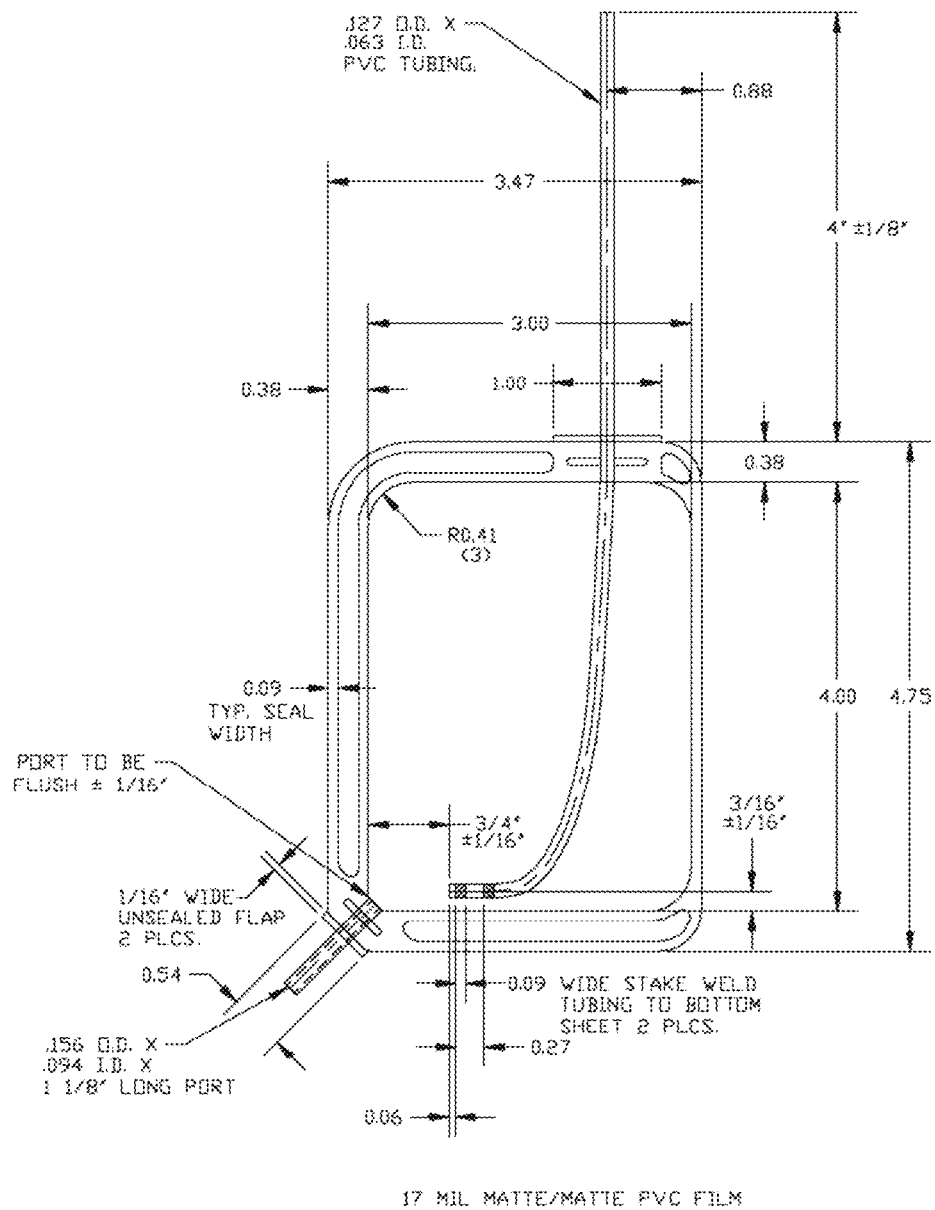
FIG. 26 depicts a schematic of the components of a concentration bag of a system described herein.
Figure 27:
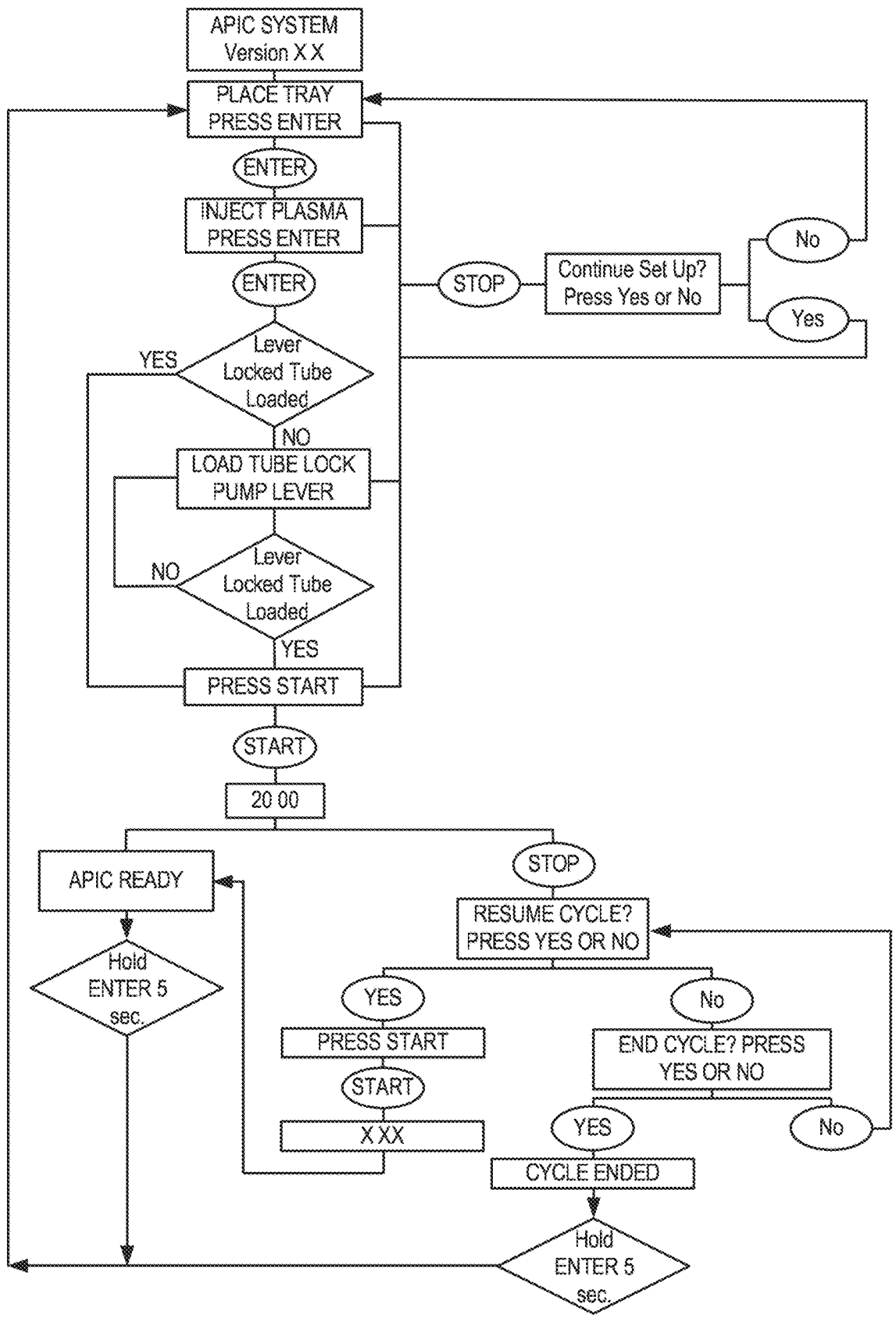
FIG. 27 depicts a schematic of a system process overview.

FIG. 24 shows an embodiment of the filtration module of the system for concentrating A2M. This particular embodiment of the filtration module is well suited to receive a supernatant 2409 of a fluid sample such as blood (not shown) that has been centrifuged. The filter module 2401 has a first filter 2410 coupled to the filter module inlet 2402. The supernatant is 2409 received and pumped from a receiving reservoir 2405 into the first filter. The first filter 2410 is typically a cross-flow filter configured to retain molecules larger than about 500 kDa in a retentate reservoir 2406. The retentate reservoir 2406 may also be the same as the receiving reservoir 2405 for receiving the supernatant 2409 of the fluid sample. The permeate 2420 of the first filter 2410 containing molecules smaller than about 500 kDa is directed to a permeate reservoir 2430 which may be a waste bag 2431. A2M is concentrated in this retentate reservoir 2406. A filter module outlet 2450 may be coupled to the retentate reservoir 2406 such that the concentrated A2M 2460 may be extracted from the retentate reservoir 2406 or pumped back through the first filter 2410.

Figure 28:
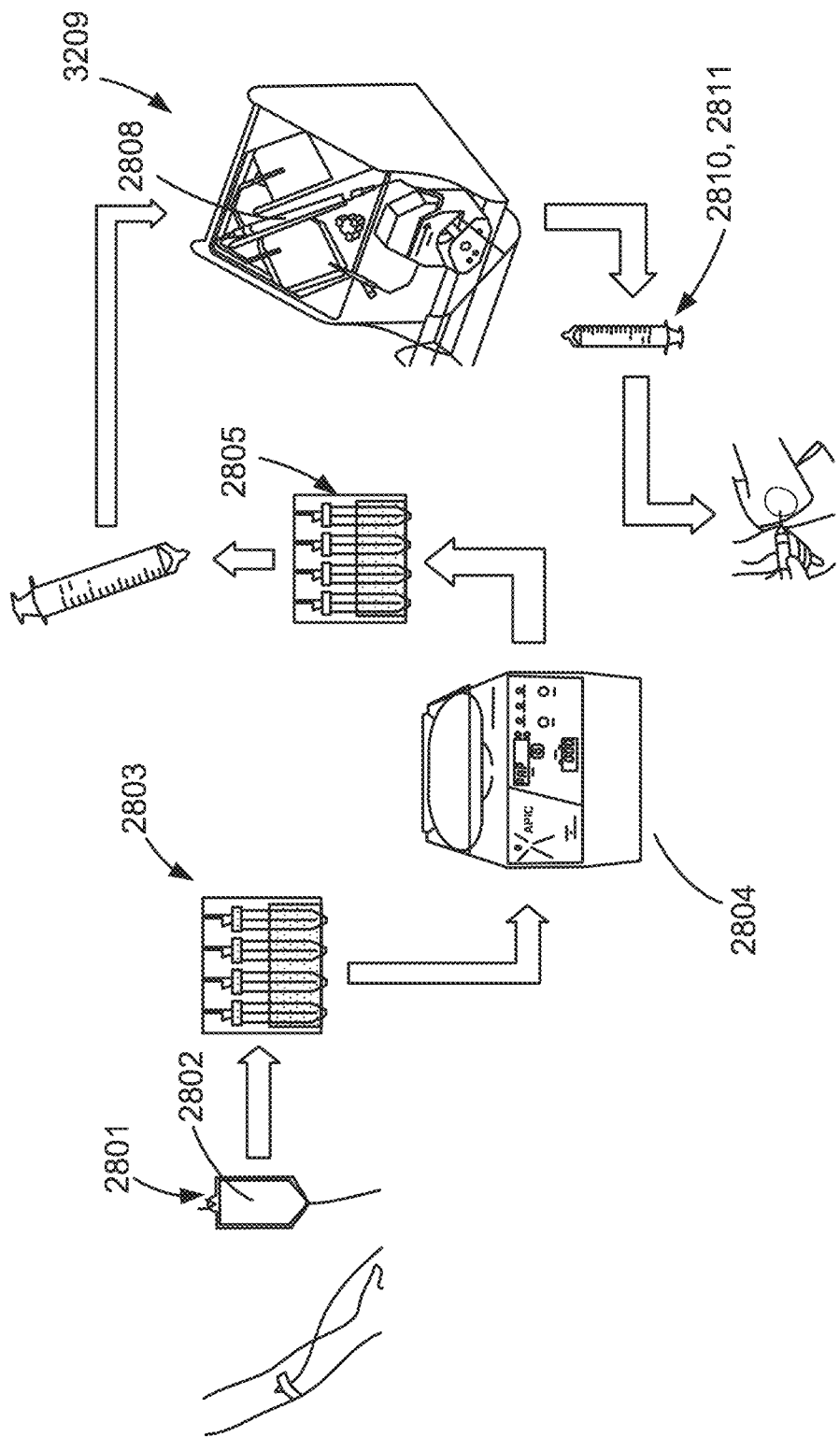
FIG. 28 depicts the components of a system described herein showing a centrifuge and a one filter system.
Figure 29:
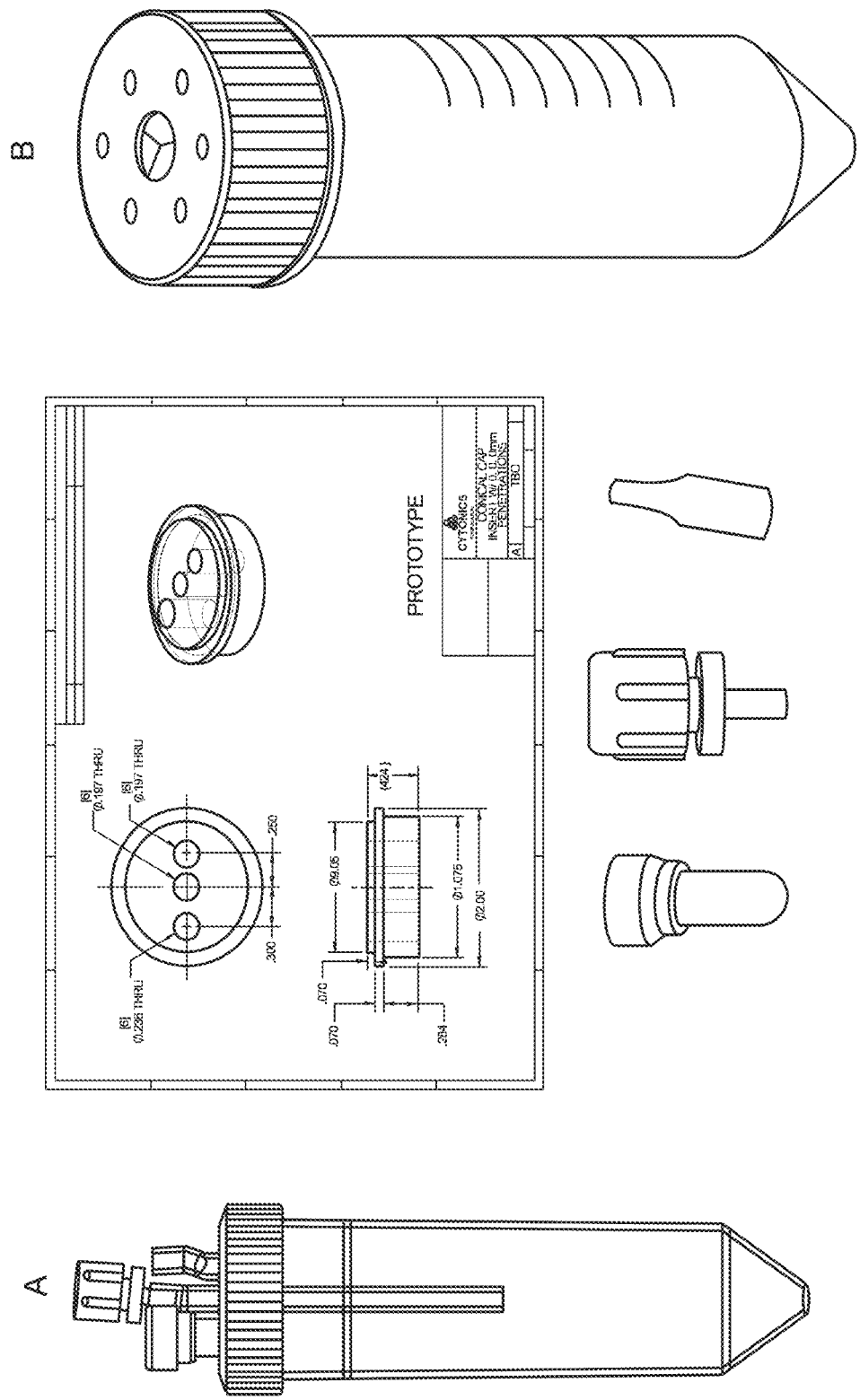
FIG. 29 depicts two different types of custom centrifuge tubes that can be used in the systems described herein.
Figure 30:
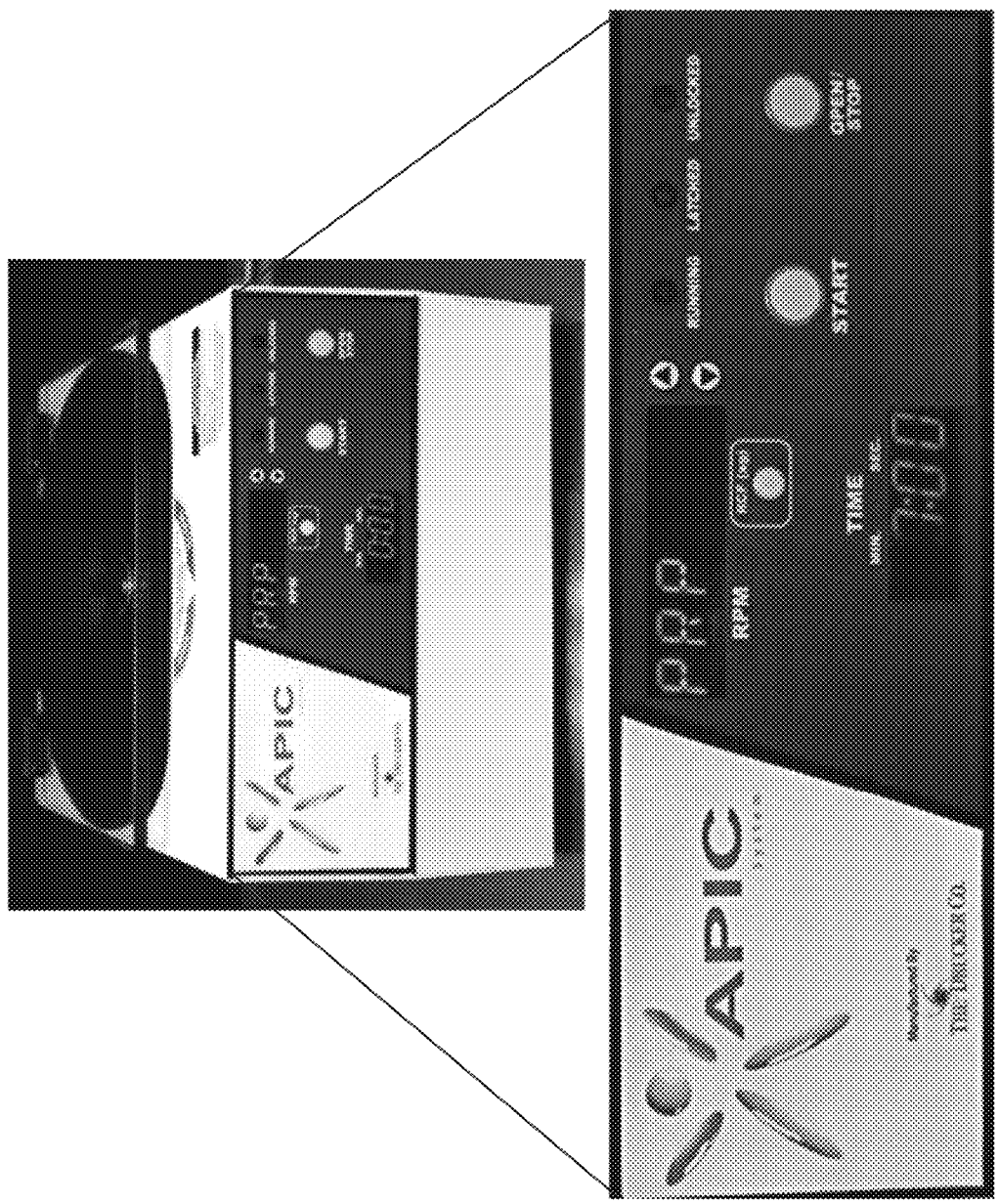
FIG. 30 depicts a custom centrifuge used in the systems described herein.
Figure 31:
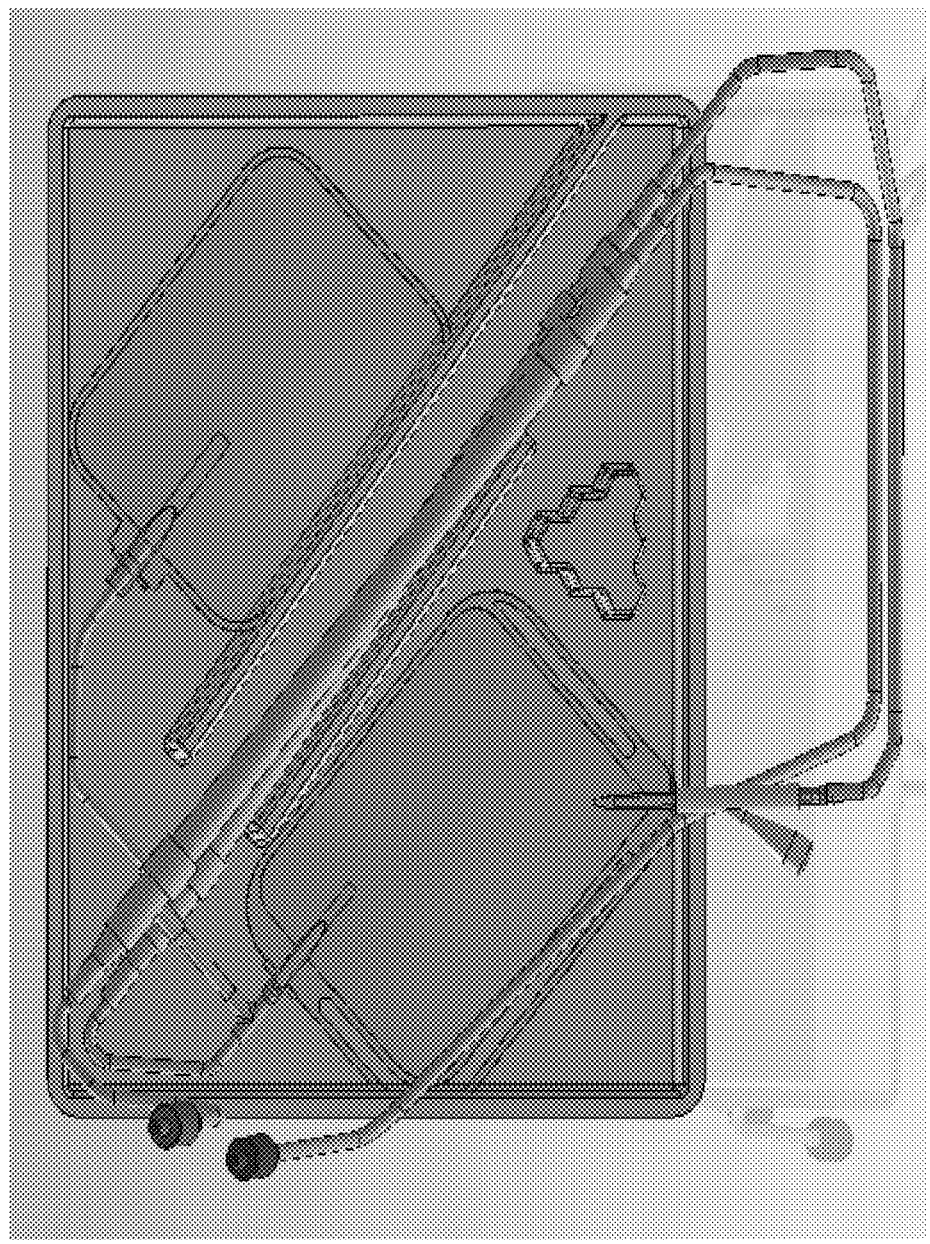
FIG. 31 depicts a schematic of the components of a concentration bag of a cell free concentration system as described herein where two filters are utilized and no centrifugation step.

FIG. 28 shows an embodiment of the system for concentrating A2M. A blood bag 2801 is shown containing the fluid sample 2802, which typically comprises blood. The fluid sample 2802 is extracted via syringe(s) 2803 and centrifuged with centrifuge 2804. The resultant supernatant 2805 containing A2M and other small molecules but not cells or large molecules is then directed to the filtration module 3209, where in the A2M is concentrated in to a serum 2810 or a plasma 2811 with at least one filter 2808 selected to retain molecules of larger in size than about 500 kDa. The filtration module 3209 may be similar to the example described in FIG. 24.

Figure 32:
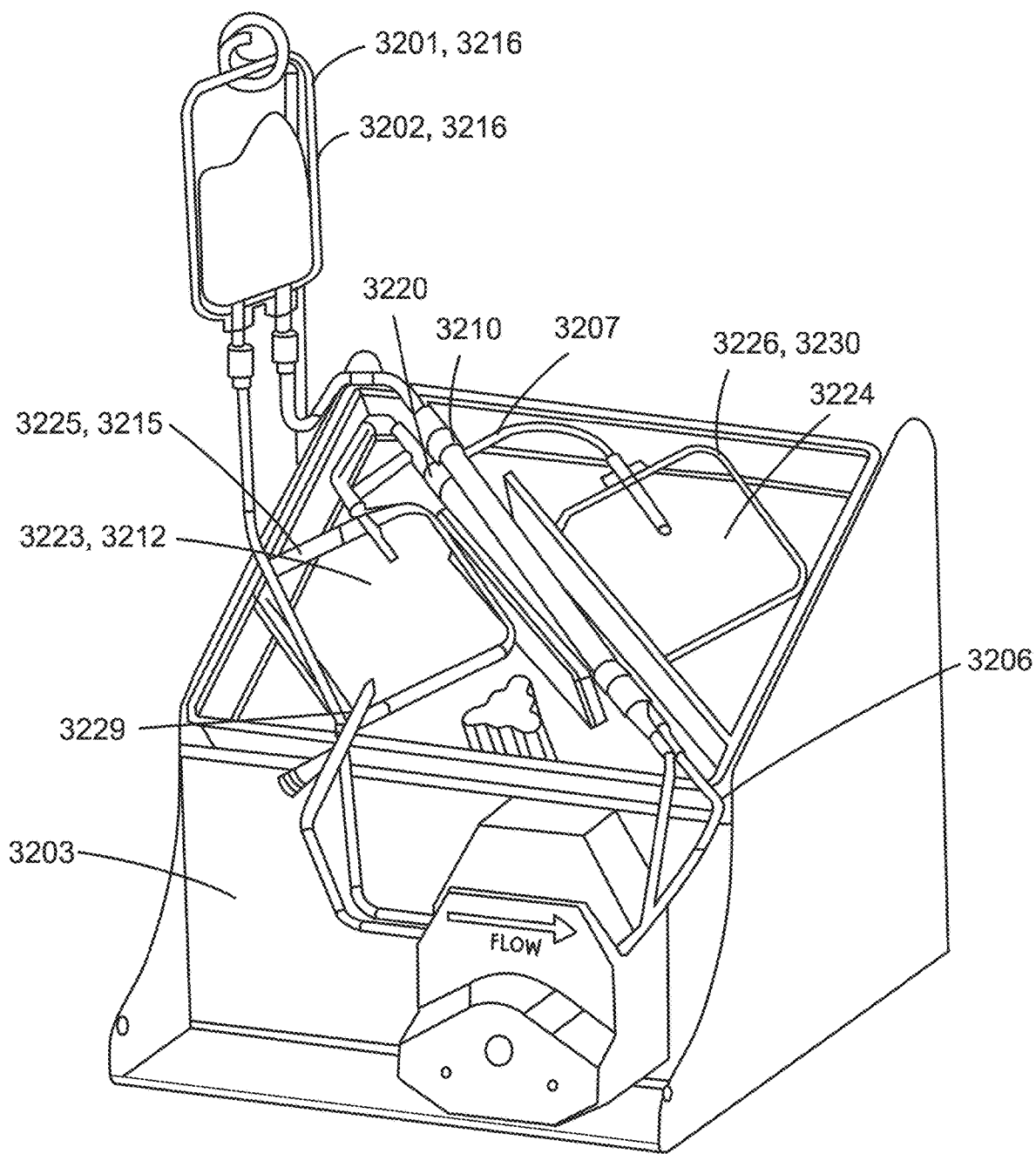
FIG. 32 depicts a schematic of a cell free concentration system as described herein with concentration component utilizing two filters.

FIG. 32 shows an embodiment of the system for concentrating A2M. A blood bag 3201 is shown containing the fluid sample 3202. The fluid sample 3202 is pumped via pump 3203 to the first filter 3210 of the filtration module 3204. The first filter 3210 shown here is a cross-flow filter configured to screen out cells, particles, and other molecules larger than 1 micron. The permeate 3212 of the first filter comprising components of the fluid sample smaller than 1 micron is directed to a first permeate reservoir 3215. The retentate 3216 of the first filter is directed to a first retentate reservoir 3216, in this particular embodiment the first retentate reservoir is also blood bag 3201. The permeate 3212 of the first filter is then directed via pump 3203 to the second filter 3220. The second filter is typically a cross-flow filter configured to retain molecules of weight more than about 500 kDa. Molecules of weight more than about 500 kDa are retained as a second retentate 3223 in a second retentate reservoir 3225. The second retentate reservoir 3225 may be the same as the first permeate reservoir 3215. Permeate of the second filter 3224 is typically directed to a second permeate reservoir 3226 in some embodiments the second permeate reservoir 3226 is a waste bag 3230. The retentate of the second filter 3223 comprises the concentrated A2M. The pump 3203 may be fluidly connected to the filtration module up stream of the filtration module inlet 3206 or downstream of the filtration module outlet 3207 or in-between inlet the filtration module 3206 and the filtration module outlet 3207 or any combination thereof. The second retentate reservoir 3225 has an access port 3229 for directing flow of the concentrated A2M (which is also the retentate of the second filter) back to the pump. Such port may be used to access the concentrated A2M, or the permeate of the first filter, or the retentate of the second filter for subsequent processing or harvesting of the concentrated A2M.

Variant A2M Polypeptides Compositions for Treatment of Pain and Inflammation

Figure 4:
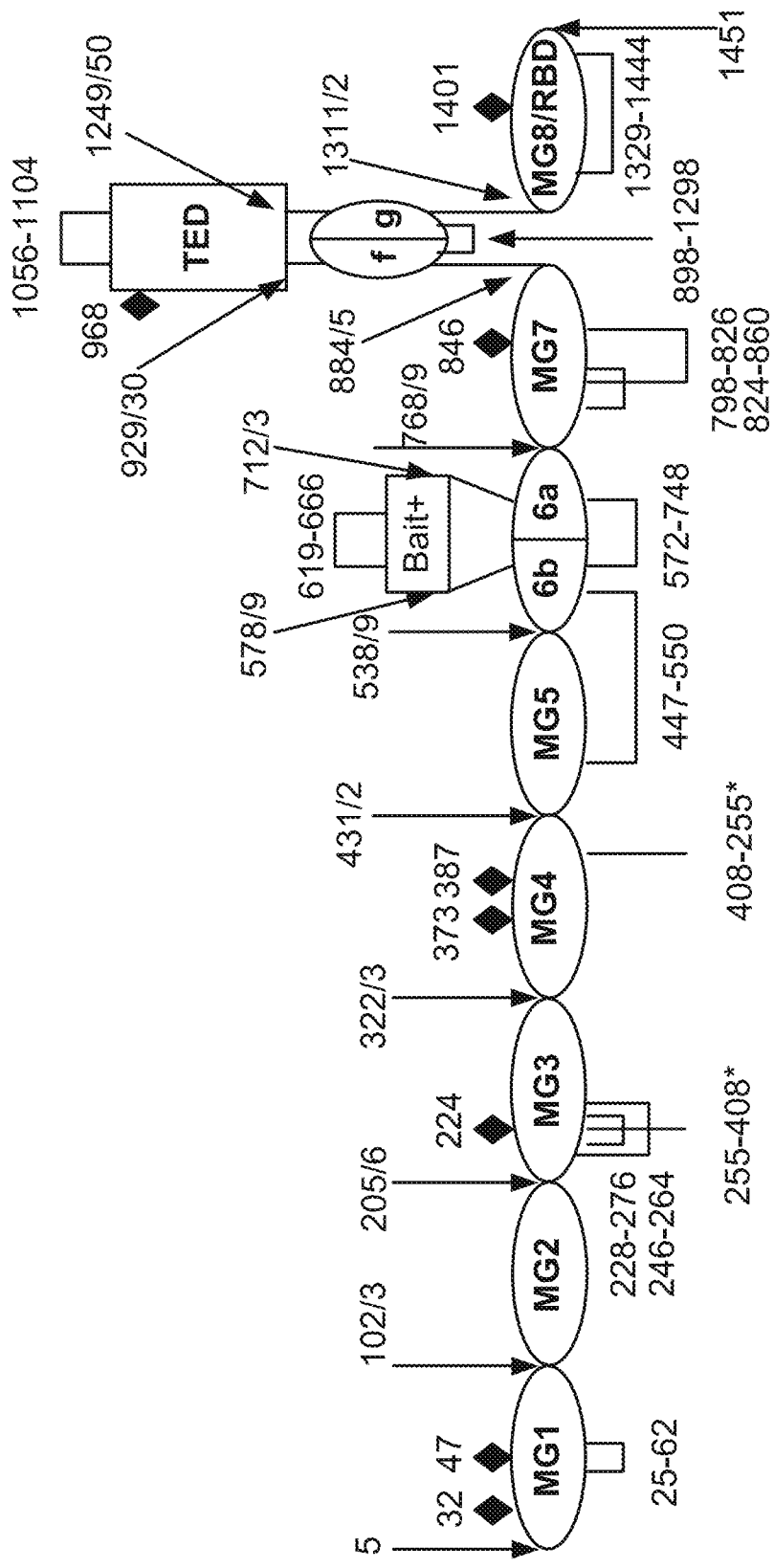
FIG. 4 depicts the A2M structure and various domains of A2M.

A2M (FIG. 4) is a general inhibitor of metalloproteases and other proteases such as ADAMTS 4 and ADAMTS 5. These proteases and others produced as a result of or prior of degeneration and inflammation can be responsible for cartilage and disc degeneration and pain in synovial joints, the spine, tendons and ligaments, and other joints, entheses and general tissues. Any of the recombinant compositions described herein can be used for treatment of a subject with a condition, disease, pain or inflammation according to any of the methods described herein.

A2M is able to inactivate an enormous variety of proteases (including serine-, cysteine-, and aspartic-metalloproteases). A2M can function as an inhibitor of fibrinolysis by inhibiting plasmin and kallikrein. A2M can function as an inhibitor of coagulation by inhibiting thrombin. Human A2M has in its structure a 38 amino acid "bait" region. The bait region varies widely in the amino acid number (27-52 amino acids) and sequence between animal species. Proteases binding and cleaving of the bait region can become bound to A2M. The protease-A2M complex can be recognized by macrophage receptors and cleared from the organism's system. A2M is able to inhibit all four classes of proteases by a unique 'trapping' mechanism. When a protease cleaves the bait region, a conformational change can be induced in the protein which can trap the protease. The entrapped enzyme can remain active against low molecular weight substrates (activity against high molecular weight substrates can be greatly reduced). Following cleavage in the bait region a thioester bond can be hydrolyzed and can mediate the covalent binding of the protein to the protease.

In one aspect, provided herein is a composition that can be a variant A2M polypeptide. A variant A2M polypeptide can be a recombinant protein, or fragments thereof, and can be produced in a host cell and purified for use in treatment of pain and inflammation conditions and diseases. A variant A2M composition can be more efficient in inhibiting proteases, have longer half-life, have a slower clearance factor, or any combination thereof compared to a wild-type A2M. A variant A2M can be a recombinant protein, or a fragment thereof, and can be produced in a host cell and purified. For example, a variant A2M recombinant protein can be produced in a host comprising bacteria, yeast, fungi, insect, or mammalian cells, or a cell free system.

Variant A2M polypeptides or fragments thereof, can also be variants or posttranslationally modified variants of A2M. A2M variant polypeptides can have an integer number of amino acid alterations such that their amino acid sequence shares at least about 60%, 70%, 80%, 85%, 90%, 95%, 97%, 98%, 99%, 99.5% or 100% identity with an amino acid sequence of a wild type A2M polypeptide. In some embodiments, A2M variant polypeptides can have an amino acid sequence sharing at least about 60%, 70%, 80%, 85%, 90%, 95%, 97%, 98%, 99%, 99.5% or 100% identity with the amino acid sequence of a wild type A2M polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The Smith Waterman algorithm can also be used to determine percent identity. Exemplary parameters for amino acid sequence comparison include the following: 1) algorithm from Needleman and Wunsch (J. Mol. Biol., 48:443-453 (1970)); 2) BLOSSUM62 comparison matrix from Hentikoff and Hentikoff (Proc. Nat. Acad. Sci. USA., 89:10915-10919 (1992)) 3) gap penalty=12; and 4) gap length penalty=4. A program useful with these parameters can be publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity–(the number of identical residues)/(alignment length in amino acid residues)*100. For this calculation, alignment length includes internal gaps but does not include terminal gaps Variant A2M polypeptides, or fragments thereof, include but are not limited to, those containing as a primary amino acid sequence all or part of the amino acid sequence encoded by SEQ ID NOs: 5-66, and fragments of these proteins, including altered sequences in which functionally equivalent amino acid residues are substituted for residues within the sequence resulting in a silent change. The variant A2M polypeptides can include all or part of the amino acid sequence encoded by SEQ ID NO: 3. The variant A2M polypeptides can be, for example, any number of between 4-20, 20-50, 50-100, 100-300, 300-600, 600-1000, 1000-1450 consecutive amino acids containing the amino acids sequences of SEQ. ID NOs. 5-66. The variant A2M polypeptide can be less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, and 1450 amino acids in length and contain, as part of the sequence: SEQ ID NOs: 5-66. Variant A2M polypeptides includes polypeptide sequences having at least 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% sequence identity or similarity to any variant A2M polypeptide containing one of SEQ ID NOs: 5-66.

The variant A2M polypeptides provided herein also include proteins characterized by amino acid sequences similar to those of purified proteins but into which modification are naturally provided or deliberately engineered. For example, modifications, in the variant A2M peptide or variant A2M DNA sequence, can be made by those skilled in the art using known techniques. Modifications of interest in the protein sequences can include the alteration, substitution, replacement, insertion or deletion of a selected amino acid residue in the coding sequence. For example, one or more of the cysteine residues can be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involves systematic substitution of single or multiple amino acids with alanine, followed by testing the resulting alanine-containing variant for biological activity. This type of analysis can be used to determine the importance of the substituted amino acid(s) in biological activity.

The bait region of A2M is a segment that is susceptible to proteolytic cleavage, and which, upon cleavage, initiates a conformational change in the A2M molecule resulting in the collapse of the structure around the protease. For the exemplary A2M sequences set forth in SEQ ID NO: 3, the bait region corresponds to amino acids 690-728. For the exemplary A2M sequences set forth in SEQ ID NO: 1 and 2, the bait region corresponds to the nucleotides encoding amino acids 690-728.

A variant A2M polypeptide can comprise a bait region of a variant A2M polypeptide. For example, a bait region of a variant A2M polypeptide can be a mutant bait region, fragment of a bait region, a bait region from another species, an isoform of a bait region, or a bait region containing multiple copies of one or more bait regions described herein, or any combination thereof. A bait region of a variant A2M polypeptide can include a plurality of protease recognition sites arranged in series and can be arranged in any order.

A bait region of a variant A2M polypeptide can have one or more protease recognition sites. For example, a bait region of a variant A2M polypeptide can have 2 or more, or 3, 4, 5, 6, 7, 8, 9, or 10 or more protease recognition sites. Protease recognition sites or substrate bait regions can be consensus sequences for serine proteases, threonine proteases, cysteine proteases, aspartate proteases, metalloproteases, glutamic acid proteases, or any combination thereof compared to a wild type A2M protein. A variant A2M polypeptide can be characterized by an enhanced specific inhibition of serine proteases, threonine proteases, cysteine proteases, aspartate proteases, metalloproteases, glutamic acid proteases, or any combination thereof. A variant A2M polypeptide can be characterized by an enhanced nonspecific inhibition of serine proteases, threonine proteases, cysteine proteases, aspartate proteases, metalloproteases, glutamic acid proteases, or any combination thereof compared to a wild type A2M protein.

A bait region of a variant A2M polypeptide can have one or more mutant base regions. For example, a bait region of a variant A2M polypeptide can have 2 or more, or 3, 4, 5, 6, 7, 8, 9, or 10 or more mutant base regions. A bait region of a variant A2M polypeptide can have one or more bait region fragments. For example, a bait region of a variant A2M polypeptide can have 2 or more, or 3, 4, 5, 6, 7, 8, 9, or 10 or more bait region fragments. A fragment of a bait region of a variant A2M polypeptide can be a fragment of any of SEQ ID NOs: 5-66.

A bait region of a variant A2M polypeptide can have one or more mutant amino acids that are different than those amino acids in a wild-type A2M polypeptide. For example, a bait region of a variant A2M polypeptide can have 2 or more, or 3, 4, 5, 6, 7, 8, 9, or 10 or more mutant amino acids that are different than those amino acids in a wild-type A2M polypeptide. A bait region of a variant A2M polypeptide can have one or more mutant amino acid regions that are different than those regions in a wild-type A2M polypeptide. For example, a bait region of a variant A2M polypeptide can have 2 or more, or 3, 4, 5, 6, 7, 8, 9, or 10 or more mutant amino acid regions that are different than those regions in a wild-type A2M polypeptide. A mutant bait region of a variant A2M polypeptide can replace or substitute a bait region in a wild-type A2M polypeptide. A mutant bait region of a variant A2M polypeptide can be any of SEQ ID NOs: 5-66.

The A2M variant polypeptides provided herein also include A2M variant proteins characterized by amino acid sequences similar to those of purified A2M variant. Isolated or purified variant A2M polypeptides can have one or more amino acid residues within the polypeptide that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

A bait region of a variant A2M polypeptide can have one or more bait region isoforms. For example, a bait region of a variant A2M polypeptide can have 2 or more, or 3, 4, 5, 6, 7, 8, 9, or 10 or more bait region isoforms. A bait region of a variant A2M polypeptide can have one or more mutant or engineered bait regions. For example, a bait region of a variant A2M polypeptide can have 2 or more, or 3, 4, 5, 6, 7, 8, 9, or 10 or more mutant or engineered bait regions.

A bait region of a variant A2M polypeptide can have one or more copies of one or more bait regions. The one or more bait regions can be the same bait regions (repeats), different bait regions, or any combination thereof. For example, a bait region of a variant A2M polypeptide can have 2 or more, or 3, 4, 5, 6, 7, 8, 9, or 10 or more copies of one or more bait regions, wherein the one or more bait regions can be the same bait regions (repeats), different bait regions, or any combination thereof.

A variant A2M polypeptide can comprise one or more bait regions derived from different organisms, different species of an organism, or a combination thereof. For example, a variant A2M polypeptide can have 2 or more, or 3, 4, 5, 6, 7, 8, 9, or 10 or more bait regions derived from different organisms, different species of an organism, or a combination thereof. One or more bait regions derived from different organisms can be derived from one or more different organisms and not from different species of an organism. For example, one or more modified bait regions can be derived from 2 or more, or 3, 4, 5, 6, 7, 8, 9, or 10 or more different organisms and not contain 2 or more bait regions derived from different species of an organism. One or more bait regions derived from different species of an organism can be derived from one or more different species of an organism and not from different organisms. For example, one or more modified bait regions can be derived from 2 or more, or 3, 4, 5, 6, 7, 8, 9, or 10 or more different species of an organism and not contain 2 or more bait regions derived from different organism. The modified bait regions can be derived from any animal, insect, plant, bacteria, viral, yeast, fish, reptile, amphibian, or fungi. The modified bait regions can be derived from any animal with A2M or homologous protein, such as pig, mouse, rat, rabbit, cat, dog, frog, monkey, horse or goat.

A variant A2M polypeptide can comprise one or more bait regions of variant A2M polypeptides. For example, a variant A2M polypeptide can have 2 or more, or 3, 4, 5, 6, 7, 8, 9, or 10 or more bait region of variant A2M polypeptides. One or more bait region of a variant A2M polypeptides can be derived from one or more different species. For example, one or more bait regions of variant A2M polypeptides can be derived from 2 or more, or 3, 4, 5, 6, 7, 8, 9, or 10 or more different species. The bait region of variant A2M polypeptides can be derived from any animal, insect, plant, bacteria, viral, yeast, fish, reptile, amphibian, or fungi species.

A variant A2M polypeptide can have a plurality of protease recognition sites that can be one or more protease substrate bait regions from one or more proteins other than A2M.

A variant A2M polypeptide can have a plurality of protease recognition sites that can be one or more protease substrate bait regions from A2M. A variant A2M polypeptide can have a plurality of protease recognition sites that can be one or more protease substrate bait regions from one or more non-natural protein sequences. The non-natural protein sequences can comprise one or more protease recognition sites in series and can function as bait for proteases. A variant A2M polypeptide can have a plurality of protease recognition sites that can be one or more protease substrate bait regions from or any of the combination of bait regions described herein. A variant A2M polypeptide can have any number of protease bait regions arranged in series. A variant A2M polypeptide can have any number of protease bait regions from any species and can be arranged in series. One or more protease substrate bait regions from one or more proteins other than A2M or from the one or more non-natural protein sequences can be a suicide inhibitor. For example, a variant A2M polypeptide can have 2, 3, 4, 5, 6, 7, 8, 9, 10, 11, 12, 13, 14, 15, or more suicide inhibitor bait regions. A suicide inhibitor can be operable to covalently attach a protease to A2M. Examples of known recognition sequences for exemplary ADAMTSs and MMPs in human aggrecan are indicated in Table 1. Dash shows location of proteolysis.

TABLE 1

| Protease | Aggrecan Cleavage Site Sequence |
| --- | --- |
| ADAMTSs | 370NITEGE-ARGS377 (SEQ ID NO: 67) |
| ADAMTSs | 1540TASELE-GRGTI1550 (SEQ ID NO: 68) |
| ADAMTSs | 1709TFKEEE-GLGSV1719 (SEQ ID NO: 69) |
| MMP-8 | 370NITEGE-ARGS377 (SEQ ID NO: 67) |
| MMPs | 336VDIPEN-FFG344 (SEQ ID NO: 70) |
| MMP-3 | 374ARGS-V378 (SEQ ID NO: 71) |
| MMP-13 | 379ILTVKP-IFEV388 (SEQ ID NO: 72) |

A variant A2M polypeptide can be characterized by at least about a 10% increase in protease inhibitory effectiveness compared to the protease inhibitory effectiveness of a wild type A2M protein. For example, a variant A2M polypeptide can be characterized by at least about a 20, 25%, 30%, 35%, 40%, 45%, 50%, 55%, 60%, 65%, 70%, 75%, 80%, 85%, 90%, 95%, or 100% increase in protease inhibitory effectiveness when compared to the protease inhibitory effectiveness of a wild type A2M protein. A variant A2M polypeptide can be characterized by an increase in protease inhibitory effectiveness compared to the protease inhibitory effectiveness of a wild type A2M protein. For example, a variant A2M polypeptide can be characterized by an 1.2, 1.2, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times increase in protease inhibitory effectiveness compared to the protease inhibitory effectiveness of a wild type A2M protein.

A variant A2M polypeptide can be characterized as having an increased ability to inhibit one or more proteases compared to a wild-type A2M polypeptide. A variant A2M polypeptide can have an ability to inhibit one or more proteases that is at least 1.5 times higher than the ability of a wild-type A2M polypeptide to inhibit the one or more proteases. For example, a variant A2M polypeptide can have an ability to inhibit one or more proteases that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to inhibit the one or more proteases. A variant A2M polypeptide can have an ability to inhibit one or more proteases that is from 1.5-100 times higher than the ability of a wild-type A2M polypeptide to inhibit the one or more proteases. For example, a variant A2M polypeptide can have an ability to inhibit one or more proteases that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to inhibit the one or more proteases.

The one or more proteases can include a matrix metalloprotease, such as MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11), Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xcol4, *xenopus* collagenase), MMP19 (RASI-1, stromelysin-4), MMP20 (Enamelysin), MMP21 (X-MMP), MMP23A (CA-MMP), MMP23B MMP24 (MT5-MMP), MMP25 (MT6-MMP), MMP26 (Matrilysin- 2, endometase), MMP27 (MMP-22, C-MMP), MMP28 (Epilysin); A Disintegrin and Metalloproteinase with Thrombospondin Motifs protease, such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMPSTE2; and acetylcholinesterase.

A variant A2M polypeptide can be characterized as having an increased ability to prevent FAC formation compared to a wild-type A2M polypeptide. A variant A2M polypeptide can have an ability to prevent FAC formation that is at least 1.5 times higher than the ability of a wild-type A2M polypeptide to prevent FAC formation. For example, a variant A2M polypeptide can have an ability to prevent FAC formation that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to prevent FAC formation. A variant A2M polypeptide can have an ability to prevent FAC formation that is from 1.5-100 times higher than the ability of a wild-type A2M polypeptide to prevent FAC formation. For example, a variant A2M polypeptide can have an ability to prevent FAC formation that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to prevent FAC formation.

One aspect of the invention is a method for determining the enhanced inhibition of a protease by a variant A2M polypeptide comprising: a) providing a variant A2M polypeptide comprising a sequence of one or more of SEQ ID NOs 5-66; b) contacting the variant A2M polypeptide with the protease and a substrate cleaved by the protease; c) contacting a wild-type A2M polypeptide with the protease and the substrate cleaved by the protease; and d) comparing the amount of cleavage of the substrate from step b) to the amount of cleavage of the substrate from step c), thereby determining the enhanced inhibition of the protease by the variant A2M polypeptide.

Enzymatic glycoconjugation reactions can be targeted to glycosylation sites and to residues that are attached to glycosylation sites. The targeted glycosylation sites can be sites native to a wild-type A2M protein, native to a variant A2M polypeptide or, alternatively, they can be introduced into a wild-type A2M or variant A2M polypeptide by mutation. Thus, a method for increasing the in vivo half life of a variant A2M polypeptide is provided by the methods of the invention.

A variant A2M polypeptide can include an amino acid sequence that mutated to insert, remove or relocate one or more glycosylation site in the protein. When a site is added or relocated, it is not present or not present in a selected location in the wild-type A2M peptide. The mutant glycosylation site can be a point of attachment for a modified glycosyl residue that can be enzymatically conjugated to the glycosylation site. Using the methods of the invention, the glycosylation site can be shifted to any efficacious position on the peptide. For example, if the native glycosylation site is sufficiently proximate or within the bait region of variant A2M polypeptide peptide that conjugation interferes with the ability to bind a protease, inhibit a protease, or a combination thereof, it is within the scope of the invention to engineer a variant A2M polypeptide that includes a glycosylation site as modified or removed from the bait as necessary to provide a biologically active variant A2M polypeptide.

Any glycosyltransferase or method of their use known in the art can be used for in vitro enzymatic synthesis of variant A2M polypeptides with custom designed glycosylation patterns, various glycosyl structures, or a combination thereof possible. See, for example, U.S. Pat. Nos. 5,876,980; 6,030,815; 5,728,554; 5,922,577; and WO/9831826; US2003180835; and WO 03/031464.

The present invention provides methods of improving or lengthening the in vivo half-lives of variant A2M polypeptides by conjugating a water-soluble polymer to the variant A2M polypeptides through an intact glycosyl linking group. In an exemplary embodiment, covalent attachment of polymers, such as polyethylene glycol (PEG), to such variant A2M polypeptides affords variant A2M polypeptides having in vivo residence times, and pharmacokinetic and pharmacodynamic properties, enhanced relative to the unconjugated variant A2M polypeptide.

The polymer backbone of the water-soluble polymer can be poly(ethylene glycol) (PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_n$ in which R represents the core moiety, such as glycerol or pentaerythritol, and n represents the number of arms. Many other polymers are also suitable for the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. Although the molecular weight of each chain of the polymer backbone can vary, it is typically in the range of from about 100 Da to about 100,000 Da often from about 6,000 Da to about 80,000 Da.

A variant A2M polypeptide can further comprise PEG. A variant A2M polypeptide can have one or more mutant or modified glycosylation sites. The modified glycosylation sites can comprise PEG. For example, a variant A2M polypeptide can have 2, 3, 4, 5, 6, 7, 8, 9, 10, 11, 12, 13, 14, 15, or more mutant or modified glycosylation sites. The conjugation or addition of PEG to a variant A2M polypeptide with one or more modified or abnormal glycosylation sites can result in a variant A2M polypeptide with a longer half life than the half life of a wild-type A2M protein without PEG when disposed within a subject, such as a joint or spine disc of a subject. The conjugation or addition of PEG to a variant A2M polypeptide with one or more modified or abnormal glycosylation sites can result in a variant A2M polypeptide with a longer half life than the half life of a variant A2M polypeptide without one or more modified glycosylation sites without PEG when disposed within a subject, such as a joint or spine disc of a subject. The conjugation or addition of PEG to a variant A2M polypeptide with one or more modified or abnormal glycosylation sites can result in a variant A2M polypeptide with a longer half life than the half life of a variant A2M polypeptide with one or more modified glycosylation sites without PEG when disposed within a subject, such as a joint or spine disc of a subject. For example, a variant A2M polypeptide with one or more modified or abnormal glycosylation sites with PEG can have half life that is 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times the half life of a wild type A2M protein without PEG, a variant A2M polypeptide with one or more modified glycosylation sites without PEG, or a variant A2M polypeptide without one or more modified glycosylation sites without PEG. For example, a variant A2M polypeptide with one or more modified or abnormal glycosylation sites with PEG can have half life that is 2 times the half life of a wild type A2M protein composition with one or more modified or abnormal glycosylation sites without PEG when disposed within a joint or spine disc of a subject.

The present invention further provides isolated polypeptides encoded by the nucleic acid fragments of the present invention or by degenerate variants of the nucleic acid fragments of the present invention. By "degenerate variant" can be intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

Fragments of the A2M variants of the present invention which are capable of exhibiting biological activity are also encompassed by the present invention. Fragments of the A2M variants can be in linear form or they can be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments can be fused to carrier molecules such as immunoglobulins for many purposes, including increasing the valency of protein binding sites. The present invention also provides both full-length and mature forms (for example, without a signal sequence or precursor sequence) of the disclosed A2M variants. The protein coding sequence can be identified in the sequence listing by translation of the disclosed nucleotide sequences. The mature form of such A2M variants can be obtained by expression of a full-length polynucleotide in a suitable mammalian cell or other host cell. The sequence of the mature form of the A2M variants can be also determinable from the amino acid sequence of the full-length form. Where A2M variants of the present invention are membrane bound, soluble forms of the A2M variants are also provided. In such forms, part or all of the regions causing the A2M variants to be membrane bound are deleted so that the A2M variants are fully secreted from the cell in which it can be expressed. A2M variant compositions of the present invention can further comprise an acceptable carrier, such as a hydrophilic, e.g., pharmaceutically acceptable, carrier.

Variant A2M Polynucleotide Compositions

As used herein, "A2M polynucleotide," when used with reference to SEQ ID NOs: 1 or 2, means the polynucleotide sequence of SEQ ID NO: 1 or 2, or fragments thereof, as well as any nucleic acid variants which include one or more insertions, deletions, mutations, or a combination thereof. The insertions, deletions, and mutations are preferably within the polynucleotide sequence encoding the bait region of the A2M protein. Similarly, "A2M cDNA", "A2M coding sequence" or "A2M coding nucleic acid", when used with reference to SEQ ID NOs: 1 or 2, means the nucleic acid sequences of SEQ ID NOs: 1 or 2, or fragments thereof, as well as nucleic acid variants which include one or more mutations, insertions, deletions, or a combination thereof. The A2M polynucleotides, or fragments thereof, can be manipulated using conventional techniques in molecular biology so as to create variant A2M recombinant polynucleotide constructs, encoding the variant A2M polypeptides that express variant A2M polypeptides. Variant A2M polynucleotides include nucleotide sequences having at least 99%, 98%, 97%, 96%, 95%, 94%, 93%, 92%, 91%, 90%, 89%, 88%, 87%, 86%, or 85% sequence identity to SEQ ID NOs: 1 and 2. A2M coding sequences includes nucleotide sequences having at least 99%, 98%, 97%, 96%, 95%, 94%, 93%, 92%, 91%, 90%, 89%, 88%, 87%, 86%, or 85% sequence identity to any one of SEQ ID NOs: 1 and 2.

In one aspect, provided herein is a variant A2M polynucleotide nucleotide composition. Numerous polynucleotide sequences encoding wild-type A2M proteins from various organisms have been determined. Any A2M DNA sequence identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene. Alternatively, a nucleic acid sequence encoding an A2M polypeptide can be isolated from a human cDNA or genomic DNA library using standard cloning techniques such as polymerase chain reaction (PCR), where homology-based primers can often be derived from a known nucleic acid sequence encoding an A2M polypeptide.

cDNA libraries suitable for obtaining a coding sequence for a wild-type A2M polypeptide can be obtained commercially or can be constructed. The general methods of isolating mRNA, making cDNA by reverse transcription, ligating cDNA into a recombinant vector, transfecting into a recombinant host for propagation, screening, and cloning are well known. Upon obtaining an amplified segment of nucleotide sequence by PCR, the segment can be further used as a probe to isolate the full-length polynucleotide sequence encoding the wild-type A2M protein from the cDNA library. A similar procedure can be followed to obtain a full length sequence encoding a wild-type A2M protein from a human genomic library. Human genomic libraries are commercially available or can be constructed according to various art-recognized methods. In general, to construct a genomic library, the DNA is first extracted from a tissue where a peptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization.

Based on sequence homology, degenerate oligonucleotides can be designed as primer sets and PCR can be performed under suitable conditions to amplify a segment of nucleotide sequence from a cDNA or genomic library. Using the amplified segment as a probe, the full-length nucleic acid encoding a wild-type A2M protein can be obtained Upon acquiring a nucleic acid sequence encoding a wild-type A2M protein, the coding sequence can be subcloned into a vector, for instance, an expression vector, so that a recombinant wild-type A2M protein can be expressed mutated into a variant A2M polypeptide of the invention produced from the resulting construct. Further modifications to the wild-type A2M protein coding sequence, for example, nucleotide substitutions, may be subsequently made to alter the bait region of the A2M protein.

The present invention further provides isolated polypeptides encoded by the polynucleotides, or fragments thereof, of the present invention or by degenerate variants of the polynucleotides, or fragments thereof, of the present invention. Preferred polynucleotides, or fragments thereof, of the present invention are the ORFs that encode A2M variants.

A variant A2M polynucleotide can be made by mutating the polynucleotide sequence encoding a wild-type A2M protein. This can be achieved by using any known mutagenesis methods. Exemplary modifications to a wild-type A2M polynucleotide for accepting variant bait regions described herein include those in SEQ ID NO 2. Exemplary modifications to an A2M nucleotide include inserting or substituting a nucleotide sequence encoding a variant bait region of SEQ ID NO 5-66 into the wild-type A2M polynucleotide sequence of SEQ ID NO: 1 and the variant A2M acceptor polynucleotide sequence of SEQ ID NO 2. Mutagenesis procedures can be used separately or in combination to produce variants of a set of nucleic acids, and hence variants of encoded polypeptides. Kits for mutagenesis are commercially available.

In one aspect, provided herein are methods of making any of the variant A2M polynucleotides. A method of making a variant A2M polynucleotide can comprise inserting or substituting a variant bait region into a wild-type A2M polynucleotide sequence or substantially similar sequence. The substantially similar sequence can be SEQ ID NO 2. One aspect of the invention is a method for making a variant A2M polynucleotide comprising: a) providing a vector containing a variant A2M polynucleotide comprising a sequence of SEQ ID NO 2; b) digesting the vector containing a variant A2M polynucleotide with restriction endonucleases to form a linear vector; c) ligating one end of the one or more polynucleotides encoding one or more of the non-natural bait regions of SEQ ID NOs 5-66 to one end of the linear vector; and d) ligating the other end of the one or more polynucleotides encoding one or more of the non-natural bait regions of SEQ ID NOs 5-66 to the other end of the linear vector, thereby forming a vector containing a variant A2M polynucleotide comprising the non-natural bait regions of SEQ ID NOs 5-66.

Protein Production

A variety of methodologies known in the art can be utilized to obtain any one of the isolated A2M variant proteins of the present invention. At the simplest level, the amino acid sequence can be synthesized using commercially available peptide synthesizers. Such polypeptides can be synthesized with or without a methionine on the amino terminus. Chemically synthesized polypeptides can be oxidized using methods set forth in these references to form disulfide bridges. The synthetically constructed A2M variant sequences, by virtue of sharing primary, secondary or tertiary structural and/or conformational characteristics with A2M variants can possess biological properties in common therewith, including protease inhibitory activity. This technique can be particularly useful in producing small peptides and fragments of larger polypeptides. Fragments are useful, for example, in generating antibodies against the A2M variants. Thus, they can be employed as biologically active or immunological substitutes for natural, purified A2M variants in screening of therapeutic compounds and in immunological processes for the development of antibodies.

The A2M variant polypeptides of the present invention can alternatively be purified from cells which have been altered to express the desired A2M variant. As used herein, a cell can be said to be altered to express a desired A2M variant polypeptide or protein when the cell, through genetic manipulation, can be made to produce a A2M variant polypeptide which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the A2M variant polypeptides of the present invention.

A variant A2M polypeptide can be a recombinant protein, or fragments thereof, and can be produced in a host cell or in vitro system. Recombinant polypeptides and protein promoters can be inserted in such a manner that it can be operatively produced in a host cell, for example, a bacterial culture or lower eukaryotes such as yeast or insects or in prokaryotes or any host know in the art. A variant A2M recombinant protein can be produced in a bacterium, yeast, fungi, insect, or mammalian host cell, or a cell free system. For example, a variant A2M polypeptide can be produced in *Escherichia coli, Bacillus subtilis, Salmonella typhimurium, Corynebacterium, Saccharomyces cerevisiae, Schizosaccharomyces pombe Kluyveromyces* strains, *Candida, Pichia pastoris*, baculovirus-infected insect cells, or mammalian cells such as COS cells, BHK cells, 293 cells, 3T3 cells, NSO hybridoma cells, baby hamster kidney (BHK) cells, PER.C6™ human cells, HEK293 cells or *Cricetulus griseus* (CHO) cells. A variant A2M polypeptide can be produced by transient expression, stable cell lines, BacMam-mediated transient transduction, or cell-free protein production.

The variant A2M polypeptides can also be produced by operably linking the isolated variant A2M polynucleotides to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference.

Figure 23:
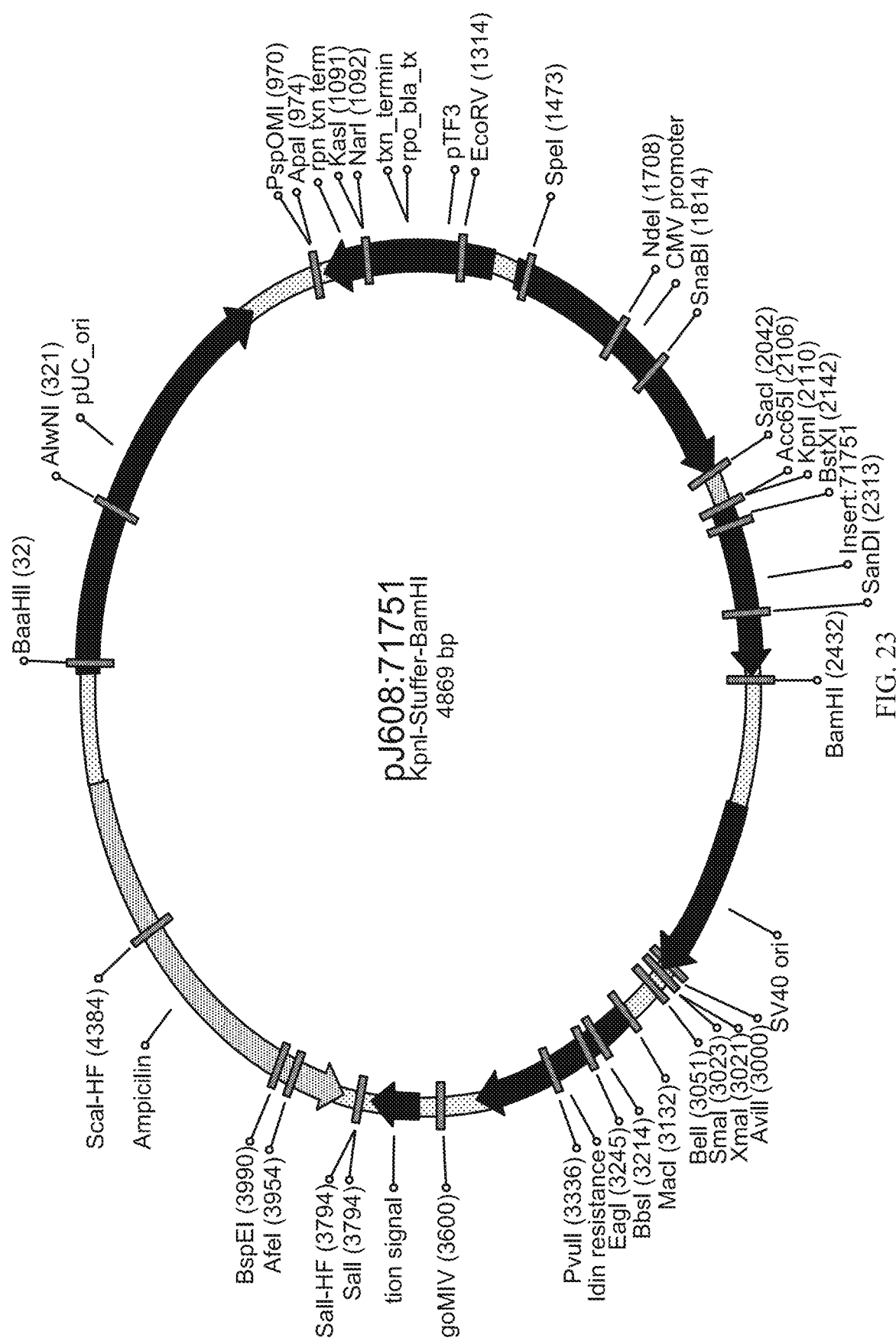
FIG. 23 depicts a Vector Map of pJ608 mammalian expression vector. The ORF sequence coding for wild-type and variant A2M is cloned in between the Kpn1 and BamH1 restriction sites.

In mammalian host cells, a number of viral-based expression systems can be utilized. In cases where an adenovirus is used as an expression vector, the variant A2M nucleotide sequence of interest can be ligated to an adenovirus transcription/translation control complex, for example, the late promoter and tripartite leader sequence. This chimeric gene can then be inserted in the adenovirus genome by in vitro or in vivo recombination. Insertion in a non-essential region of the viral genome can result in a recombinant virus that is viable and capable of expressing the variant A2M gene product in infected hosts. Specific initiation signals can also be required for efficient translation of inserted nucleotide sequences. These signals include the ATG initiation codon and adjacent sequences. In cases where an entire variant A2M gene or cDNA, including its own initiation codon and adjacent sequences, is inserted into the appropriate expression vector, for example, a pJ608 mammalian expression vector (FIG. 23) no additional translational control signals are needed. Exogenous translational control signals, such as the ATG initiation codon, can be provided.

Host cells can be genetically engineered to contain the variant A2M polynucleotides of the invention. For example, such host cells can contain variant A2M polynucleotides introduced into the host cell using known transformation, transfection or infection methods. As used herein, a cell capable of expressing a variant A2M polynucleotide can be "transformed." The variant A2M polypeptides of the invention can be prepared by culturing transformed host cells under culture conditions suitable to express the recombinant protein. Any procedure for introducing foreign nucleotide sequences into host cells may be used. Non-limiting examples include the use of calcium phosphate transfection, transfection, DEAE, dextran-mediated transfection, microinjection, lipofection, polybrene, protoplast fusion, electroporation (Davis, L. et al., Basic Methods in Molecular Biology (1986)), liposomes, microinjection, plasma vectors, viral vectors, and any other well known methods for introducing cloned genomic DNA, cDNA, synthetic DNA, or other foreign genetic material into a host cell. A genetic engineering procedure capable of successfully introducing at least one gene into the host cell capable of expressing the variant A2M polynucleotide can be used.

The present invention still further provides host cells engineered to express the variant A2M polynucleotides of the invention, wherein the variant A2M polynucleotides are operative with a regulatory sequence heterologous to the host cell which drives expression of the variant A2M polynucleotides in the cell. Knowledge of A2M-like DNA allows for modification of cells to permit, or increase, expression of A2M-like polypeptide. Cells can be modified, for example, by homologous recombination, to provide increased variant A2M polypeptide expression by replacing, in whole or in part, the naturally occurring A2M derived from the SV40 viral genome, for example, SV40 macroglobulin-like promoter with all or part of a heterologous promoter so that the cells' variant A2M sites can be used to provide the required non-transcribed polypeptide and can be expressed at higher levels.

For long-term, high-yield production of recombinant variant A2M polypeptides, stable expression is preferred. For example, cell lines that stably express the variant A2M sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the variant A2M gene product. Such engineered cell lines are particularly useful in screening and evaluation of compounds that affect the endogenous activity of the variant A2M gene product. A number of selection systems can be used, including but not limited to the herpes simplex virus thymidine kinase, hypoxanthine-guanine phosphoribosyltransferase, and adenine phosphoribosyltransferase genes can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin.

Variant A2M polynucleotide sequences can be engineered so as to modify processing or expression of the protein. For example, and not by way of limitation, the variant A2M polynucleotides can be combined with a promoter sequence and/or ribosome binding site, or a signal sequence can be inserted upstream of variant A2M polynucleotide sequences to permit secretion of the variant A2M polypeptide and thereby facilitate harvesting or bioavailability. Additionally, a variant A2M polynucleotide can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis.

Further, nucleic acids encoding other proteins or domains of other proteins can be joined to nucleic acids encoding variant A2M polypeptides or fragments thereof so as to create a fusion protein. Nucleotides encoding fusion proteins can include, but are not limited to, a full length variant or wild-type A2M protein, a truncated variant or wild-type A2M protein or a peptide fragment of a variant or wild type A2M protein fused to an unrelated protein or peptide, such as for example, a transmembrane sequence, which anchors the A2M peptide fragment to the cell membrane; an Ig Fc domain which increases the stability and half life of the resulting fusion protein; maltose binding protein (MBP), glutathione-S-transferase (GST) or thioredoxin (TRX), a His tag, an enzyme, fluorescent protein, luminescent protein which can be used as a marker, for example, an A2M-Green Fluorescent Protein fusion protein. The fusion proteins can be used for affinity purification.

The variant A2M nucleic acids and polypeptides can also be expressed in organisms so as to create a transgenic organism. Desirable transgenic plant systems having one or more of these sequences include Arabadopsis, Maize, and *Chlamydomonas*. Desirable insect systems having one or more of the variant A2M polynucleotides and/or polypeptides include, for example, *D. melanogaster* and *C. elegans*. Animals of any species, including, but not limited to, amphibians, reptiles, birds, mice, rats, rabbits, guinea pigs, pigs, micro-pigs, goats, dogs, cats, and non-human primates, e.g., baboons, monkeys, and chimpanzees can be used to generate variant A2M containing transgenic animals. Transgenic organisms desirably exhibit germline transfer of variant A2M nucleic acids and polypeptides described herein.

A variety of methodologies known in the art can be utilized to obtain any one of the isolated polypeptides or proteins of the present invention. At the simplest level, the amino acid sequence can be synthesized using commercially available peptide synthesizers. The synthetically constructed protein sequences, by virtue of sharing primary, secondary or tertiary structural and/or conformational characteristics with proteins can possess biological properties in common therewith, including protein activity. This technique can be particularly useful in producing small peptides and fragments of larger polypeptides. Fragments are useful, for example, in generating antibodies against the native polypeptide. Thus, they can be employed as biologically active or immunological substitutes for natural, purified proteins in screening of therapeutic compounds and in immunological processes for the development of antibodies. The polypeptides and proteins of the present invention can alternatively be purified from cells which have been altered to express the desired polypeptide or protein. As used herein, a cell can be said to be altered to express a desired polypeptide or protein when the cell, through genetic manipulation, can be made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells in a suitable culture medium, and purifying the protein from the cells or the culture in which the cells are grown. For example, the methods can include a process for producing a polypeptide in which a host cell containing a suitable expression vector that includes a polynucleotide of the invention can be cultured under conditions that allow expression of the encoded polypeptide. The polypeptide can be recovered from the culture, conveniently from the culture medium, or from a lysate prepared from the host cells and further purified. Preferred embodiments include those in which the protein produced by such process can be a full length or mature form of the protein, such as A2M. In an alternative method, the polypeptide or protein can be purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological or immunological activity include fragments comprising greater than about 100 amino acids, or greater than about 200 amino acids, and fragments that encode specific protein domains. The purified polypeptides can be used in in vitro binding assays which are well known in the art to identify molecules which bind to the polypeptides. These molecules include but are not limited to, for example, small molecules, molecules from combinatorial libraries, antibodies or other proteins. The molecules identified in a binding assay can then be tested for antagonist or agonist activity in in vivo tissue culture or animal models that are well known in the art. In brief, the molecules can be titrated into a plurality of cell cultures or animals and then tested for either cell or animal death or prolonged survival of the animal or cells.

The resulting expressed variant A2M polypeptides can then be purified from a culture, for example, from culture medium or cell extracts, using known purification processes, such as affinity chromatography, gel filtration, and ion exchange chromatography. The purification of the variant A2M polypeptides can also include an affinity column containing agents which will bind to the protein; one or more column steps over such affinity resins as concanavalin A-agarose, heparin-Toyopearl™ or Cibacron blue 3GA Sepharose™; one or more steps involving hydrophobic interaction chromatography using such resins as phenyl ether, butyl ether, or propyl ether; or immunoaffinity chromatography. Alternatively, the protein of the invention can also be expressed in a form which will facilitate purification. For example, a protein can be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.). Finally, one or more reverse-phase high performance liquid chromatography (RP-HPLC) steps employing hydrophobic RP-HPLC media, for example, silica gel having pendant methyl or other aliphatic groups, can be employed to further purify the protein. Any combination of the foregoing purification procedures can also be employed to provide a substantially homogeneous isolated or purified recombinant variant A2M polypeptide. The variant A2M polypeptides purified can be substantially free of other mammalian proteins and can be defined in accordance with the present invention as an "isolated protein."

Agents for Inhibition of FAC Formation

Also provided herein are methods to inhibit the one or more steps of the fibronectin-aggrecan complex formation cycle (FACC) in a human with a condition or disease (FIG. 1). An agent can be administered to a subject with a condition or disease. An agent can be wild-type A2M protein or a composition described herein, such as a purified form of A2M, or an A2M enriched sample, or a variant A2M polypeptide as described herein. An agent can be an agent that is not a purified form of A2M concentrated from autologous blood. An agent can be an inhibitor or an antagonist. An inhibitor or antagonist can be a compound or composition that directly or indirectly, partially or totally blocks activity, decreases, prevents, delays activation, inactivates, desensitizes, or down regulates the activity or expression of a target biomarker. Antagonists can be, for example, polypeptides, such as antibodies, and soluble receptors, as well as nucleic acids such as siRNA or antisense RNA, as well as naturally occurring and synthetic biomarker antagonists, including small chemical molecules.

An agent can be compound that has a pharmacological activity. Agents can include compositions described herein or compounds that are known drugs, compounds for which pharmacological activity has been identified but that are undergoing further therapeutic evaluation, and compounds that are members of collections and libraries that are to be screened for a pharmacological activity. An agent can be organic or inorganic chemical such a peptide, protein, including antibodies, small molecules and natural products.

An agent can comprise an antibody. An antibody can be a polypeptide comprising a framework region from an immunoglobulin gene or fragments thereof that specifically binds and recognizes an antigen. The recognized immunoglobulin genes can include the kappa, lambda, alpha, gamma, delta, epsilon, and mu constant region genes, as well as the myriad immunoglobulin variable region genes. Light chains can be classified as either kappa or lambda. Heavy chains can be classified as gamma, mu, alpha, delta, or epsilon, which in turn define the immunoglobulin classes, IgG, IgM, IgA, IgD and IgE, respectively. An antibody can encompass plural referents unless the context clearly indicates otherwise. In some instances a plurality of the antibodies can belong to the same antibody species, e.g., in the case of monoclonal antibodies, while in some cases different antibodies species are encompassed the by phrase "an antibody", e.g., a polyclonal antibodies. An exemplary immunoglobulin (antibody) structural unit can comprise a tetramer. Each tetramer can be composed of two identical pairs of polypeptide chains, each pair having one "light" (about 25 kDa) and one "heavy" chain (about 50-70 kDa). The N-terminus of each chain can define a variable region of about 100 to 110 or more amino acids primarily responsible for antigen recognition. The terms variable light chain ($V_L$) and variable heavy chain (VH) can refer to these light and heavy chains respectively. Antibodies can exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer can be a Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. An antibody can also be an antibody fragment either produced by the modification of whole antibodies, or those synthesized de novo using recombinant DNA methodologies (e.g., single chain Fv) or those identified using phage display libraries (see, e.g., McCafferty et al., Nature 348:552-554 (1990)). When referring to treatment methods, antibodies that are chimeric, human, humanized or otherwise specific to the species to be treated can be used.

An agent can be an antibody that binds to the FAC but not to the individual components of the complex separately. An agent can comprise an antibody that binds to aggrecan or any variation thereof, thereby inhibiting formation of the FAC complex. An agent can comprise an antibody, such as a monoclonal antibody, that binds to aggrecan G3 lectin domain. The antibody can bind to aggrecan G3 and prevent the formation of FAC and inflammation. An agent can comprise an antibody that binds to fibronectin or any variant thereof, thereby inhibiting formation of the FAC complex. An agent can comprise an antibody that binds to a PAMP receptor recognition domain of aggrecan, a DAMP receptor recognition domain of aggrecan, or both, thereby inhibiting activation of monocytes and other cells. Other cells can be macrophages, fibroblast, T-cells, B-cells, neutrophils, platelets, synoviocytes, chondrocytes and other cells involved in inflammation. An agent can comprise an antibody that binds to a PAMP receptor recognition domain of fibronectin, a DAMP receptor recognition domain of fibronectin, or both, thereby inhibiting activation of monocytes and other cells.

An agent that prevents or inhibits FAC formation can be a recombinant aggrecan G3 domain, wherein the domain contains the aggrecan G3 lectin domain and competitively binds to fibronectin; wherein the domain lacks the Pathogen Associated Molecular Patterns (PAMP) and the Damage Associated Molecular Patterns (DAMP) receptor recognition domains. Recombinant aggrecan G3 lectin domain can competitively bind to fibronectin. A recombinant aggrecan G3 domain can lack the cell activation domain and can slow down, inhibit, or prevent FAC formation and inflammation.

An agent that prevents or inhibits FAC formation can be a wild-type A2M protein or a recombinant fibronectin fragment, wherein the fragment comprises a G3 binding domain and binds to aggrecan, wherein the G3 binding domain the PAMP, receptor recognition domain, the DAMP receptor recognition domain, or both. A recombinant fibronectin fragment can competitively bind to aggrecan.

An agent that prevents or inhibits FAC formation can be a soluble form of the PAMP receptor or DAMP receptor that binds to the PAMP domain of aggrecan G3, the DAMP domain of aggrecan G3, or both, thereby inhibiting activation of monocytes and other cells to produce proinflammatory cytokines, chemokines, proteases, or any combination thereof.

An agent that prevents or inhibits FAC formation can be a soluble form of the PAMP receptor or DAMP receptor that binds to the PAMP domain of fibronectin, the DAMP domain of fibronectin, or both, thereby inhibiting activation of monocytes and other cells to produce proinflammatory cytokines, chemokines, proteases, or any combination thereof. An agent can be an inhibitor of fibroblast cells and can inhibit production of increased levels fibronectin, recruitment of other fibroblast cells, or both.

An agent that prevents or inhibits FAC formation can be a small molecule. A small molecule can be identified using one or more high-throughput screening methods. A small molecule can inhibit FAC formation, inhibit activation of monocytes; inhibit increased production of fibronectin; inhibit recruitment of fibroblast cells; or bind to the DAMP domain of fibronectin, bind to the DAMP domain of aggrecan G3, bind to the PAMP domain of fibronectin, or bind to the PAMP domain of aggrecan G3, thereby inhibiting activation of cells to produce proinflammatory cytokines, chemokines, proteases, or any combination thereof. In A small molecule can inhibit FAC formation by competitively binding to fibronectin or aggrecan. In some embodiments, the small molecule binds to the FAC complex and resulting in dissociation or degradation of the FAC complex. Inhibiting the formation of the fibronectin-aggrecan complex (FAC) can comprise inhibiting one or more steps in FAC formation or a step in the FAC formation cycle (FACC).

One or more steps in FAC formation or the FACC can comprise production of fibronectin in the ECM, production of proteases and metalloproteases, production of inflammatory cytokines and chemokines, degradation of aggrecan in cartilage, or increasing the aggrecan G3 domain fragment concentration.

In any of the methods herein, an agent can be a medicament used to treat joint injury or inflammation. Thus, one can administer to a subject, along with a composition comprising an elevated concentration of A2M, a variant A2M polypeptide, or a wild-type A2M protein, an effective amount of one or more other medicament (where a composition comprising an elevated concentration of A2M or variant A2M polynucleotide (e.g., compositions described herein) can be a first medicament). The one or more other medicaments can include, for example, an immunosuppressive agent, a cytokine antagonist such as a cytokine antibody, an integrin antagonist (e.g., antibody), a corticosteroid, or any combination thereof. The type of such second medicament can depend on various factors, including the type of inflammation and/or joint damage, the severity of the inflammation and/or joint damage, the condition and age of the subject, the type and dose of the first medicament employed, etc. Examples of such additional medicaments include an immunosuppressive agent (such as mitoxantrone (NOVANTRONE®), MTX, cyclophosphamide, chlorambucil, leflunomide, and azathioprine), intravenous immunoglobulin (gamma globulin), lymphocyte-depleting therapy (e.g., mitoxantrone, cyclophosphamide, CAMPATH™ antibodies, anti-CD4, cladribine, a polypeptide construct with at least two domains comprising a de-immunized, autoreactive antigen or its fragment that can be specifically recognized by the Ig receptors of autoreactive B-cells (WO 2003/68822), total body irradiation, and bone marrow transplantation), integrin antagonist or antibody (e.g., an LFA-1 antibody such as efalizumab/RAPTIVA® commercially available from Genentech, or an alpha 4 integrin antibody such as natalizumab/ANTEGREN® available from Biogen, or others as noted above), drugs that treat symptoms secondary or related to inflammation and/or joint damage such as those noted herein, steroids such as corticosteroid (e.g., prednisolone, methylprednisolone such as SOLU-MEDROL™ methylprednisolone sodium succinate for injection, prednisone such as low-dose prednisone, dexamethasone, or glucocorticoid, e.g., via joint injection, including systemic corticosteroid therapy), nonlymphocyte-depleting immunosuppressive therapy (e.g., MMF or cyclosporine), a TNF-α inhibitor such as an antibody to TNF-α or its receptor or TNFR-Ig (e.g., etanercept), DMARD, NSAID, plasmapheresis or plasma exchange, trimethoprim-sulfamethoxazole (BACTRIM™, SEPTRA™), MMF, H2-blockers or proton-pump inhibitors (during the use of potentially ulcerogenic immunosuppressive therapy), levothyroxine, cyclosporin A (e.g., SANDIMMUNE®), somatostatin analogue, a DMARD or NSAID, cytokine 25 antagonist such as antibody, anti-metabolite, immunosuppressive agent, rehabilitative surgery, radioiodine, thyroidectomy, anti-IL-6 receptor antagonist/antibody (e.g., ACTEMRA™ (tocilizumab)), or another B-cell antagonist such as BR3-Fc, TACI-Ig, anti-BR3 antibody, anti-CD40 receptor or anti-CD40 ligand (CD154), agent blocking CD4O-CD40 ligand, epratuzumab (anti-CD22 antibody), lumiliximab (anti-CD23 30 antibody), or anti-CD20 antibody such as rituximab or 2H7 antibody. Known inhibitors such as chelators of known aggrecanases or MMP's can be administered to a subject in need thereof in amount effective to inhibit or slow down the release of aggrecan fragments which in effect will reduce or eliminate the formation of the fibronectin aggrecan complexes thereby giving relief to the subject from the pain.

Diagnostic Methods

Methods for detecting biomarkers, such as a wild-type A2M protein, to identify sites in the spine or joint that are a source of pain can be used to diagnose, or assist in the diagnosis be of, subjects with pain syndromes related to the anatomic structure and physiologic function of the spine or joint. For example, the identification of fibronectin-aggrecan complexes in a biological sample, such as a biological sample from the epidural space, intervertebral disc, or facet joint can be used to diagnose, or assist in the diagnosis be of radiculopathy, facet joint pain or discogenic pain.

The amount of a biomarker, such as A2M, that can indicate a specific location in the spine as a source of pain for a particular subject can depend on numerous factors, including, but not limited to, the age, sex, medical history, etc., of the patient, the site that the biological sample was extracted from, and the assay format used to detect the biomarker. In some embodiments, the level and/or concentration of A2M in a biological sample may be quantified or directly compared with a control sample. In some embodiments, the level and/or concentration of A2M in a biological sample may not be quantified or directly compared with a control sample, but can rather be detected relative to a "diagnostic absence" or "diagnostic presence" of A2M.

A "diagnostic absence" can refer to an amount and/or concentration of A2M in a biological that indicates the absence or likelihood of the absence of pain or inflammation causing pathology or injury at the location from which the sample was taken. A diagnostic absence can be detectable in a simple assay giving a positive or negative result. A positive or negative result can be determined based on the amount and/or concentration of A2M in the biological sample. Detection of a level and/or concentration of A2M corresponding to a diagnostic absence of A2M indicates the absence of a pain-causing pathology or injury at the location from which the sample was taken. In some embodiments, a diagnostic absence of A2M can be a concentration of A2M in a biological sample from about 0-30 µg/ml. For example, a diagnostic absence of A2M can be a concentration of A2M in a biological sample from about 0-30 µg/ml, 0-25 µg/ml, 0-20 µg/ml, 0-15 µg/ml, 0-10 µg/ml, 0-5 µg/ml, 5-30 µg/ml, 5-25 µg/ml, 5-20 µg/ml, 5-15 µg/ml, 5-10 µg/ml, 10-30 µg/ml, 10-25 µg/ml, 10-20 µg/ml, 10-15 m/ml, 15-30 µg/ml, 15-25 µg/ml, 15-20 µg/ml, 20-30 µg/ml, or 20-25 µg/ml. In some embodiments, a diagnostic absence of A2M can be a concentration of A2M in a biological sample from about 0-40 µg/ml. For example, a diagnostic absence of A2M can be a concentration of A2M in a biological sample from about 0-40 µg/ml, 5-40 µg/ml, 10-40 µg/ml, 15-40 µg/ml, 20-40 µg/ml, 25-40 µg/ml, 30-40 µg/ml, or 35-40 µg/ml.

In some embodiments, a diagnostic absence of A2M in a biological sample can be at least about 1.5, 2, 3, 4, 5, 6, 7, 8, 9, 10, 20, 30, 40, 50, 60, 70, 80, 90, 100, 200, 500, 1000 or more fold lower than a control sample.

A "diagnostic presence" can refer to an amount and/or concentration of A2M in a biological that indicates the presence or likelihood of the presence of pain or inflammation causing pathology or injury at the location from which the sample was taken. A diagnostic presence can be detectable in a simple assay giving a positive or negative result. A positive or negative result can be determined based on the amount and/or concentration of A2M in the biological sample. Detection of a level and/or concentration of A2M corresponding to a diagnostic presence of A2M indicates the presence of a pain-causing pathology or injury at the location from which the sample was taken. In some embodiments, a diagnostic presence of A2M can be a concentration of A2M in a biological sample of at least about 31 µg/ml, 32 µg/ml, 33 µg/ml, 34 µg/ml, 35 µg/ml, 36 µg/ml, 37 µg/ml, 38 µg/ml, or 39 µg/ml. In some embodiments, a diagnostic presence of A2M can be a concentration of A2M in a biological sample of at least about 40 µg/ml. For example, a diagnostic presence of A2M can be a concentration of A2M in a biological sample of at least about 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, 95 µg/ml, 100 µg/ml, 110 µg/ml, 120 µg/ml, 130 µg/ml, 140 µg/ml, 145 µg/ml, 150 µg/ml, 160 µg/ml, 170 µg/ml, 180 µg/ml, 190 µg/ml, 200 µg/ml, 220 µg/ml, 240 µg/ml, 250 µg/ml, 260 µg/ml, 280 µg/ml, 300 µg/ml, 320 µg/ml, 340 µg/ml, 360 µg/ml, 380 µg/ml, 400 µg/ml, 420 µg/ml, 440 µg/ml, 460 µg/ml, 480 µg/ml, 500 µg/ml, or more.

In some embodiments, a diagnostic presence of A2M can be a concentration of A2M in a biological sample from about 40-500 µg/ml. For example, a diagnostic presence of A2M can be a concentration of A2M in a biological sample from about 50-500 µg/ml, 60-500 µg/ml, 70-500 µg/ml, 80-500 m/ml, 90-500 µg/ml, 100-500 µg/ml, 125-5004 ml, 150-5004 ml, 175-500, 200-500 µg/ml, 250-500 m/ml, 300-500 µg/ml, 400-500 µg/ml, 50-60 µg/ml, 50-70 µg/ml, 50-80 µg/ml, 50-90 µg/ml, 50-100 m/ml, 50-125 µg/ml, 50-150 µg/ml, 50-175 µg/ml, 50-200 µg/ml, 50-250 µg/ml, 50-300 µg/ml, 50-400 m/ml, 60-70 µg/ml, 60-80 µg/ml, 60-90 µg/ml, 60-100 µg/ml, 60-125 µg/ml, 60-150 µg/ml, 60-175 µg/ml, 60-200 µg/ml, 60-250 µg/ml, 60-300 µg/ml, 60-400 µg/ml, 70-80 µg/ml, 70-90 µg/ml, 70-100 µg/ml, 70-125 µg/ml, 70-150 µg/ml, 70-175 µg/ml, 70-200 µg/ml, 70-250 µg/ml, 70-300 µg/ml, 70-400 µg/ml, 80-90 µg/ml, 80-100 µg/ml, 80-125 µg/ml, 80-150 µg/ml, 80-175 µg/ml, 80-200 m/ml, 80-250 µg/ml, 80-300 µg/ml, 80-400 µg/ml, 90-100 µg/ml, 90-125 µg/ml, 90-150 µg/ml, 90-175 µg/ml, 90-200 µg/ml, 90-250 µg/ml, 90-300 µg/ml, 90-400 µg/ml, 100-125 µg/ml, 100-150 µg/ml, 100-175 µg/ml, 100-200 m/ml, 100-250 µg/ml, 100-300 µg/ml, 100-4004 ml, 125-1504 ml, 125-175 µg/ml, 125-2004 ml, 125-2504 ml, 125-3004 ml, 125-400 µg/ml, 150-175 µg/ml, 150-200 µg/ml, 150-2504 ml, 150-3004 ml, 150-4004 ml, 175-200 µg/ml, 175-250 µg/ml, 175-300 µg/ml, 175-4004 ml, 200-2504 ml, 200-3004 ml, 200-400 µg/ml, 250-300 µg/ml, 250-400 µg/ml, or 300-4004 ml.

In some embodiments, a diagnostic presence of A2M in a biological sample can be at least about 1.5, 2, 3, 4, 5, 6, 7, 8, 9, 10, 20, 30, 40, 50, 60, 70, 80, 90, 100, 200, 500, 1000 or more fold higher than a control sample.

The disclosed methods can be used regardless of whether A2M is normally present, or expected to be present, in a particular control sample. For example, A2M may not be detectable in certain normal spine samples (such as, for example, in a disc space or epidural space lavasate) using a particular assay, resulting in a complete absence of A2M complexes in a control biological sample. For example, A2M cannot be detectable in certain normal joint samples (such as, for example, in a synovial fluid sample) using a particular assay, resulting in a complete absence of A2M in a control biological sample. For such biological samples, a diagnostic presence can refer to any detectable amount of A2M using that same assay. In other instances, however, there can be a detectable level of A2M present in normal or control samples and a diagnostic absence represents a level that can be lower than the normal level, preferably representing a statistically significant decrease over the normal level.

Control samples can be samples that are taken from an individual or a group of individuals not experiencing inflammation or pain, such as spinal or joint pain. Alternatively, control samples can be obtained from a source not suspected to be a source of pain or inflammation, such as a level of the spine not suspected to be a source of pain. For example, in a subject experiencing discogenic pain, the control sample can be obtained from an unaffected or asymptomatic disc space of the same patient. Control samples can be samples that are taken from an individual or a group of individuals not experiencing joint-related pain. Alternatively, control samples can be obtained from unaffected or asymptomatic joints from the subject being tested. Particularly suitable joints to obtain control samples from are joints that are unaffected or asymptomatic contra-lateral to the joint being tested for a diagnostic presence of A2M. For example, in a subject experiencing left knee pain, the control sample can be obtained from the right knee of the same subject, provided that the right knee can be unaffected or asymptomatic.

The level of a biomarker, such as A2M, need not be quantified for a diagnostic absence or presence to be detected. Rather, any method of determining whether A2M is present at levels lower or higher than in a normal or control can be used. In addition, a diagnostic absence or presence does not refer to any absolute quantity of A2M, but rather to an amount that, depending on the biological sample, assay conditions, medical condition of the patient, etc., can be sufficient to distinguish the level in an affected patient from a normal or control patient.

The presence, absence or level of A2M present at a particular level within the spine can be used to diagnose, or assist in the diagnosis be of, a particular type of spinal pain, such as discogenic, facetogenic or radiculopathic pain. Additionally, or alternatively, the presence, absence, or level of A2M in a spinal sample can be used to distinguish pain that results from spinal pathology or injury from pain originating from another source, such as muscular pain.

The presence, absence, or level of A2M present in a particular joint can be used to diagnose, or assist in the diagnosis be of, a particular type of joint-related pain, including, but not limited to, osteoarthritis, meniscal pathology, rotator cuff tears, tendon or ligament pathology, chondrosis, or myofascial pain. In some embodiments, the presence, absence, or level of A2M in a joint can be indicative of pathology or injury in that particular joint. Additionally, or alternatively, the presence, absence, or level of A2M in a joint sample can be used to distinguish joint-related pain from pain from another anatomical or physiological source, such as the spine. For example, the absence or low level of A2M in a joint sample compared to a control sample can be used to distinguish joint-related pain from radiculopathic pain.

The presence, absence, or change over time in the level of A2M in a biological sample can be used to designate a patient as candidate for a particular treatment. A spinal sample obtained from the patient can be analyzed for the presence or absence of A2M. The patient can be selected for treatment if A2M is not detected in the spinal sample. The type of treatment can be then tailored to the severity of the condition as determined by the presence, absence, or level of A2M.

The level A2M present at a specific site can also be useful to determine a prognosis for the subject being tested. For example, the level of A2M present in a spinal sample can indicate the extent of an acute injury to the spine and can assist a practitioner in determining to what extent successful repair or healing of the injury or pathology can be achieved.

Methods for detecting A2M to identify joints as sites for treating joint-related pain can be used to diagnose, or assist in the diagnosis of, subjects with pain syndromes related to the anatomic structure and physiologic function of the synovial joints of the appendicular skeleton. For example, the identification of A2M in a joint can be used to diagnose, or assist in the diagnosis of osteoarthritis, meniscal pathology, rotator cuff tears, tendon or ligament pathology, chondrosis, or myofascial pain.

Detection of A2M can be used alone, or in combination with other diagnostic approaches to diagnose joint-related pain. Exemplary diagnostic approaches include, but are not limited to, medical history and physical examination, x-ray radiography, MIll and intra-articular injection. The presence of A2M can however be used to diagnose injury and administer treatment at a particular location irrespective of whether injury was detectable by other methods, e.g., an MRI. The patient will typically be treated by administration of a therapeutic agent to the site of injury or pathology, i.e., the site of presence of A2M.

The diagnostic methods of the present invention can include determination of the expression levels of a set of nucleic acid molecules comprising polynucleotide sequences coding for a protein marker. The diagnostic methods of the present invention can include the determination of expression levels of a plurality (i.e., one or more, e.g., at least 2, at least 3, at least 4, at least 5, at least 6, at least 7, at least 8, at least 9, at least 10 or more) of polypeptides in a biological sample obtained from a subject. Determination of protein expression levels in the practice of the inventive methods can be performed by any suitable method (see, for example, E. Harlow and A. Lane, "Antibodies: A Laboratories Manual", 1988, Cold Spring Harbor Laboratory: Cold Spring Harbor, N.Y.).

The disclosed methods can also be used to assess the efficacy of a treatment or a course of treatment. For example, in a patient with joint pain or radiculopathy testing positive for a diagnostic positive of A2M, such as wild-type A2M protein, indicative or radiculopathy, the efficacy of an anti-inflammatory treatment can be assessed by monitoring, over time, the levels of A2M. A decrease in the levels of A2M in a biological sample taken from a patient following a treatment, compared to a level in a sample taken from the same patient before, or earlier in, the treatment, can indicate efficacious treatment. An increase or lack of change in the levels of A2M in a biological sample taken from a patient following a treatment, compared to a level in a sample taken from the same patient before, or earlier in, the treatment, can indicate a non-efficacious treatment.

Inflammation biomarkers for diagnostic methods can be A2M, chemokines, cytokines, fibronectin, or aggrecan polypeptides in any ratio, in addition to other inflammatory mediators, extracellular matrix molecules or their breakdown products, signal transduction mediators, proteases and their inhibitors, and neurotransmitter receptors including, but not limited to IL-6, Prostaglandin E2, NO, IFN gamma, 5HT, RANTES, MCP-1, IL-1ra, TNF-α, Procollagens, CTX II, ARGS, aggrecan fragments, fibronectin fragments, FAC, COMP, CS 846, chondroitin fragments, sRAGE, MMP-3, MMP-13 and other MMPs, ADAMTS-4, aggrecanases, NF-kappa-B, p38 MAP kinase, DR5/DcR2. The biomarkers can include full length polypeptides or can include fragments of polypeptides.

Any known method for detecting the presence of polypeptides in a biological sample can be used to qualitatively or quantitatively detect the presence of A2M in biological samples, such as spinal or joint samples. Suitable methods include, but are not limited to, chromatographic methods, selective binding assays, mass spectrometry, spectrophotometry, or combinations thereof.

Exemplary binding assays include immunoassays, such as enzyme-linked immunosorbent assays. Immunoassays can be used to qualitatively or quantitatively analyze a spinal sample for the presence of A2M. A general overview of the applicable technology can be found in a number of readily available manuals, e.g., Harlow & Lane, Cold Spring Harbor Laboratory Press, Using Antibodies: A Laboratory Manual (1999).

The disclosed methods and kits can utilize selective binding partners of inflammation biomarkers to identify their presence or determine their levels in samples from the spine or joint. The selective binding partners can be antibodies, or other biomolecules that specifically bind to A2M, or fragments or complexes thereof.

Monoclonal or polyclonal antibodies can be used. The antibodies can be any known in the art, including commercially available antibodies. It is well known to those of skill in the art that the type, source and other aspects of an antibody to be used can be a consideration to be made in light of the assay in which the antibody can be used. In some instances, antibodies that will recognize its antigen target (for instance, an epitope or multiple epitopes from A2M) on a Western blot might not be applicable to all ELISA or ELISpot assay and vice versa.

Antibodies, antibody fragments, or single chain antibodies to be used can be produced using techniques for producing monoclonal or polyclonal antibodies that are well known in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g. Huse et al., Science 246:1275-1281 (1989); Ward et al., Nature 341:544-546 (1989)).

A number of immunogens from A2M can be used to produce antibodies specifically reactive with A2M and fragments thereof. For example, a recombinant A2M or an antigenic fragment thereof, can be isolated using methods well known to those of skill in the art. Recombinant protein can be expressed in eukaryotic or prokaryotic cells. Recombinant protein can be the typically used immunogen for the production of monoclonal or polyclonal antibodies. Alternatively, synthetic peptides derived from the known sequences A2M and conjugated to a carrier protein can be used as an immunogen. Naturally-occurring protein can also be used either in pure or impure form. The product can be then injected into an animal capable of producing antibodies. Either monoclonal or polyclonal antibodies can be generated, for subsequent use in immunoassays to measure the protein.

Antibodies that specifically bind to complexes containing A2M can be used as specific binding partners.

Non-antibody polypeptides can be used as specific binding agents for the detection of A2M, or fragments or complexes thereof. A large number of proteins that specifically bind to A2M are known in the art. Exemplary proteins that can be used as selective binding partners of A2M include, but are not limited to soluble receptors, cytokines and growth factors that are known to bind A2M, modified proteases that can bind to A2M and not trigger the conformation change.

Once selective binding partners are available, each specific biomarker can be detected by a variety of selective binding assays, including immunoassay methods. For a review of immunological and immunoassay procedures, see Basic and Clinical Immunology (Stites & Terr eds., 7th ed. 1991). Moreover, the disclosed selective binding assays can be performed in any of several configurations. Several immunoassay configurations are reviewed extensively in Enzyme Immunoassay (Maggio, ed., 1980).

Methods for detecting the presence and/or measuring a level of A2M in a spinal or joint sample, can use specific binding partners A2M, or fragments or complexes thereof. The methods generally include contacting the spinal or joint sample with specific binding partner for A2M, or fragments or complexes thereof, purifying a desired fraction from the sample, and detecting binding between the specific binding partner and molecules of the sample.

Detection of specific binding of the specific binding partners with molecules of the sample, when compared to a suitable control, can be an indication that biomarkers are present in the sample. A variety of methods to detect specific protein interactions are known in the art and can be used in the method. Methods include competitive assays and non-competitive assays.

Suitable methods include, but are not limited to, Western blot, immunoprecipitation, ELISA and radio-immunoassays. Methods for performing these and other suitable assays are known in the art. In general, the specific binding partner used to detect the biomarker will be delectably labeled, either directly or indirectly. The spinal or joint sample can be brought into contact with and immobilized on a solid support or carrier, such as a membrane (i.e. nitrocellulose) or polystyrene or magnetic beads that can be capable of immobilizing cells, cell particles, or soluble proteins. The support can then be washed with suitable buffers, followed by contacting with a detectably-labeled selective binding partner.

In specific binding assays, it can be desirable to minimize the amount of non-specific binding that occurs, particularly when the specific binding partner can be attached to a substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used. In addition to, or in place of proteinaceous material, various detergents and/or salt can be incorporated into the immunoassay to minimize non-specific interactions. Throughout the assays, incubation and/or washing steps can be required after each combination of reagents. Incubation and washing times will depend upon several factors, including the assay format, the affinity of the specific binding partner for the biomarker, the volume of solution, concentrations.

A positive control for an inflammation biomarker can be used in the detection assays, for example to calibrate the detection assay. A2M can be from different sources, for example from different species. A2M can be recombinant, natural or a combination thereof.

In general, protein expression levels can be determined by contacting a biological sample isolated from a subject with binding agents for one or more of the protein markers; detecting, in the sample, the levels of polypeptides that bind to the binding agents; and comparing the levels of polypeptides in the sample with the levels of polypeptides in a control sample. A binding agent can be an entity or composition such as a polypeptide or antibody that specifically binds to a protein marker. A binding agent can specifically bind to a polypeptide if it reacts and/or interacts at a detectable level with the polypeptide, but does not react and/or interact detectably with peptides containing unrelated sequences or sequences of different polypeptides.

The binding agent can be a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

The binding agent can be an antibody specific for a protein marker of the invention. Suitable antibodies for use in the methods of the present invention include monoclonal and polyclonal antibodies, immunologically active fragments (e.g., Fab or (Fab)$_2$ fragments), antibody heavy chains, humanized antibodies, antibody light chains, and chimeric antibodies. Antibodies, including monoclonal and polyclonal antibodies, fragments and chimeras, can be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof can be bound. The bound antibodies can then be eluted from the column using a buffer with a high salt concentration.

Instead of being prepared, antibodies to be used in the methods of the present invention can be obtained from scientific or commercial sources.

The binding agent can be directly or indirectly labeled with a detectable moiety. The role of a detectable agent can be to facilitate the detection step of the diagnostic method by allowing visualization of the complex formed by binding of the binding agent to the protein marker (or analog or fragment thereof). The detectable agent can be selected such that it generates a signal which can be measured and whose intensity can be related or proportional to the amount of protein marker present in the sample being analyzed. Methods for labeling biological molecules such as polypeptides and antibodies are well-known in the art (see, for example, "Affinity Techniques. Enzyme Purification B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Specific binding to an antibody, for example, when referring to a protein or peptide, can be a binding reaction that can be determinative of the presence of the protein in a heterogeneous population of proteins and other biologics. Thus, under designated immunoassay conditions, the specified antibodies can bind to a particular protein or protein complex at least two times the background and do not substantially bind in a significant amount to other proteins present in the sample. Specific binding between a binding agent, e.g., an antibody and a protein, for instance, a biomarker, can be the ability of a capture- or detection-agent to preferentially bind to a particular antigen that can be present in a mixture; e.g., a biological sample. In some embodiments, specific binding can refer to a dissociation constant (KD) that can be less than about $10^{-6}$ M; preferably, less than about $10^{-5}$ M; and, most preferably, less than about $10^{-9}$ M.

Specific binding assays, including immunoassays, can use a labeling agent to specifically bind to and allow for the detection of the complex formed by the specific binding partner and the detected analyte. A label or detectable moiety can be a composition detectable by spectroscopic, photochemical, biochemical, radiographic, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels can be incorporated into nucleic acids, proteins and antibodies at any position. Any method known in the art for conjugating the antibody to the label can be employed, e.g., using methods described in Hermanson, Bioconjugate Techniques 1996, Academic Press, Inc., San Diego.

The labeling agent can be a part of the specific binding partner used to detect the analyte. Alternatively, the labeling agent can be a third moiety, such a secondary antibody, which specifically binds to the complex formed by the specific binding partner and the detected analyte. Other proteins capable of specifically binding immunoglobulin constant regions, such as protein A or protein G, can also be used as the label agent. These proteins exhibit a strong affinity for immunoglobulin constant regions from a variety of species (see, e.g. Kronval et al., J. Immunol. 111: 1401-1406 (1973); Akerstrom et al., J. Immunol. 135:2589-2542 (1985)). The labeling agent can be modified with a detectable moiety, such as biotin, to which another molecule can specifically bind, such as streptavidin. A variety of detectable moieties are well-known to those skilled in the art.

The detectable label can be any material having a detectable physical or chemical property. Many useful detectable labels are known in the art and include any label that can be detectable by spectroscopic, photochemical, biochemical, immunochemical, radiographic, electrical, optical or chemical means. The choice of label can depend on the sensitivity required, the ease of conjugation with the compound, stability requirements, available instrumentation, and disposal provisions. Useful labels include magnetic beads (e.g., DYNABEADS®), fluorescent dyes (e.g., fluorescein isothiocyanate, Texas red, rhodamine, and the like), radiolabels (e.g., 3H, 125I, 35S, 14C, or 32P), enzymes (e.g., horseradish peroxidase, alkaline phosphatase and others commonly used in an ELISA), and calorimetric labels such as colloidal gold or colored glass or plastic beads (e.g., polystyrene, polypropylene, latex, etc.).

Non-radioactive labels are often attached by indirect means. Generally, a ligand molecule (e.g., biotin) can be covalently bound to the molecule. The ligand then binds to another molecules (e.g., streptavidin) molecule, which can be either inherently detectable or covalently bound to a signal system, such as a detectable enzyme, a fluorescent compound, or a chemiluminescent compound. The ligands and their targets can be used in any suitable combination with antibodies that recognize the biomarkers, or secondary antibodies that recognize the antibodies to the biomarkers.

The molecules can also be conjugated directly to signal generating compounds, for example, by conjugation with an enzyme or fluorophore. Enzymes that can be used as labels will primarily be hydrolases, particularly phosphatases, esterases and glycosidases, or oxidotases, particularly peroxidases. Exemplary fluorescent compounds include, but are not limited to, fluorescein and its derivatives, rhodamine and its derivatives, dansyl and µMbelliferone. Exemplary chemiluminescent compounds include, but are not limited to, luciferin and 2,3-dihydrophthalazinediones. Means of detecting labels are well known to those of skill in the art.

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) can be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents can be indirectly immobilized using second binding agents specific for the first binding agents (e.g., mouse antibodies specific for the protein markers can be immobilized using sheep anti-mouse IgG Fc fragment specific antibody coated on the carrier or support).

Protein expression levels in the diagnostic methods of the present invention can be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay can be competitive or noncompetitive. Methods of detection and quantification of the signal generated by the complex formed by binding of the binding agent with the protein marker will depend on the nature of the assay and of the detectable moiety (e.g., fluorescent moiety). Alternatively, the protein expression levels can be determined using mass spectrometry based methods or image (including use of labeled ligand) based methods known in the art for the detection of proteins. Other suitable methods include proteomics-based methods.

Determination of expression levels of nucleic acid molecules in the practice of the inventive methods can be performed by any suitable method, including, but not limited to, Southern analysis, Northern analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554, 527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples can be constructed using conventional methods known in the art. Suitable probes can be based on nucleic acid sequences encoding at least about 5 sequential amino acids from regions of nucleic acids encoding a protein marker, and preferably comprise about 15 to about 50 nucleotides. A nucleic acid probe can be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well known in the art (for a review of labeling protocols, label detection techniques and recent developments in the field, see, for example, L. J. Kricka, Ann Clin. Biochem. 2002, 39: 114-129; R. P. van Gijlswijk et al., Expert Rev. Mol. Diagn. 2001, 1: 81-91; and S. Joos et al., J. Biotechno 1. 1994, 35:135-153).

Nucleic acid probes can be used in hybridization techniques to detect polynucleotides encoding the protein markers. The technique can generally involve contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker can involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least about 60%, preferably at least about 75% and more preferably at least about 90% identity to a portion of nucleic acids encoding a protein marker.

Hybridization and amplification techniques described herein can be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker can be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436, 327; 5,472,672; 5,527,681; 5,529,756; 5,545,531; 5,554, 501; 5,561,071; 5,571,639; 5,593,839; 5,599,695; 5,624, 711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; 1. 1. Chen et al., Genomics, 1998, 51: 313324; U.S. Pat. Nos. 5,143,854; 5,445,934; 5,807,522; 5,837, 832; 6,040,138; 6,045,996; 6,284,460; and 6,607, 885).

Any biomarker binding agent, such as an antibody, can be labeled with a radiolabel or a fluorescent label. A labeled biomarker binding agent can be administered into a subject, by any suitable method, such as by injection. In some embodiments, a labeled biomarker binding agent can be administered locally, such as to a site of pain or inflammation, for example, a joint or spine disc. The labeled biomarker binding agent can be detected by any suitable means known in the art. Exemplary instruments that can be used to detect radiolabeled agents or fluorescent agents after administration to a subject include, but are not limited to, instruments for IVIS Imaging™ (Calipur), bioluminescence imaging (BLI), fluorescence-lifetime imaging (FLI) microscopy, X-ray radiography, ultrasound imaging, computed tomography (CT) imaging, single-photon emission computed tomography (SPECT), positron emission tomography (PET), magnetic resonance imaging (MRI), or any combination thereof. A labeled biomarker agent can bind to its respective biomarker upon administration of the agent into a subject. In some embodiments, the intensity of the signal from the label and the region in a subject's body where the label accumulates can indicate a painful or inflamed disc or joint where treatment is needed. For example, a fluorescently labeled antibody to A2M can be injected into a subject and can bind to the A2M of the subject in a knee joint where the label can accumulate and can indicate the knee joint is in need of treatment.

Therapeutic Methods

Once the site from which the pain can be originating can be identified by the presence of A2M, any method known in the art can be used to treat the pain, or to treat the pathology that can be causing the pain. For example, if radiculopathy or discogenic pain or facet pain has been diagnosed, any number of methods known in the art for treating spinal pain can be applied to treat the patient. Suitable methods include, but are not limited to, laminotomy, laminectomy, discectomy, microdiscectomy, percutaneous discectomy, endoscopic discectomy, laser discectomy, foramenotomy, fusion, prolotherapy, other surgical decompressions, decompression with fusion with or without instrumentation.

Pain in the spine can also be treated by standard non-surgical methods, including administration of steroidal or non-steroidal anti-inflammatory agents. Non-steroidal anti-inflammatory (NSAID) agents are well known in the art. Non-steroidal agents, including NSAIDs such as ibuprofen, aspirin or paracetamol can be used. Steroids, such as glucocorticoids, which reduce inflammation by binding to cortisol receptors, can also be used for treatment.

Any number of methods known in the art for treating joint-related pain can be applied to treat the patient. Suitable methods include surgical and non-surgical methods including, but not limited to, arthroscopic debridement or administration of steroidal or non-steroidal anti-inflammatory agents.

Any of the compositions described herein can be used for enhancing the nonspecific inhibition of one or more proteases in a human or non-human animal experiencing or susceptible to one or more conditions selected from the group of arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof. An autologous A2M composition, variant A2M polypeptide, and/or agent that prevents, slows or alters FAC formation can be administered to an animal to reduce one or more protease activities in an animal.

An autologous A2M composition, variant A2M polypeptide, and/or agent that prevents, slows or alters FAC formation can be used for inhibiting proteases. An autologous A2M composition and/or a variant A2M polypeptide can be used for treatment of pain and inflammation conditions and diseases. An autologous A2M composition and/or a variant A2M polypeptide can be used to prevent, slow, or alter FAC formation. A variant A2M can be more efficient than a wild-type A2M polypeptide in inhibiting proteases, have a longer half-life, have a slower clearance factor, or any combination thereof.

Any of the compositions, agents or formulations described herein, such an autologous A2M composition, variant A2M polypeptide, and/or agent that prevents, slows or alters FAC formation can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual), oral, intra-articular or inhalation routes of administration. An autologous A2M composition, variant A2M polypeptide, and/or agent that prevents, slows or alters FAC formation can also be administered using bioerodible inserts, bare-metal stents (BMS), or drug-eluting stents (DES or coated stents, or medicated stents), and can be delivered directly to spinal structures, such as intervertebral discs, the epidural space and facet joints, or to diarthroidal joints. An autologous A2M composition, variant A2M polypeptide, and/or agent that prevents, slows or alters FAC formation can be formulated in dosage forms appropriate for each route of administration. An autologous A2M composition, variant A2M polypeptide and/or agent that prevents, slows or alters FAC formation that are not peptides or polypeptides, can additionally be formulated for enteral administration.

An autologous A2M composition, variant A2M polypeptide, and/or agent that prevents, slows or alters FAC formation disclosed herein can be administered to a subject in a therapeutically effective amount. The precise dosage will vary according to a variety of factors such as subject dependent variables, such as age, the injury or pathology being treated, and the treatment being affected. The exact dosage can be chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

For some compositions, such as an autologous A2M composition, variant A2M polypeptide, and/or agent that prevents, slows or alters FAC formation disclosed herein, as further studies are conducted information will emerge regarding appropriate dosage levels for treatment of various conditions in various subjects, and the ordinary skilled worker, considering the therapeutic context, age, and general health of the recipient, will be able to ascertain proper dosing. The selected dosage depends upon the route of administration, and on the duration of the treatment desired. Generally dosage levels can include 0.1 to 40 mg/kg of body weight daily. Generally, for local injection or infusion, dosages can be lower. Depending on the composition and site of administration, dosage levels can be between about 1 to 500,000 mg, in a volume between about 0.1 to 10 mL. For example, dosage levels can be between about 5 to 450 mg, 5 to 400 mg, 5 to 350 mg, 5 to 300 mg, 5 to 250 mg, 5 to 200 mg, 5 to 150 mg, 5 to 100 mg, 5 to 500 mg, 5 to 25 mg, 100 to 150 mg, 100 to 200 mg, 100 to 250 mg, 100 to 300 mg, 100 to 350 mg, 100 to 400 mg, 100 to 450 mg, or 100 to 500 mg in a volume between about 0.1 to 9 mL, 0.1 to 8 mL, 0.1 to 7 mL, 0.1 to 6 mL, 0.1 to 5 mL, 0.1 to 4 mL, 0.1 to 3 mL, 0.1 to 2 mL, 0.1 to 1 mL, 0.1 to 0.9 mL, 0.1 to 0.7 mL, 0.1 to 0.6 mL, 0.1 to 0.5 mL, 0.1 to 0.4 mL, 0.1 to 0.3 mL, 0.1 to 0.2 mL, 1 to 9 mL, 1 to 8 mL, 1 to 7 mL, 1 to 6 mL, 1 to 5 mL, 1 to 4 mL, 1 to 3 mL, or 1 to 2 mL. Normal dosage amounts of various variant A2M polypeptides or nucleic acids, or fragment thereof can vary from any number between approximately 1 to 500,000 micrograms, up to a total dose of about 50 grams, depending upon the route of administration. Desirable dosages include, for example, 250 ug, 500 ug, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, 10 g, 20 g, 30 g, 40 g, and 50 g.

The dose of the variant A2M polypeptide, or fragment thereof, can be administered to produce a tissue or blood concentration or both from approximately any number between 0.1 µM to 500 mM. Desirable doses produce a tissue or blood concentration or both of about any number between 1 to 800 µM. Preferable doses produce a tissue or blood concentration of greater than about any number between 10 µM to about 500 µM. Preferable doses are, for example, the amount of active ingredient required to achieve a tissue or blood concentration, or both, of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 145 µM, 150 µM, 160 µM, 170 µM, 180 µM, 190 µM, 200 µM, 220 µM, 240 µM, 250 µM, 260 µM, 280 µM, 300 µM, 320 µM, 340 µM, 360 µM, 380 µM, 400 µM, 420 µM, 440 µM, 460 µM, 480 µM, and 500 µM. Although doses that produce a tissue concentration of greater than 800 µM are not preferred, they can be used with some embodiments of the invention. A constant infusion of the variant A2M polypeptide, or fragment thereof, can also be provided so as to maintain a stable concentration in the tissues as measured by blood levels.

Any composition described herein, including an autologous A2M composition, variant A2M polypeptide, and/or agent that prevents, slows or alters FAC formation can be administered in an aqueous solution by parenteral, intradiscal, intrafacet, intrathecal, epidural or joint injection. Any composition described herein can be administered directly into the area of the spine or joint that can be the source of pain in the subject. For example, when fibronectin-aggrecan complexes are detected in the epidural space, a variant A2M polypeptide that inhibits proteases or that prevents FAC formation can be administered by direct injection into the epidural space. Alternatively, variant A2M polypeptide that inhibits proteases or that prevents FAC formation can be administered by direct injection into the disc space, facet joint, or diarthroidial joint when fibronectin-aggrecan complexes are detected in these spaces. In some embodiments, aggrecan can include any naturally-occurring variants and splice variants of aggrecan, versican, brevican and neurocan, and any variants of aggrecan, versican, brevican and neurocan due to splicing by different cell types. In some embodiments, fibronectin can include any naturally occurring fibronectin variants including approximately 20 known splice variants associated with a disease or a disorder and fibronectin variants due to different splicing by different cell types.

A composition or formulation or agent can also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations can be lyophilized and redissolved or resuspended immediately before use. The formulation can be sterilized by, for example, filtration through a bacteria retaining filter, by incorporating sterilizing agents into the compositions, by irradiating the compositions, or by heating the compositions.

Any composition described herein, including an autologous A2M composition, variant A2M polypeptide, and/or agent that prevents, slows or alters FAC formation can also be administered in controlled release formulations. Controlled release polymeric devices can be made for long term release systemically following implantation of a polymeric device (rod, cylinder, film, or disc) or injection (microparticles). The matrix can be in the form of microparticles such as microspheres, where peptides are dispersed within a solid polymeric matrix or microcapsules, where the core can be of a different material than the polymeric shell, and the peptide can be dispersed or suspended in the core, which can be liquid or solid in nature. Unless specifically defined herein, microparticles, microspheres, and microcapsules are used interchangeably. Alternatively, the polymer can be cast as a thin slab or film, ranging from nanometers to four centimeters, a powder produced by grinding or other standard techniques, or even a gel such as a hydrogel.

Either non-biodegradable or biodegradable matrices can be used for delivery of any composition described herein, although biodegradable matrices are preferred. These can be natural or synthetic polymers, although synthetic polymers are preferred due to the better characterization of degradation and release profiles. The polymer can be selected based on the period over which release can be desired. In some cases linear release can be most useful, although in others a pulse release or "bulk release" can provide more effective results. The polymer can be in the form of a hydro gel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection which will typically deliver a dosage that can be much less than the dosage for treatment of an entire body or systemic delivery. These can be implanted or injected subcutaneously, into the muscle, fat, or swallowed.

Any of the compositions described herein, such as an autologous A2M composition, variant A2M polypeptide, and/or agent that prevents, slows or alters FAC formation, can be used in the treatment of a condition or a disease. For example, a condition or disease can be tendon condition, ligament condition, joint injury, spine injury, or inflammation, Alzheimer's disease, cerebral amyloid angiopathy, multiple sclerosis, congenital anti-thrombin deficiency, rheumatoid arthritis, growth of various tumors, coronary or limb ischemia, retinopathies, and regulation of immune response to tumors and viral infections. Others include Acne vulgaris, Alzheimer's disease, arthritis, asthma, acne, allergies and sensitivities, Autoimmune diseases, atherosclerosis, bronchitis, cancer, carditis, Crohn's disease, colitis, chronic pain, cirrhosis, Celiac disease, Chronic prostatitis, dermatitis diverticulitis, dementia, dermatitis, diabetes, dry eyes, edema, emphysema, eczema, fibromyalgia, gastroenteritis, gingivitis, Glomerulonephritis, Hypersensitivities, hepatitislupus erythematous, acid reflux/heartburn, heart disease, hepatitis, high blood pressure, insulin resistance, Interstitial cystitis, Inflammatory bowel diseases, irritable bowel syndrome (IBS), joint pain/arthritis/rheumatoid arthritis, metabolic syndrome (syndrome X), myositis, nephritis, obesity, osteopenia, osteoporosis, Pelvic inflammatory disease, Parkinson's disease, periodontal disease, polyarteritis, polychondritis, psoriasis, Reperfusion injury, Rheumatoid arthritis, Sarcoidosis, scleroderma, sinusitis, Sjögren's syndrome, spastic colon, systemic candidiasis, tendonitis, Transplant rejection, ulcerative colitcis, UTI's, Vasculitis, and vaginitis.

In some embodiments, an autologous A2M composition, variant A2M polypeptide and/or agent that prevents, slows or alters FAC formation that are not peptides or polypeptides, can be used in the treatment of cancer. For example, particularly by an autologous A2M composition, variant A2M polypeptide and/or agent that prevents, slows or alters FAC formation that are not peptides or polypeptides, can be administered directly into a tumor, such as a solid tumor, by injection or another suitable means.

An autoimmune disease can be a disease or disorder arising from and directed against an individual's own tissues or organs or a co-segregate or manifestation thereof or resulting condition therefrom. In many of these autoimmune and inflammatory disorders, a number of clinical and laboratory markers can exist, including, but not limited to, hypergammaglobulinemia, high levels of auto-antibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B-cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis.

Each of these pathways can participate to different degrees in the pathology of autoimmune diseases. "Autoimmune disease" can be an organ-specific disease (i.e., the immune response can be specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, SLE, RA, polymyositis, etc.). Preferred such diseases include autoimmune rheumatologic disorders (such as, for example, RA, Sjogren's syndrome, scleroderma, lupus such as SLE and lupus nephritis, polymyositis, dermatomyositis, cryoglobulinemia, antiphospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis be (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, MS, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, posttransfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, MS, Sjogren's syndrome, Graves' disease, IDDM, pernicious anemia, thyroiditis, and glomerulonephritis.

Any of the compositions described herein can be isolated from a blood sample and can be suitable for delivery into one or more joints or into the spine. One or more joints can be one or more synovial, diarthrodial, amphiarthrodial, synarthrodial, symphyseal, or cartilaginous joints. A joint can be a wrist, spinal, vertebral, cervical, shoulder, elbow, carpal, metacarpal, phalangeal, acromioclavicular, sternoclavicular, scapular, costal, sacroiliac, hip, knee, ankle tarsal, articulations of a foot or hand, axillary articulations, or a metatarsal.

A joint can refer to any diarthoidal (also called synovial) joints. A joint can be any joint containing bone, articular cartilage, a joint capsule, a synovial tissue lining, or lubricating synovial fluid inside a joint capsule. Cartilage components of a joint can be a chondral component. A component of the knee can be a meniscal component. In some embodiments, a synovial joint can be a shoulder or wrist or ankle or hip or elbow, or the small joints of the fingers or toes. A joint can be a normal joint or a control joint. A normal or control joint can be a joint that can be an insignificant source of pain to a subject. The level of pain that can be present in a normal joint typically may not impact the function or quality of the patient's life to the degree that the patient seeks medical care. A joint sample or sample from a joint can be a sample of tissue or fluid from a joint including, but not limited to, ex vivo and in vivo synovial fluid samples and joint or tissue lavages. A joint sample or sample from a joint can be a biological sample.

Any of the compositions described herein, such as an autologous A2M composition, variant A2M polypeptide, and/or agent that prevents, slows or alters FAC formation, can be used in the treatment of pain, such as pain associated with a condition or a disease of the current disclosure.

Pain can be radicular pain, radiculopathy, radiculopathic pain and sciatica and can be radiating pain of the extremities which emanates from the spinal root level or "radic" along the path of one or more irritated lumbar nerve roots. In the case of sciatica, this can originate from the L4, L5 and/or L6 or transitional vertebrae if present and/or sacroiliac spinal nerve roots, which make up the sciatic nerve. Radiating pain can be also possible from the high lumbar disc herniations in the l3, l2 or l1 regions or from any cervical nerve root in the case of a cervical disc herniation, cervical nerve root irritation or cervical disc degeneration. This pain can differ from pain resulting from a facet joint or other spinal structure, which can be classified as "referred" pain. Radiating pain can be also possible from the high lumbar disc herniations in the L3, L2 or L1 regions or cervical spine regions.

Pain can be discogenic pain and can be spinal related pain that generates from an intervertebral disc. The intervertebral disc suffers from reduced functionality in association with a loss of hydration from the nucleus pulposus. The reduction in functionality coincides with damage in the annulus fibrosus. This weakening can lead to anatomic lesions such as bulging, prolapsed, extruded, or sequestered disc. This weakening can also lead to possible biochemical lesions resulting from leakage of the disc contents that can manifest in back pain or aforementioned chemical radiculopathy.

Pain can be facet joint pain or facetogenic pain and can be pain generating from a facet joint, facet joints, or zygapophysial joints that are paired, true synovial joints endowed with cartilage, capsule, meniscoid, and synovial membrane. Spinal-pain or spine related pain includes, but is not limited to, discogenic, facetogenic and radiculopathic pain.

Pain can be acute pain and can be pain lasting up to six months, e.g., five months, four months, three months, two months, four weeks, three weeks, two weeks, one week, six days, five days, four days, three days, two days or one day or less. Chronic pain can be pain of duration longer than six months.

Any subject described herein can be treated with any of the compositions described herein. In some embodiments, a subject can be diagnosed with a condition or disease before or after being diagnosed with a condition or disease, such as by the methods described in U.S. Pat. No. 7,709,215 and U.S. Publication No.: US 2010/0098684A1. In some embodiments, a subject can be treated with any composition described herein, before or after being diagnosed with a condition or disease.

Subjects

Subjects can include any subject that presents with pain in the spine or joint. In some embodiments, a subject can be selected for the detection of A2M. Preferably the subject can be human. Subjects can be experiencing any pain, such as pain associated with the spine, including, but not limited to, discogenic, facetogenic or radiculopathic pain.

Subjects can be suspected of experiencing pain associated with any anatomic structure of a joint including, but not limited to, bone, articular cartilage, or the synovial tissue lining. Joints can include, but are not limited to, large diarthrodial (synovial) joints (e.g. knee, hip, shoulder), small diarthrodial (synovial) joints (e.g. elbow, wrist, ankle, zygoapophyseal or facet joints of spine), and amphiarthrodial joints (e.g. sacroiliac joint, sternoclavicular joint, tempomandibular joint ("TMJ")). Subjects can be experiencing acute joint-related pain, or can suffer from chronic joint-related pain. These can be related to degenerative disease (e.g. osteoarthritis), myofascial pain syndromes, inflammatory or crystalline arthritides, or other enthesopathies, tendon/ligament injuries or degeneration, or soft tissue pathology outside the musculoskeletal system.

In some embodiments, a subject may have been experiencing joint-related or spine-related pain for 30 or 25 weeks or less. In some embodiments, a subject may have been experiencing joint-related or spine-related pain for 20, 15, 10, 8, or 6 weeks, or less. Subjects can be of either sex and can be of any age. Subjects may be experiencing acute or chronic pain.

A subject can be human or non-human animal. For example, the animal can be a mammal, such as a mouse, rat, rabbit, cat, dog, monkey, horse or goat. A subject can be a virus, bacterium, *mycoplasma*, parasite, fungus, or plant, or animal, such as a mammal, for example, a human.

In some embodiments, a subject can be diagnosed as needing treatment with any of the compositions described herein. For example, a subject can be diagnosed as needing treatment with an A2M enriched sample or an agent that can prevent FAC formation.

Samples

Any of the autologous compositions described herein can be derived from a biological sample. Preferably, the autologous compositions described herein are isolated from a blood sample and suitable for delivery into one or more joints or into the spine. Biological samples can also include sections of tissues such as biopsy samples, frozen sections taken for histologic purposes, and lavage samples. A biological sample can be from a virus, bacterium, *mycoplasma*, parasite, fungus, or plant. A biological sample can be from an animal, such as a mammal, for example, a human, non-human primate, rodent, caprine, bovine, ovine, equine, canine, feline, mouse, rat, rabbit, horse or goat.

A biological sample can be a tissue sample or bodily fluid, such as a human bodily fluid. For example, the bodily fluid can be blood, sera, plasma, lavage, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocyl cavity fluid, or µMbilical cord blood. One or more of the biological sample(s) can comprise a cell, such as a stem cell, undifferentiated cell, differentiated cell, or cell from a diseased subject or subject with a specific condition. A biological sample can be blood, a cell, a population of cells, a quantity of tissue, fluid, or lavasate from a joint of a subject. A biological sample can comprise cells from cartilaginous tissue or can be free of cells. A biological sample can be substantially depleted of a common serum protein, such as, but not limited to, albumin or IgG. Depletion can comprise filtration, fractionation, or affinity purification.

Biological samples can be collected by any non-invasive means, such as, for example, by drawing blood from a subject, or using fine needle aspiration or needle biopsy. Alternatively, biological samples can be collected by an invasive method, including, for example, surgical biopsy.

A biological sample can comprise disease or condition specific proteins. A biological sample can be from a subject with a disease or condition or from a subject without a disease or condition. In some embodiments, a biological sample can be from a subject diagnosed with a disease or condition or from a subject not diagnosed with or without a disease or condition. A diagnosis can be made by any of the methods described herein. A biological sample can be from a subject at one time point and another biological sample can be from a subject at a later or earlier time point, wherein the subject can be the same or a different subject. For example, the subject may have a disease or condition or have been diagnosed with a disease or condition, and samples can be taken as the disease or condition progresses. A biological sample can be from a subject pretreatment and another biological sample can be from a subject at post treatment, wherein the subject can be the same or different subject. A biological sample can be from a subject non-responsive to treatment and another biological sample can be from a subject responsive to a treatment. Biological samples can be from the same or different species. One or more biological samples can be from the same subject or from a different subject from which one or more other biological samples were obtained.

A spine sample or sample from the spine can be a sample of tissue or fluid from the spine or added to the spine (lavage) including, but not limited to, spinal disc samples, epidural samples, and facet joint samples. A spine sample or sample from the spine can be a biological sample. Any number of methods known in the art can be used to retrieve sample from the spine for the detection of inflammation biomarkers. These methods include, but are not limited to, methods for obtaining samples from the epidural space, the intervertebral disc space and the facet joint space. Any number of methods known in the art can be used to obtain joint samples for the detection of inflammation biomarkers. Suitable methods include, but are not limited to, percutaneous or open aspiration, biopsy, or lavage.

The methods of the invention can be applied to the study of any type of biological samples allowing one or more biomarkers to be assayed. A biological sample can be a fresh or frozen sample collected from a subject, or archival samples with known diagnosis, treatment and/or outcome history.

The inventive methods can be performed on the biological sample itself without or with limited processing of the sample. The inventive methods can be performed at the single cell level (e.g., isolation of cells from the biological sample). Multiple biological samples can be taken from the same tissue/body part in order to obtain a representative sampling of the tissue.

Any of the method described herein can be performed on a protein extract prepared from the biological sample. The methods can also be performed on extracts containing one or more of: membrane proteins, nuclear proteins, and cytosolic proteins. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, and Invitrogen Corp. (Carlsbad, Calif.). After the protein extract has been obtained, the protein concentration of the extract can be standardized to a value being the same as that of the control sample in order to allow signals of the protein markers to be quantitated. Such standardization can be made using photometric or spectrometric methods or gel electrophoresis.

Any of the method described herein can be performed on nucleic acid molecules extracted from the biological sample. For example, RNA can be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA can then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

After extraction, mRNA can be amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions can be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-911910-18-2); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998), which are all incorporated by reference herein in their entireties.

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art can recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described as these can vary. It is also to be understood that the terminology used herein is for the purpose of describing particular embodiments only, and is not intended to limit the scope of the present disclosure which can be limited only by the appended claims.

Unless defined otherwise, all technical and scientific terms used herein have the meanings that would be commonly understood by one of skill in the art in the context of the present specification.

It should be noted that as used herein and in the appended claims, the singular forms "a," "an," and "the" include plural reference unless the context clearly dictates otherwise. Thus, for example, reference to "a nucleotide" includes a plurality of such nucleotides; reference to "the nucleotide" is a reference to one or more nucleotides and equivalents thereof known to those skilled in the art, and so forth.

The term "and/or" shall in the present context be understood to indicate that either or both of the items connected by it are involved. While preferred embodiments of the present disclosure have been shown and described herein, it can be obvious to those skilled in the art that such embodiments are provided by way of example only. Numerous variations, changes, and substitutions can now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Sequences:

SEQ ID NO 1: Wild-type A2M precursor protein - complete vector DNA sequence including tag sequences for easier purification.

```
   1 CTCATGACCA AAATCCCTTA ACGTGAGTTA CGCGCGCGTC GTTCCACTGA GCGTCAGACC
  61 CCGTAGAAAA GATCAAAGGA TCTTCTTGAG ATCCTTTTTT TCTGCGCGTA ATCTGCTGCT
 121 TGCAAACAAA AAAACCACCG CTACCAGCGG TGGTTTGTTT GCCGGATCAA GAGCTACCAA
 181 CTCTTTTTCC GAAGGTAACT GGCTTCAGCA GAGCGCAGAT ACCAAATACT GTTCTTCTAG
 241 TGTAGCCGTA GTTAGCCCAC CACTTCAAGA ACTCTGTAGC ACCGCCTACA TACCTCGCTC
 301 TGCTAATCCT GTTACCAGTG GCTGCTGCCA GTGGCGATAA GTCGTGTCTT ACCGGGTTGG
 361 ACTCAAGACG ATAGTTACCG GATAAGGCGC AGCGGTCGGG CTGAACGGGG GGTTCGTGCA
 421 CACAGCCCAG CTTGGAGCGA ACGACCTACA CCGAACTGAG ATACCTACAG CGTGAGCTAT
 481 GAGAAAGCGC CACGCTTCCC GAAGGGAGAA AGGCGGACAG GTATCCGGTA AGCGGCAGGG
 541 TCGGAACAGG AGAGCGCACG AGGGAGCTTC CAGGGGGAAA CGCCTGGTAT CTTTATAGTC
 601 CTGTCGGGTT TCGCCACCTC TGACTTGAGC GTCGATTTTT GTGATGCTCG TCAGGGGGGC
 661 GGAGCCTATG GAAAAACGCC AGCAACGCGG CCTTTTTACG GTTCCTGGCC TTTTGCTGGC
 721 CTTTTGCTCA CATGTTCTTT CCTGCGTTAT CCCCTGATTC TGTGGATAAC CGTATTACCG
 781 CCTTTGAGTG AGCTGATACC GCTCGCCGCA GCCGAACGAC CGAGCGCAGC GAGTCAGTGA
 841 GCGAGGAAGC GGAAGGCGAG AGTAGGGAAC TGCCAGGCAT CAAACTAAGC AGAAGGCCCC
 901 TGACGGATGG CCTTTTTGCG TTTCTACAAA CTCTTTCTGT GTTGTAAAAC GACGGCCAGT
 961 CTTAAGCTCG GCCCCCTGGG GCGGTTCTGA TAACGAGTAA TCGTTAATCC GCAAATAACG
1021 TAAAAACCCG CTTCGGCGGG TTTTTTTATG GGGGGAGTTT AGGGAAAGAG CATTTGTCAG
1081 AATATTTAAG GGCGCCTGTC ACTTTGCTTG ATATATGAGA ATTATTTAAC CTTATAAATG
1141 AGAAAAAAGC AACGCACTTT AAATAAGATA CGTTGCTTTT TCGATTGATG AACACCTATA
1201 ATTAAACTAT TCATCTATTA TTTATGATTT TTTGTATATA CAATATTTCT AGTTTGTTAA
1261 AGAGAATTAA GAAAATAAAT CTCGAAAATA ATAAAGGGAA AATCAGTTTT TGATATCAAA
1321 ATTATACATG TCAACGATAA TACAAAATAT AATACAAACT ATAAGATGTT ATCAGTATTT
1381 ATTATCATTT AGAATAAATT TTGTGTCGCC CTTAATTGTG AGCGGATAAC AATTACGAGC
1441 TTCATGCACA GTGGCGTTGA CATTGATTAT TGACTAGTTA TTAATAGTAA TCAATTACGG
1501 GGTCATTAGT TCATAGCCCA TATATGGAGT TCCGCGTTAC ATAACTTACG GTAAATGGCC
1561 CGCCTGGCTG ACCGCCCAAC GACCCCCGCC CATTGACGTC AATAATGACG TATGTTCCCA
1621 TAGTAACGCC AATAGGGACT TTCCATTGAC GTCAATGGGT GGAGTATTTA CGGTAAACTG
1681 CCCACTTGGC AGTACATCAA GTGTATCATA TGCCAAGTAC GCCCCCTATT GACGTCAATG
1741 ACGGTAAATG GCCCGCCTGG CATTATGCCC AGTACATGAC CTTATGGGAC TTTCCTACTT
1801 GGCAGTACAT CTACGTATTA GTCATCGCTA TTACCATGGT GATGCGGTTT TGGCAGTACA
1861 TCAATGGGCG TGGATAGCGG TTTGACTCAC GGGGATTTCC AAGTCTCCAC CCCATTGACG
1921 TCAATGGGAG TTTGTTTTGG CACCAAAATC AACGGGACTT TCCAAAATGT CGTAACAACT
1981 CCGCCCCATT GACGCAAATG GGCGGTAGGC GTGTACGGTG GGAGGTCTAT ATAAGCAGAG
2041 CTCTCTGGCT AACTAGAGAA CCCACTGCTT ACTGGCTTAT CGAAATTAAT ACGACTCACT
2101 ATAGGGGTAC CTGCCACCAT GGGGAAAAAC AAACTGCTGC ATCCAAGCCT GGTCCTGCTG
2161 CTGCTGGTTC TGCTGCCTAC TGACGCCTCT GTGAGCGGAA AGCCCCAGTA TATGGTTCTG
2221 GTCCCGTCCC TGCTGCACAC CGAGACCACA GAAAAGGGT GCGTGCTGCT GTCTTACCTG
2281 AATGAAACAG TGACTGTTAG TGCCTCACTG GAGAGTGTGC GCGGAAATCG TTCACTGTTC
2341 ACCGATCTGG AGGCGGAAAA CGATGTGCTG CATTGCGTCG CATTTGCTGT GCCAAAAAGC
2401 TCCTCTAATG AAGAAGTGAT GTTCCTGACC GTCCAGGTGA AGGGCCCTAC ACAGGAATTC
2461 AAAAAACGCA CTACCGTTAT GGTCAAAAAC GAGGATAGCC TGGTGTTTGT TCAGACAGAC
2521 AAATCCATCT ATAAGCCTGG TCAGACTGTG AAGTTCCGGG TGGTTAGCAT GGATGAAAAT
2581 TTTCACCCCC TGAACGAGCT GATTCCACTG GTGTACATCC AGGACCCTAA AGGCAACCGC
2641 ATCGCCCAGT GGCAGTCTTT CCAGCTGGAA GGCGGTCTGA AGCAGTTTAG TTTCCCTCTG
2701 AGTTCAGAGC CGTTTCAGGG TTCTTATAAA GTCGTGGTTC AGAAAAAGAG TGGGGGACGT
2761 ACTGAACATC CTTTTACCGT TGAAGAGTTC GTCCTGCCGA AATTTGAGGT CCAGGTGACG
2821 GTTCCCAAGA TTATCACAAT TCTGGAAGAG GAAATGAACG TGAGCGTGTG CGGACTGTAT
2881 ACCTACGGCA AACCAGTGCC TGGTCACGTT ACAGTCAGTA TCTGCCGTAA GTACTCAGAT
2941 GCAAGCGACT GTCATGGCGA AGATTCACAG GCTTTTTGCG AGAAGTTCAG CGGCCAGCTG
3001 AACTCCCACG GTTGCTTCTA TCAGCAGGTG AAAACCAAGT TTTTCAGCT GAAACGGAAG
3061 GAGTACGAAA TGAAACTGCA TACAGAAGCC CAGATTCAGG AAGAAGGCAC CGTCGTGGAA
3121 CTGACTGGTC GTCAGAGCTC CGAGATTACC CGGACAATCA CTAAACTGAG CTTCGTGAAG
3181 GTTGATTCCC ACTTTCGGCA GGGGATTCCC TTTTTCGGAC AGGTGCGCCT GGTTGACGGG
3241 AAAGGAGTTC CGATCCCCAA CAAAGTGATC TTTATTCGCG GCAATGAAGC CAACTATTAC
3301 AGCAACGCGA CAACTGATGA GCATGGGCTG GTGCAGTTCA GTATCAATAC CACAAACGTG
3361 ATGGGAACCT CACTGACAGT CCGCGTGAAT TATAAAGACC GTTCACCGTG TTATGGCTAC
3421 CAGTGGGTGA GCGAGGAACA CGAGGAAGCC CACCATACCG CGTACCTGGT TTTCAGCCCC
3481 TCCAAATCTT TTGTCCATCT GGAACCTATG TCTCACGAGC TGCCGTGCGG CCATACCCAG
3541 ACAGTGCAGG CACATTATAT TCTGAACGGC GGCACCCTGC TGGGTCTGAA AAAGCTGAGC
3601 TTTTATTACC TGATTATGGC TAAGGGGGGA ATCGTCCGCA CTGGCACCCA CGGTCTGCTG
3661 GTTAAACAGG AAGATATGAA GGGCCATTTC AGTATTTCAA TCCCTGTTAA AGCGACATT
3721 GCTCCGGTCG CCCGTCTGCT GATCTATGCC GTGCTGCCAA CCGGCGATGT TATCGGTGAC
3781 TCCGCCAAAT ACGATGTGGA GAATTGTCTG GCGAACAAGG TTGACCTGAG CTTTTCCCCC
3841 TCTCAGAGTC TGCCAGCGTC TCATGCACAT CTGCGTGTGA CCGCAGCCCC TCAGAGCGTT
3901 TGCGCTCTGC GTGCAGTGGA TCAGTCCGTG CTGCTGATGA AGCCAGACGC AGAACTGTCT
3961 GCTAGCAGCG TGTATAATCT GCTGCCTGAG AAAGATCTGA CCGGGTTCCC AGGACCTCTG
4021 AACGATCAGG ATGACGAAGA CTGTATTAAT CGCCACAACG TGTATATTAA TGGGATCACA
4081 TACACTCCGG TTTCAAGCAC CAACGAAAAA GATATGTACA GCTTCCTGGA GGACATGGGT
4141 CTGAAAGCGT TTACCAATTC CAAGATCCGG AAACCCAAGA TGTGCCCACA GCTGCAGCAG
4201 TATGAAATGC ACGGACCTGA GGGTCTGCGT GTGGGCTTTT ACGAATCTGA TGTGATGGGA
4261 CGTGGTCATG CACGTCTGGT TCATGTCGAG GAACCACACA CCGAAACAGT GCGTAAATAC
4321 TTCCCTGAGA CCTGGATTTG GGACCTGGTT GTGGTGAACT CCGCGGGTGT GGCAGAAGTG
4381 GGTGTTACCG TCCCGGATAC TATTACCGAA TGGAAGCAG GTGCCTTCTG TCTGTCTGAG
4441 GATGCAGGGC TGGGAATCTC CTCTACAGCC TCTCTGCGCG CGTTTCAGCC CTTTTTCGTC
4501 GAACTGACTA TGCCATATAG CGTGATTCGT GGCGAGGCAT TCACTCTGAA AGCTACCGTG
4561 CTGAATTACC TGCCCAAGTG CATCCGCGTG AGCGTGCAGC TGGAAGCTAG TCCCGCCTTT
```

```
                                    Sequences:

4621 CTGGCGGTCC CAGTGGAGAA GGAACAGGCA CCGCACTGCA TTTGTGCTAA CGGCCGGCAG
4681 ACTGTTTCCT GGGCCGTCAC CCCCAAATCT CTGGGTAATG TGAACTTCAC CGTTTCAGCA
4741 GAGGCTCTGG AAAGCCAGGA GCTGTGCGGC ACCGAAGTCC CATCCGTGCC TGAGCATGGT
4801 CGCAAAGATA CAGTCATCAA GCCTCTGCTG GTTAACCGG AAGGCCTGGA GAAGGAAACT
4861 ACCTTTAATT CTCTGCTGTG CCCAAGTGGC GGTGAAGTGT CCGAGGAACT GTCTCTGAAA
4921 CTGCCGCCCA ACGTGGTCGA GGAATCTGCC CGTGCGTCAG TTAGCGTCCT GGGGGATATT
4981 CTGGGAAGTG CCATGCAGAA TACCCAGAAC CTGCTGCAGA TGCCGTATGG CTGTGGCGAG
5041 CAGAATATGG TTCTGTTTGC GCCCAACATC TATGTCCTGG ATTACCTGAA TGAAACACAG
5101 CAGCTGACTC CTGAAATCAA AGCAAGGCA ATCGGGTATC TGAATACCGG ATACCAGCGG
5161 CAGCTGAACT ATAAGCACTA CGACGGCTCC TATTCTACCT TCGGCGAACG GTACGGTCGC
5221 AATCAGGGGA ACACTTGGCT GACCGCCTTT GTGCTGAAAA CCTTTGCCCA GGCTCGCGCC
5281 TATATCTTTA TTGATGAGGC CCATATTACA CAGGCGCTGA TCTGGCTGTC ACAGCGCCAG
5341 AAGGACAACG GGTGTTTCCG TAGTTCAGGA AGCCTGCTGA ACAATGCCAT CAAAGGCGGC
5401 GTCGAGGATG AAGTGACACT GAGCGCATAC ATTACTATCG CTCTGCTGGA AATCCCTCTG
5461 ACAGTGACTC ACCCGGTGGT TCGCAATGCT CTGTTTTGCC TGGAAAGTGC ATGGAAAACA
5521 GCTCAGGAAG GCGATCACGG ATCACACGTG TATACTAAGG CACTGCTGGC GTACGCATTC
5581 GCTCTGGCCG GCAACCAGGA TAAACGTAAA GAAGTGCTGA AATCACTGAA TGAGGAAGCA
5641 GTTAAAAAGG ACAACAGCGT CCACTGGGAA CGGCCGCAGA AACCCAAGGC TCCAGTGGGT
5701 CACTTTTATG AGCCTCAGGC ACCGAGTGCT GAGGTGGAAA TGACCTCATA TGTTCTGCTG
5761 GCATACCTGA CCGCACAGCC TGCCCCCACA TCAGAAGATC TGACAAGCGC CACTAATATT
5821 GTGAAATGGA TCACCAAGCA GCAGAACGCG CAGGGCGGTT TTAGCTCCAC CCAGGACACA
5881 GTCGTGGCAC TGCACGCTCT GTCTAAATAT GGGGCAGCTA CCTTCACACG CACTGGAAAG
5941 GCCGCGCAAG TGACTATTCA GTCTAGTGGC ACCTTTTCAA GCAAGTTCCA GGTGGATAAC
6001 AATAACCGTC TGCTGCTGCA GCAGGTGTCC CTGCCCGAAC TGCCAGGCGA GTACTCTATG
6061 AAAGTCACTG GGGAAGGATG CGTGTATCTG CAGACCTCCC TGAAATACAA TATTCTGCCC
6121 GAGAAAGAAG AATTTCCATT CGCACTGGGC GTGCAGACCC TGCCTCAGAC ATGCGATGAA
6181 CCGAAGGCTC ATACTTCTTT TCAGATCAGT CTGTCAGTGA GCTATACCGG GTCCCGCTCT
6241 GCCAGTAACA TGGCGATTGT GGATGTGAAA ATGGTGAGTG GATTCATCCC TCTGAAACCG
6301 ACTGTGAAGA TGCTGGAACG GAGTAATCAC GTTTCACGCA CCGAGGTCTC CTCTAACCAT
6361 GTGCTGATCT ACCTGGATAA AGTGTCCAAT CAGACACTGT CTCTGTTTTT CACTGTGCTG
6421 CAGGATGTCC CCGTGCGTGA CCTGAAACCA GCCATTGTTA AGGTCTATGA TTATTACGAA
6481 ACCGACGAGT TCGCGATCGC AGAATACAAC GCGCCGTGCA GCAAAGACCT GGGGAATGCT
6541 GACTACAAGG ACGACGACGA CAAGGGGGCA AGCCACCACC ATCACCATCA CTAAGGATCC
6601 AAAATCAGCC TCGACTGTGC CTTCTAGTTG CCAGCCATCT GTTGTTTGCC CCTCCCCCGT
6661 GCCTTCCTTG ACCCTGGAAG GTGCCACTCC CACTGTCCTT TCCTAATAAA ATGAGGAAAT
6721 TGCATCACAA CACTCAACCC TATCTCGGTC TATTCTTTTG ATTTATAAGG GATTTTGCCG
6781 ATTTCGGCCT ATTGGTTAAA AAATGAGCTG ATTTAACAAA AATTTAACGC GAATTAATTC
6841 TGTGGAATGT GTGTCAGTTA GGGTGTGGAA AGTCCCCAGG CTCCCCAGCA GGCAGAAGTA
6901 TGCAAAGCAT GCATCTCAAT TAGTCAGCAA CCAGGTGTGG AAAGTCCCCA GGCTCCCCAG
6961 CAGGCAGAAG TATGCAAAGC ATGCATCTCA ATTAGTCAGC AACCATAGTC CCGCCCCTAA
7021 CTCCGCCCAT CCCGCCCCTA ACTCCGCCCA GTTCCGCCCA TTCTCCGCCC CATGGCTGAC
7081 TAATTTTTTT TATTTATGCA GAGGCCGAGG CCGCCTCTGC CTCTGAGCTA TTCCAGAAGT
7141 AGTGAGGAGG CTTTTTTGGA GGCCTAGGCT TTTGCAAAAA GCTCCCGGGA GCTTGTATAT
7201 CCATTTTCGG ATCTGATCAG CACGTGTTGA CAATTAATCA TCGGCATAGT ATATCGGCAT
7261 AGTATAATAC GACAAGGTGA GGAACTAAAC CATGGCCAAG CCTTTGTCTC AAGAAGAATC
7321 CACCCTCATT GAAAGAGCAA CGGCTACAAT CAACAGCATC CCCATCTCTG AAGACTACAG
7381 CGTCGCCAGC GCAGCTCTCT CTAGCGACGG CCGCATCTTC ACTGGTGTCA ATGTATATCA
7441 TTTTACTGGG GGACCTTGTG CAGAACTCGT GGTGCTGGGC ACTGCTGCTG CTGCGGCAGC
7501 TGGCAACCTG ACTTGTATCG TCGCGATCGG AAATGAGAAC AGGGGCATCT TGAGCCCCTG
7561 CGGACGGTGC CGACAGGTGC TTCTCGATCT GCATCCTGGG ATCAAAGCCA TAGTGAAGGA
7621 CAGTGATGGA CAGCCGACGG CAGTTGGGAT TCGTGAATTG CTGCCCTCTG GTTATGTGTG
7681 GGAGGGCTAA CACGTGCTAC GAGATTTCGA TTCCACCGCC GCCTTCTATG AAAGGTTGGG
7741 CTTCGGAATC GTTTTCCGGG ACGCCGGCTG GATGATCCTC CAGCGCGGGG ATCTCATGCT
7801 GGAGTTCTTC GCCCACCCCA ACTTGTTTAT TGCAGCTTAT AATGGTTACA AATAAAGCAA
7861 TAGCATCACA AATTTCACAA ATAAAGCATT TTTTTCACTG CATTCTAGTT GTGGTTTGTC
7921 CAAACTCATC AATGTATCTT ATCATGTCTG TATACCGTCG ACCTCTAGCT AGAGCTTGGC
7981 GTAATCATGG TCATTACCAA TGCTTAATCA GTGAGGCACC TATCTCAGCG ATCTGTCTAT
8041 TTCGTTCATC CATAGTTGCC TGACTCCCCG TCGTGTAGAT AACTACGATA CGGGAGGGCT
8101 TACCATCTGG CCCCAGCGCT GCGATGATAC CGCGAGAACC ACGCTCACCG GCTCCGGATT
8161 TATCAGCAAT AAACCAGCCA GCCGGAAGGG CCGAGCGCAG AAGTGGTCCT GCAACTTTAT
8221 CCGCCTCCAT CCAGTCTATT AATTGTTGCC GGGAAGCTAG AGTAAGTAGT TCGCCAGTTA
8281 ATAGTTTGCG CAACGTTGTT GCCATCGCTA CAGGCATCGT GGTGTCACGC TCGTCGTTTG
8341 GTATGGCTTC ATTCAGCTCC GGTTCCCAAC GATCAAGGCG AGTTACATGA TCCCCCATGT
8401 TGTGCAAAAA AGCGGTTAGC TCCTTCGGTC CTCCGATCGT TGTCAGAAGT AAGTTGGCCG
8461 CAGTGTTATC ACTCATGGTT ATGGCAGCAC TGCATAATTC TCTTACTGTC ATGCCATCCG
8521 TAAGATGCTT TTCTGTGACT GGTGAGTACT CAACCAAGTC ATTCTGAGAA TAGTGTATGC
8581 GGCGACCGAG TTGCTCTTGC CCGGCGTCAA TACGGGATAA TACCGCGCCA CATAGCAGAA
8641 CTTTAAAAGT GCTCATCATT GGAAAACGTT CTTCGGGGCG AAAACTCTCA AGGATCTTAC
8701 CGCTGTTGAG ATCCAGTTCG ATGTAACCCA CTCGTGCACC CAACTGATCT TCAGCATCTT
8761 TTACTTTCAC CAGCGTTTCT GGGTGAGCAA AAACAGGAAG GCAAAATGCC GCAAAAAAGG
8821 GAATAAGGGC GACACGGAAA TGTTGAATAC TCATATTCTT CCTTTTTCAA TATTATTGAA
8881 GCATTTATCA GGGTTATTGT CTCATGAGCG GATACATATT TGAATGTATT TAGAAAAATA
8941 AACAAATAGG GGTCAGTGTT ACAACCAATT AACCAATTCT GAACATTATC GCG

SEQ ID NO 2: Complete vector DNA sequence of the of the acceptor mutant.
   1 CTCATGACCA AATCCCTTA ACGTGAGTTA CGCGCGCGTC GTTCCACTGA GCGTCAGACC
  61 CCGTAGAAAA GATCAAAGGA TCTTCTTGAG ATCCTTTTTT TCTGCGCGTA ATCTGCTGCT
```

| | |
|---|---|
| | Sequences: |

```
 121 TGCAAACAAA AAAACCACCG CTACCAGCGG TGGTTTGTTT GCCGGATCAA GAGCTACCAA
 181 CTCTTTTTCC GAAGGTAACT GGCTTCAGCA GAGCGCAGAT ACCAAATACT GTTCTTCTAG
 241 TGTAGCCGTA GTTAGCCCAC CACTTCAAGA ACTCTGTAGC ACCGCCTACA TACCTCGCTC
 301 TGCTAATCCT GTTACCAGTG GCTGCTGCCA GTGGCGATAA GTCGTGTCTT ACCGGGTTGG
 361 ACTCAAGACG ATAGTTACCG GATAAGGCGC AGCGGTCGGG CTGAACGGGG GGTTCGTGCA
 421 CACAGCCCAG CTTGGAGCGA ACGACCTACA CCGAACTGAG ATACCTACAG CGTGAGCTAT
 481 GAGAAAGCGC CACGCTTCCC GAAGGGAGAA AGGCGGACAG GTATCCGGTA AGCGGCAGGG
 541 TCGGAACAGG AGAGCGCACG AGGGAGCTTC CAGGGGGAAA CGCCTGGTAT CTTTATAGTC
 601 CTGTCGGGTT TCGCCACCTC TGACTTGAGC GTCGATTTTT GTGATGCTCG TCAGGGGGGC
 661 GGAGCCTATG GAAAACGCC AGCAACGCGG CCTTTTTACG GTTCCTGGCC TTTTGCTGGC
 721 CTTTTGCTCA CATGTTCTTT CCTGCGTTAT CCCCTGATTC TGTGGATAAC CGTATTACCG
 781 CCTTTGAGTG AGCTGATACC GCTCGCCGCA GCCGAACGAC CGAGCGCAGC GAGTCAGTGA
 841 GCGAGGAAGC GGAAGGCGAG AGTAGGGAAC TGCCAGGCAT CAAACTAAGC AGAAGGCCCC
 901 TGACGGATGG CCTTTTTGCG TTTCTACAAA CTCTTTCTGT GTTGTAAAAC GACGGCCAGT
 961 CTTAAGCTCG GGCCCCTGG GCGGTTCTGA TAACGAGTAA TCGTTAATCC GCAAATAACG
1021 TAAAAACCCG CTTCGGCGGG TTTTTTATG GGGGGAGTTT AGGGAAAGAG CATTTGTCAG
1081 AATATTTAAG GGCGCCTGTC ACTTTGCTTG ATATATGAGA ATTATTTAAC CTTATAAATG
1141 AGAAAAAAGC AACGCACTTT AAATAAGATA CGTTGCTTTT TCGATTGATG AACACCTATA
1201 ATTAAACTAT TCATCTATTA TTTATGATTT TTTGTATATA CAATATTTCT AGTTTGTTAA
1261 AGAGAATTAA GAAAATAAAT CTCGAAAATA ATAAAGGGAA AATCAGTTTT TGATATCAAA
1321 ATTATACATG TCAACGATAA TACAAATAT AATACAAACT ATAAGATGTT ATCAGTATTT
1381 ATTATCATTT AGAATAAATT TTGTGTCGCC CTTAATTGTG AGCGGATAAC AATTACGAGC
1441 TTCATGCACA GTGGCGTTGA CATTGATTAT TGACTAGTTA TTAATAGTAA TCAATTACGG
1501 GGTCATTAGT TCATAGCCCA TATATGGAGT TCCGCGTTAC ATAACTTACG GTAAATGCCC
1561 CGCCTGGCTG ACCGCCCAAC GACCCCCGCC CATTGACGTC AATAATGACG TATGTTCCCA
1621 TAGTAACGCC AATAGGGACT TTCCATTGAC GTCAATGGGT GGAGTATTTA CGGTAAACTG
1681 CCCACTTGGC AGTACATCAA GTGTATCATA TGCCAAGTAC GCCCCCTATT GACGTCAATG
1741 ACGGTAAATG GCCCGCCTGG CATTATGCCC AGTACATGAC CTTATGGGAC TTTCCTACTT
1801 GGCAGTACAT CTACGTATTA GTCATCGCTA TTACCATGGT GATGCGGTTT TGGCAGTACA
1861 TCAATGGGCG TGGATAGCGG TTTGACTCAC GGGGATTTCC AAGTCTCCAC CCCATTGACG
1921 TCAATGGGAG TTTGTTTTGG CACCAAAATC AACGGGACTT TCCAAAATGT CGTAACAACT
1981 CCGCCCCATT GACGCAAATG GGCGGTAGGC GTGTACGGTG GGAGGTCTAT ATAAGCAGAG
2041 CTCTCTGGCT AACTAGAGAA CCCACTGCTT ACTGGCTTAT CGAAATTAAT ACGACTCACT
2101 ATAGGGGTAC CTGCCACCAT GGGGAAAAAC AAACTGCTGC ATCCAAGCCT GGTCCTGCTG
2161 CTGCTGGTTC TGCTGCCTAC TGACGCCTCT GTGAGCGGAA AGCCCCAGTA TATGGTTCTG
2221 GTCCCGTCCC TGCTGCACAC CGAGACCACA GAAAAGGCGT GCGTGCTGCT GTCTTACCTG
2281 AATGAAACAG TGACTGTTAG TGCCTCACTG GAGAGTGTGC GCGGAAATCG TTCACTGTTC
2341 ACCGATCTGG AGGCGGAAAA CGATGTGCTG CATTGCGTCG CATTTGCTGT GCCAAAAAGC
2401 TCCTCTAATG AAGAAGTGAT GTTCCTGACC GTCCAGGTGA AGGGCCCTAC ACAGGAATTC
2461 AAAAAACGCA CTACCGTTAT GGTCAAAAAC GAGGATAGCC TGGTGTTTGT TCAGACAGAC
2521 AAATCCATCT ATAAGCCTGG TCAGACTGTG AAGTTCCGGG TGGTTAGCAT GGATGAAAAT
2581 TTTCACCCCC TGAACGAGCT GATTCCACTG GTGTACATCC AGGACCCTAA AGGCAACCGC
2641 ATCGCCCAGT GGCAGTCTTT CCAGCTGGAA GGCGGTCTGA AGCAGTTTAG TTTCCCTCTG
2701 AGTTCAGAGC CGTTTCAGGG TTCTTATAAA GTCGTGGTTC AGAAAAAGAG TGGGGGACGT
2761 ACTGAACATC CTTTTACCGT TGAAGAGTTC GTCCTGCCGA AATTTGAGGT CCAGGTGACA
2821 GTTCCCAAGA TTATCACAAT TCTGGAAGAG GAAATGAACG TGAGCGTGTG CGGACTGTAT
2881 ACCTACGGCA AACCAGTGCC TGGTCACGTT ACAGTCAGTA TCTGCCGTAA GTACTCAGAT
2941 GCAAGCGACT GTCATGGCGA AGATTCACAG CTTTTTGCG AGAAGTTCAG CGGCCAGCTG
3001 AACTCCCACG GTTGCTTCTA TCAGCAGGTG AAAACCAGG TTTTTCAGCT GAAACGGAAG
3061 GAGTACGAAA TGAAACTGCA TACAGAAGCC CAGATTCAGG AAGAAGGCAC CGTCGTGGAA
3121 CTGACTGGTC GTCAGAGCTC CGAGATTACC CGGACAATCA CTAAACTGAG CTTCGTGAAG
3181 GTTGATTCCC ACTTTCGGCA GGGGATTCCC TTTTTCGGAC AGGTGCGCCT GGTTGACGGG
3241 AAAGGAGTTC CGATCCCCAA CAAAGTGATC TTTATTCGGC GCAATGAAGC CAACTATTAC
3301 AGCAACGCGA CAACTGATGA GCATGGGCTG GTGCAGTTCA GTATCAATAC CACAAACGTG
3361 ATGGGAACCT CACTGACAGT CCGCGTGAAT TATAAAGACC GTTCACCGTG TTATGGCTAC
3421 CAGTGGGTGA GCGAGGAACA CGAGGAAGCC CACCATACCG CGTACCTGGT TTTCAGCCCC
3481 TCCAAATCTT TTGTCCATCT GGAACCTATG TCTCACGAGC TGCCGTGCGG CCATACCCAG
3541 ACAGTGCAGG CACATTATAT TCTGAACGGC GGCACCCTGC TGGGTCTGAA AAAGCTGAGC
3601 TTTTATTACC TGATTATGGC TAAGGGGGGA ATCGTCCGCA CTGGCACCCA CGGTCTGCTG
3661 GTTAAACAGG AAGATATGAA GGGCCATTTC AGTATTTCAA TCCCTGTTAA AAGCGACATT
3721 GCTCCGGTCG CCCGTCTGCT GATCTATGCC GTGCTGCCAA CCGGCGATGT TATCGGTGAC
3781 TCCGCCAAAT ACGATGTGGA GAATTGTCTG GCGAACAAGG TTGACCTGAG CTTTTCCCCC
3841 TCTCAGAGTC TGCCAGCGTC TCATGCACAT CTGCGTGTGA CCGCAGCCCC TCAGAGCGTT
3901 TGCGCTCTGC GTGCAGTGGA TCAGTCCGTG CTGCTGATGA AGCCAGACGC AGAACTGTCT
3961 GCTAGCAGCG TGTATAATCT GCTGCCTGAG AAAGATCTGA CCGGGTTCCC AGGACCTCTG
4021 AACGATCAGG ATGACGAAGA CTGTATTAAT CGCCACACAG TGTATATTAA TGGGATCACA
4081 TACACTCCGG TTTCAAGCAC CAACGAAAAA GATATGTACA GCTTCCTGGA GGACATGGGT
4141 CTGAAAGCGT TTACCAATTC CAAGATCCGG AAACCCAAG ATGTGCCCAC AGCTCGAGCA
4201 GTATGAAATG CACGGACCTG AGGGTCTGCG TGTGGGCTTT TACGAATCTG ATGTGATGGG
4261 ACGTGGTCAT GCACGTCTGG TTCATGTCGA GGAACCACAC ACCGAAAAGC TTCGTAAATA
4321 CTTCCCTGAG ACCTGGATTT GGGACCTGGT TGTGGTGAAC TCCGCGGGTG TGGCAGAAGT
4381 GGGTGTTACC GTCCCGGATA CTATTACCGA ATGGAAAGCA GGTGCCTTCT GTCTGTCTGA
4441 GGATGCAGGG CTGGGAATCT CCTCTACAGC CTCTCTGCGC GCGTTTCAGC CCTTTTTCGT
4501 CGAACTGACT ATGCCATATA GCGTGATTCG TGGCGAGGCA TTCACTCTGA AGCTACCGT
4561 GCTGAATTAC CTGCCCAAGT GCATCCGCGT GAGCGTGCAG CTGGAAGCTA GTCCCGCCTT
4621 TCTGGCGGTC CCAGTGGAGA AGGAACAGGC ACCGCACTGG ATTTGTGCTA ACGGCCGGCA
4681 GACTGTTTCC TGGGCCGTCA CCCCCAAATC TCTGGGTAAT GTGAACTTCA CCGTTTCAGC
```

-continued

Sequences:

```
4741 AGAGGCTCTG GAAAGCCAGG AGCTGTGCGG CACCGAAGTC CCATCCGTGC CTGAGCATGG
4801 TCGCAAAGAT ACAGTCATCA AGCCTCTGCT GGTTGAACCG GAAGGCCTGG AGAAGGAAAC
4861 TACCTTTAAT TCTCTGCTGT GCCCAAGTGG CGGTGAAGTG TCCGAGGAAC TGTCTCTGAA
4921 ACTGCCGCCC AACGTGGTCG AGGAATCTGC CCGTGCGTCA GTTAGCGTCC TGGGGGATAT
4981 TCTGGGAAGT GCCATGCAGA ATACCCAGAA CCTGCTGCAG ATGCCGTATG CTGTGGCGA
5041 GCAGAATATG GTTCTGTTTG CGCCCAACAT CTATGTCCTG GATTACCTGA ATGAAACACA
5101 GCAGCTGACT CCTGAAATCA AAAGCAAGGC AATCGGGTAT CTGAATACCG GATACCAGCG
5161 GCAGCTGAAC TATAAGCACT ACGACGGCTC CTATTCTACC TTCGGCGAAC GGTACGGTCG
5221 CAATCAGGGG AACACTTGGC TGACCGCCTT TGTGCTGAAA ACCTTTGCCC AGGCTCGCGC
5281 CTATATCTTT ATTGATGAGG CCCATATTAC ACAGGCGCTG ATCTGGCTGT CACAGCGCCA
5341 GAAGGACAAC GGGTGTTTCC GTAGTTCAGG AAGCCTGCTG AACAATGCCA TCAAAGGCGG
5401 CGTCGAGGAT GAAGTGACAC TGAGCGCATA CATTACTATC GCTCTGCTGG AAATCCCTCT
5461 GACAGTGACT CACCCGGTGG TTCGCAATGC TCTGTTTTGC CTGGAAAGTG CATGGAAAAC
5521 AGCTCAGGAA GGCGATCACG GATCACACGT GTATACTAAG GCACTGCTGG CGTACGCATT
5581 CGCTCTGGCC GGCAACCAGG ATAAACGTAA AGAAGTGCTG AAATCACTGA ATGAGGAAGC
5641 AGTTAAAAAG GACAACAGCG TCCACTGGGA ACGGCCGCAG AAACCCAAGG CTCCAGTGGG
5701 TCACTTTTAT GAGCCTCAGG CACCGAGTGC TGAGGTGGAA ATGACCTCAT ATGTTCTGCT
5761 GGCATACCTG ACCGCACAGC CTGCCCCCAC ATCAGAAGAT CTGACAAGCG CCACTAATAT
5821 TGTGAAATGG ATCACCAAGC AGCAGAACGC GCAGGGCGGT TTTAGCTCCA CCCAGGACAC
5881 AGTCGTGGCA CTGCACGCTC TGTCTAAATA TGGGGCAGCT ACCTTCACGC GCACTGGAAA
5941 GGCCGCGCAA GTGACTATTC AGTCTAGTGG CACCTTTTCA AGCAAGTTCC AGGTGGATAA
6001 CAATAACCGT CTGCTGCTGC AGCAGGTGTC CCTGCCCGAA CTGCCAGGCG AGTACTCTAT
6061 GAAAGTCACT GGGGAAGGAT GCGTGTATCT GCAGACCTCC CTGAAATACA ATATTCTGCC
6121 CGAGAAAGAA GAATTTCCAT TCGCACTGGG CGTGCAGACC CTGCCTCAGA CATGCGATGA
6181 ACCGAAGGCT CATACTTCTT TTCAGATCAG TCTGTCAGTG AGCTATACCG GGTCCCGCTC
6241 TGCCAGTAAC ATGGCGATTG TGGATGTGAA ATGGTGAGT GGATTCATCC CTCTGAAACC
6301 GACTGTGAAG ATGCTGGAAC GGAGTAATCA CGTTTCACGC ACCGAGGTCT CCTCTAACCA
6361 TGTGCTGATC TACCTGGATA AAGTGTCCAA TCAGACACTG TCTCTGTTTT TCACTGTGCT
6421 GCAGGATGTC CCCGTGCGTG ACCTGAAACC AGCCATTGTT AAGGTCTATG ATTATTACGA
6481 AACCGACGAG TTCGCGATCG CAGAATACAA CGCGCCGTGC AGCAAAGACC TGGGGAATGC
6541 TGACTACAAG GACGACGACG ACAAGGGGGC AAGCCACCAC CATCACCATC ACTAAGGATC
6601 CAAAATCAGC CTCGACTGTG CCTTCTAGTT GCCAGCCATC TGTTGTTTGC CCCTCCCCCG
6661 TGCCTTCCTT GACCCTGGAA GGTGCCACTC CCACTGTCCT TTCCTAATAA AATGAGGAAA
6721 TTGCATCACA ACACTCAACC CTATCTCGGT CTATTCTTTT GATTTATAAG GGATTTTGCC
6781 GATTTCGGCC TATTGGTTAA AAAATGAGCT GATTTAACAA AAATTTAACG CGAATTAATT
6841 CTGTGGAATG TGTGTCAGTT AGGGTGTGGA AAGTCCCCAG GCTCCCCAGC AGGCAGAAGT
6901 ATGCAAAGCA TGCATCTCAA TTAGTCAGCA ACCAGGTGTG GAAAGTCCCC AGGCTCCCCA
6961 GCAGGCAGAA GTATGCAAAG CATGCATCTC AATTAGTCAG CAACCATAGT CCCGCCCCTA
7021 ACTCCGCCCA TCCCGCCCCT AACTCCGCCC AGTTCCGCCC ATTCTCCGCC CCATGGCTGA
7081 CTAATTTTTT TTATTTATGC AGAGGCCGAG GCCGCCTCTG CCTCTGAGCT ATTCCAGAAG
7141 TAGTGAGGAG GCTTTTTTGG AGGCCTAGGC TTTTGCAAAA AGCTCCCGGG AGCTTGTATA
7201 TCCATTTTCG GATCTGATCA GCACGTGTTG ACAATTAATC ATCGGCATAG TATATCGGCA
7261 TAGTATAATA CGACAAGGTG AGGAACTAAA CCATGGCCAA GCCTTTGTCT CAAGAAGAAT
7321 CCACCCTCAT TGAAAGAGCA ACGGCTACAA TCAACAGCAT CCCCATCTCT GAAGACTACA
7381 GCGTCGCCAG CGCAGCTCTC TCTAGCGACG GCCGCATCTT CACTGGTGTC AATGTATATC
7441 ATTTTACTGG GGGACCTTGT GCAGAACTCG TGGTGCTGGG CACTGCTGCT GCTGCGGCAG
7501 CTGGCAACCT GACTTGTATC GTCGCGATCG GAAATGAGAA CAGGGGCATC TTGAGCCCCT
7561 GCGGACGGTG CCGACAGGTG CTTCTCGATC TGCATCCTGG GATCAAAGCC ATAGTGAAGG
7621 ACAGTGATGG ACAGCCGACG GCAGTTGGGA TTCGTGAATT GCTGCCCTCT GGTTATGTGT
7681 GGGAGGGCTA ACACGTGCTA CGAGATTTCG ATTCCACCGC CGCCTTCTAT GAAAGGTTGG
7741 GCTTCGGAAT CGTTTTCCGG GACGCCGGCT GGATGATCCT CCAGCGCGGG GATCTCATGC
7801 TGGAGTTCTT CGCCCACCCC AACTTGTTTA TTGCAGCTTA TAATGGTTAC AAATAAAGCA
7861 ATAGCATCAC AAATTTCACA AATAAAGCAT TTTTTTCACT GCATTCTAGT TGTGGTTTGT
7921 CCAAACTCAT CAATGTATCT TATCATGTCT GTATACCGTC GACCTCTAGC TAGAGCTTGG
7981 CGTAATCATG GTCATTACCA ATGCTTAATC AGTGAGGCAC CTATCTCAGC GATCTGTCTA
8041 TTTCGTTCAT CCATAGTTGC CTGACTCCCC GTCGTGTAGA TAACTACGAT ACGGGAGGGC
8101 TTACCATCTG GCCCCAGCGC TGCGATGATA CCGCGAGAAC CACGCTCACC GGCTCCGGAT
8161 TTATCAGCAA TAAACCAGCC AGCCGGAAGG GCCGAGCGCA GAAGTGGTCC TGCAACTTTA
8221 TCCGCCTCCA TCCAGTCTAT TAATTGTTGC CGGGAAGCTA GAGTAAGTAG TTCGCCAGTT
8281 AATAGTTTGC GCAACGTTGT TGCCATCGCT ACAGGCATCG TGGTGTCACG CTCGTCGTTT
8341 GGTATGGCTT CATTCAGCTC CGGTTCCCAA CGATCAAGGC GAGTTACATG ATCCCCCATG
8401 TTGTGCAAAA AAGCGGTTAG CTCCTTCGGT CCTCCGATCG TTGTCAGAAG TAAGTTGGCC
8461 GCAGTGTTAT CACTCATGGT TATGGCAGCA CTGCATAATT CTCTTACTGT CATGCCATCC
8521 GTAAGATGCT TTTCTGTGAC TGGTGAGTAC TCAACCAAGT CATTCTGAGA ATAGTGTATG
8581 CGGCGACCGA GTTGCTCTTG CCCGGCGTCA ATACGGGATA ATACCGCGCC ACATAGCAGA
8641 ACTTTAAAAG TGCTCATCAT TGGAAAACGT TCTTCGGGGC GAAAACTCTC AAGGATCTTA
8701 CCGCTGTTGA GATCCAGTTC GATGTAACCC ACTCGTGCAC CCAACTGATC TTCAGCATCT
8761 TTTACTTTCA CCAGCGTTTC TGGGTGAGCA AAAACAGGAA GGCAAATGC CGCAAAAAAG
8821 GGAATAAGGG CGACACGGAA ATGTTGAATA CTCATATTCT TCCTTTTTCA ATATTATTGA
8881 AGCATTTATC AGGGTTATTG TCTCATGAGC GGATACATAT TTGAATGTAT TTAGAAAAAT
8941 AAACAAATAG GGGTCAGTGT TACAACCAAT TAACCAATTC TGAACATTAT CGCG
```

SEQ ID NO 3: Amino Acid Sequence of Tagged wild-type human A2M
```
  1 MGKNKLLHPS LVLLLLVLLP TDASVSGKPQ YMVLVPSLLH TETTEKGCVL LSYLNETVTV
 61 SASLESVRGN RSLFTDLEAE NDVLHCVAFA VPKSSSNEEV MFLTVQVKGP TQEFKKRTTV
121 MVKNEDSLVF VQTDKSIYKP GQTVKFRVVS MDENFHPLNE LIPLVYIQDP KGNRIAQWQS
181 FQLEGGLKQF SFPLSSEPFQ GSYKVVVQKK SGGRTEHPFT VEEFVLPKFE VQVTVPKIIT
```

```
                              Sequences:

241 ILEEEMNVSV CGLYTYGKPV PGHVTVSICR KYSDASDCHG EDSQAFCEKF SGQLNSHGCF
 301 YQQVKTKVFQ LKRKEYEMKL HTEAQIQEEG TVVELTGRQS SEITRTITKL SFVKVDSHFR
 361 QGIPFFGQVR LVDGKGVPIP NKVIFIRGNE ANYYSNATTD EHGLVQFSIN TTNVMGTSLT
 421 VRVNYKDRSP CYGYQWVSEE HEEAHHTAYL VFSPSKSFVH LEPMSHELPC GHTQTVQAHY
 481 ILNGGTLLGL KKLSFYYLIM AKGGIVRTGT HGLLVKQEDM KGHFSISIPV KSDIAPVARL
 541 LIYAVLPTGD VIGDSAKYDV ENCLANKVDL SFSPSQSLPA SHAELRVTAA PQSVCALRAV
 601 DQSVLLMKPD AELSASSVYN LLPEKDLTGF PGPLNDQDDE DCINRHNVYI NGITYTPVSS
 661 TNEKDMYSFL EDMGLKAFTN SKIRKPKMCP QLQQYEMHGP EGLRVGFYES DVMGRGHARL
 721 VHVEEPHTET VRKYFPETWI WDLVVVNSAG VAEVGVTVPD TITEWKAGAF CLSEDAGLGI
 781 SSTASLRAFQ PFFVELTMPY SVIRGEAFTL KATVLNYLPK CIRVSVQLEA SPAFLAVPVE
 841 KEQAPHCICA NGRQTVSWAV TPKSLGNVNF TVSAEALESQ ELCGTEVPSV PEHGRKDTVI
 901 KPLLVEPEGL EKETTFNSLL CPSGGEVSEE LSLKLPPNVV EESARASVSV LGDILGSAMQ
 961 NTQNLLQMPY GCGEQNMVLF APNIYVLDYL NETQQLTPEI KSKAIGYLNT GYQRQLNYKH
1021 YDGSYSTFGE RYGRNQGNTW LTAFVLKTFA QARAYIFIDE AHITQALIWL SQRQKDNGCF
1081 RSSGSLLNNA IKGGVEDEVT LSAYITIALL EIPLTVTHPV VRNALFCLES AWKTAQEGDH
1141 GSHVYTKALL AYAFALAGNQ DKRKEVLKSL NEEAVKKDNS VHWERPQKPK APVGHFYEPQ
1201 APSAEVEMTS YVLLAYLTAQ PAPTSEDLTS ATNIVKWITK QQNAQGGFSS TQDTVVALHA
1261 LSKYGAATFT RTGKAAQVTI QSSGTFSSKF QVDNNNRLLL QQVSLPELPG EYSMKVTGEG
1321 CVYLQTSLKY NILPEKEEFP FALGVQTLPQ TCDEPKAHTS FQISLSVSYT GSRSASNMAI
1381 VDVKMVSGFI PLKPTVKMLE RSNHVSRTEV SSNHVLIYLD KVSNQTLSLF FTVLQDPVPR
1441 DLKPAIVKVY DYYETDEFAI AEYNAPCSKD LGNADYKDDD DKGASHHHHHH

SEQ ID NO 4: Amino Acid Sequence of the Acceptor Mutant.
   1 MGKNKLLHPS LVLLLLVLLP TDASVSGKPQ YMVLVPSLLH TETTEKGCVL LSYLNETVTV
  61 SASLESVRGN RSLFTDLEAE NDVLHCVAFA VPKSSSNEEV MFLTVQVKGP TQEFKKRTTV
 121 MVKNEDSLVF VQTDKSIYKP GQTVKFRVVS MDENFHPLNE LIPLVYIQDP KGNRIAQWQS
 181 FQLEGGLKQF SFPLSSEPFQ GSYKVVVQKK SGGRTEHPFT VEEFVLPKFE VQVTVPKIIT
 241 ILEEEMNVSV CGLYTYGKPV PGHVTVSICR KYSDASDCHG EDSQAFCEKF SGQLNSHGCF
 301 YQQVKTKVFQ LKRKEYEMKL HTEAQIQEEG TVVELTGRQS SEITRTITKL SFVKVDSHFR
 361 QGIPFFGQVR LVDGKGVPIP NKVIFIRGNE ANYYSNATTD EHGLVQFSIN TTNVMGTSLT
 421 VRVNYKDRSP CYGYQWVSEE HEEAHHTAYL VFSPSKSFVH LEPMSHELPC GHTQTVQAHY
 481 ILNGGTLLGL KKLSFYYLIM AKGGIVRTGT HGLLVKQEDM KGHFSISIPV KSDIAPVARL
 541 LIYAVLPTGD VIGDSAKYDV ENCLANKVDL SFSPSQSLPA SHAHLRVTAA PQSVCALRAV
 601 DQSVLLMKPD AELSASSVYN LLPEKDLTGF PGPLNDQDDE DCINRHNVYI NGITYTPVSS
 661 TNEKDMYSFL EDMGLKAFTN SKIRKPKMCP QLEQYEMHGP EGLRVGFYES DVMGRGHARL
 721 VHVEEPHTEK LRKYFPETWI WDLVVVNSAG VAEVGVTVPD TITEWKAGAF CLSEDAGLGI
 781 SSTASLRAFQ PFFVELTMPY SVIRGEAFTL KATVLNYLPK CIRVSVQLEA SPAFLAVPVE
 841 KEQAPHCICA NGRQTVSWAV TPKSLGNVNF TVSAEALESQ ELCGTEVPSV PEHGRKDTVI
 901 KPLLVEPEGL EKETTFNSLL CPSGGEVSEE LSLKLPPNVV EESARASVSV LGDILGSAMQ
 961 NTQNLLQMPY GCGEQNMVLF APNIYVLDYL NETQQLTPEI KSKAIGYLNT GYQRQLNYKH
1021 YDGSYSTFGE RYGRNQGNTW LTAFVLKTFA QARAYIFIDE AHITQALIWL SQRQKDNGCF
1081 RSSGSLLNNA IKGGVEDEVT LSAYITIALL EIPLTVTHPV VRNALFCLES AWKTAQEGDH
1141 GSHVYTKALL AYAFALAGNQ DKRKEVLKSL NEEAVKKDNS VHWERPQKPK APVGHFYEPQ
1201 APSAEVEMTS YVLLAYLTAQ PAPTSEDLTS ATNIVKWITK QQNAQGGFSS TQDTVVALHA
1261 LSKYGAATFT RTGKAAQVTI QSSGTFSSKF QVDNNNRLLL QQVSLPELPG EYSMKVTGEG
1321 CVYLQTSLKY NILPEKEEFP FALGVQTLPQ TCDEPKAHTS FQISLSVSYT GSRSASNMAI
1381 VDVKMVSGFI PLKPTVKMLE RSNHVSRTEV SSNHVLIYLD KVSNQTLSLF FTVLQDPVPR
1441 DLKPAIVKVY DYYETDEFAI AEYNAPCSKD LGNADYKDDD DKGASHHHHH H SEQ ID NOs 5-66: Amino Acid Sequences of Variant Bait Regions.
SEQ ID NO 5:   LEQYEMHGPE GLRVGKEEEG LGSIPENFFG VSELEGRGSK L
SEQ ID NO 6:   LEQYEMHGPE GLRVGIPENF FGVSELEGRG SKEEEGLGSK L
SEQ ID NO 7:   LEQYEMHGPE GLRVGSELEG RGSKEEEGLG SIPENFFGVK L
SEQ ID NO 8:   LEQYEMHGPE GLRVGKEEEG LGSSELEGRG STAQEAGEGK L
SEQ ID NO 9:   LEQYEMHGPE GLRVGIPENF FGVFYESDVM GRGHARLVHV EEPHTKLL
SEQ ID NO 10:  LEQYEMHGPE GLRVGKEEEG LGSFYESDVM GRGHARLVHV EEPHTKLL
SEQ ID NO 11:  LEQYEMHGPE GLRVGSELEG RGSFYESDVM GRGHARLVHV EEPHTKLL
SEQ ID NO 12:  LEQYEMHGPE GLRVGEAIPM SIPFYESDVM GRGHARLVHV EEPHTKLL
SEQ ID NO 13:  LEQYEMHGPE GLRVGTAQEA GEGFYESDVM GRGHARLVHV EEPHTKLL
SEQ ID NO 14:  LEQYEMHGPE GLRVGVSQEL GQRFYESDVM GRGHARLVHV EEPHTKLL
SEQ ID NO 15:  LEQYEMHGPE GLRVGTEGEA RGSFYESDVM GRGHARLVHV EEPHTKLL
SEQ ID NO 16:  LEQYEMHGPE GLRVGTSEDL VVQFYESDVM GRGHARLVHV EEPHTKLL
SEQ ID NO 17:  LEQYEMHGPE GLRVGEGEGE GEGFYESDVM GRGHARLVHV EEPHTKLL
SEQ ID NO 18:  LEQYEMHGPE GLRVGGEEGV EEGFYESDVM GRGHARLVHV EEPHTKLL
SEQ ID NO 19:  LEQYEMHGPE GLRVGGARGL EGFYESDVMG RGHARLVHVE EPHTKL
SEQ ID NO 20:  LEQYEMHGPE GLRVGPPGL APGFYESDVM GRGHARLVHV EEPHTKLL
SEQ ID NO 21:  LEQYEMHGPE GLRVGGEPEG AKGFYESDVM GRGHARLVHV EEPHTKLL
SEQ ID NO 22:  LEQYEMHGPE GLRVGEEEGG GFYESDVMGR GHARLVHVEE PHTKL
SEQ ID NO 23:  LEQYEMHGPE GLRVGGYPGS SRGFYESDVM GRGHARLVHV EEPHTKLL
SEQ ID NO 24:  LEQYEMHGPE GLRVGGARGL EGGFAGLPNG GEEGVEEGKL
SEQ ID NO 25:  LEQYEMHGPE GLRVGESESE GGGGGSLLGE FEVEGGFAGL PNGKL
SEQ ID NO 26:  LEQYEMHGPE GLRVGGFKEG VEGEIEEGGG FKEGVEGKL
SEQ ID NO 27:  LEQYEMHGPE GLRVGESESE GGFAGLPNGK EEEGLGSIPE NFFGVKL
SEQ ID NO 28:  LEQYEMHGPE GLRVGIPENF FGVTSEDLVV QEAIPMSIPK L
SEQ ID NO 29:  LEQYEMHGPE GLRVGEAIPM SIPTSEDLVV QIPENFFGVK L
SEQ ID NO 30:  LEPAGAARGE SESEGGFFGF PIGERESTGG DRGLPIGENE AGGKL
SEQ ID NO 31:  LETEGRGERE AQGEFPEVEG EEEGGGPEKE TGGEREAQGK L
```

-continued

Sequences:

```
SEQ ID NO 32: LEARGLEGGG GGSLLGGYPG SSRGGFKEGV EGGPAGAARG KL
SEQ ID NO 33: LEPGLAPGGE EGVEEGGPEE GVEEGGFKEG VEGEPESSGK L
SEQ ID NO 34: LEEGEARGST AQEAGEGPKE EEGLGSSELE GRGSPVSQEL GQRKL
SEQ ID NO 35: LEAQEAGEGK EEEGLGSPVS QELGQRSELE GRGSPTEGEA RGSKL
SEQ ID NO 36: LEEEEGLGSK EEEGLGSPKE EEGLGSKEEE GLGSPKEEEG LGSKL
SEQ ID NO 37: LEELEGRGSK EEEGLGSIPE NFFGVFYESD VMGRGHARLV HVEEPHTKL
SEQ ID NO 38: LEENFFGVTE GEARGSPTSE DLVVQKEEEG LGSEAIPMSI PKL
SEQ ID NO 39: LEIPMSIPKE EEGLGSIPEN FFGVTEGEAR GSPTSEDLVV QKL
SEQ ID NO 40: LELQQYEMHG PEGLRVGEAI PMSIPIPENF FGVKEEEGLG SKL
SEQ ID NO 41: LEEEGVEEGK EEEGLGSGPA GAARGSELEG RGSPTEGEAR GSKL
SEQ ID NO 42: LEPESSGEAI PMSIPTSEDL VVQIPENFFG VEAEGTGGER GVLGKL
SEQ ID NO 43: LEGGGSLLGE PEPEGEREAQ GGVEGVELGG FKEGVEGEQE GRGKL
SEQ ID NO 44: LESQELGQRE SESEGSELEG RGSGFKEGVE GKEEEGLGSG FFGFPIGKL
SEQ ID NO 45: LEQYEMHGPK EEEGLGSSEL EGRGSEAIPM SIPTIPENFF GVVEEPHTKL
SEQ ID NO 46: LEQYEMHGPS ELEGRGSIPE NFFGVEAIPM SIPTSEDLVV QIVEEPHTKL
SEQ ID NO 47: LEQYEMHGPE GEGEGEGIPE NFFGVSEDLV VQISELEGRG SVEEPHTKL
SEQ ID NO 50: LEQYEMHGPI PENFFGVSEL EGRGSEAIPM SIPTEGEGEG EGVEEPHTKL
SEQ ID NO 51: LEQYEMHGPS ELEGRGSEAI PMSIPTKEEE GLGSIPENFF GVVEEPHTKL
SEQ ID NO 52: LEQYEMHGPE AIPMSIPTEG EGEGEGIPEN FFGVSEDLVV QIVEEPHTKL
SEQ ID NO 53: LEQYEMHGPS EDLVVQIEGE GEGEGIPENF FGVEAIPMSI PTVEEPHTKL
SEQ ID NO 54: LEQYEMHGPE GEGEGEGISE DLVVQIPENF FGVKEEEGLG SVEEPHTKL
SEQ ID NO 55: LEQYEMHGPE GEGEGEGIPE NFFGVSELEG RGSSEDLVVQ IVEEPHTKL
SEQ ID NO 56: LEQYEMHGPI PENFFGVEGE GEGESELEGR GSSEDLVVQI VEEPHTKL
SEQ ID NO 57: LEQYEMHGPS ELEGRGSIPE NFFGVKEEEG LGSSEDLVVQ IVEEPHTKL
SEQ ID NO 58: LEQYEMHGPI PENFFGVSEL EGRGSSEDLV VQIKEEEGLG SVEEPHTKL
SEQ ID NO 59: LEQYEMHGPK EEEGLGSIPE NFFGVSELEG RGSEGEGEGE GVEEPHTKL
SEQ ID NO 60: LEQYEMHGPS EDLVVQIKEE EGLGSIPENF FGVSELEGRG SVEEPHTKL
SEQ ID NO 61: LEQYEMHGPS EDLVVQIEGE GEGEGIPENF FGVKEEEGLG SVEEPHTKL
SEQ ID NO 62: LEQYEMHGPS EDLVVQIEGE GEGEGIPENF FGVEAIPMSI PTEPHTKL
SEQ ID NO 63: LEQYEMHGPE GEGEGEGIPE NFFGVEAIPM SIPTSELEGR GSEPHTKL
SEQ ID NO 64: LEQYEMHGPE AIPMSIPTSE LEGRGSIPEN FFGVEGEGEG EGEPHTKL
SEQ ID NO 65: LEQYEMHGPS ELEGRGSIPE NFFGVEGEGE GEGKEEEGLG SVEEPHTKL
SEQ ID NO 66: LEQYEMHGPI PENFFGVSED LVVQIEGEGE GEGEAIPMSI PTEPHTKL
```

EXAMPLES

Figure 3:
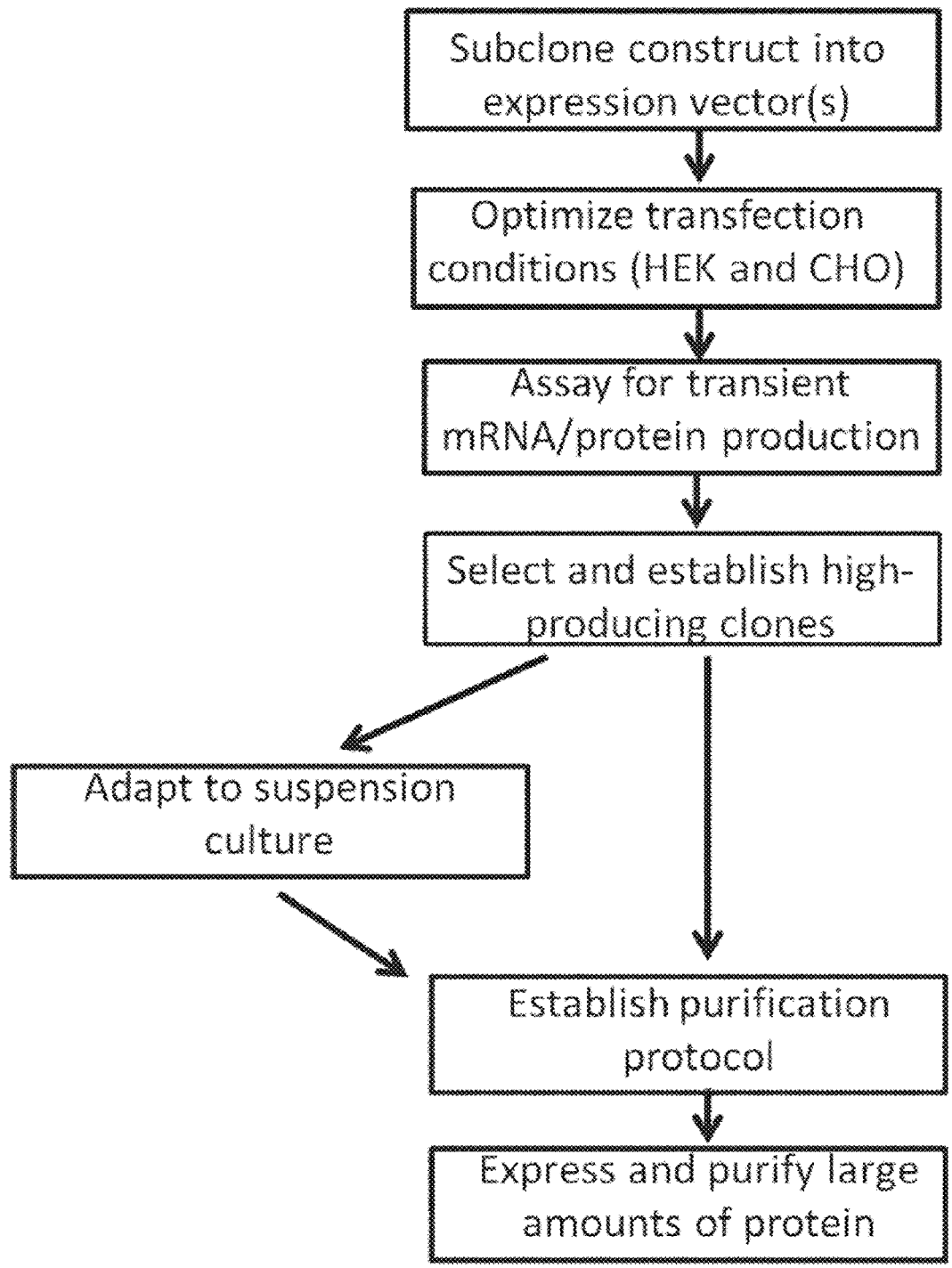
FIG. 3 depicts a flow chart of the steps for construct or protein expression.
Figure 15:
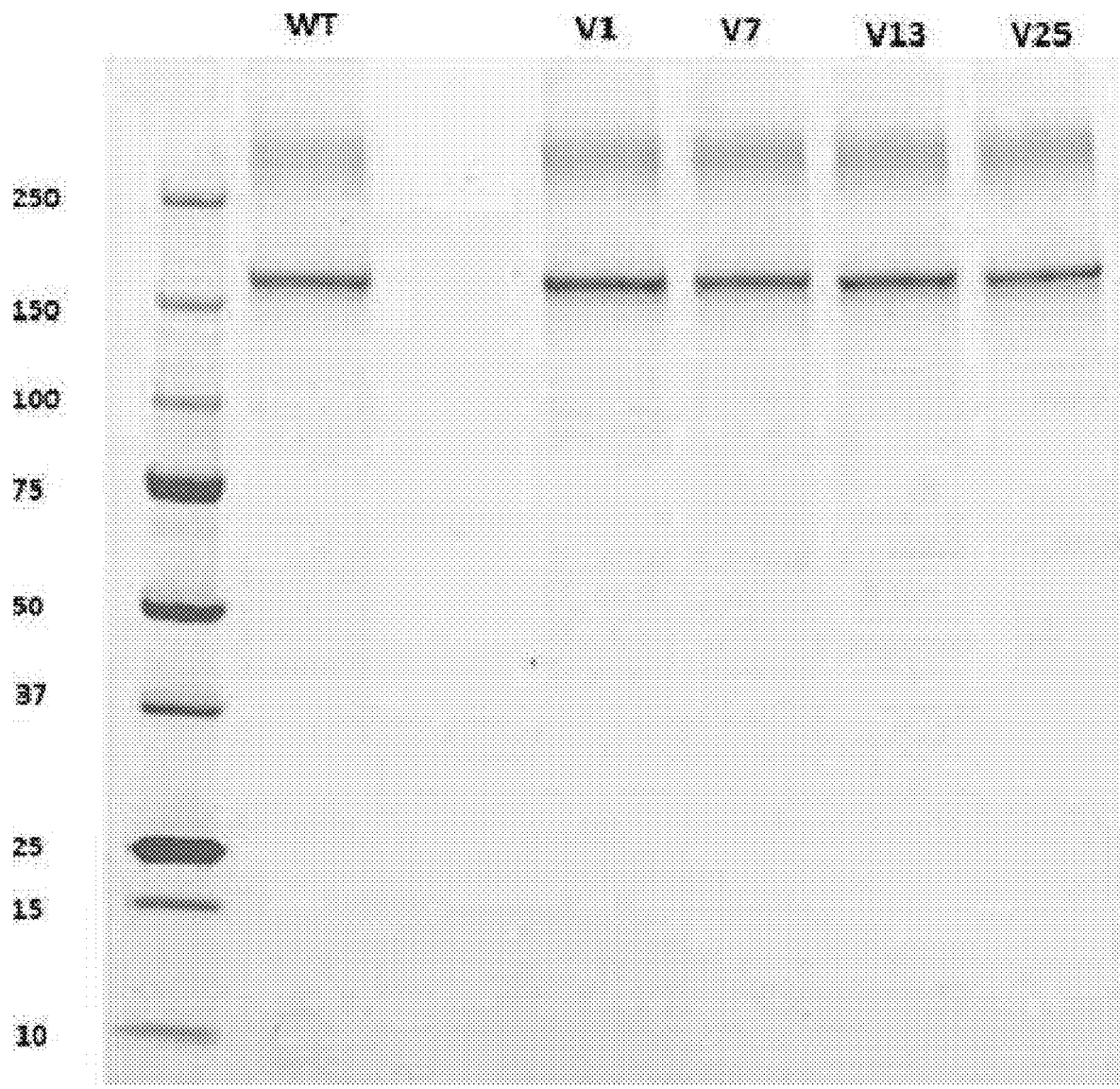
FIG. 15 is a depiction of a pseudocolored stain-free SDS-PAGE gel of a representative purification of tagged wild-type A2M and the four selected variable bait region A2M proteins. The theoretical molecular weight of a monomer of wild-type A2M is 163 KDa, not including glycosylation. The blurry band above 250 KDa is comprised of dimeric A2M that is not thoroughly reduced during sample preparation or covalently bound dimer through amino acid modification mechanisms.
Figure 16:
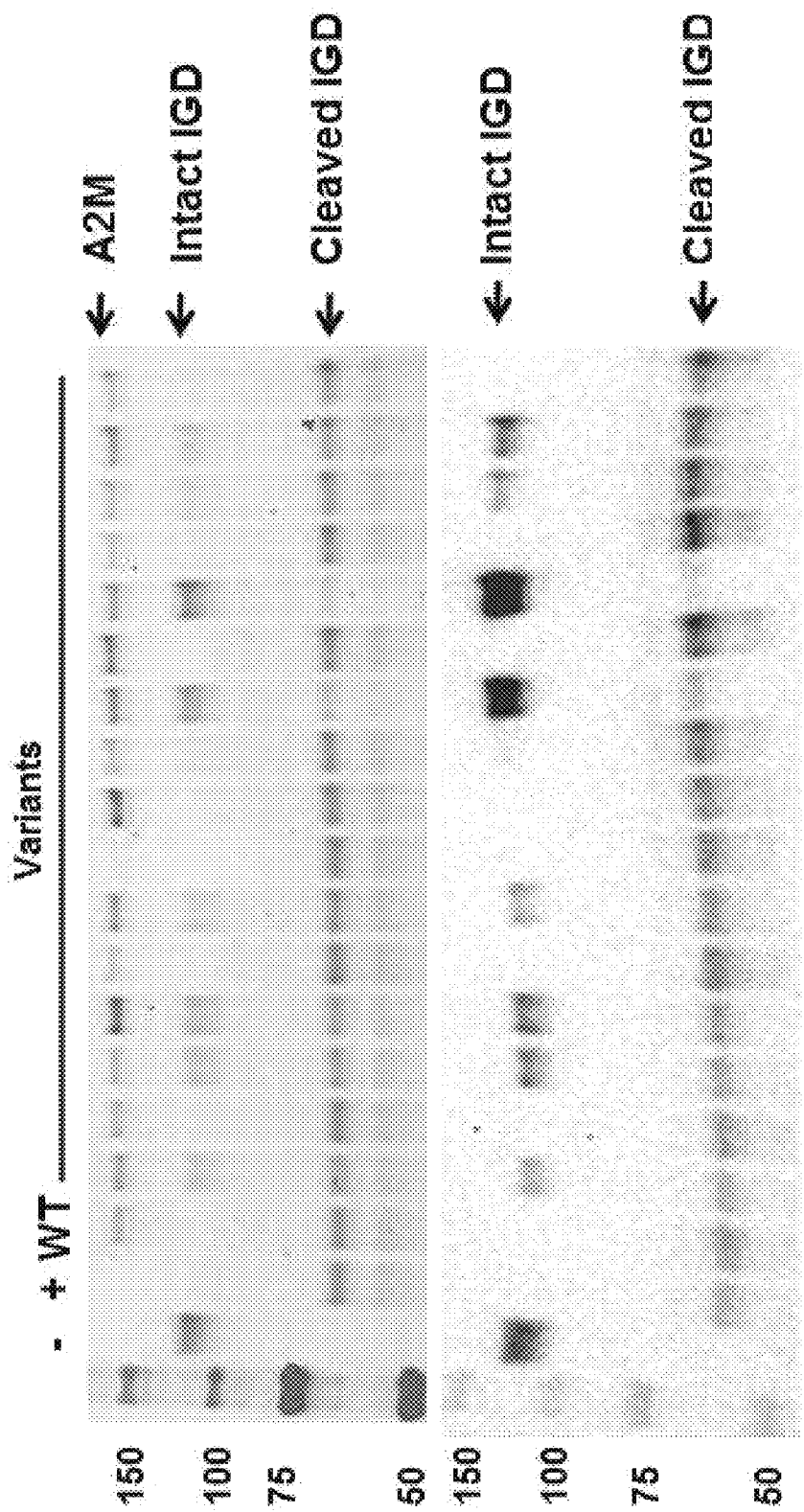
FIG. 16 is a depiction of a pseudocolored stain-free SDS-PAGE gel (top) and Western blot (bottom) of a representative screening assay for inhibition of ADAMTS-5 cleavage of aggrecan IGD domain (IGD fragment) by wild-type (WT) and bait region substituted A2M. The negative control is IGD fragment protein alone; the positive control is IGD fragment plus ADAMTS-5. ADAMTS-5, Wild-type and variant A2M were each kept at 50 nM, and the A2M and ADAMTS-5 were pre-mixed for 10 min. before addition of IGD fragment. The primary antibody for the Western blot was an anti-Aggrecan G1-IGD-G2 polyclonal antibody (R&D).
Figure 17A:
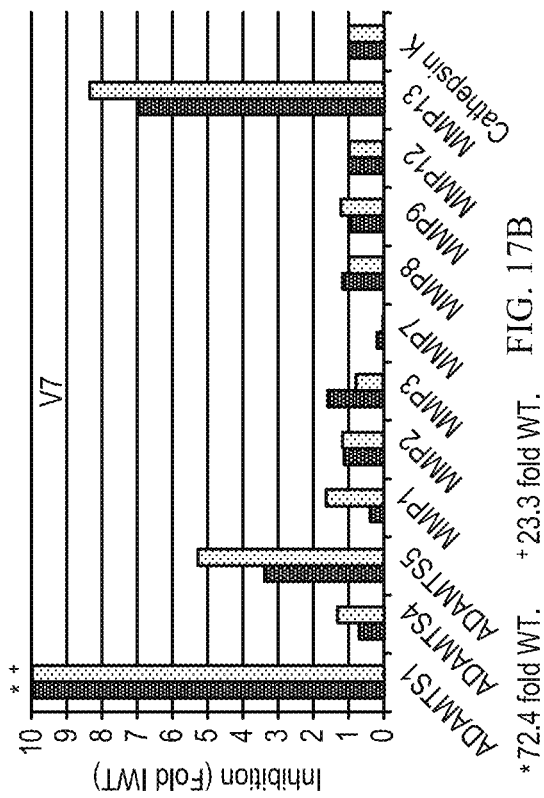
FIG. 17A, FIG. 17B, FIG. 17C, and FIG. 17D are exemplary graphs depicting a comparison of the relative inhibitory characteristics of the four chosen variants vs. various MMPs and ADAMTS-4 and -5 as determined by the two IGD screening experiments. In each case the unit for the y-axis is multiples of the wild-type inhibition of each protease.
Figure 17B:
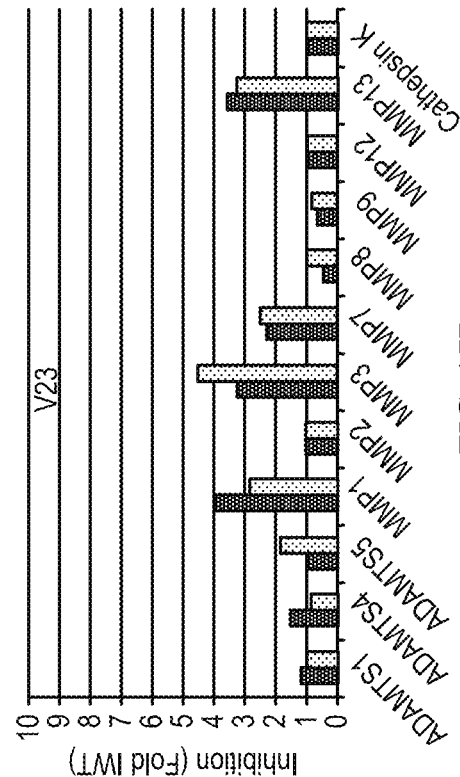
Figure 17C:
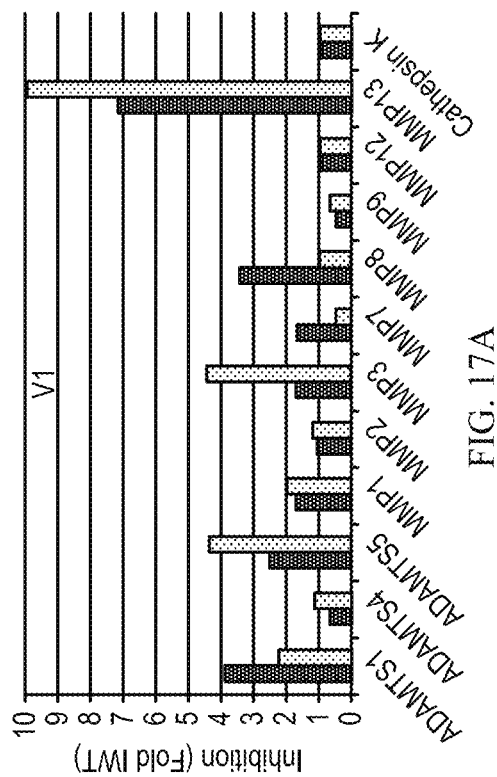
Figure 17D:
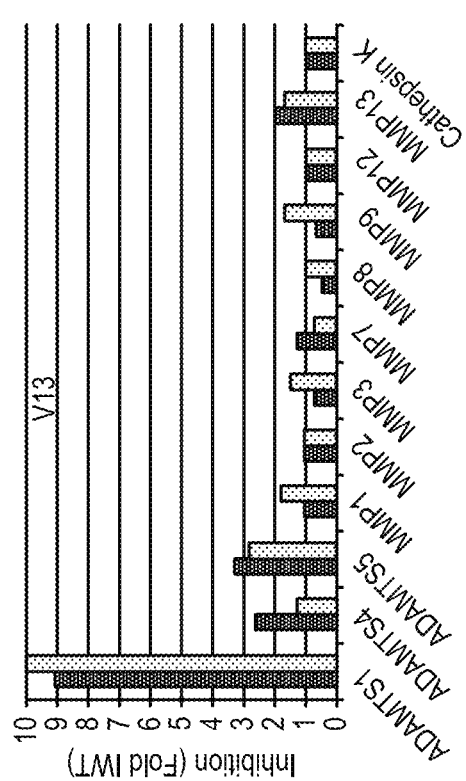
Figure 19:
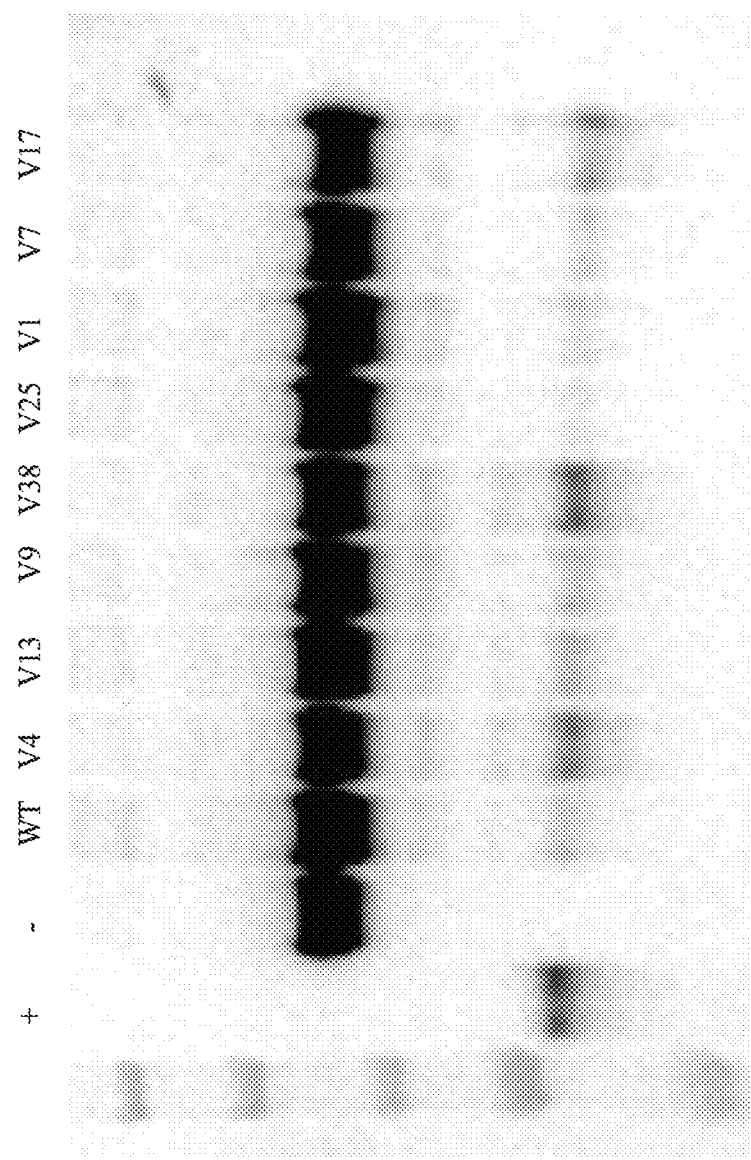
FIG. 19 depicts a western blot analysis of a cleavage assay using IGD fragment as a substrate in the presence of the MMP3.
Figure 21:
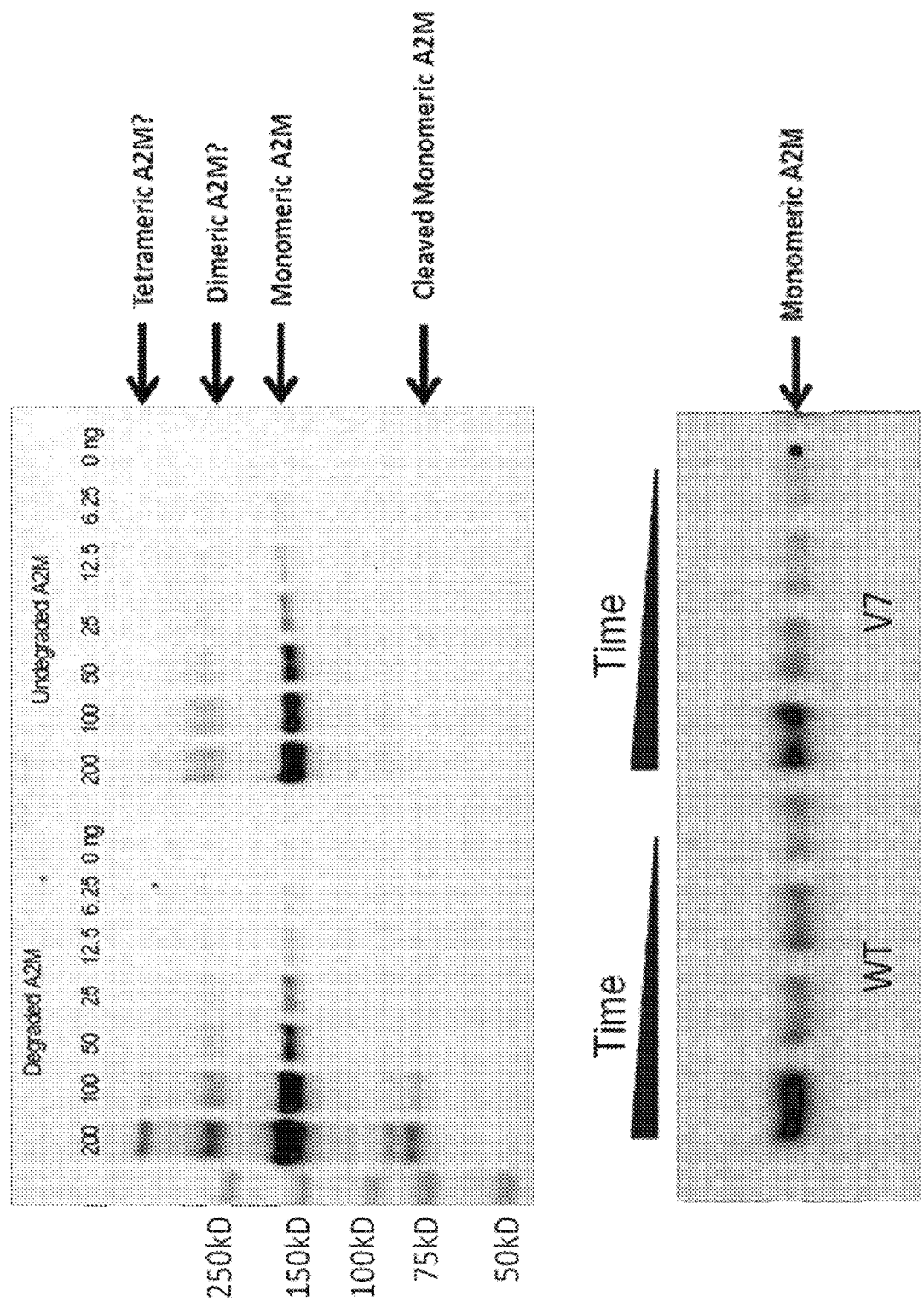
FIG. 21 depicts Western blots showing the control blot of degraded and non-degraded forms of A2M as a function of the known amount of protein indicated (top) and the cleavage of various A2M polypeptides over time in the presence of a protease (bottom). The control blot can be used to quantify the amount of cleaved A2M, which is directly proportional to the rate of protease inhibition.

Example 1—Generation and Selection of HEK293 Clones Expressing Recombinant A2M Recombinant A2M wild type sequence was expressed in HEK293F cells. Hek293F cells are plated adherently and allowed to attach overnight. Cells are transfected with XTreme Gene HP (Roche) and DNA in a 6 uL reagent:2 ug DNA ratio. Cells are grown for 48 hours at 5% CO2 and 37 degrees Celsius. Forty-eight hours after transfection media samples are taken to confirm success of the transfection via an ELISA assay that quantifies A2M protein. Cells are split so as to be in logarithmic growth phase and selection antibiotic (blasticidin) is added at 10 µg/mL (selection concentration determined experimentally). Cells are selected in antibiotic until all of the negative control cells are dead (usually about 4 to 5 days). Another media sample is taken at this point to confirm that this newly established pool is still producing protein. Upon confirmation of protein production cells are plated at a density of ~100 cells/10 cm dish with 7.5 µg/mL blasticidin (maintenance concentration determined experimentally). This plating density is sparse enough that cells will be spaced far enough apart to allow each cell to grow into an individual colony. These colonies are collected using cloning cylinders (Sigma) and plated in a 24 well plate to allow further cell growth. Once cells become confluent in the 24 well plate an ELISA is performed on a media sample again to screen for the highest producing clone. High-expressing clones were selected and used for production of A2M. The chosen clones were expanded and adapted to suspension (FIG. 3). Suspension adaption was completed by slowly changing the media to a serum-free media while the cells are in shaker flasks. Once the culture is in suspension, protein can be collected by simply spinning the cells out of the media. The A2M containing supernatants were subjected to purification for A2M. The higher cell number per volume of media results in a higher protein concentration per milliliter of media. High purity samples were obtained after two chromatography methods. A yield of ~12 mg/L (adherent pool) was typical (FIG. 15).

Figures 7A, 7B:
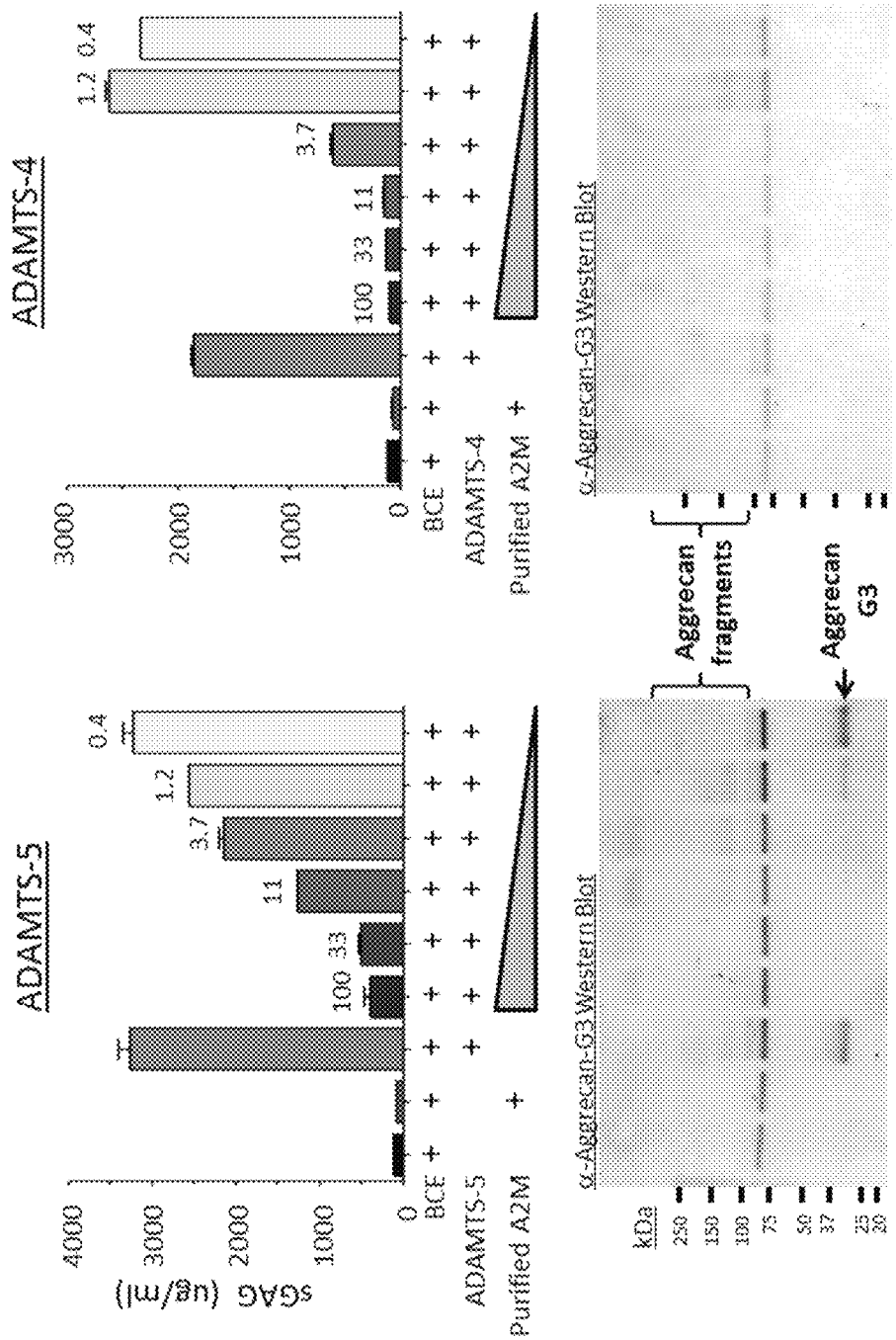
FIG. 7A depicts the sulfated glycosaminoglycan (sGAG) released upon cartilage catabolism in a BCE model with and without treatment of ADAMTS-5 and treatment with or without a serial dilution of purified A2M (top). Western Blots of the samples (bottom) demonstrate ADAMTS-5 degradation of cartilage produced an Aggrecan G3 fragment and higher molecular weight Aggrecan fragments, which were inhibited by treatment with A2M in a dose dependent manner. Values above the columns indicate the concentration of A2M (µg/ml) needed to inhibit ADATMS-5. An 85 kDa non-specific band is also visible, which was apparent in media-only controls (data not shown).
FIG. 7B depicts the sulfated glycosaminoglycan (sGAG) released upon cartilage catabolism in a BCE model with and without treatment of ADAMTS-4 and treatment with or without a serial dilution of purified A2M (top). Western Blot analysis with α-Aggrecan G3 antibody (bottom) of the samples demonstrates ADAMTS-4 degradation of cartilage produced high molecular weight Aggrecan C-terminal fragments containing the G3 domain. Cartilage catabolism is inhibited by A2M in a dose dependent manner and reduces the release of cartilage aggrecan fragments. An 85 kDa non-specific band is also visible, which was apparent in media-only controls (data not shown).

Example 2—Inhibition of ADAMTS-5- and ADAMTS-4-Induced Damage of Cartilage with A2M Bovine Cartilage Explants (BCEs) were treated with 500 ng/ml ADAMTS-5 or ADAMTS-4 for 2 days, with a 3-fold serial dilution of purified A2M (FIG. 7A, B). Concentration of A2M tested were 100, 33.3, 11.1, 3.7, 1.2, 0.4 µg/mL. The A2M inhibited cartilage catabolism in a concentration dependent manner. The IC50 for inhibiting 500 ng/ml of ADAMTS-5 was calculated to be ~7 µg/ml A2M (a 1:1 molar ratio). Maximum inhibition was observed in ~90% with 100 µg/ml A2M (a 14:1 molar ratio). The A2M was shown to block formation of Aggrecan G3 fragments (FIG. 7A, B) and FAC formation (FIG. 9).

Example 3—Comparison of APIC Retentate and Filtrate

Figures 10A, 10B:
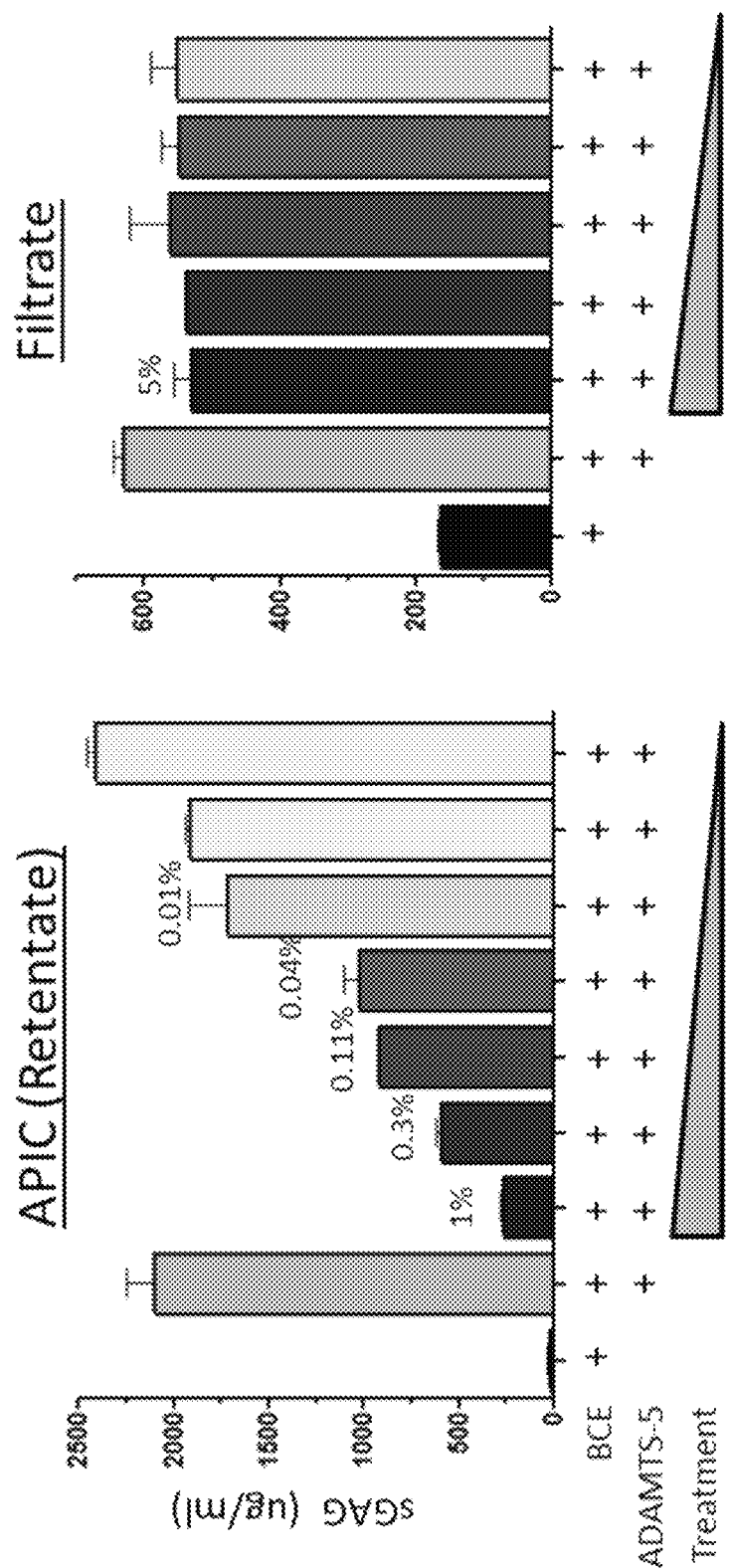
FIG. 10A and FIG. 10B are exemplary graphs depicting two bar graphs demonstrating the ability of APIC (Retentate from the 500 kDa filter) and the Filtrate to prevent cartilage degradation. Cartilage catabolism was induced in the BCE model with ADAMTS-5, which could be inhibited with serial dilution of APIC (left, Retentate), but not the Filtrate which is devoid of A2M (right, Filtrate). The numbers above the columns represent the percentage of APIC (v/v) or filtrate in the culture media. The inhibitory potential in 5% of Filtrate is equivalent to 0.01% of APIC; thus the process of producing APIC concentrates >99% of the chondroprotective effects of blood.

Fresh cartilage was treated with APIC containing ~7 mg/ml A2M. Cartilage catabolism was efficiently blocked by 1% v/v of the Retentate of the APIC production process (concentration of proteins >500 kDa in size), but not by the Filtrate (contains proteins <500 kDa), even at 5% v/v (FIG. 10). The chondroprotective effects of APIC were dose dependent. The inability of Filtrate to protect cartilage from catabolism by ADAMTS-5 demonstrates that APIC concentrates >99% of the protective factors of autologous blood.

Example 4—APIC Blocks Cartilage Catabolism in an Osteoarthritis Model

Figures 6A, 6B:
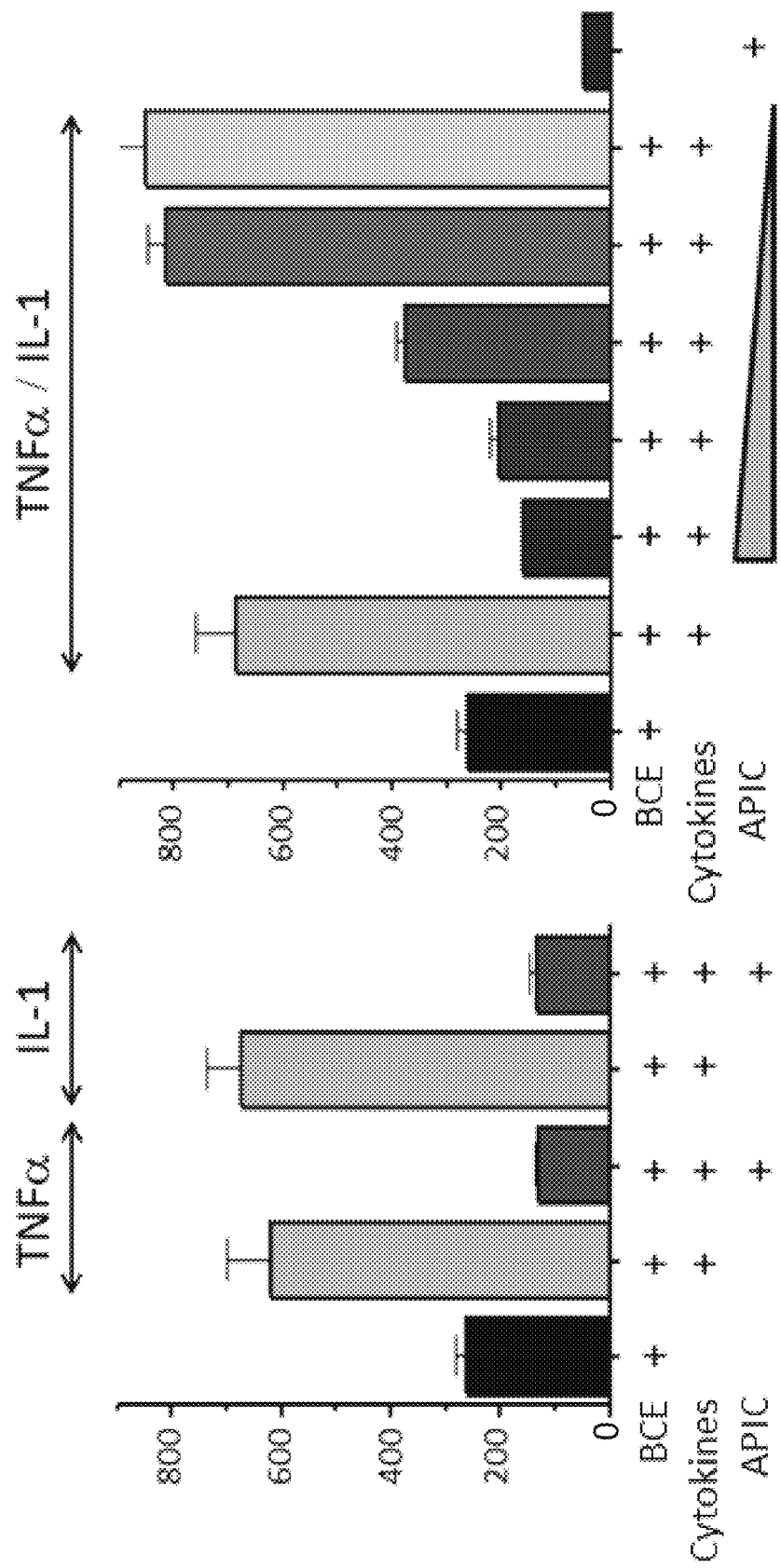
FIG. 6A depicts a graph showing Bovine Cartilage Explants (BCE) treated with pro-inflammatory cytokines TNF-α and IL-1β to induce cartilage catabolism. Cartilage catabolism with each cytokines separately is demonstrated by the release of sulfated Glycosaminoglycans (sGAG) into the culture media. Treatment with APIC-PRP efficiently inhibits cartilage catabolism by each pro-inflammatory cytokine separately.
FIG. 6B depicts a graph showing Bovine Cartilage Explants (BCE) treated with the combination of pro-inflammatory cytokines TNF-α and IL-1β to induce cartilage catabolism. Treatment with APIC-PRP efficiently inhibited cartilage catabolism by the combination of pro-inflammatory cytokines in a dose dependent manner.

Fresh cartilage was treated with TNF-α or IL-1βeta to induce chondrocytes to secrete proteases, similar to the pathology of osteoarthritis (FIG. 6). Cartilage catabolism was detected as increased sulfated glycosaminoglycans (sGAG) in the culture media. Treatment with pro-inflammatory cytokines induced cartilage catabolism which treatment with APIC was shown to block in a dose-dependent manner.

Example 5—Cytokine Profile of Monocytes Treated with APIC

Figure 11:
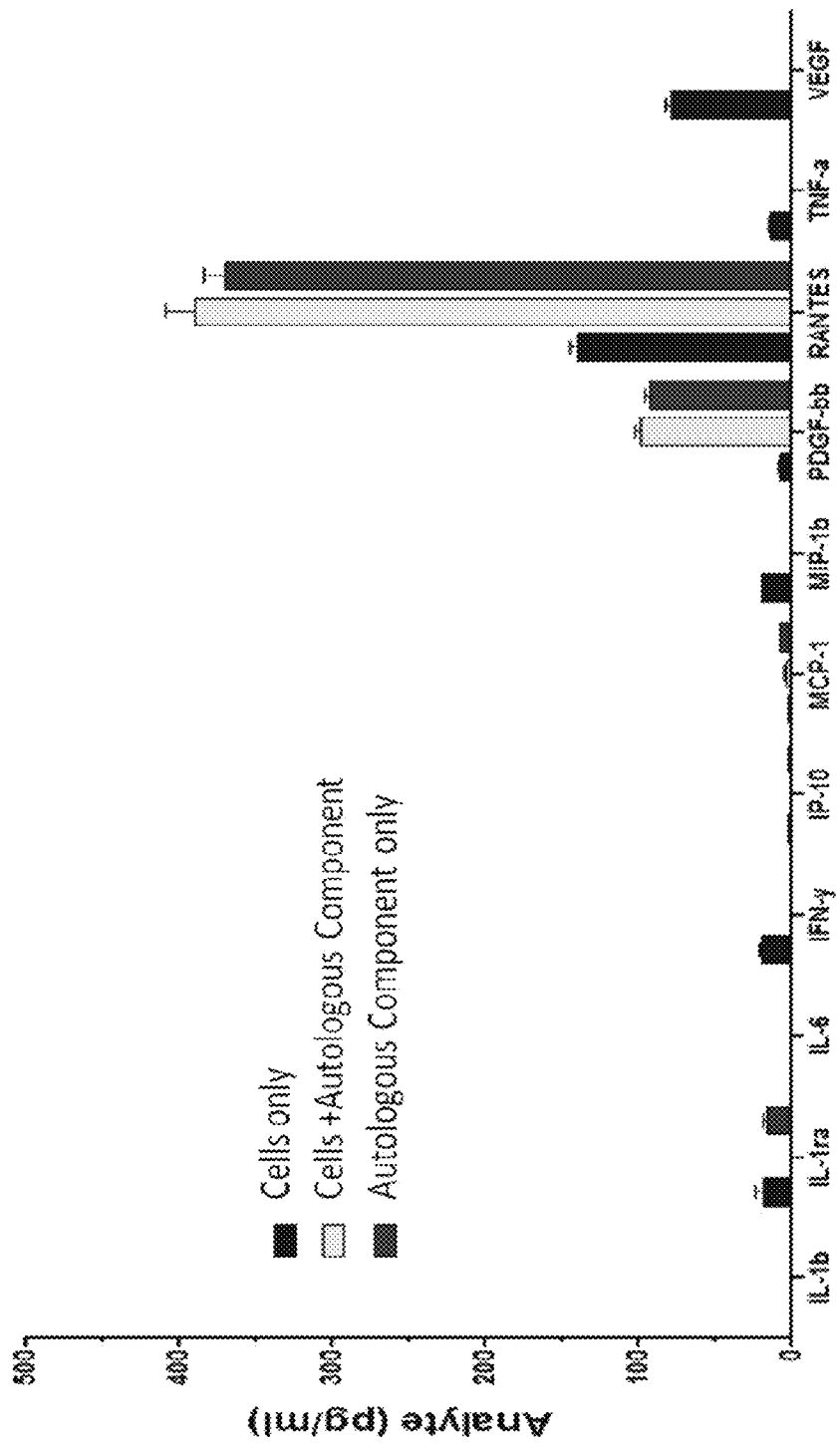
FIG. 11 is a bar graph depicting the effects of treatment of THP-1 monocytes with autologous APIC for two days in culture. No activation of the monocytes was observed through monitoring with a panel of cytokines, chemokines, and growth factors (Left to right: IL-1β, IL-1 receptor agonist (IL-1ra), IL-6, IFN-γ, IP-10, MCP-10, MIP-1β, PDGF-ββ, RANTES, TNF-α, and VEGF).

THP-1 monocyte cells were treated with or without APIC for 2 days and the activation of the cells was monitored by secretion of cytokines and growth factors into the medium. THP-1 did not show a change in the cytokines profile tested (FIG. 11). Similar results were seen in E6-1 T-cells and SW982 fibroblast cells.

Example 6—Design and Synthesis of Tagged Wild-Type A2M Expression Construct

A DNA sequence coding for the wild-type A2M precursor protein (SEQ ID NO. 1) was synthesized by GenScript based on the RefSeq amino acid sequence of human A2M precursor protein (RefSeq #NP_000005.2) (SEQ ID NO. 3). The codons used in the construct were optimized by GenScript for mammalian codon usage bias, GC content, CpG dinucleotide content, mRNA secondary structure, cryptic splicing sites, premature polyadenylation sites, internal chi and ribosome binding sites, negative CpG islands, RNA instability motifs, repeat sequences, and restriction endonuclease sites. A sequence encoding a fusion tag (DYKDDDDK-GASHHHHHH (SEQ ID NO. 73)) was added to the natural end of the protein sequence, followed by a STOP codon. The expression construct was given a Kpn1 restriction site at the 5' end and a BamH1 restriction site at the 3' end. This construct was cloned into a pUC57 vector. The insert encoding the expression construct was extracted from the pUC57 vector via double digestion with Kpn1 and BamH1 followed by agarose gel electrophoresis and gel extraction of the fragment. This insert was ligated into a pJ608 mammalian expression vector (DNA 2.0) behind a cytomegalovirus (CMV) promoter (FIG. 23) and transformed into E. coli strain GC10 (Genessee Scientific). This step is performed to maintain and propagate the vector. The sequence of the expression construct was verified by DNA sequencing (Genewiz).

Example 7—Design of Acceptor Construct for Variable Bait Regions

The wild-type expression construct was mutated to allow switching of bait region sequences by first introducing XhoI and HindIII restriction sites flanking the sequence encoding the bait region. This was done via two sequential site-directed mutagenesis reactions using the wild-type expression construct as the template. The sequence of the mutant "acceptor" construct was verified by DNA sequencing of the bait region by Genewiz (SEQ ID NO 2). The corresponding amino acid sequence is SEQ ID No 4. The mutations in the DNA sequence necessarily result in three amino acid substitutions in the protein Q693E on the N-terminal side of the bait region and T730K and V731L on the C-terminal of the bait region. These mutations could not be avoided because the natural DNA sequence does not have restriction endonuclease sites that could be used to remove the bait sequence. These mutations are included in the new bait regions design. The preservation of function of the acceptor mutant was verified by its ability to inhibit trypsin (see below), and it was tested versus other proteases as part of the evaluation of the designed bait regions.

Example 8—Design and Creation of Variable Bait Region Expression Constructs 60 novel bait region amino acid sequences (SEQ ID NOs: 5-66) were designed based on the known cleavage sites of human aggrecan by ADAMTS-4, ADAMTS-5, and various MMPs (Fosang et al., Eur. Cells and Mat., Vol. 15, 2008, pp. 11-26) (Table 1). Some constructs retained part or the entirety of the wild-type A2M bait sequence, but with an insertion of non-native amino acids (SEQ ID NOs: 5-66). Several pUC57 plasmids, each containing DNA insert sequences encoding between one and six bait region sequences, were synthesized by GenScript and delivered to us as a lyophilized powder. Each insert sequence contains an XhoI site at the 5' end and a HindIII site at the 3' end for ligation into the acceptor construct. Each insert plasmid, along with the acceptor plasmid, was reconstituted in water and double digested overnight with 20 U of XhoI and HindIII to liberate the insert sequences, and the digested plasmids were separated by electrophoresis on a 1% agarose gel and visualized under UV light. Bands corresponding to the insert and acceptor length were extracted from the gel via a Qiagen Qiaquick Gel Extraction Kit as per the kit instructions. The concentration of DNA obtained from each extraction was determined using a Qubit fluorimeter (Invitrogen). Ligation of inserts into the region of the acceptor encoding the bait region was undertaken in a semi-random fashion, by mixing the extracted insert fragment(s) from each insert vector digestion with 50 ng of digested acceptor plasmid in a 3:1 molar ratio of insert:plasmid. Ligation was achieved using a Quick Ligation kit (New England Biolabs) according to the kit instructions. The mixture of ligated plasmids was then transformed into E. coli strain GC10 (Genessee Scientific) and spread onto Luria broth/agar plates containing 100 µg/mL ampicillin to generate single colonies of transformants. 5 mL Luria broth cultures of individual colonies from each ligation reaction were grown and the plasmid DNA contained within each extracted via a Qiagen QiaPrep miniprep kit according to the kit instructions. These plasmids were sent to Genewiz for sequence confirmation using a primer that anneals to the sequence of the A2M construct just upstream of the bait region. The individual chromatogram traces were analyzed for the presence of heterogeneity in the sequence, and the sequences of the individual inserts confirmed.

Example 9—Expression of A2M Variants

A2M variants were expressed in HEK293F cells (Gibco) by transient transfection of each construct in suspension cells. Cells were grown to a density of 550,000 cells/mL in a Erlenmeyer cell culture flask containing 20 mL of FreeStyle F17 medium (Invitrogen) containing 1× GlutaMax (Gibco) on a rotator at a speed of 125 rpm inside a 37° C.

incubator containing an 8% CO2/air mixture. Cells were transfected by mixing 20 µg of plasmid DNA of each construct (wild-type or variant) in a 1:2 (w/v) ratio with TransIT Pro plus 10 µL TransIT Boost (Mirus) 15 minutes before addition to media. Cells were maintained in the same conditions for three days after transfection before the media containing secreted recombinant protein was removed for protein purification (FIG. 3).

Example 10—Purification of A2M Variants

Since the A2M expression construct encodes the precursor A2M protein, the expressed and processed recombinant protein is secreted into the cell culture medium via the natural A2M secretion signal. Secreted recombinant wild-type A2M and A2M bait region variants were purified from the transfected cell culture media by Immobilized Metal Affinity Chromatography using the 6× His tag (SEQ ID NO. 74) at the C-terminus of each construct. The media removed from the transfected cells was centrifuged at 17,500G for 15 minutes to remove all cells. Imidazole was added to the clarified media to a final concentration of 10 mM. 1 mL of HisPur Cobalt resin slurry (Pierce) was added to the sample and allowed to equilibrate with shaking on a rocker at 4° C. for one hour. The beads were collected by centrifugation at 700G for 2 minutes and the supernatant discarded. The beads were washed three times in 10 mL of a buffer of 50 mM Tris-Cl, 150 mM NaCl, 10 mM imidazole, pH 7.4, each time the beads were collected by centrifugation at 700G, and the supernatant removed and discarded. The protein was eluted by mixing of 2 mL of elution buffer (wash buffer containing 200 mM imidazole) with the beads and centrifuging for 2 minutes at 700G. The supernatant was collected and retained, and the elution repeated a total of three times. The purified proteins contained in the sample were then concentrated to 100 µL volume (typically between 100 µg/mL and 600 µg/mL-) using an Amicon spin filter with a NMCO of 100 KDa. During concentration the imidazole containing buffer was exhaustively exchanged for 50 mM HEPES, 150 mM NaCl, 10 mM $CaCl_2$, 100 µm $ZnCl_2$, 0.05% (w/v) Brij-35, pH 7.4 (HNZCB buffer). The concentration of the protein was determined using BCA (Pierce) and 660 nm (Pierce) assays. 1 µg of each purified protein was mixed with reducing SDS-PAGE loading buffer, heated for five minutes at 95° C., and loaded onto a 7.5% Tris-glycine SDS-PAGE stain-free gel (Bio-rad). The gel was developed by exposing to UV light for five minutes, and a picture taken of the total protein bands. The purity of the recombinant A2M was estimated to be consistently greater than 90% across all variants and wild-type proteins (FIG. 15).

Figure 22:
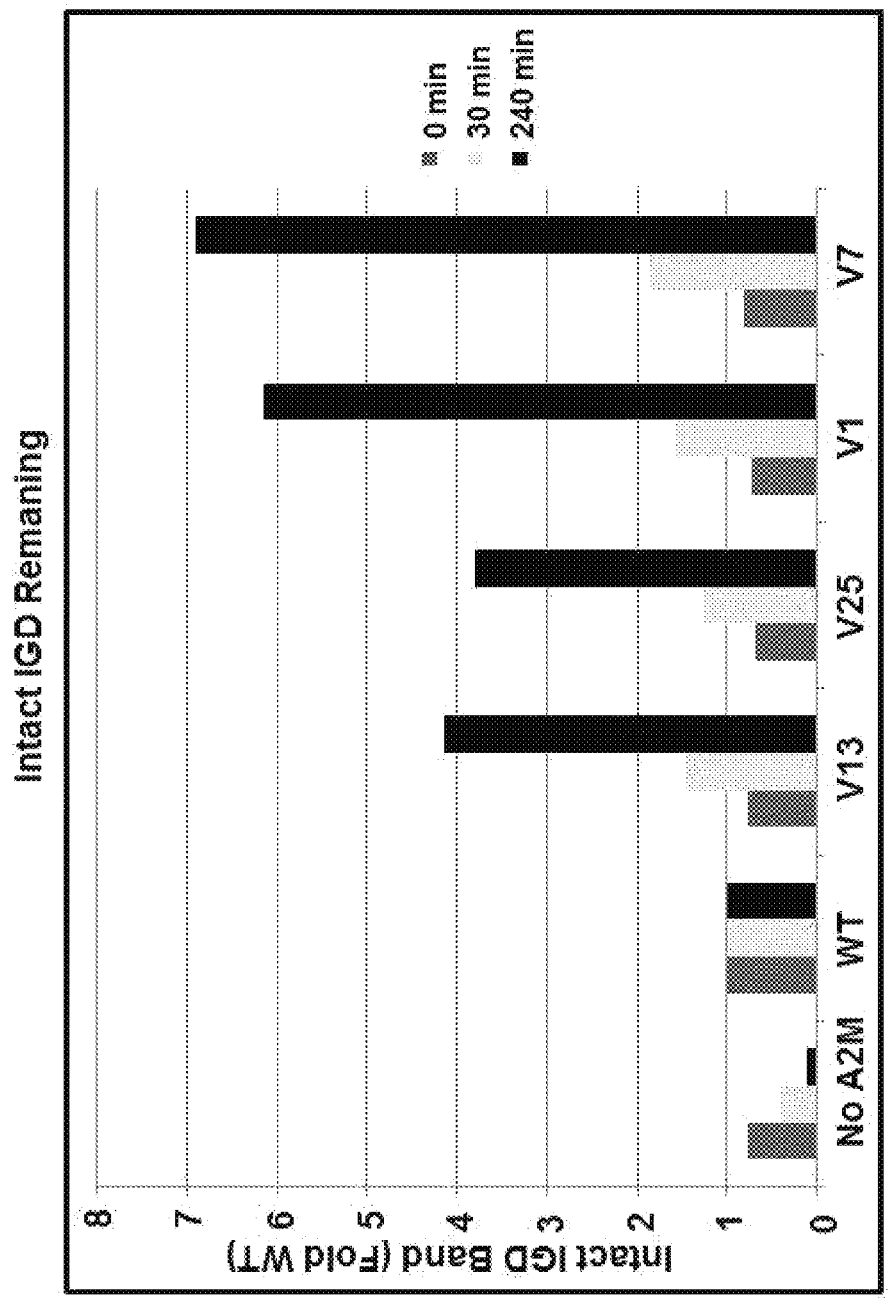
FIG. 22 depicts the protective effect of the A2M wild type vs. some of the variants of the digestion of IGD domain from a mixture of proteases. 10 nM of each MMP1, MMP3, MMP7, MMP13, ADAMTS4 and ADAMTS5 were mixed and used to digest IGD in the presence or absence of A2M wild type and A2M variants.

Example 11—Screening of Inhibition Abilities of ADAMTSs and MMPs by A2M Variants Forty A2M variants containing SEQ ID Nos.: 5-44 and the tagged wild-type protein were screened for their comparative ability to inhibit proteolysis of a recombinant IDG fragment of human aggrecan which consist of the G1, G2, and interglobular domains (R&D) by ADAMTS-4, ADAMTS-5, and MMP13. Screening the effectiveness of these variants for the inhibition of each of these enzymes was done in the same manner taking in consideration the rate of the proteolytic activity of each protease. The amount of IGD fragment in each sample was held constant at 0.1 µg, whereas the amount of protease varied depending on the activity of the protease toward IGD fragment. Since each of the variants and wild-type A2M vary greatly in the kinetics of bind to each protease, some showed complete inhibition with no pre-incubation of A2M with the protease, where others showed some inhibition if incubated with the protease for 10 minutes, and others showed no inhibition even after a pre-incubation of A2M with the protease. Two independent assays were performed on each A2M variant: one in which the protease, IGD fragment, and A2M were all added at the same time (no pre-incubation), and one in which the protease and A2M were pre-incubated at room temperature for ten minutes before addition of the IGD fragment, in order to detect slower inhibitors binding to the proteases. For the experiment with no pre-incubation of protease with A2M, 5 µL of 150 nM tagged wild-type A2M or an A2M variant in HNZCB buffer was added to a microcentrifuge tube. 5 µL of 40 µg/mL IGD fragment was then added to the same tube and mixed. Finally 5 µL of 150 nM (ADAMTS-4 and ADAMTS-5, a 1:1 A2M:protease molar ratio) or 75 nM (MMP13—a 2:1 A2M:protease molar ratio) protease was added to the tube. For the experiment with a 10 minute pre-incubation, 5 µL of each A2M was mixed with 5 µL of protease 10 minutes before addition of 5 µL of IGD fragment. All samples were incubated at 37° C. for one hour before being stopped by addition of 2× reducing SDS-PAGE loading buffer (Bio-rad) and heating for 5 min. at 95° C. 15 µL of each sample was loaded onto a 7.5% Tris-Glycine Stain Free Gel (Bio-Rad) and run at 150 V for 1 hour. Total protein was visualized and imaged under UV light as per gel instructions. The proteins were then blotted onto a nitrocellulose membrane via an iBlot (Invitrogen) dry blotting system using a transfer time of seven minutes, blocked for one hour using TBS casein blocking solution (Bio-rad), and probed using an anti-IGD fragment goat polyclonal antibody (R&D Biosystems catalog #AF1220) at a concentration of 0.1 µg/mL in TBS-T. The blot was washed three times with TBS-T and probed with an HRP-conjugated anti-goat IgG polyclonal antibody (Sigma catalog #A5420) at 0.1 µg/mL in casein blocking solution. The blots were developed using ECL Plus chemiluminescence kits (Pierce) according to the manufacturer instructions. The Western blots were imaged in a ChemiDoc imager system (Bio-rad). Each IGD fragment band on the Western (intact and degraded IGD fragment) was quantified using ImageLab software. The amount of degradation of IGD fragment in the presence of each A2M variant was quantified by comparing the intensities of the degraded and intact IGD fragment bands (FIGS. 16-20), and the inhibitory capacity of each variant was compared to a wild-type A2M sample that was prepared along with each batch of variants. From this initial round of screening, eight variants were selected for further screening against MMP1, MMP2, MMP3, MMP8, MMP9, MMP12, and Cathepsin K (all enzymes are recombinant human constructs and purchased from R&D). The comparison of the inhibitory capacity of each variant was done by taking the ratio of the intensity of the degraded band to the intact band with the exception of MMP9 and MMP13 which degraded IGD fragment in such a manner that cleaved fragments did not appear on the Western blot. In these cases the comparison was done based solely on the intensity of the remaining intact IGD fragment band. Additionally, ADAMTS-1 and MMP7 only cleaved the IGD fragment perceptibly; therefore, accurate inhibition measurements could not be quantified. In these cases all of the variants were judged to be essentially equivalent to wild-type with respect to these two proteases. After evaluating all inhibition data, four variants were selected based on improved or at least equivalent inhibition characteristics against all proteases tested (FIGS. 17-21) or a mixture of proteases known to degrade cartilage (FIG. 22).

Example 12—Screening of A2M Variants vs. Trypsin and Chymotrypsin

To verify that the four selected A2M variants are still capable of inhibiting the general proteases trypsin and chymotrypsin to a similar degree as the wild-type protein, the variants were tested in a fluorescent proteolysis assay (Twining, S. S., *Anal. Biochem.* Vol. 143, 1984, pp. 30-34). In this assay, one monitors the increase in fluorescence emission from a FITC-labeled protein substrate that is caused by a proteolysis-dependent release of the fluorophore. Two experiments were done on each variant: one in which the molar ratio of A2M:protease is held at 1:1, and another in which the A2M is reduced to 0.5:1. 40 µL of wild-type or variant A2M at a concentration of 100 nM (for the 1:1 ratio) or 50 nM (for the 0.5:1 ratio) in HNZCB buffer was mixed with 100 µL of bovine trypsin (Sigma) at 40 nM and incubated at room temp for 5 minutes. Into this mixture 70 µL of 40 µg/mL FTC-casein substrate (Pierce) was added, mixed, and immediately pipetted into three wells of a 384 well plate (65 µL/well) The plate was placed into a Cary Eclipse fluorimeter and read in kinetic mode (single wavelength) with excitation wavelength of 485 nm and emission wavelengths of 519 nm for fifteen minutes, during which time the rate of casein degradation by the protease remains approximately linear. The emission intensity was averaged for the three sample wells, plotted vs. time, and a straight line fitted to the data from each sample and control (FIG. 18, left). The slope of the fitted line was taken as a measure of the protease activity remaining in solution. Comparison of the four chosen A2M variants to the wild-type protein shows that the variants are all capable of inhibiting trypsin and chymotrypsin approximately equally to the wild-type A2M (FIG. 18, right).

Example 13—Preparation of Blood for Autologous Therapy 120 mL of whole human blood was obtained from a subject by venipuncture. 38 mL aliquots of the blood were collected into two or more hematologic collection bottles with a suitable volume of citrate dextrose solution A ("ACD-A") in each collection bottle. The collection bottles with blood/ACD-A were placed into a fixed angle rotor centrifuge, and centrifuged at predetermined velocities and times under ambient temperature conditions. Approximately 15 mL of plasma was aliquoted from each tube with a serological pipette, leaving approximately 1 mL, of plasma above the level of the buffy coat so as not to disturb the precipitated cells. This process was repeated for the collection bottles in one or more centrifuge spin cycles to yield a volume 45 mL of total plasma from a total blood draw of 120 mL. The plasma was pooled into a separate sterile hematologic collection bag. The compositions described herein can be mixed with autograft or allograft tissue, such as bone, before administration to a subject.

Example 14—Pump Drive for Systems

This example describes the operating characteristics and limits for a Pump Drive (Pump Drive, Fixed Speed, 100-240 VAC) for use with the Easy-Load II Pump Head. This Pump Drive is intended to process APIC PRP through the filtration procedure. The Pump Drive is not patient connected. The APIC PRP will be removed after the filtration process is complete and collected through the use of a syringe. The following are features along with an indication of how the pump drive will meet these requirements.

FEATURE: 100-240 VAC, 50/60 Hz operations. IMPLEMENTATION: A medical grade, auto-sensing, switching power supply will be incorporated to allow 100-240 VAC operations FEATURE: IEC Power Cord Connector. IMPLEMENTATION: The Pump Drive will be supplied with a 10' long hospital grade power cord. The power cord will connector to the Pump Drive via an IEC input connector on the medical grade AC inlet.

FEATURE: Power Indicator, Complete light & 2-Line, 15 character digital display. IMPLEMENTATION: No separate power indicator or "complete" light will be implemented. A 2-Line LCD display will be used to display Pump Drive operations. When the display is illuminated, power is ON. When an operational cycle is "complete"—a message will be displayed on the 2-Line LCD display.

FEATURE: Power (On/Off) switch on front of unit. IMPLEMENTATION: Power (On/Off) switch will be located on the rear of the Pump Drive for safety and EMC purposes. The rear location will help minimize and ensure all creepage and clearance distances are met with regard to the AC mains.

FEATURE: Interlock (motor disable when pump head open). IMPLEMENTATION: An interlock will be incorporated into the pump head and pump drive to disable the motor when the occlusion bed is opened and the rotor assembly is exposed during tube set changes.

FEATURE: 3.1 ml/sec±2%. IMPLEMENTATION: A digital motor control system with encoder feedback will be utilized to ensure the motor speed is regulated to within ±2%.

FEATURE: Masterflex L/S Easy-Load II Pump Head: Single channel, fixed occlusion; 4-roller, stainless steel rotor; Compatible with tubing size 16, ⅛" ID; Material: Polyphenylene Sulfide; Automated tubing retainers. IMPLEMENTATION: An Easy-Load II with a standard thin wall, stainless steel rotor assembly will be used. The Easy-Load II pump head accommodates all of the requested features.

FEATURE: Control Panel with Stop, Start/Confirm buttons and Up/Down arrows.

IMPLEMENTATION: A—5 key Keypad will be utilized for operator entries. Note—to reduce lead time, an existing 7-key keypad will be utilized on the prototype Pumps.

FEATURE: Operations—Count Down timer. IMPLEMENTATION: The Pump Drive will be programmed to include a countdown timer.

FEATURE: Rubber peg feet. IMPLEMENTATION: Rubber feet will be utilized to ensure that the Pump Drive is stable and will not slide off a table or shelf.

FEATURE: Custom housing with 30° platform. IMPLEMENTATION: A painted aluminum custom enclosure will be utilized per an industrial design.

FEATURE: Pump drive to be private labeled. IMPLEMENTATION: Front and rear panel labeling will be specific color, text and content requirements.

FEATURE: Instruction Manual. IMPLEMENTATION: An instruction manual will be supplied with the Pump Drive. In addition, this Pump Drive is designed to meet UL and cUL requirements to comply with UL Mode of operation—Continuous Intended Use:

The systems described herein, such as the Autologous Platelet Integrated Concentration ("APIC") System is indicated for the rapid preparation of autologous platelet rich plasma/platelet poor plasma from a small sample of blood at the patient's point of care. The platelet rich plasma/platelet poor plasma is mixed with autograft and/or allograft bone prior to application to a bony defect for improving bone graft handling characteristics.

Product Specification

The following list is the design-input specifications for a Pump Drive of the system: Power Input: 100 VAC-240 VAC, 50/60 Hz; Operating Temperature: 15° C.-35° C.; Shipping Test: ISTA 3A; Storage Temperature: −10° C.-65° C.; Humidity: 10%-90%; Speed Range: 232 rpm, (ref. 3.1 ml/sec.=186 ml/min.); Max. Load 30 psi (disposable); Line Regulation+/−2%; Load Regulation+/−2%; Speed Regulation+/−2%

Functional Description

The Pump Drive can provide flow (speed) at a rate of 3.1 mUsec. (186 ml/min). The flow rate can be programmed or factory set. The user can follow the instructions for use to enable the Pump Drive. The Pump Drive can be programmed to stop after 30 minutes of operation. A pump head interlock circuit can remove power to the motor when the pump head rotor and rollers are exposed.

The Pump Drive can comprise the following main parts: a universal power supply, 24 VDC permanent magnet DC, 5.9:1 gear motor w/encoder, a motor drive controller board, an Easy-Load II Pump Head, 2-Line LCD display, 5-key Keypad and a two piece aluminum enclosure. The universal power supply is a purchased part, which is designed and UL listed for medical applications. The power supply can be mounted on the rear of the chassis. The 24 VDC gear motor with encoder, are purchased as an assembled set. The motor/gearbox shaft will be coupled to the pump head shaft using a flexible coupler. The motor drive controller board is located on the chassis. The EZ Load II Pump Head consists of a stainless steel rotor and rollers. On the back of the enclosure can be a medical grade, dual fused AC Inlet and the ON/OFF switch. The front of the enclosure comprises the Easy-Load II Pump Head, 2-Line LCD display & a 5-key Keypad. The pump drive can be mounted on a table or shelf.

Product Operation

Place tube set into the pump head. Secure pump head cam latch.

Connect line cord to the AC entry module on the rear panel, connect line cord to the AC mains. Turn rear power switch to the ON position. ON/OFF—A switch mounted on the back panel of the enclosure. Switches power from the mains to the universal power supply, which powers the electronics and motor. KEYPAD—A 5-key keypad mounted on the front panel. START—Key press will enable the Pump Drive (motor operating). STOP—Key press will disable the Pump Drive (motor stopped). ENTER—Key press will enable operator to confirm operator setting and sequence to the next operational display. YES—Key press will enable operator to confirm operator setting and sequence to the next operational display. NO—Key press will enable operator to confirm operator setting and sequence to the next operational display. While the Pump is operational (running), all keys should be disabled except the STOP key.

Mechanical Inputs

Tubing selection—L/S size 16 tubing. ⅛" ID×¼" OD×1/16" wall. Ref: 0.8 ml per rev.

Operator Related Outputs

LCD Display: A two-line LCD display will provide instructions and status to the user. At power up the upper line will read: "APIC SYSTEM" "Version X.X" (X.X=the latest software revision). After the initial power up display the display changes to: "PLACE TRAY" "PRESS ENTER." After enter is pressed, display changes to: "INJECT PLASMA" "PRESS ENTER." After enter is pressed, display changes to: "LOAD TUBE" "LOCK PUMP LEVER." Pump Head Lever is locked, (interlock is enabled); display changes to: "PRESS START."

Pump starts to operate . . . display to indicate (time counting down) "30:00." When time reaches 0:00, Pump Operation to stop, display to read:"CONCENTRATION DONE?" "PRESS YES OR NO." If YES is pressed, display to read: "APIC READY." If NO is pressed, display to read: "PRESS START" "TO CONTNUE." After start is pressed, pump operation to start, display to indicate time counting down: "5:00." When time reaches 0:00, Pump Operation to stop, display to read: "CONCENTRATION DONE?" "SELECT YES OR NO." If YES is pressed, display to read: "APIC READY." If NO is pressed—the 5 minute cycle repeats. The STOP key versus Pump Operations: The STOP key is always active. If STOP is pressed prior to initiating pump cycle, display changes to: "CONTINUE SET UP?" "PRESS YES OR NO." If YES is pressed, display returns to display when STOP was pressed. If NO is pressed, display to read: "PLACE TRAY" "PRESS ENTER." If STOP is pressed during pump cycle, display to read: "RESUME CYCLE?" "PRESS YES OR NO." If YES is pressed, display to read: "PRESS START." START is pressed, Pump operation resumes and display shows time of pressing "STOP" (X:XX). NO is pressed, and display reads: "END CYCLE?" "PRESS YES OR NO." YES is pressed, pump operation terminates and display reads: "0 00." NO is pressed, pump operation resumes, and cycle repeats. The Pump Head—An L/S Easy Load II Pump Head comprises:

Single channel, fixed occlusion. 4-roller, stainless steel rotor. Compatible with L/S 16 size tubing, ref. ⅛" ID. Material: Polyphenylene Sulfide. Automated, spring loaded tubing retainers MECHANICAL OUTPUTS Speed setting (rpm) 232; Max. Load continuous (psi) 30 (generated by the disposable); Number of pump heads 1; Line Regulation: ±2; (% of Max RPM); Load Regulation: ±2; (% of Max RPM); Speed Regulation±2; (% of Max RPM). "Load" is defined as the maximum load for which all specifications apply, measured at the gearbox output. "Line Regulation" is defined as the change in speed when line voltage is changed from nominal to minimum or nominal to maximum.

"Load Regulation" is defined as the change in speed when the load is changed from nominal to zero or nominal to maximum.

Example 15—System Overview

The APIC PRP System (FIGS. 24-30) can contain three components for producing APIC PRP; High Speed Bench Top Centrifuge; Peristaltic Pump w/Custom Housing; and Disposables Kit for Collection, Separation, and Administration of APIC PRP. The APIC System can separate and concentrate a patient's own blood for therapeutic use by a physician. 60 cc to 120 cc of a patient's blood can be drawn in to a collection bag, then transferred to centrifuge tubes.

The tubes can be centrifuged and the recovered plasma is then drawn off and transferred to a concentration bag. The pump can circulate the blood through a Tangential Flow Filter concentrating the APIC PRP down to a 5 cc to 10 cc of APIC. The APIC can then be used by Physicians as they deem necessary and appropriate. The system can include: Industry Standard Centrifuge and Peristaltic Pump, Private Labeled and Customized for APIC, Low Cost Disposable with Filtration, Majority of Disposable Components are PPS, Minimal number of steps. The system can include: Integrated Centrifuge and Pump Separation, Custom Ergonomic Design, Lower Cost Equipment w/Smaller Footprint, Lower Cost and Less Disposables, Ease Of Use=Set It And Forget It APIC Cell Free Concentration Kit: No Centrifugation; Direct Connection of Blood Collection Bag to Concentration Bag; Two Filters Example 16—In Vitro Cartilage Degradation Assay To test the hypotheses that cartilage catabolism caused by proinflammatory cytokines and cartilage-degrading metalloproteinases (ADAMTS) can be inhibited by preparations of Leukocyte-rich PRP (LR-PRP) or Autologous Platelet Integrated Concentrate (APIC-PRP) a controlled in vitro cartilage degradation assay was performed. BCE was treated with ADAMTS-5, TNF-α or IL-1β in the presence or absence of LR-PRP or APIC-PRP. Cartilage catabolism was measured following 2 or 3 days in culture by proteoglycan release via the presence of sulfated glycosaminoglycan (sGAG) in the media. Bovine articular cartilage explants (BCE, 200 tit mg) were isolated from 1-1.5 year-old heifers and are equilibrated 3 days in culture. BCE cultures were treated for 3 days with or without a 33% (v/v) Leukocyte rich platelet-rich Plasma (LR-PRP), blood, or APIC-PRP prepared from the same patient. Protease digestion of cartilage with 500 ng/ml ADAMTS-5 for 2 days was inhibited with a 2-fold serial dilution of APIC-PRP [$ED_{50}$=0.1% v/v]. For cytokine-induced cartilage catabolism, BCE was incubated 3 days in SFM with or without 80 ng/ml human TNF-α or 8 ng/ml human IL-1β. Cartilage degradation was inhibited with the addition of 5 mg/ml A2M or 30% (v/v) APIC-PRP. To demonstrate a dose-response curve of APIC-PRP, 3-fold serial dilutions of APIC-PRP [ED50=3% v/v] were used to inhibit TNF-α/1L-1p induced cartilage degradation. Cartilage catabolism was measured in culture supernatant by proteoglycan release via the presence of sulfated glycosaminoglycan (sGAG) using a DMMB assay with chondroitin sulphate standard curve. Cartilage degradation in 200 mg BCE was induced by addition of LR-PRP (33% v/v), demonstrating it as a source of cartilage catabolism. Treatment with proinflammatory cytokines (80 ngiml TNF-α or 8 ng/ml IL-1β), ADAMTS-5 (500 ng/ml) also resulted in increased sGAG in the medium. Addition of APIC-PRP inhibited cartilage catabolism induced by cytokines, metalloproteinases or LR-PRP in a dose dependent manner. The addition of LR-PRP at the highest concentration used in the APIC-PRP study reduced but did not inhibit cartilage catabolism induced by cytokines or MMP's measured by the release of sGAG in the medium (data not shown). Osteoarthritis (OA) is characterized by progressive degeneration of articular cartilage. The BCE model is representative of studying putative therapeutics in OA. This study demonstrates that Leukocyte-rich PRP (LR-PRP) contributed to cartilage catabolism, but APIC-PRP protected cartilage from degradation by known OA mediators. This activity can be explained by the 5-10 fold increased concentration of A2M in APIC-PRP over its concentration in blood. This conclusion is in agreement with experiments that demonstrate the protective effect of A2M on cartilage. This improved understanding of cartilage biology and metabolism should lead to clinical trials of APIC-PRP in humans.

Example 17—Chondroprotective Effect in Rabbit Model

The pathology ad osteoarthritis involves the upregulation of inflammatory mediators and preleases such as matrix metalloproteases (MMPs) A2M is a naturally occurring plasma glycoprotein that is a potent protease inhibitor. A2M is behaved to modulate cartilage catabolism by its ability to bind, trap and clear MMPs. Though A2M functions throughout multiple tissues and extracellular spaces, it does not normally reach high levels within the intrarticular joint space. The ability of the Autologous Protease Inhibitor Concentrate (APIC-Cell Free), which concentrates A2M from the blood, was tested to inhibit cartilage catabolism, and thereby attenuate the development of osteoarthritis in a ACL-T rabbit model. The rabbit model represents a functional load-bearing in vivo anatomical model for the evaluation of osteoarthritis, which exhibits mechanical properties, morphological structures, and healing capacity similar to human tissues. Female 8-12 months old New Zealand white rabbits were used in this study. This rabbit model represents a functional load-bearing in vivo anatomical model for the evaluation of osteoarthritis which exhibits mechanical properties, morphological structures and healing capacity similar to human tissue. Multiple Injection Cohort (Group 1): 6 rabbits received ACL-T surgery on the right knee and sham surgery on the left knee. Four injections of 0.3 mL Autologous Protease Inhibitor Concentrate (APIC-Cell Free) were prepared from the rabbit blood and were administered on day 1. 4, 14, and 28 following the ACL knee injury. Rabbits received an equivalent volume of the sterile isotonic saline in the contra-lateral control knee. The rabbits were monitored for 6 weeks, then sacrificed for cartilage degeneration assessment. Control Group (Group 2): 6 rabbits received ACL-T surgery on the right knee without sham surgery on the left knee. These rabbits were the control group and accordingly did not receive any treatment.

Autologous A2M Concentrate Preparation

Figure 12:
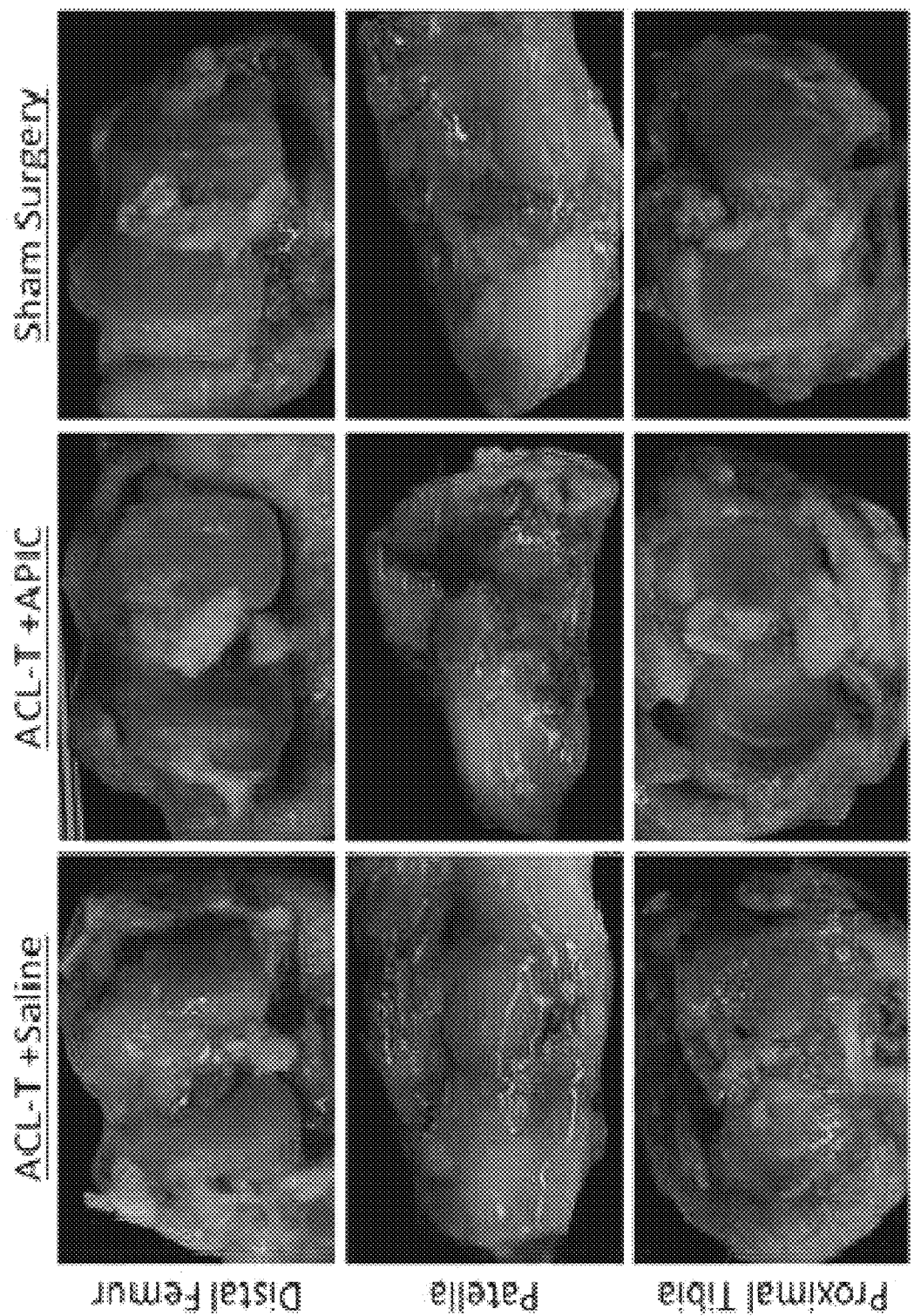
FIG. 12 depicts macroscopic images of rabbit knees 6 weeks after ACL-T surgery and treatment with saline or APIC cell free. Sham surgeries without ACL-T were performed as a control.
Figures 13A, 13B:
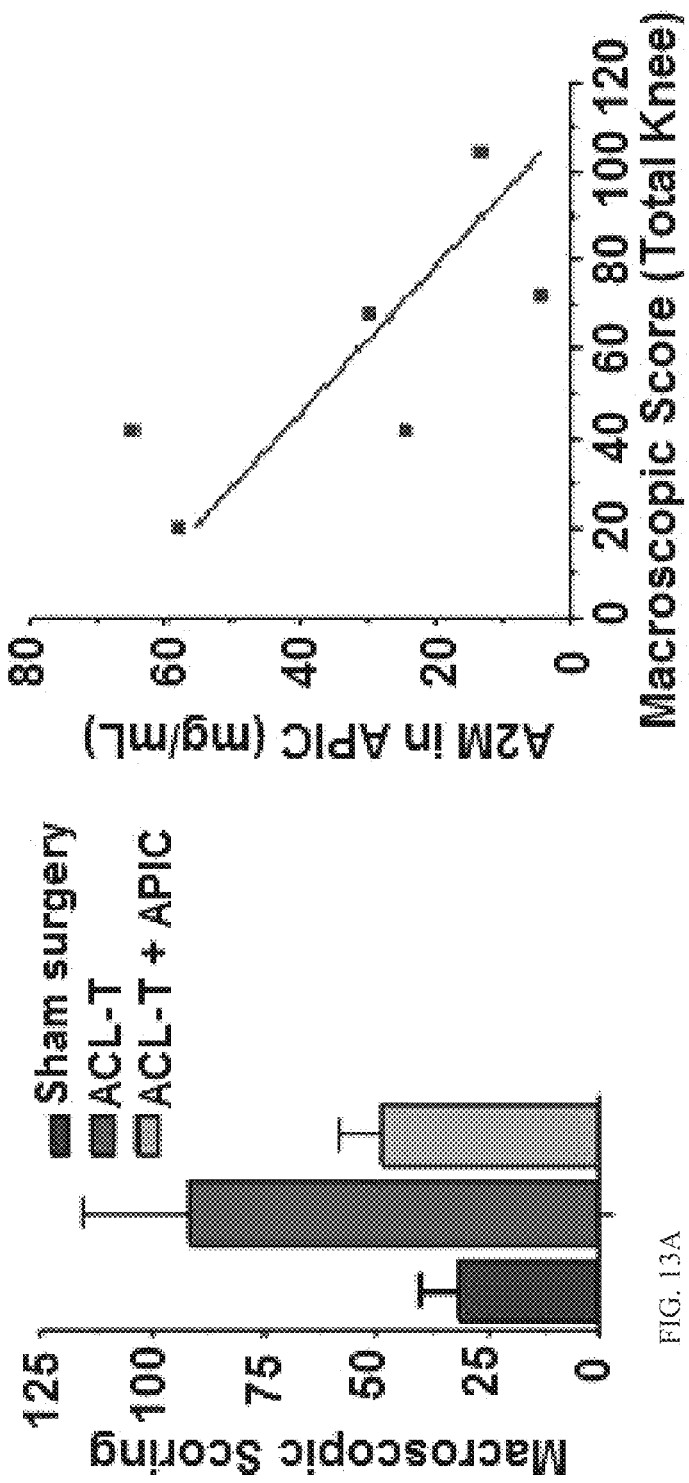
FIG. 13A depicts a graph of macroscopic evaluation for the experiments shown in FIG. 12. The values shown are the average of the macroscopic evaluation of 6 rabbits.
FIG. 13B depicts a graph of macroscopic evaluation, showing an inverse correlation of A2M in APIC cell free treatment and cartilage degradation for the experiments shown in FIG. 12.

Prior to the ACL injury, 20 mL of blood was removed from each animal in group 1 and used to prepare the APIC Cell Free concentrate using a series of filters. Every rabbit received the protease inhibitor concentrate from its own blood. Six weeks after the ACL-T operation the animal was sacrificed for macroscopic and microscopic knee joint cartilage evaluation to determine OA progression Macroscopic and Histological Analyses For macroscopic evaluation, the distal femoral condyles and tibial plateau surfaces were analyzed and lesions were classified using a validated 0 to 8 scale as previously described. The locations of the lesions in the joint were recorded by a specific nine-area grid of each joint surface, following the classification of the International Cartilage Repair Society (OARSI), which was adapted to the rabbit knee by Lindhorst et al. After macroscopic examination. Isolated femoral and tibial samples were feed and decalcified for histological (microscopic evaluation). Macroscopic evaluation of the femur and tibia demonstrated features consistent with cartage catabolism consistent with OA. Treatment with APIC Cell Free considerably improved cartilage appearance, similar to the sham surgery control (FIGS. 12-14). Application of APIC reduced cartilage degradation by 53+/−20% compared to untreated controls (mean±SEM. p=0.0086) (FIGS. 13A and B). The concentration of A2M in the APIC Cell Free varied front 5-65 mg/ml. There was a dose-dependent correlation between higher concentrations of A2M in the API Cell Free and decreased OARSI total knee score on the macroscopic evaluation (FIGS. 13A and B). There was also a dose-dependent therapeutic benefit to APIC Cell Free treatment observed in sum OARSI histopathology evaluations of Safarin-O staining ($r^2$=0.73), Structure ($r^2$=0.76), Chondrocyte density ($r^2$=0.50), and Cluster Formation ($r^2$=0.97) (FIG. 14). The data suggests that the Autologous Protease inhibitor Concentrate (APIC-Cell Free), which contains 9-10 times the A2M concentration in blood, has a chondroprotective effect on an osteoarthritis rabbit model.

Example 18—Effect of A2M on BCEs

To test the hypothesis that the addition of proinflammatory cytokines or cartilage-degrading metalloproteinases (ADAMTS and MMP) stimulate cartilage degradation that will be inhibited by A2M, a controlled in vitro cartilage degradation assay was performed. Bovine Cartilage Explants (BCE) were treated with or without proinflammatory cytokines (TNF-α or IL-1β) or cartilage-degrading metalloproteinases (ADAMTS-5, ADAMTS-4, MMP-7, or MMP-12) in the presence or absence of purified A2M.

Bovine articular cartilage explants (BCE. 100±4 mg) were isolated from 1-1.5 year-old heifers and were equilibrated 3 days in culture. To degrade cartilage by protease digestions, BCE was incubated 2 days in Serum-free Media (SFM) with or without 500 ng/mL ADAMTS-4 or ADAMTS-5 and 3-5 µg/mL of MMP-3, MMP-7, MMP-12, or MMP-13. MMP-3 was activated with chymotrypsin before application on BCE. For cytokine-induced cartilage catabolism, BCE (200+/−4 mg) was incubated 3 days in SFM with or without 80 ng/ml human TNF-α and 8 ng/mL human 1L-1β. Cartilage degradation was inhibited with the addition of 100 µg/mL of purified human A2M for protease digestion or 5 mg/mL A2M for cytokine-induced degradation.

Cartilage catabolism was measured in culture supernatant by 1) proteoglycan release via the presence of sulfated glycosaminoglycan (sGAG) and 2) the presence of cartilage proteoglycan fragments by Bio-Rad Stainless SDS-PAGE and Aggrecan G3 fragments by Western blotting.

Fibronectin and Aggrecan Complexes (FAC) were formed by combining degraded cartilage matrix proteoglycans from the BCE experiments with Fibronectin and Synovial Fluid and incubating for 4 hours. Newly formed FAC was measured by the FACT ELISA, with the alteration of using an α-Aggrecan G3 antibody needed to recognize bovine aggrecan.

The $IC_{50}$ needed to inhibit cartilage catabolism by 500 mg/mL proteases was 7 µg/mL A2M for ADAMTS-5 and 3 µg/mL for ADAMTS-4. Addition of 5 mg/mL A2M also inhibited cartilage catabolism induced by TNF-α or IL-1β. Further, A2M blocked production of Aggrecan G3 fragments, which form complexes with fibronectin and are a marker for pain and degrading joints. (FIGS. 7-10).

What is claim is:

1. A composition comprising a recombinant alpha-2-macroglobulin (A2M) polypeptide comprising a non-natural bait region, wherein:
   (a) the non-natural bait region comprises:
      (i) a sequence with 100% sequence identity to at least 24 contiguous amino acid residues of SEQ ID NO: 47, and
      (ii) two or more protease recognition sequences;
   (b) the non-natural bait region replaces the bait region of a wild-type A2M polypeptide with a sequence according to SEQ ID NO: 3; and
   (c) the non-natural bait region has at least 70% identity to the entirety of SEQ ID NO: 47.

2. The composition of claim 1, wherein the non-natural bait region has at least 78% sequence identity to the entirety of SEQ ID NO: 47.

3. The composition of claim 1, wherein the non-natural bait region has at least 80% sequence identity to the entirety of SEQ ID NO: 47.

4. The composition of claim 1, wherein the non-natural bait region has at least 90% sequence identity to the entirety of SEQ ID NO: 47.

5. The composition of claim 1, wherein the non-natural bait region consists of the amino acid sequence according to SEQ ID NO: 47.

6. The composition of claim 1, wherein the recombinant A2M polypeptide further comprises a glycosylation site that is not present in the wild-type A2M polypeptide.

7. The composition of claim 6, wherein a polyethylene glycol (PEG) is covalently attached to the glycosylation site.

8. The composition of claim 1, wherein the non-natural bait region comprises a consensus sequence for a protease selected from the group consisting of a serine protease, a threonine protease, a cysteine protease, an aspartate protease, a metalloprotease, a glutamic acid protease, and combinations thereof.

9. The composition of claim 1, wherein the non-natural bait region comprises a consensus sequence for a protease selected from the group consisting of a matrix metalloproteinase (MMP), a disintegrin and metalloproteinase with thrombospondin motifs (ADAMTS), chymotrypsin, trypsin, elastase, a compliment factor, a clotting factor, thrombin, plasmin, subtilisin, neprilysin, procollagen peptidase, thermolysin, pregnancy-associated plasma protein A, bone morphogenetic protein 1, lysostaphin, insulin degrading enzyme, zinc metallopeptidase STE2 (ZMPSTE2), acetylcholinesterase, and combinations thereof.

10. The composition of claim 1, wherein the two or more protease recognition sequences comprises a protease recognition sequence from a non-A2M protein.

11. The composition of claim 1, wherein the non-natural bait region comprises a protease recognition sequence operable to covalently attach a protease to the recombinant A2M polypeptide.

12. The composition of claim 1, wherein the recombinant A2M polypeptide comprises a sequence with at least 80% identity to SEQ ID NO: 4.

13. A pharmaceutical composition comprising the composition of claim 1 and a pharmaceutically acceptable excipient.

* * * * *

SEQUENCE LISTING

<160> NUMBER OF SEQ ID NOS: 76

<210> SEQ ID NO 1
<211> LENGTH: 8993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ctcatgacca aaatccctta acgtgagtta cgcgcgcgtc gttccactga gcgtcagacc        60
ccgtagaaaa gatcaaagga tcttcttgag atccttttt tctgcgcgta atctgctgct       120
tgcaaacaaa aaaaccaccg ctaccagcgg tggtttgttt gccggatcaa gagctaccaa       180 ctcttttttcc gaaggtaact ggcttcagca gagcgcagat accaaatact gttcttctag       240
tgtagccgta gttagcccac cacttcaaga actctgtagc accgcctaca tacctcgctc       300
tgctaatcct gttaccagtg gctgctgcca gtggcgataa gtcgtgtctt accgggttgg       360
actcaagacg atagttaccg gataaggcgc agcggtcggg ctgaacgggg ggttcgtgca       420
cacagcccag cttggagcga acgacctaca ccgaactgag atacctacag cgtgagctat       480
gagaaagcgc cacgcttccc gaagggagaa aggcggacag gtatccggta agcggcaggg       540
tcggaacagg agagcgcacg agggagcttc caggggggaaa cgcctggtat ctttatagtc       600
ctgtcgggtt tcgccacctc tgacttgagc gtcgatttt gtgatgctcg tcagggggc        660 ggagcctatg gaaaaacgcc agcaacgcgg ccttttacg gttcctggcc ttttgctggc       720
cttttgctca catgttcttt cctgcgttat ccctgattc tgtggataac cgtattaccg       780
cctttgagtg agctgatacc gctcgccgca gccgaacgac cgagcgcagc gagtcagtga       840
```

```
gcgaggaagc ggaaggcgag agtagggaac tgccaggcat caaactaagc agaaggcccc    900
tgacggatgg cctttttgcg tttctacaaa ctctttctgt gttgtaaaac gacggccagt    960
cttaagctcg ggcccctgg gcggttctga taacgagtaa tcgttaatcc gcaaataacg    1020
taaaaaccg cttcggcggg ttttttatg ggggagttt agggaaagag catttgtcag    1080
aatatttaag ggcgcctgtc actttgcttg atatatgaga attatttaac cttataaatg    1140
agaaaaagc aacgcacttt aaataagata cgttgctttt tcgattgatg aacacctata    1200
attaaactat tcatctatta tttatgattt tttgtatata caatatttct agtttgttaa    1260
agagaattaa gaaataaat ctcgaaaata ataagggaa aatcagtttt tgatatcaaa    1320
attatacatg tcaacgataa tacaaaatat aatacaaact ataagatgtt atcagtattt    1380
attatcattt agaataaatt ttgtgtcgcc cttaattgtg agcggataac aattacgagc    1440
ttcatgcaca gtggcgttga cattgattat tgactagtta ttaatagtaa tcaattacgg    1500
ggtcattagt tcatagccca tatatggagt tccgcgttac ataacttacg gtaaatggcc    1560
cgcctggctg accgcccaac gacccccgcc cattgacgtc aataatgacg tatgttccca    1620
tagtaacgcc aatagggact ttccattgac gtcaatgggt ggagtattta cggtaaactg    1680
cccacttggc agtacatcaa gtgtatcata tgccaagtac gccccctatt gacgtcaatg    1740
acggtaaatg gcccgcctgg cattatgccc agtacatgac cttatgggac tttcctactt    1800
ggcagtacat ctacgtatta gtcatcgcta ttaccatggt gatgcggttt tggcagtaca    1860
tcaatgggcg tggatagcgg tttgactcac ggggatttcc aagtctccac cccattgacg    1920
tcaatgggag tttgttttgg caccaaaatc aacgggactt tccaaaatgt cgtaacaact    1980
ccgccccatt gacgcaaatg ggcggtaggc gtgtacggtg ggaggtctat ataagcagag    2040
ctctctggct aactagagaa cccactgctt actggcttat cgaaattaat acgactcact    2100
ataggggtac ctgccaccat ggggaaaaac aaactgctgc atccaagcct ggtcctgctg    2160
ctgctggttc tgctgcctac tgacgcctct gtgagcggaa agcccagta tatggttctg    2220
gtcccgtccc tgctgcacac cgagaccaca gaaaagggt gcgtgctgct gtcttacctg    2280
aatgaaacag tgactgttag tgcctcactg gagagtgtgc gcggaaatcg ttcactgttc    2340
accgatctgg aggcggaaaa cgatgtgctg cattgcgtcg catttgctgt gccaaaaagc    2400
tcctctaatg aagaagtgat gttcctgacc gtccaggtga agggccctac acaggaattc    2460
aaaaaacgca ctaccgttat ggtcaaaaac gaggatagcc tggtgtttgt tcagacagac    2520
aaatccatct ataagcctgg tcagactgtg aagttccggg tggttagcat ggatgaaaat    2580
tttcaccccc tgaacgagct gattccactg gtgtacatcc aggaccctaa aggcaaccgc    2640
atcgcccagt ggcagtcttt ccagctggaa ggcggtctga agcagtttag ttttcctctg    2700
agttcagagc cgtttcaggg ttcttataaa gtcgtggttc agaaaaagag tggggacgt    2760
actgaacatc ctttaccgt tgaagagttc gtcctgccga aatttgaggt ccaggtgacc    2820
gttcccaaga ttatcacaat tctggaagag gaaatgaacg tgagcgtgtg cggactgtat    2880
acctacggca aaccagtgcc tggtcacgtt acagtcagta tctgccgtaa gtactcagat    2940
gcaagcgact gtcatggcga agattcacag gcttttgcg agaagttcag cggccagctg    3000
aactcccacg gttgcttcta tcagcaggtg aaaaccaagg ttttttcagct gaaacggaag    3060
gagtacgaaa tgaaactgca tacagaagcc cagattcagg aagaaggcac cgtcgtggaa    3120
ctgactggtc gtcagagctc cgagattacc cggacaatca ctaaactgag cttcgtgaag    3180
gttgattccc actttcggca ggggattccc tttttcggac aggtgcgcct ggttgacggg    3240
```

```
aaaggagttc cgatccccaa caaagtgatc tttattcgcg gcaatgaagc caactattac    3300
agcaacgcga caactgatga gcatgggctg gtgcagttca gtatcaatac cacaaacgtg    3360
atgggaacct cactgacagt ccgcgtgaat tataaagacc gttcaccgtg ttatggctac    3420
cagtgggtga gcgaggaaca cgaggaagcc caccataccg cgtacctggt tttcagcccc    3480
tccaaatctt ttgtccatct ggaacctatg tctcacgagc tgccgtgcgg ccatacccag    3540
acagtgcagg cacattatat tctgaacggc ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt    3720
gctccggtcg cccgtctgct gatctatgcc gtgctgccaa ccggcgatgt tatcggtgac    3780
tccgccaaat acgatgtgga gaattgtctg gcgaacaagg ttgacctgag ctttccccc     3840
tctcagagtc tgccagcgtc tcatgcacat ctgcgtgtga ccgcagcccc tcagagcgtt    3900
tgcgctctgc gtgcagtgga tcagtccgtg ctgctgatga gccagacgc agaactgtct     3960
gctagcagcg tgtataatct gctgcctgag aaagatctga ccgggttccc aggacctctg    4020
aacgatcagg atgacgaaga ctgtattaat cgccacaacg tgtatattaa tgggatcaca    4080
tacactccgg tttcaagcac caacgaaaaa gatatgtaca gcttcctgga ggacatgggt    4140
ctgaaagcgt ttaccaattc caagatccgg aaacccaaga tgtgcccaca gctgcagcag    4200
tatgaaatgc acggacctga gggtctgcgt gtgggctttt acgaatctga tgtgatggga    4260
cgtggtcatg cacgtctggt tcatgtcgag gaaccacaca ccgaaacagt gcgtaaatac    4320
ttccctgaga cctggatttg ggacctggtt gtggtgaact ccgcgggtgt ggcagaagtg    4380
ggtgttaccg tcccggatac tattaccgaa tggaaagcag gtgccttctg tctgtctgag    4440
gatgcagggc tgggaatctc ctctacagcc tctctgcgcg cgtttcagcc cttttttcgtc   4500
gaactgacta tgccatatag cgtgattcgt ggcgaggcat tcactctgaa agctaccgtg    4560
ctgaattacc tgcccaagtg catccgcgtg agcgtgcagc tggaagctag tcccgccttt    4620
ctggcggtcc cagtggagaa ggaacaggca ccgcactgca tttgtgctaa cggccggcag    4680
actgttcct gggccgtcac ccccaaatct ctgggtaatg tgaacttcac cgtttcagca     4740
gaggctctgg aaagccagga gctgtgcggc accgaagtcc catccgtgcc tgagcatggt    4800
cgcaaagata cagtcatcaa gcctctgctg gttgaaccgg aaggcctgga agggaaact     4860
acctttaatt ctctgctgtg cccaagtggc ggtgaagtgt ccgaggaact gtctctgaaa    4920
ctgccgccca acgtggtcga ggaatctgcc cgtgcgtcag ttagcgtcct gggggatatt    4980
ctgggaagtg ccatgcagaa tacccagaac ctgctgcaga tgccgtatgg ctgtggcgag    5040
cagaatatgg ttctgtttgc gcccaacatc tatgtcctgg attacctgaa tgaaacacag    5100
cagctgactc ctgaaatcaa aagcaaggca atcgggtatc tgaataccgg ataccagcgg    5160
cagctgaact ataagcacta cgacggctcc tattctacct tcggcgaacg gtacggtcgc    5220
aatcagggga cacttggct gaccgccttt gtgctgaaaa cctttgccca ggctcgcgcc     5280
tatatcttta ttgatgaggc ccatattaca caggcgctga tctggctgtc acagcgccag    5340
aaggacaacg ggtgtttccg tagttcagga agcctgctga caatgccat caaaggcggc     5400
gtcgaggatg aagtgacact gagcgcatac attactatcg ctctgctgga aatccctctg    5460
acagtgactc acccggtggt tcgcaatgct ctgttttgcc tggaaagtgc atggaaaaca    5520
gctcaggaag gcgatcacgg atcacacgtg tatactaagg cactgctggc gtacgcattc    5580
```

```
gctctggccg gcaaccagga taaacgtaaa gaagtgctga atcactgaa tgaggaagca    5640
gttaaaaagg acaacagcgt ccactgggaa cggccgcaga acccaaggc tccagtgggt    5700
cacttttatg agcctcaggc accgagtgct gaggtggaaa tgacctcata tgttctgctg    5760
gcatacctga ccgcacagcc tgcccccaca tcagaagatc tgacaagcgc cactaatatt    5820
gtgaaatgga tcaccaagca gcagaacgcg cagggcggtt ttagctccac ccaggacaca    5880
gtcgtggcac tgcacgctct gtctaaatat ggggcagcta ccttcacacg cactggaaag    5940
gccgcgcaag tgactattca gtctagtggc acctttcaa gcaagttcca ggtggataac    6000
aataaccgtc tgctgctgca gcaggtgtcc ctgcccgaac tgccaggcga gtactctatg    6060
aaagtcactg gggaaggatg cgtgtatctg cagacctccc tgaaatacaa tattctgccc    6120
gagaaagaag aatttccatt cgcactgggc gtgcagaccc tgcctcagac atgcgatgaa    6180
ccgaaggctc atacttcttt tcagatcagt ctgtcagtga gctataccgg gtcccgctct    6240
gccagtaaca tggcgattgt ggatgtgaaa atggtgagtg gattcatccc tctgaaaccg    6300
actgtgaaga tgctggaacg gagtaatcac gtttcacgca ccgaggtctc ctctaaccat    6360
gtgctgatct acctggataa agtgtccaat cagacactgt ctctgttttt cactgtgctg    6420
caggatgtcc ccgtgcgtga cctgaaacca gccattgtta aggtctatga ttattacgaa    6480
accgacgagt tcgcgatcgc agaatacaac gcgccgtgca gcaaagacct ggggaatgct    6540
gactacaagg acgacgacga caaggggggca agccaccacc atcaccatca ctaaggatcc    6600
aaaatcagcc tcgactgtgc cttctagttg ccagccatct gttgtttgcc cctccccgt    6660
gccttccttg accctggaag gtgccactcc cactgtcctt tcctaataaa atgaggaaat    6720
tgcatcacaa cactcaaccc tatctcggtc tattcttttg atttataagg gattttgccg    6780
atttcggcct attggttaaa aaatgagctg atttaacaaa atttaacgc gaattaattc    6840
tgtggaatgt gtgtcagtta gggtgtggaa agtccccagg ctccccagca ggcagaagta    6900
tgcaaagcat gcatctcaat tagtcagcaa ccaggtgtgg aaagtcccca ggctccccag    6960
caggcagaag tatgcaaagc atgcatctca attagtcagc aaccatagtc ccgcccctaa    7020
ctccgcccat cccgccccta actccgccca gttccgccca ttctccgccc catggctgac    7080
taattttttt tatttatgca gaggccgagg ccgcctctgc ctctgagcta ttccagaagt    7140
agtgaggagg cttttttgga ggcctaggct tttgcaaaaa gctcccggga gcttgtatat    7200
ccatttttcgg atctgatcag cacgtgttga caattaatca tcggcatagt atatcggcat    7260
agtataatac gacaaggtga ggaactaaac catggccaag cctttgtctc aagaagaatc    7320
caccctcatt gaaagagcaa cggctacaat caacagcatc cccatctctg aagactacag    7380
cgtcgccagc gcagctctct ctagcgacgg ccgcatcttc actggtgtca atgtatatca    7440
ttttactggg ggaccttgtg cagaactcgt ggtgctgggc actgctgctg ctgcggcagc    7500
tggcaacctg acttgtatcg tcgcgatcgg aaatgagaac aggggcatct tgagcccctg    7560
cggacggtgc cgacaggtgc ttctcgatct gcatcctggg atcaaagcca tagtgaagga    7620
cagtgatgga cagccgacgg cagttgggat tcgtgaattg ctgccctctg gttatgtgtg    7680
ggagggctaa cacgtgctac gagatttcga ttccaccgcc gccttctatg aaaggttggg    7740
cttcggaatc gttttccggg acgccggctg gatgatcctc cagcgcgggg atctcatgct    7800
ggagttcttc gcccacccca acttgtttat tgcagcttat aatggttaca ataaagcaa     7860
tagcatcaca aatttcacaa ataaagcatt ttttcactg cattctagtt gtggtttgtc    7920
caaactcatc aatgtatctt atcatgtctg tataccgtcg acctctagct agagcttggc    7980
```

```
gtaatcatgg tcattaccaa tgcttaatca gtgaggcacc tatctcagcg atctgtctat    8040
ttcgttcatc catagttgcc tgactccccg tcgtgtagat aactacgata cgggagggct    8100
taccatctgg ccccagcgct gcgatgatac cgcgagaacc acgctcaccg gctccggatt    8160
tatcagcaat aaaccagcca gccggaaggg ccgagcgcag aagtggtcct gcaactttat    8220
ccgcctccat ccagtctatt aattgttgcc gggaagctag agtaagtagt tcgccagtta    8280
atagtttgcg caacgttgtt gccatcgcta caggcatcgt ggtgtcacgc tcgtcgtttg    8340
gtatggcttc attcagctcc ggttcccaac gatcaaggcg agttacatga tcccccatgt    8400
tgtgcaaaaa agcggttagc tccttcggtc ctccgatcgt tgtcagaagt aagttggccg    8460
cagtgttatc actcatggtt atggcagcac tgcataattc tcttactgtc atgccatccg    8520
taagatgctt ttctgtgact ggtgagtact caaccaagtc attctgagaa tagtgtatgc    8580
ggcgaccgag ttgctcttgc ccggcgtcaa tacgggataa taccgcgcca catagcagaa    8640
ctttaaaagt gctcatcatt ggaaaacgtt cttcggggcg aaaactctca aggatcttac    8700
cgctgttgag atccagttcg atgtaaccca ctcgtgcacc caactgatct tcagcatctt    8760
ttactttcac cagcgtttct gggtgagcaa aaacaggaag gcaaaatgcc gcaaaaaagg    8820
gaataagggc gacacggaaa tgttgaatac tcatattctt ccttttcaa tattattgaa    8880 gcatttatca gggttattgt ctcatgagcg gatacatatt tgaatgtatt tagaaaaata    8940
acaaataggg gtcagtgtt acaaccaatt aaccaattct gaacattatc gcg           8993

<210> SEQ ID NO 2
<211> LENGTH: 8994
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctcatgacca aaatccctta acgtgagtta cgcgcgcgtc gttccactga gcgtcagacc      60
ccgtagaaaa gatcaaagga tcttcttgag atccttttt tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg gctgctgcca gtggcgataa gtcgtgtctt accgggttgg     360
actcaagacg atagttaccg gataaggcgc agcggtcggg ctgaacgggg ggttcgtgca     420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc     600
ctgtcgggtt tcgccacctc tgacttgagc gtcgatttt tgtgatgctcg tcagggggggc     660 ggagcctatg gaaaaacgcc agcaacgcgg cctttttacg gttcctggcc ttttgctggc     720
cttttgctca catgttcttt cctgcgttat cccctgattc tgtggataac cgtattaccg     780
cctttgagtg agctgatacc gctcgccgca gccgaacgac cgagcgcagc gagtcagtga     840
gcgaggaagc ggaaggcgag agtagggaac tgccaggcat caaactaagc agaaggcccc     900
tgacggatgg ccttttttgcg tttctacaaa ctctttctgt gttgtaaaac gacggccagt     960
cttaagctcg ggcccctgg gcggttctga taacgagtaa tcgttaatcc gcaaataacg    1020
```

```
taaaaacccg cttcggcggg ttttttttatg gggggagttt agggaaagag catttgtcag    1080
aatatttaag ggcgcctgtc actttgcttg atatatgaga attatttaac cttataaatg    1140
agaaaaaagc aacgcacttt aaataagata cgttgctttt tcgattgatg aacacctata    1200
attaaactat tcatctatta tttatgattt tttgtatata caatatttct agtttgttaa    1260
agagaattaa gaaataaat ctcgaaaata ataagggaa aatcagtttt tgatatcaaa      1320
attatacatg tcaacgataa tacaaaatat aatacaaact ataagatgtt atcagtattt    1380
attatcattt agaataaatt ttgtgtcgcc cttaattgtg agcggataac aattacgagc    1440
ttcatgcaca gtggcgttga cattgattat tgactagtta ttaatagtaa tcaattacgg    1500
ggtcattagt tcatagccca tatatggagt tccgcgttac ataacttacg gtaaatggcc    1560
cgcctggctg accgcccaac gacccccgcc cattgacgtc aataatgacg tatgttccca    1620
tagtaacgcc aatagggact ttccattgac gtcaatgggt ggagtattta cggtaaactg    1680
cccacttggc agtacatcaa gtgtatcata tgccaagtac gccccctatt gacgtcaatg    1740
acggtaaatg gcccgcctgg cattatgccc agtacatgac cttatgggac tttcctactt    1800
ggcagtacat ctacgtatta gtcatcgcta ttaccatggt gatgcggttt tggcagtaca    1860
tcaatgggcg tggatagcgg tttgactcac ggggatttcc aagtctccac cccattgacg    1920
tcaatgggag tttgttttgg caccaaaatc aacgggactt tccaaaatgt cgtaacaact    1980
ccgccccatt gacgcaaatg gcggtaggc gtgtacggtg ggaggtctat ataagcagag    2040
ctctctggct aactagagaa cccactgctt actggcttat cgaaattaat acgactcact    2100 atagggtac ctgccaccat ggggaaaaac aaactgctgc atccaagcct ggtcctgctg    2160
ctgctggttc tgctgcctac tgacgcctct gtgagcggaa agccccagta tatggttctg    2220
gtcccgtccc tgctgcacac cgagaccaca gaaaagggt gcgtgctgct gtcttacctg    2280
aatgaaacag tgactgttag tgcctcactg gagagtgtgc gcggaaatcg ttcactgttc    2340
accgatctgg aggcggaaaa cgatgtgctg cattgcgtcg catttgctgt gccaaaaagc    2400
tcctctaatg aagaagtgat gttcctgacc gtccaggtga agggcccctac acaggaattc    2460 aaaaaacgca ctaccgttat ggtcaaaaac gaggatagcc tggtgtttgt tcagacagac    2520
aaatccatct ataagcctgg tcagactgtg aagttccggg tggttagcat ggatgaaaat    2580
tttcaccccc tgaacgagct gattccactg gtgtacatcc aggaccctaa aggcaaccgc    2640
atcgcccagt ggcagtcttt ccagctggaa ggcggtctga agcagtttag tttccctctg    2700
agttcagagc cgtttcaggg ttcttataaa gtcgtggttc agaaaaagag tgggggacgt    2760
actgaacatc ctttttaccgt tgaagagttc gtcctgccga aatttgaggt ccaggtgacc    2820
gttcccaaga ttatcacaat tctggaagag gaaatgaacg tgagcgtgtg cggactgtat    2880
acctacggca aaccagtgcc tggtcacgtt acagtcagta tctgccgtaa gtactcagat    2940
gcaagcgact gtcatggcga agattcacag gcttttttgcg agaagttcag cggccagctg    3000
aactcccacg gttgcttcta tcagcaggtg aaaaccaagg ttttttcagct gaaacggaag    3060 gagtacgaaa tgaaactgca tacagaagcc cagattcagg aagaaggcac cgtcgtggaa    3120
ctgactggtc gtcagagctc cgagattacc cggacaatca ctaaactgag cttcgtgaag    3180
gttgattccc actttcggca ggggattccc tttttcggac aggtgcgcct ggttgacggg    3240
aaaggagttc cgatccccaa caaagtgatc tttattcgcg gcaatgaagc caactattac    3300
agcaacgcga caactgatga gcatgggctg gtgcagttca gtatcaatac cacaaacgtg    3360
```

-continued

```
atgggaacct cactgacagt ccgcgtgaat tataaagacc gttcaccgtg ttatggctac    3420
cagtgggtga gcgaggaaca cgaggaagcc caccataccg cgtacctggt tttcagcccc    3480
tccaaatctt ttgtccatct ggaacctatg tctcacgagc tgccgtgcgg ccatacccag    3540
acagtgcagg cacattatat tctgaacggg ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt    3720
gctccggtcg cccgtctgct gatctatgcc gtgctgccaa ccggcgatgt tatcggtgac    3780
tccgccaaat acgatgtgga gaattgtctg gcgaacaagg ttgacctgag cttttccccc    3840
tctcagagtc tgccagcgtc tcatgcacat ctgcgtgtga ccgcagcccc tcagagcgtt    3900
tgcgctctgc gtgcagtgga tcagtccgtg ctgctgatga agccagacgc agaactgtct    3960
gctagcagcg tgtataatct gctgcctgag aaagatctga ccgggttccc aggacctctg    4020
aacgatcagg atgacgaaga ctgtattaat cgccacaacg tgtatattaa tgggatcaca    4080
tacactccgg tttcaagcac caacgaaaaa gatatgtaca gcttcctgga ggacatgggt    4140
ctgaaagcgt ttaccaattc caagatccgg aaaccccaag atgtgcccac agctcgagca    4200
gtatgaaatg cacggacctg agggtctgcg tgtgggcttt tacgaatctg atgtgatggg    4260
acgtggtcat gcacgtctgg ttcatgtcga ggaaccacac accgaaaagc ttcgtaaata    4320
cttccctgag acctggattt gggacctggt tgtggtgaac tccgcgggtg tggcagaagt    4380
gggtgttacc gtcccggata ctattaccga atggaaagca ggtgccttct gtctgtctga    4440
ggatgcaggg ctgggaatct cctctacagc ctctctgcgc gcgtttcagc ccttttttcgt    4500 cgaactgact atgccatata gcgtgattcg tggcgaggca ttcactctga aagctaccgt    4560
gctgaattac ctgcccaagt gcatccgcgt gagcgtgcag ctggaagcta gtcccgcctt    4620
tctggcggtc ccagtggaga aggaacaggc accgcactgc atttgtgcta acggccggca    4680 gactgttttcc tgggccgtca cccccaaatc tctgggtaat gtgaacttca ccgtttcagc    4740
agaggctctg gaaagccagg agctgtgcgg caccgaagtc ccatccgtgc tgagcatgg    4800 tcgcaaagat acagtcatca agcctctgct ggttgaaccg gaaggcctgg agaaggaaac    4860
tacctttaat tctctgctgt gcccaagtgg cggtgaagtg tccgaggaac tgtctctgaa    4920
actgccgccc aacgtggtcg aggaatctgc ccgtgcgtca gttagcgtcc tgggggatat    4980
tctgggaagt gccatgcaga ataccagaa cctgctgcag atgccgtatg ctgtggcga    5040 gcagaatatg gttctgtttg cgcccaacat ctatgtcctg gattacctga atgaaacaca    5100
gcagctgact cctgaaatca aaagcaaggc aatcgggtat ctgaataccg gataccagcg    5160
gcagctgaac tataagcact acgacggctc ctattctacc ttcggcgaac ggtacggtcg    5220
caatcagggg aacacttggc tgaccgcctt tgtgctgaaa cctttgccc aggctcgcgc    5280 ctatatcttt attgatgagg cccatattac acaggcgctg atctggctgt cacacgccca    5340
gaaggacaac gggtgtttcc gtagttcagg aagcctgctg aacaatgcca tcaaaggcgg    5400
cgtcgaggat gaagtgacac tgagcgcata cattactatc gctctgctgg aaatccctct    5460
gacagtgact caccggtgg ttcgcaatgc tctgttttgc ctggaaagtg catggaaaac    5520
agctcaggaa ggcgatcacg gatcacacgt gtatactaag gcactgctgg cgtacgcatt    5580
cgctctggcc ggcaaccagg ataaacgtaa agaagtgctg aaatcactga atgaggaagc    5640
agttaaaaag gacaacagcg tccactggga acggccgcag aaacccaagg ctccagtggg    5700 tcactttttat gagcctcagg caccgagtgc tgaggtggaa atgacctcat atgttctgct    5760
```

```
ggcatacctg accgcacagc ctgccccac atcagaagat ctgacaagcg ccactaatat    5820
tgtgaaatgg atcaccaagc agcagaacgc gcagggcggt tttagctcca cccaggacac    5880
agtcgtggca ctgcacgctc tgtctaaata tggggcagct accttcacac gcactggaaa    5940
ggccgcgcaa gtgactattc agtctagtgg caccttttca agcaagttcc aggtggataa    6000
caataaccgt ctgctgctgc agcaggtgtc cctgcccgaa ctgccaggcg agtactctat    6060
gaaagtcact ggggaaggat gcgtgtatct gcagacctcc ctgaaataca atattctgcc    6120
cgagaaagaa gaatttccat tcgcactggg cgtgcagacc ctgcctcaga catgcgatga    6180
accgaaggct catacttctt ttcagatcag tctgtcagtg agctataccg ggtcccgctc    6240
tgccagtaac atggcgattg tggatgtgaa aatggtgagt ggattcatcc ctctgaaacc    6300
gactgtgaag atgctggaac ggagtaatca cgtttcacgc accgaggtct cctctaacca    6360
tgtgctgatc tacctggata aagtgtccaa tcagacactg tctctgtttt tcactgtgct    6420
gcaggatgtc cccgtgcgtg acctgaaacc agccattgtt aaggtctatg attattacga    6480
aaccgacgag ttcgcgatcg cagaatacaa cgcgccgtgc agcaaagacc tggggaatgc    6540
tgactacaag gacgacgacg acaagggggc aagccaccac catcaccatc actaaggatc    6600
caaaatcagc ctcgactgtg ccttctagtt gccagccatc tgttgtttgc cctcccccg    6660 tgccttcctt gaccctggaa ggtgccactc ccactgtcct ttcctaataa aatgaggaaa    6720
ttgcatcaca acactcaacc ctatctcggt ctattctttt gatttataag ggattttgcc    6780
gatttcggcc tattggttaa aaaatgagct gatttaacaa aaatttaacg cgaattaatt    6840
ctgtggaatg tgtgtcagtt agggtgtgga aagtccccag gctccccagc aggcagaagt    6900
atgcaaagca tgcatctcaa ttagtcagca accaggtgtg gaaagtcccc aggctcccca    6960
gcaggcagaa gtatgcaaag catgcatctc aattagtcag caaccatagt cccgccccta    7020
actccgccca tcccgcccct aactccgccc agttccgccc attctccgcc ccatggctga    7080 ctaattttt ttatttatgc agaggccgag gccgcctctg cctctgagct attccagaag    7140
tagtgaggag gcttttttgg aggcctaggc ttttgcaaaa agctcccggg agcttgtata    7200 tccatttcg gatctgatca gcacgtgttg acaattaatc atcggcatag tatatcggca    7260
tagtataata cgacaaggtg aggaactaaa ccatggccaa gcctttgtct caagaagaat    7320
ccaccctcat tgaaagagca acggctacaa tcaacagcat ccccatctct gaagactaca    7380
gcgtcgccag cgcagctctc tctagcgacg gccgcatctt cactggtgtc aatgtatatc    7440
attttactgg gggaccttgt gcagaactcg tggtgctggg cactgctgct gctgcggcag    7500
ctggcaacct gacttgtatc gtcgcgatcg gaaatgagaa cagggcatc ttgagcccct    7560 gcggacggtg ccgacaggtg cttctcgatc tgcatcctgg gatcaaagcc atagtgaagg    7620
acagtgatgg acagccgacg gcagttggga ttcgtgaatt gctgccctct ggttatgtgt    7680
gggagggcta acacgtgcta cgagatttcg attccaccgc cgccttctat gaaaggttgg    7740
gcttcggaat cgttttccgg gacgccggct ggatgatcct ccagcgcggg gatctcatgc    7800
tggagttctt cgcccacccc aacttgttta ttgcagctta taatggttac aaataaagca    7860
atagcatcac aaatttcaca aataaagcat ttttttcact gcattctagt tgtggtttgt    7920
ccaaactcat caatgtatct tatcatgtct gtataccgtc gacctctagc tagagcttgg    7980
cgtaatcatg gtcattacca atgctttaatc agtgaggcac ctatctcagc gatctgtcta    8040
tttcgttcat ccatagttgc ctgactcccc gtcgtgtaga taactacgat acgggagggc    8100
```

-continued

```
ttaccatctg gccccagcgc tgcgatgata ccgcgagaac cacgctcacc ggctccggat    8160
ttatcagcaa taaaccagcc agccggaagg gccgagcgca gaagtggtcc tgcaacttta    8220
tccgcctcca tccagtctat taattgttgc cgggaagcta gagtaagtag ttcgccagtt    8280
aatagtttgc gcaacgttgt tgccatcgct acaggcatcg tggtgtcacg ctcgtcgttt    8340
ggtatggctt cattcagctc cggttcccaa cgatcaaggc gagttacatg atcccccatg    8400
ttgtgcaaaa aagcggttag ctccttcggt cctccgatcg ttgtcagaag taagttggcc    8460
gcagtgttat cactcatggt tatggcagca ctgcataatt ctcttactgt catgccatcc    8520
gtaagatgct tttctgtgac tggtgagtac tcaaccaagt cattctgaga atagtgtatg    8580
cggcgaccga gttgctcttg cccggcgtca atacgggata ataccgcgcc acatagcaga    8640
actttaaaag tgctcatcat tggaaaacgt tcttcggggc gaaaactctc aaggatctta    8700
ccgctgttga gatccagttc gatgtaaccc actcgtgcac ccaactgatc ttcagcatct    8760
tttactttca ccagcgtttc tgggtgagca aaaacaggaa ggcaaaatgc cgcaaaaaag    8820
ggaataaggg cgacacggaa atgttgaata ctcatattct ccttttttca atattattga    8880
agcatttatc agggttattg tctcatgagc ggatacatat ttgaatgtat ttagaaaaat    8940
aaacaaatag gggtcagtgt tacaaccaat taaccaattc tgaacattat cgcg          8994
```

<210> SEQ ID NO 3
<211> LENGTH: 1491
<212> TYPE: PRT
<213> ORGANISM: Homo sapiens
<220> FEATURE:
<223> OTHER INFORMATION: Tagged wild-type human A2M polypeptide
<400> SEQUENCE: 3

```
Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205
```

-continued

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                    245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                    325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                    405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                    485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                    565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asp Glu

```
                625                 630                 635                 640
Asp Cys Ile Asn Arg His Asn Val Tyr Ile Asn Gly Ile Thr Tyr Thr
                    645                 650                 655
Pro Val Ser Ser Thr Asn Glu Lys Asp Met Tyr Ser Phe Leu Glu Asp
                660                 665                 670
Met Gly Leu Lys Ala Phe Thr Asn Ser Lys Ile Arg Lys Pro Lys Met
            675                 680                 685
Cys Pro Gln Leu Gln Gln Tyr Glu Met His Gly Pro Glu Gly Leu Arg
        690                 695                 700
Val Gly Phe Tyr Glu Ser Asp Val Met Gly Arg Gly His Ala Arg Leu
705                 710                 715                 720
Val His Val Glu Glu Pro His Thr Glu Thr Val Arg Lys Tyr Phe Pro
                725                 730                 735
Glu Thr Trp Ile Trp Asp Leu Val Val Asn Ser Ala Gly Val Ala
                    740                 745                 750
Glu Val Gly Val Thr Val Pro Asp Thr Ile Thr Glu Trp Lys Ala Gly
                755                 760                 765
Ala Phe Cys Leu Ser Glu Asp Ala Gly Leu Gly Ile Ser Ser Thr Ala
        770                 775                 780
Ser Leu Arg Ala Phe Gln Pro Phe Val Glu Leu Thr Met Pro Tyr
785                 790                 795                 800
Ser Val Ile Arg Gly Glu Ala Phe Thr Leu Lys Ala Thr Val Leu Asn
                805                 810                 815
Tyr Leu Pro Lys Cys Ile Arg Val Ser Val Gln Leu Glu Ala Ser Pro
                820                 825                 830
Ala Phe Leu Ala Val Pro Val Glu Lys Glu Gln Ala Pro His Cys Ile
        835                 840                 845
Cys Ala Asn Gly Arg Gln Thr Val Ser Trp Ala Val Thr Pro Lys Ser
    850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
                885                 890                 895
Asp Thr Val Ile Lys Pro Leu Leu Val Glu Pro Glu Gly Leu Glu Lys
                900                 905                 910
Glu Thr Thr Phe Asn Ser Leu Leu Cys Pro Ser Gly Gly Glu Val Ser
                915                 920                 925
Glu Glu Leu Ser Leu Lys Leu Pro Pro Asn Val Val Glu Glu Ser Ala
        930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
                965                 970                 975
Met Val Leu Phe Ala Pro Asn Ile Tyr Val Leu Asp Tyr Leu Asn Glu
                980                 985                 990
Thr Gln Gln Leu Thr Pro Glu Ile Lys Ser Lys Ala Ile Gly Tyr Leu
                995                 1000                1005
Asn Thr Gly Tyr Gln Arg Gln Leu Asn Tyr Lys His Tyr Asp Gly
        1010                1015                1020
Ser Tyr Ser Thr Phe Gly Glu Arg Tyr Gly Arg Asn Gln Gly Asn
        1025                1030                1035
Thr Trp Leu Thr Ala Phe Val Leu Lys Thr Phe Ala Gln Ala Arg
        1040                1045                1050
```

```
Ala Tyr Ile Phe Ile Asp Glu Ala His Ile Thr Gln Ala Leu Ile
1055                1060                1065

Trp Leu Ser Gln Arg Gln Lys Asp Asn Gly Cys Phe Arg Ser Ser
1070                1075                1080

Gly Ser Leu Leu Asn Asn Ala Ile Lys Gly Gly Val Glu Asp Glu
1085                1090                1095

Val Thr Leu Ser Ala Tyr Ile Thr Ile Ala Leu Leu Glu Ile Pro
1100                1105                1110

Leu Thr Val Thr His Pro Val Val Arg Asn Ala Leu Phe Cys Leu
1115                1120                1125

Glu Ser Ala Trp Lys Thr Ala Gln Glu Gly Asp His Gly Ser His
1130                1135                1140

Val Tyr Thr Lys Ala Leu Leu Ala Tyr Ala Phe Ala Leu Ala Gly
1145                1150                1155

Asn Gln Asp Lys Arg Lys Glu Val Leu Lys Ser Leu Asn Glu Glu
1160                1165                1170

Ala Val Lys Lys Asp Asn Ser Val His Trp Glu Arg Pro Gln Lys
1175                1180                1185

Pro Lys Ala Pro Val Gly His Phe Tyr Glu Pro Gln Ala Pro Ser
1190                1195                1200

Ala Glu Val Glu Met Thr Ser Tyr Val Leu Leu Ala Tyr Leu Thr
1205                1210                1215

Ala Gln Pro Ala Pro Thr Ser Glu Asp Leu Thr Ser Ala Thr Asn
1220                1225                1230

Ile Val Lys Trp Ile Thr Lys Gln Gln Asn Ala Gln Gly Gly Phe
1235                1240                1245

Ser Ser Thr Gln Asp Thr Val Val Ala Leu His Ala Leu Ser Lys
1250                1255                1260

Tyr Gly Ala Ala Thr Phe Thr Arg Thr Gly Lys Ala Ala Gln Val
1265                1270                1275

Thr Ile Gln Ser Ser Gly Thr Phe Ser Ser Lys Phe Gln Val Asp
1280                1285                1290

Asn Asn Asn Arg Leu Leu Leu Gln Gln Val Ser Leu Pro Glu Leu
1295                1300                1305

Pro Gly Glu Tyr Ser Met Lys Val Thr Gly Glu Gly Cys Val Tyr
1310                1315                1320

Leu Gln Thr Ser Leu Lys Tyr Asn Ile Leu Pro Glu Lys Glu Glu
1325                1330                1335

Phe Pro Phe Ala Leu Gly Val Gln Thr Leu Pro Gln Thr Cys Asp
1340                1345                1350

Glu Pro Lys Ala His Thr Ser Phe Gln Ile Ser Leu Ser Val Ser
1355                1360                1365

Tyr Thr Gly Ser Arg Ser Ala Ser Asn Met Ala Ile Val Asp Val
1370                1375                1380

Lys Met Val Ser Gly Phe Ile Pro Leu Lys Pro Thr Val Lys Met
1385                1390                1395

Leu Glu Arg Ser Asn His Val Ser Arg Thr Glu Val Ser Ser Asn
1400                1405                1410

His Val Leu Ile Tyr Leu Asp Lys Val Ser Asn Gln Thr Leu Ser
1415                1420                1425

Leu Phe Phe Thr Val Leu Gln Asp Val Pro Val Arg Asp Leu Lys
1430                1435                1440
```

```
Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala Asp Tyr Lys Asp Asp Asp Lys Gly Ala Ser His His His
    1475                1480                1485

His His His
    1490

<210> SEQ ID NO 4
<211> LENGTH: 1491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
                100                 105                 110

Glu Phe Lys Lys Arg Thr Thr Val Met Val Lys Asn Glu Asp Ser Leu
            115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300
```

```
Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
                355                 360                 365

Val Arg Leu Val Asp Gly Lys Gly Val Pro Ile Pro Asn Lys Val Ile
                370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
                435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
                515                 520                 525

Pro Val Lys Ser Asp Ile Ala Pro Val Ala Arg Leu Leu Ile Tyr Ala
                530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
                595                 600                 605

Pro Asp Ala Glu Leu Ser Ala Ser Val Tyr Asn Leu Leu Pro Glu
                610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
                675                 680                 685

Cys Pro Gln Leu Glu Gln Tyr Glu Met His Gly Pro Glu Gly Leu Arg
                690                 695                 700

Val Gly Phe Tyr Glu Ser Asp Val Met Gly Arg Gly His Ala Arg Leu
705                 710                 715                 720
```

```
Val His Val Glu Glu Pro His Thr Glu Lys Leu Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
                755                 760                 765

Ala Phe Cys Leu Ser Glu Asp Ala Gly Leu Gly Ile Ser Ser Thr Ala
        770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
            805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
        850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
            885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
                980                 985                 990

Thr Gln Gln Leu Thr Pro Glu Ile Lys Ser Lys Ala Ile Gly Tyr Leu
            995                 1000                1005

Asn Thr Gly Tyr Gln Arg Gln Leu Asn Tyr Lys His Tyr Asp Gly
    1010                1015                1020

Ser Tyr Ser Thr Phe Gly Glu Arg Tyr Gly Arg Asn Gln Gly Asn
    1025                1030                1035

Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
    1055                1060                1065

Trp Leu Ser Gln Arg Gln Lys Asp Asn Gly Cys Phe Arg Ser Ser
    1070                1075                1080

Gly Ser Leu Leu Asn Asn Ala Ile Lys Gly Gly Val Glu Asp Glu
    1085                1090                1095

Val Thr Leu Ser Ala Tyr Ile Thr Ile Ala Leu Leu Glu Ile Pro
    1100                1105                1110

Leu Thr Val Thr His Pro Val Val Arg Asn Ala Leu Phe Cys Leu
    1115                1120                1125

Glu Ser Ala Trp Lys Thr Ala Gln Glu Gly Asp His Gly Ser His
```

```
            1130                1135                1140
Val Tyr Thr Lys Ala Leu Leu Ala Tyr Ala Phe Ala Leu Ala Gly
    1145                1150                1155

Asn Gln Asp Lys Arg Lys Glu Val Leu Lys Ser Leu Asn Glu Glu
    1160                1165                1170

Ala Val Lys Lys Asp Asn Ser Val His Trp Glu Arg Pro Gln Lys
    1175                1180                1185

Pro Lys Ala Pro Val Gly His Phe Tyr Glu Pro Gln Ala Pro Ser
    1190                1195                1200

Ala Glu Val Glu Met Thr Ser Tyr Val Leu Leu Ala Tyr Leu Thr
    1205                1210                1215

Ala Gln Pro Ala Pro Thr Ser Glu Asp Leu Thr Ser Ala Thr Asn
    1220                1225                1230

Ile Val Lys Trp Ile Thr Lys Gln Gln Asn Ala Gln Gly Gly Phe
    1235                1240                1245

Ser Ser Thr Gln Asp Thr Val Val Ala Leu His Ala Leu Ser Lys
    1250                1255                1260

Tyr Gly Ala Ala Thr Phe Thr Arg Thr Gly Lys Ala Ala Gln Val
    1265                1270                1275

Thr Ile Gln Ser Ser Gly Thr Phe Ser Ser Lys Phe Gln Val Asp
    1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
    1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
    1340                1345                1350

Glu Pro Lys Ala His Thr Ser Phe Gln Ile Ser Leu Ser Val Ser
    1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala Asp Tyr Lys Asp Asp Asp Lys Gly Ala Ser His His His
    1475                1480                1485

His His His
    1490

<210> SEQ ID NO 5
<211> LENGTH: 41
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 5

Leu Glu Gln Tyr Glu Met His Gly Pro Glu Gly Leu Arg Val Gly Lys
1               5                   10                  15

Glu Glu Glu Gly Leu Gly Ser Ile Pro Glu Asn Phe Phe Gly Val Ser
            20                  25                  30

Glu Leu Glu Gly Arg Gly Ser Lys Leu
        35                  40

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Glu Gln Tyr Glu Met His Gly Pro Glu Gly Leu Arg Val Gly Ile
1               5                   10                  15

Pro Glu Asn Phe Phe Gly Val Ser Glu Leu Glu Gly Arg Gly Ser Lys
            20                  25                  30

Glu Glu Glu Gly Leu Gly Ser Lys Leu
        35                  40

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Glu Gln Tyr Glu Met His Gly Pro Glu Gly Leu Arg Val Gly Ser
1               5                   10                  15

Glu Leu Glu Gly Arg Gly Ser Lys Glu Glu Glu Gly Leu Gly Ser Ile
            20                  25                  30

Pro Glu Asn Phe Phe Gly Val Lys Leu
        35                  40

<210> SEQ ID NO 8
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Glu Gln Tyr Glu Met His Gly Pro Glu Gly Leu Arg Val Gly Lys
1               5                   10                  15

Glu Glu Glu Gly Leu Gly Ser Ser Glu Leu Glu Gly Arg Gly Ser Thr
            20                  25                  30

Ala Gln Glu Ala Gly Glu Gly Lys Leu
        35                  40

<210> SEQ ID NO 9
<211> LENGTH: 48
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 9

Leu Glu Gln Tyr Glu Met His Gly Pro Glu Gly Leu Arg Val Gly Ile
1               5                   10                  15

Pro Glu Asn Phe Phe Gly Val Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 10
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Glu Gln Tyr Glu Met His Gly Pro Glu Gly Leu Arg Val Gly Lys
1               5                   10                  15

Glu Glu Glu Gly Leu Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 11
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Glu Gln Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 12
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Glu Gln Tyr Glu Met His Gly Pro Glu Gly Leu Arg Val Gly Glu
1               5                   10                  15

Ala Ile Pro Met Ser Ile Pro Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 13
<211> LENGTH: 48

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Glu Gln Tyr Glu Met His Gly Pro Glu Gly Leu Arg Val Gly Thr
1               5                   10                  15

Ala Gln Glu Ala Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 14
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Glu Gln Tyr Glu Met His Gly Pro Glu Gly Leu Arg Val Gly Val
1               5                   10                  15

Ser Gln Glu Leu Gly Gln Arg Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Glu Gln Tyr Glu Met His Gly Pro Glu Gly Leu Arg Val Gly Thr
1               5                   10                  15

Glu Gly Glu Ala Arg Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 16
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Glu Gln Tyr Glu Met His Gly Pro Glu Gly Leu Arg Val Gly Thr
1               5                   10                  15

Ser Glu Asp Leu Val Val Gln Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 17
```

```
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Glu Gln Tyr Glu Met His Gly Pro Glu Gly Leu Arg Val Gly Gly
1               5                   10                  15

Glu Glu Gly Val Glu Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 19
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Glu Gln Tyr Glu Met His Gly Pro Glu Gly Leu Arg Val Gly Gly
1               5                   10                  15

Ala Arg Gly Leu Glu Gly Phe Tyr Glu Ser Asp Val Met Gly Arg Gly
            20                  25                  30

His Ala Arg Leu Val His Val Glu Glu Pro His Thr Lys Leu
        35                  40                  45

<210> SEQ ID NO 20
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Glu Gln Tyr Glu Met His Gly Pro Glu Gly Leu Arg Val Gly Gly
1               5                   10                  15

Pro Pro Gly Leu Ala Pro Gly Phe Tyr Glu Ser Asp Val Met Gly Arg
            20                  25                  30

Gly His Ala Arg Leu Val His Val Glu Glu Pro His Thr Lys Leu Leu
        35                  40                  45
```

```
<210> SEQ ID NO 21
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Glu Gln Tyr Glu Met His Gly Pro Glu Gly Leu Arg Val Gly Gly
1               5                   10                  15

Glu Pro Glu Gly Ala Lys Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Glu Gln Tyr Glu Met His Gly Pro Glu Gly Leu Arg Val Gly Glu
1               5                   10                  15

Glu Glu Gly Gly Gly Phe Tyr Glu Ser Asp Val Met Gly Arg Gly His
            20                  25                  30

Ala Arg Leu Val His Val Glu Glu Pro His Thr Lys Leu
        35                  40                  45

<210> SEQ ID NO 23
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Leu Glu Gln Tyr Glu Met His Gly Pro Glu Gly Leu Arg Val Gly Gly
1               5                   10                  15

Tyr Pro Gly Ser Ser Arg Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Leu Glu Gln Tyr Glu Met His Gly Pro Glu Gly Leu Arg Val Gly Gly
1               5                   10                  15

Ala Arg Gly Leu Glu Gly Gly Phe Ala Gly Leu Pro Asn Gly Gly Glu
            20                  25                  30

Glu Gly Val Glu Glu Gly Lys Leu
        35                  40
```

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Glu Gln Tyr Glu Met His Gly Pro Glu Gly Leu Arg Val Gly Glu
1               5                   10                  15

Ser Glu Ser Glu Gly Gly Gly Gly Ser Leu Leu Gly Glu Phe Glu
            20                  25                  30

Val Glu Gly Gly Phe Ala Gly Leu Pro Asn Gly Lys Leu
        35                  40                  45

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Glu Gln Tyr Glu Met His Gly Pro Glu Gly Leu Arg Val Gly Gly
1               5                   10                  15

Phe Lys Glu Gly Val Glu Gly Glu Ile Glu Gly Gly Gly Phe Lys
            20                  25                  30

Glu Gly Val Glu Gly Lys Leu
        35

<210> SEQ ID NO 27
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Glu Gln Tyr Glu Met His Gly Pro Glu Gly Leu Arg Val Gly Glu
1               5                   10                  15

Ser Glu Ser Glu Gly Gly Phe Ala Gly Leu Pro Asn Gly Lys Glu Glu
            20                  25                  30

Glu Gly Leu Gly Ser Ile Pro Glu Asn Phe Phe Gly Val Lys Leu
        35                  40                  45

<210> SEQ ID NO 28
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Glu Gln Tyr Glu Met His Gly Pro Glu Gly Leu Arg Val Gly Ile
1               5                   10                  15

Pro Glu Asn Phe Phe Gly Val Thr Ser Glu Asp Leu Val Val Gln Glu
            20                  25                  30

Ala Ile Pro Met Ser Ile Pro Lys Leu
        35                  40

```
<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Leu Glu Gln Tyr Glu Met His Gly Pro Glu Gly Leu Arg Val Gly Glu
1               5                   10                  15

Ala Ile Pro Met Ser Ile Pro Thr Ser Glu Asp Leu Val Val Gln Ile
            20                  25                  30

Pro Glu Asn Phe Phe Gly Val Lys Leu
        35                  40

<210> SEQ ID NO 30
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Glu Pro Ala Gly Ala Ala Arg Gly Glu Ser Glu Ser Glu Gly Gly
1               5                   10                  15

Phe Phe Gly Phe Pro Ile Gly Glu Arg Glu Ser Thr Gly Gly Asp Arg
            20                  25                  30

Gly Leu Pro Ile Gly Glu Asn Glu Ala Gly Gly Lys Leu
        35                  40                  45

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Leu Glu Thr Glu Gly Arg Gly Glu Arg Glu Ala Gln Gly Glu Phe Pro
1               5                   10                  15

Glu Val Glu Gly Glu Glu Gly Gly Gly Pro Glu Lys Glu Thr Gly
            20                  25                  30

Gly Glu Arg Glu Ala Gln Gly Lys Leu
        35                  40

<210> SEQ ID NO 32
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Leu Glu Ala Arg Gly Leu Glu Gly Gly Gly Gly Ser Leu Leu Gly
1               5                   10                  15

Gly Tyr Pro Gly Ser Ser Arg Gly Gly Phe Lys Glu Gly Val Glu Gly
            20                  25                  30

Gly Pro Ala Gly Ala Ala Arg Gly Lys Leu
```

35                  40

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Leu Glu Pro Gly Leu Ala Pro Gly Gly Glu Glu Gly Val Glu Glu Gly
1               5                   10                  15

Gly Pro Glu Glu Val Glu Glu Gly Phe Lys Glu Gly Val Glu
            20                  25                  30

Gly Glu Pro Glu Ser Ser Gly Lys Leu
        35                  40

<210> SEQ ID NO 34
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Leu Glu Glu Gly Glu Ala Arg Gly Ser Thr Ala Gln Glu Ala Gly Glu
1               5                   10                  15

Gly Pro Lys Glu Glu Glu Gly Leu Gly Ser Ser Glu Leu Glu Gly Arg
            20                  25                  30

Gly Ser Pro Val Ser Gln Glu Leu Gly Gln Arg Lys Leu
        35                  40                  45

<210> SEQ ID NO 35
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Leu Glu Ala Gln Glu Ala Gly Glu Gly Lys Glu Glu Glu Gly Leu Gly
1               5                   10                  15

Ser Pro Val Ser Gln Glu Leu Gly Gln Arg Ser Glu Leu Glu Gly Arg
            20                  25                  30

Gly Ser Pro Thr Glu Gly Glu Ala Arg Gly Ser Lys Leu
        35                  40                  45

<210> SEQ ID NO 36
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Leu Glu Glu Glu Glu Gly Leu Gly Ser Lys Glu Glu Glu Gly Leu Gly
1               5                   10                  15

Ser Pro Lys Glu Glu Glu Gly Leu Gly Ser Lys Glu Glu Glu Gly Leu
            20                  25                  30

Gly Ser Pro Lys Glu Glu Glu Gly Leu Gly Ser Lys Leu
            35                  40                  45

<210> SEQ ID NO 37
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Glu Glu Leu Glu Gly Arg Gly Ser Lys Glu Glu Glu Gly Leu Gly
1               5                   10                  15

Ser Ile Pro Glu Asn Phe Phe Gly Val Phe Tyr Glu Ser Asp Val Met
            20                  25                  30

Gly Arg Gly His Ala Arg Leu Val His Val Glu Glu Pro His Thr Lys
        35                  40                  45

Leu

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Glu Glu Asn Phe Phe Gly Val Thr Glu Gly Glu Ala Arg Gly Ser
1               5                   10                  15

Pro Thr Ser Glu Asp Leu Val Val Gln Lys Glu Glu Glu Gly Leu Gly
            20                  25                  30

Ser Glu Ala Ile Pro Met Ser Ile Pro Lys Leu
        35                  40

<210> SEQ ID NO 39
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Glu Ile Pro Met Ser Ile Pro Lys Glu Glu Glu Gly Leu Gly Ser
1               5                   10                  15

Ile Pro Glu Asn Phe Phe Gly Val Thr Glu Gly Glu Ala Arg Gly Ser
            20                  25                  30

Pro Thr Ser Glu Asp Leu Val Val Gln Lys Leu
        35                  40

<210> SEQ ID NO 40
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Glu Leu Gln Gln Tyr Glu Met His Gly Pro Glu Gly Leu Arg Val
1               5                   10                  15

```
Gly Glu Ala Ile Pro Met Ser Ile Pro Ile Pro Glu Asn Phe Phe Gly
            20                  25                  30

Val Lys Glu Glu Glu Gly Leu Gly Ser Lys Leu
        35                  40
```

<210> SEQ ID NO 41
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Leu Glu Glu Glu Gly Val Glu Gly Lys Glu Glu Glu Gly Leu Gly
1               5                   10                  15

Ser Gly Pro Ala Gly Ala Ala Arg Gly Ser Glu Leu Glu Gly Arg Gly
            20                  25                  30

Ser Pro Thr Glu Gly Glu Ala Arg Gly Ser Lys Leu
        35                  40
```

<210> SEQ ID NO 42
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Leu Glu Pro Glu Ser Ser Gly Glu Ala Ile Pro Met Ser Ile Pro Thr
1               5                   10                  15

Ser Glu Asp Leu Val Val Gln Ile Pro Glu Asn Phe Phe Gly Val Glu
            20                  25                  30

Ala Glu Gly Thr Gly Gly Glu Arg Gly Val Leu Gly Lys Leu
        35                  40                  45
```

<210> SEQ ID NO 43
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Leu Glu Gly Gly Gly Ser Leu Leu Gly Glu Pro Glu Pro Glu Gly Glu
1               5                   10                  15

Arg Glu Ala Gln Gly Gly Val Glu Gly Val Glu Leu Gly Gly Phe Lys
            20                  25                  30

Glu Gly Val Glu Gly Glu Gln Glu Gly Arg Gly Lys Leu
        35                  40                  45
```

<210> SEQ ID NO 44
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Leu Glu Ser Gln Glu Leu Gly Gln Arg Glu Ser Glu Ser Glu Gly Ser
1               5                   10                  15
```

Glu Leu Glu Gly Arg Gly Ser Gly Phe Lys Glu Gly Val Glu Gly Lys
                20                  25                  30

Glu Glu Glu Gly Leu Gly Ser Gly Phe Phe Gly Phe Pro Ile Gly Lys
                35                  40                  45

Leu

<210> SEQ ID NO 45
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Glu Gln Tyr Glu Met His Gly Pro Lys Glu Glu Gly Leu Gly
1               5                   10                  15

Ser Ser Glu Leu Glu Gly Arg Gly Ser Glu Ala Ile Pro Met Ser Ile
                20                  25                  30

Pro Thr Ile Pro Glu Asn Phe Phe Gly Val Val Glu Glu Pro His Thr
            35                  40                  45

Lys Leu
    50

<210> SEQ ID NO 46
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Leu Glu Gln Tyr Glu Met His Gly Pro Ser Glu Leu Glu Gly Arg Gly
1               5                   10                  15

Ser Ile Pro Glu Asn Phe Phe Gly Val Glu Ala Ile Pro Met Ser Ile
                20                  25                  30

Pro Thr Ser Glu Asp Leu Val Val Gln Ile Val Glu Glu Pro His Thr
            35                  40                  45

Lys Leu
    50

<210> SEQ ID NO 47
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Asp Leu Val Val Gln
                20                  25                  30

Ile Ser Glu Leu Glu Gly Arg Gly Ser Val Glu Glu Pro His Thr Lys
            35                  40                  45

Leu

<210> SEQ ID NO 48

<400> SEQUENCE: 48

000

<210> SEQ ID NO 49

<400> SEQUENCE: 49

000

<210> SEQ ID NO 50
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Leu Glu Gln Tyr Glu Met His Gly Pro Ile Pro Glu Asn Phe Phe Gly
1               5                   10                  15

Val Ser Glu Leu Glu Gly Arg Gly Ser Glu Ala Ile Pro Met Ser Ile
            20                  25                  30

Pro Thr Glu Gly Glu Gly Glu Gly Val Glu Pro His Thr
        35                  40                  45

Lys Leu
    50
```

<210> SEQ ID NO 51
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Leu Glu Gln Tyr Glu Met His Gly Pro Ser Glu Leu Glu Gly Arg Gly
1               5                   10                  15

Ser Glu Ala Ile Pro Met Ser Ile Pro Thr Lys Glu Glu Glu Gly Leu
            20                  25                  30

Gly Ser Ile Pro Glu Asn Phe Phe Gly Val Val Glu Glu Pro His Thr
        35                  40                  45

Lys Leu
    50
```

<210> SEQ ID NO 52
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Leu Glu Gln Tyr Glu Met His Gly Pro Glu Ala Ile Pro Met Ser Ile
1               5                   10                  15

Pro Thr Glu Gly Glu Gly Glu Gly Gly Ile Pro Glu Asn Phe Phe
            20                  25                  30

Gly Val Ser Glu Asp Leu Val Val Gln Ile Val Glu Glu Pro His Thr
        35                  40                  45

Lys Leu
```

```
            50

<210> SEQ ID NO 53
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Glu Ala Ile Pro Met Ser Ile Pro Thr Val Glu Glu Pro His Thr
        35                  40                  45

Lys Leu
    50

<210> SEQ ID NO 54
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Glu Gln Tyr Glu Met His Gly Pro Glu Gly Glu Gly Glu Gly Glu
1               5                   10                  15

Gly Ile Ser Glu Asp Leu Val Val Gln Ile Pro Glu Asn Phe Phe Gly
            20                  25                  30

Val Lys Glu Glu Glu Gly Leu Gly Ser Val Glu Glu Pro His Thr Lys
        35                  40                  45

Leu

<210> SEQ ID NO 55
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Leu Glu Gly Arg Gly
            20                  25                  30

Ser Ser Glu Asp Leu Val Val Gln Ile Val Glu Glu Pro His Thr Lys
        35                  40                  45

Leu

<210> SEQ ID NO 56
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56
```

```
Leu Glu Gln Tyr Glu Met His Gly Pro Ile Pro Glu Asn Phe Phe Gly
1               5                   10                  15

Val Glu Gly Glu Gly Glu Gly Glu Ser Glu Leu Glu Gly Arg Gly Ser
                20                  25                  30

Ser Glu Asp Leu Val Val Gln Ile Val Glu Pro His Thr Lys Leu
            35                  40                  45

<210> SEQ ID NO 57
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Glu Gln Tyr Glu Met His Gly Pro Ser Glu Leu Glu Gly Arg Gly
1               5                   10                  15

Ser Ile Pro Glu Asn Phe Phe Gly Val Lys Glu Glu Glu Gly Leu Gly
                20                  25                  30

Ser Ser Glu Asp Leu Val Val Gln Ile Val Glu Glu Pro His Thr Lys
            35                  40                  45

Leu

<210> SEQ ID NO 58
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Glu Gln Tyr Glu Met His Gly Pro Ile Pro Glu Asn Phe Phe Gly
1               5                   10                  15

Val Ser Glu Leu Glu Gly Arg Gly Ser Ser Glu Asp Leu Val Val Gln
                20                  25                  30

Ile Lys Glu Glu Glu Gly Leu Gly Ser Val Glu Glu Pro His Thr Lys
            35                  40                  45

Leu

<210> SEQ ID NO 59
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Glu Gln Tyr Glu Met His Gly Pro Lys Glu Glu Glu Gly Leu Gly
1               5                   10                  15

Ser Ile Pro Glu Asn Phe Phe Gly Val Ser Glu Leu Glu Gly Arg Gly
                20                  25                  30

Ser Glu Gly Glu Gly Glu Gly Glu Gly Val Glu Glu Pro His Thr Lys
            35                  40                  45

Leu

<210> SEQ ID NO 60
<211> LENGTH: 49
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Leu Glu Gln Tyr Glu Met His Gly Pro Ser Glu Asp Leu Val Val Gln
1               5                   10                  15

Ile Lys Glu Glu Glu Gly Leu Gly Ser Ile Pro Glu Asn Phe Phe Gly
            20                  25                  30

Val Ser Glu Leu Glu Gly Arg Gly Ser Val Glu Glu Pro His Thr Lys
        35                  40                  45

Leu

<210> SEQ ID NO 61
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Lys Glu Glu Glu Gly Leu Gly Ser Val Glu Glu Pro His Thr Lys
        35                  40                  45

Leu

<210> SEQ ID NO 62
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Glu Ala Ile Pro Met Ser Ile Pro Thr Glu Pro His Thr Lys Leu
        35                  40                  45

<210> SEQ ID NO 63
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Leu Glu Gln Tyr Glu Met His Gly Pro Glu Gly Glu Gly Glu Gly Glu
1               5                   10                  15

Gly Ile Pro Glu Asn Phe Phe Gly Val Glu Ala Ile Pro Met Ser Ile
            20                  25                  30

Pro Thr Ser Glu Leu Glu Gly Arg Gly Ser Glu Pro His Thr Lys Leu
```

```
            35                  40                  45

<210> SEQ ID NO 64
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Leu Glu Gln Tyr Glu Met His Gly Pro Glu Ala Ile Pro Met Ser Ile
1               5                   10                  15

Pro Thr Ser Glu Leu Glu Gly Arg Gly Ser Ile Pro Glu Asn Phe Phe
            20                  25                  30

Gly Val Glu Gly Glu Gly Glu Gly Glu Pro His Thr Lys Leu
        35                  40                  45

<210> SEQ ID NO 65
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Glu Gln Tyr Glu Met His Gly Pro Ser Glu Leu Glu Gly Arg Gly
1               5                   10                  15

Ser Ile Pro Glu Asn Phe Phe Gly Val Glu Gly Glu Gly Glu Gly Glu
            20                  25                  30

Gly Lys Glu Glu Glu Gly Leu Gly Ser Val Glu Glu Pro His Thr Lys
        35                  40                  45

Leu

<210> SEQ ID NO 66
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Glu Gln Tyr Glu Met His Gly Pro Ile Pro Glu Asn Phe Phe Gly
1               5                   10                  15

Val Ser Glu Asp Leu Val Val Gln Ile Glu Gly Glu Gly Glu Gly Glu
            20                  25                  30

Gly Glu Ala Ile Pro Met Ser Ile Pro Thr Glu Pro His Thr Lys Leu
        35                  40                  45

<210> SEQ ID NO 67
<211> LENGTH: 10
<212> TYPE: PRT
<213> ORGANISM: Homo sapiens

<400> SEQUENCE: 67

Asn Ile Thr Glu Gly Glu Ala Arg Gly Ser
1               5                   10

<210> SEQ ID NO 68
<211> LENGTH: 11
<212> TYPE: PRT
```

```
<213> ORGANISM: Homo sapiens

<400> SEQUENCE: 68

Thr Ala Ser Glu Leu Glu Gly Arg Gly Thr Ile
1               5                   10

<210> SEQ ID NO 69
<211> LENGTH: 11
<212> TYPE: PRT
<213> ORGANISM: Homo sapiens

<400> SEQUENCE: 69

Thr Phe Lys Glu Glu Glu Gly Leu Gly Ser Val
1               5                   10

<210> SEQ ID NO 70
<211> LENGTH: 9
<212> TYPE: PRT
<213> ORGANISM: Homo sapiens

<400> SEQUENCE: 70

Val Asp Ile Pro Glu Asn Phe Phe Gly
1               5

<210> SEQ ID NO 71
<211> LENGTH: 5
<212> TYPE: PRT
<213> ORGANISM: Homo sapiens

<400> SEQUENCE: 71

Ala Arg Gly Ser Val
1               5

<210> SEQ ID NO 72
<211> LENGTH: 10
<212> TYPE: PRT
<213> ORGANISM: Homo sapiens

<400> SEQUENCE: 72

Ile Leu Thr Val Lys Pro Ile Phe Glu Val
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Tyr Lys Asp Asp Asp Asp Lys Gly Ala Ser His His His His His
1               5                   10                  15

His

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 74

His His His His His His
```

```
<210> SEQ ID NO 75
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
            20                  25                  30

Gly His Ala Arg Leu Val His Val Glu Glu Pro His Thr Lys Leu
        35                  40                  45

<210> SEQ ID NO 76
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Glu Gln Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
            20                  25                  30

Gly His Ala Arg Leu Val His Val Glu Glu Pro His Thr Lys Leu
        35                  40                  45
```